United States Patent
Shibayama et al.

(10) Patent No.: US 8,969,554 B2
(45) Date of Patent: Mar. 3, 2015

(54) 6-ACYL-1,2,4-TRIAZINE-3,5-DIONE DERIVATIVE AND HERBICIDES

(75) Inventors: Atsushi Shibayama, Shizuoka (JP); Ryu Kajiki, Shizuoka (JP); Masami Kobayashi, Tokyo (JP); Takashi Mitsunari, Tokyo (JP); Atsushi Nagamatsu, Tokyo (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 13/807,590

(22) PCT Filed: May 26, 2011

(86) PCT No.: PCT/JP2011/062643
§ 371 (c)(1),
(2), (4) Date: Dec. 28, 2012

(87) PCT Pub. No.: WO2012/002096
PCT Pub. Date: Jan. 5, 2012

(65) Prior Publication Data
US 2013/0102468 A1     Apr. 25, 2013

(30) Foreign Application Priority Data

Jun. 29, 2010     (JP) .................................. 2010-148286

(51) Int. Cl.
| | | |
|---|---|---|
| *C07D 253/075* | (2006.01) |
| *C07D 401/04* | (2006.01) |
| *C07D 401/06* | (2006.01) |
| *C07D 401/08* | (2006.01) |
| *C07D 401/12* | (2006.01) |
| *C07D 401/14* | (2006.01) |
| *C07D 403/04* | (2006.01) |

(Continued)

(52) U.S. Cl.
CPC .............. *A01N 43/707* (2013.01); *A01N 43/80* (2013.01); *A01N 43/84* (2013.01); *A01N 47/02* (2013.01); *C07D 253/075* (2013.01); *C07D 401/04* (2013.01); *C07D 401/06* (2013.01); *C07D 401/08* (2013.01); *C07D 401/12* (2013.01); *C07D 401/14* (2013.01); *C07D 403/04* (2013.01); *C07D 403/06* (2013.01); *C07D 403/08* (2013.01); *C07D 405/04* (2013.01); *C07D 405/06* (2013.01); *C07D 405/08* (2013.01); *C07D 405/14* (2013.01); *C07D 409/04* (2013.01); *C07D 409/06* (2013.01); *C07D 409/08* (2013.01); *C07D 411/04* (2013.01); *C07D 411/08* (2013.01); *C07D 411/14* (2013.01); *C07D 413/04* (2013.01); *C07D 413/08* (2013.01); *C07D 413/14* (2013.01); *C07D 417/04* (2013.01); *C07D 417/08* (2013.01); *C07D 417/14* (2013.01); *C07D 401/10* (2013.01); *C07D 405/10* (2013.01); *C07D 411/10* (2013.01); *C07D 413/10* (2013.01); *C07D 417/10* (2013.01)
USPC ........... 544/182; 544/223; 504/229; 514/242; 562/400; 562/405; 562/470; 562/488; 562/492; 562/493

(58) Field of Classification Search
USPC ................... 504/229; 514/242; 544/182, 223; 562/400, 405, 470, 488, 492, 493
See application file for complete search history.

(56) References Cited

U.S. PATENT DOCUMENTS

| 4,405,779 A | 9/1983 | Wiley |
|---|---|---|
| 5,798,316 A | 8/1998 | Theodoridis |
| 6,159,903 A * | 12/2000 | Linker et al. .................. 504/229 |

FOREIGN PATENT DOCUMENTS

| CN | 87107276 A | 10/1988 |
|---|---|---|
| EP | 0073970 A1 | 3/1983 |

(Continued)

OTHER PUBLICATIONS

Daunis et al., "Analogues azotes de derives de l'acide orotique", 1977; J. Heterocyclic Chem., 14(5):729-732.*

(Continued)

*Primary Examiner* — Jane C Oswecki
(74) *Attorney, Agent, or Firm* — Mintz Levin Cohn Ferris Glovsky and Popeo, P.C.; Peter F. Corless; Richard B. Emmons

(57) ABSTRACT

Disclosed are compounds exhibiting sufficient herbicidal activity at low application dosage when they are applied to soils and foliage, and an agrochemical composition using the same, in particular herbicides. The compounds are triazine derivatives represented by following Formula 1 or salts thereof, and the herbicides containing them: [Chem. 28] wherein in the formula, $R^1$ represents a hydrogen atom; a $C_1$-$C_{12}$ alkyl group; a $C_2$-$C_6$ alkenyl group, etc., $R^2$ represents a $C_1$-$C_{12}$ alkyl group, etc., Y and Z represent an oxygen atom or a sulfur atom, and A represents a 5- or 6-membered cyclic group which may contain a nitrogen atom, an oxygen atom, or a sulfur atom.

[1]

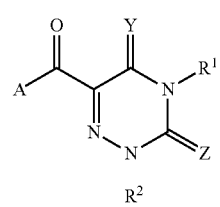

15 Claims, No Drawings

(51) Int. Cl.

| | | |
|---|---|---|
| *C07D 403/06* | (2006.01) | |
| *C07D 405/04* | (2006.01) | |
| *C07D 405/06* | (2006.01) | |
| *C07D 405/08* | (2006.01) | |
| *C07D 405/14* | (2006.01) | |
| *C07D 409/04* | (2006.01) | |
| *C07D 409/06* | (2006.01) | |
| *C07D 411/04* | (2006.01) | |
| *C07D 411/14* | (2006.01) | |
| *C07D 413/04* | (2006.01) | |
| *C07D 413/08* | (2006.01) | |
| *C07D 413/14* | (2006.01) | |
| *C07D 417/04* | (2006.01) | |
| *C07D 417/08* | (2006.01) | |
| *C07D 411/10* | (2006.01) | |
| *C07D 417/10* | (2006.01) | |
| *A01N 43/80* | (2006.01) | |
| *A01N 43/84* | (2006.01) | |
| *A01N 43/707* | (2006.01) | |
| *A01N 47/02* | (2006.01) | |
| *C07D 401/10* | (2006.01) | |
| *C07D 403/08* | (2006.01) | |
| *C07D 411/08* | (2006.01) | |
| *C07D 413/10* | (2006.01) | |
| *C07D 417/14* | (2006.01) | |
| *C07D 409/08* | (2006.01) | |
| *C07D 405/10* | (2006.01) | |

(56) References Cited

FOREIGN PATENT DOCUMENTS

| | | |
|---|---|---|
| EP | 271170 A2 | 6/1988 |
| JP | 63-156787 A | 6/1988 |
| JP | 5-51369 | 3/1993 |
| JP | 5-32641 | 9/1993 |
| JP | 8-259546 A | 10/1996 |
| JP | 2011/031658 A | 2/2011 |
| WO | 86/00072 A1 | 1/1986 |
| WO | WO86/00072 * | 1/1986 ........... C07D 253/06 |
| WO | 96/24589 A1 | 8/1996 |
| WO | 2004/048348 A1 | 6/2004 |
| WO | 2007/088876 A1 | 8/2007 |
| WO | 2008056257 A2 | 5/2008 |
| WO | 2009016841 A1 | 2/2009 |
| WO | 2011031658 A1 | 3/2011 |
| WO | WO2011/031658 A1 * | 3/2011 ........... C07D 401/04 |

OTHER PUBLICATIONS

Daunis et al., "No. 605—Etude en serie as-triazine. XIII—Preparations et proprietes de derives de l'acide thioxo-3 oxo-5 tetrahydro-2,3,4,5 as-triazine carboxylique-6"; 1973; Bulletin de la Societe Chimque de France, No. 11, Pt. 2, pp. 3178-3184.*

Daunis et al., "Analogues azotes de derives de l'acide orotique," 1977; J. Heterocyclic Chem., 14(5):729-732.*

Collection of Czechoslovak Chemical Communications (1969), 34(6), 1673-83.

The Pesticide Manual 15th Edition (2009, published by BCPC).

Daunis, J. et al., J. Heterocyclic Chem., (1977), vol. 14, No. 5, p. 729-32.

Daunis, J. et al., Bulletin de la Societe Chimque de France, (1973), No. 11, pt. 2, p. 3178-84.

Falco, E.A. et al., J. Am. Chem. Soc., (1956), vol. 58, p. 1938-41.

Office Action from corresponding Israeli Patent Application No. 222748, dated Jan. 2, 2014 (2 pages).

Office Action issued in corresponding EP Application Ser. No. 11 800 564.4 on Mar. 5, 2014, 5 pages.

Office Action issued in corresponding Chinese Application Ser. No. 100191, Mar. 3, 2014, 12 pages.

International Preliminary Report on Patentability issued on Jul. 14, 2011 for corresponding International application No. PTC/JP2011/062643 (7 pages).

Extended European Search Report for corresponding European Application Serial No. 11800564.4, Jun. 6, 2013 (6 pages).

* cited by examiner

6-ACYL-1,2,4-TRIAZINE-3,5-DIONE DERIVATIVE AND HERBICIDES

RELATED APPLICATIONS

This application is the U.S. national phase, pursuant to 35 U.S.C. §371, of PCT international application PCT/JP2011/062643, filed May 26, 2011, designating the United States and published on Jan. 5, 2012 as WO 2012/002096 A1, which claims priority to Japanese application 2010-148286, filed Jun. 29, 2010. The entire contents of the aforementioned patent applications are incorporated herein by this reference.

TECHNICAL FIELD

The present invention relates to a novel triazine derivative or its salt, and herbicides containing it as an effective component.

BACKGROUND ART

Triazine derivatives are known from "Collection of Czechoslovak Chemical Communications (1969), 34(6), 1673-83," etc., for example. However, no herbicidal activity is described for the compounds disclosed in these literatures. Although various compounds are reported as triazine-based herbicides (for example, see "The Pesticide Manual 15th Edition, 2009, published by BCPC"), they all have a 1,3,5-triazine ring. Specific examples of the 1,3,5-triazine-based agrochemicals include 2-chloro-4,6-bis-(ethylamino)-1,3,5-triazine (Simazine), 2-chloro-4-ethylamino-6-isopropylamino-1,3,5-triazine (Atrazin), 2,4-bis(ethylamino)-6-methylthio-1,3,5-triazine (Simetryn), 2,4-bis(isopropylamino)-6-methylthio-1,3,5-triazine (Prometryn), and 2-(1,2-dimethylpropylamino)-4-ethylamino-6-methylthio-1,3,5-triazine (Dimethametryn).

Further, as a 1,2,4-triazine-based agrochemical, there are known 4-amino-3-methyl-6-phenyl-1,2,4-triazine-5 (4H)-one (Metamitron), 4-amino-6-tert-butyl-3-methylthio-1,2,4-triazine-5 (4H)-one (Metribuzin), etc. It is disclosed in Japanese Patent Application Laid-Open (JP-A) No. 8-259546 that 4-(2,4-dihalogeno-5-alkoxyphenyl)-1,2,4-triazine-3,5-dione derivatives having a hydrocarbon substituent group at 6-position have a herbicidal activity. It is disclosed in JP-A No. 5-51369 that 3,5-diaryl-6-amino-1,2,4-triazine derivatives have a herbicidal activity. It is disclosed in JP-A No. 5-32641 that 3-mercapto-1,2,4-triazine derivatives have a herbicidal activity.

However, it is not known from any literatures that 6-acyl-1,2,4-triazine-3,5-dione derivatives represented by Formula 1 below have a herbicidal activity.

CITATION LIST

Patent Literature

PLT 1: Japanese Patent Application Laid-Open No. 8-259546
PLT 2: Japanese Patent Application Laid-Open No. 5-51369
PLT 3: Japanese Patent Application Laid-Open No. 5-32641

Non Patent Literature

NPL 1: Collection of Czechoslovak Chemical Communications (1969), 34(6), 1673-83.
NPL 2: The Pesticide Manual 15th Edition (2009, published by BCPC)

SUMMARY OF INVENTION

Technical Problem

Herbicides used for useful crops and useful plants are required to be a chemical preparation which can be applied to soils or leaves and exhibit a sufficient herbicidal effect with low chemical dosage. Further, as there is an increasing need concerning safety and effect on environment of a chemical substance, development of safer herbicides is waited for. The invention is devised to cope with such problems.

Solution to Problem

In order to achieve the object above, inventors of the invention synthesized many triazine compounds to study the herbicidal activity of various triazine derivatives, and intensively determined the herbicidal activity and usefulness of the compounds. As a result, it is found that, when triazine derivatives of the invention are applied to weeds or soils wherein weeds thrive, an excellent herbicidal effect is obtained for a long period of time, and therefore the invention is completed accordingly.

Thus, the present invention relates to the following (1) to (43).

(1) A triazine derivative or a salt thereof represented by following Formula 1:
[Chem. 1]

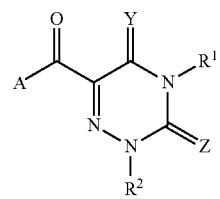

[1]

[in the formula, $R^1$ represents a hydrogen atom; a $C_1$-$C_{12}$ alkyl group; a $C_2$-$C_6$ alkenyl group; a $C_2$-$C_6$ alkynyl group; a $C_3$-$C_6$ cycloalkyl group; a $C_3$-$C_6$ cycloalkenyl group; a $C_3$-$C_6$ cycloalkyl $C_1$-$C_6$ alkyl group; a $C_1$-$C_6$ haloalkyl group; a $C_2$-$C_6$ haloalkenyl group; a $C_2$-$C_6$ haloalkynyl group; a $C_3$-$C_6$ halocycloalkyl group; a $C_3$-$C_6$ halocycloalkyl $C_1$-$C_6$ allyl group; an amino $C_1$-$C_6$ alkyl group; a nitro $C_1$-$C_6$ alkyl group; a $C_1$-$C_6$ alkylamino $C_1$-$C_6$ alkyl group; a di($C_1$-$C_6$ alkyl)amino $C_1$-$C_6$ alkyl group; a $C_1$-$C_6$ alkylthio $C_1$-$C_6$ allyl group; a $C_1$-$C_6$ alkylsulfinyl $C_1$-$C_6$ alkyl group; a $C_1$-$C_6$ allylsulfonyl $C_1$-$C_6$ alkyl group; a $C_1$-$C_6$ haloalkylthio $C_1$-$C_6$ alkyl group; a $C_1$-$C_6$ haloalkylsulfinyl $C_1$-$C_6$ alkyl group; a $C_1$-$C_6$ haloalkylsulfonyl $C_1$-$C_6$ alkyl group; a $C_1$-$C_6$ alkoxy $C_1$-$C_6$ alkyl group; a hydroxy $C_1$-$C_6$ alkyl group; a phenyl $C_1$-$C_6$ alkoxy $C_1$-$C_6$ alkyl group (phenyl in the group may be substituted with one substituent group selected from Substituent group α or 2 to 5 substituent groups that are the same or different from each other and selected from Substituent group α); a $C_1$-$C_6$ alkoxy $C_1$-$C_6$ alkoxy $C_1$-$C_6$ alkyl group; a $C_3$-$C_6$ cycloalkyloxy $C_1$-$C_6$ alkyl group; a $C_3$-$C_6$ cycloalkyl $C_1$-$C_6$ alkyloxy $C_1$-$C_6$ alkyl group; a phenyloxy $C_1$-$C_6$ alkyl group (the phenyl in the group may be substituted with 1 to 5 identical or different substituents selected from the Substituent group α); a phenylthio $C_1$-$C_6$ alkyl group (the phenyl in the group may be substituted with 1 to 5 identical or different substituents selected from the Substituent group α); a phenylsulfinyl $C_1$-$C_6$ alkyl group (the phenyl in the group may be substituted with 1 to 5 identical or different substituents selected from the Substituent group α); a phenylsulfonyl $C_1$-$C_6$ alkyl group (the phenyl in the group may be substituted with 1 to 5 identical or different substituents selected from the Substituent group α); a $C_1$-$C_6$ haloalkoxy $C_1$-$C_6$ alkyl group; a phenyl group which may be substituted with one or more substituents selected from the Substituent group α; a phenyl $C_1$-$C_6$ alkyl group which may be substituted with one or more substituents selected from the Substituent group α; a phenyl $C_2$-$C_6$ alkenyl group which may be substituted with one or more substituents selected from the Substituent group α; a phenyl $C_2$-$C_6$ alkynyl group which may be substituted with one or more substituents selected from the Substituent group α; a $C_1$-$C_6$ alkoxyimino $C_1$-$C_6$ alkyl group; a phenoxyimino $C_1$-$C_6$ alkyl group which may be substituted with one or more substituents selected from the Substituent group α; a di($C_1$-$C_6$ alkoxy) $C_1$-$C_6$ alkyl group; a ($R^{31}R^{32}N$—C=O) $C_1$-$C_6$ alkyl group; a $C_1$-$C_6$ alkoxycarbonyl $C_1$-$C_6$ alkyl group; a $C_1$-$C_6$ alkylcarbonyl $C_1$-$C_6$ alkyl group; a $C_1$-$C_6$ alkylcarbonyloxy $C_1$-$C_6$ alkyl group; a $C_1$-$C_6$ alkylidene aminooxy $C_1$-$C_6$ alkyl group; a formyl $C_1$-$C_6$ alkyl group; a $C_1$-$C_6$ alkylthio $C_1$-$C_6$ alkoxy $C_1$-$C_6$ alkyl group; a $C_1$-$C_6$ alkylsulfinyl $C_1$-$C_6$ alkoxy $C_1$-$C_6$ alkyl group; a $C_1$-$C_6$ alkylsulfonyl $C_1$-$C_6$ alkoxy $C_1$-$C_6$ alkyl group; a cyano $C_1$-$C_6$ alkoxy $C_1$-$C_6$ alkyl group; a cyano $C_1$-$C_6$ alkyl group; a $C_2$-$C_6$ alkylidene amino group; a di($C_1$-$C_{10}$ alkyl)amino $C_1$-$C_6$ alkylidene amino group; a $NR^{31}R^{32}$ group; a $C_1$-$C_6$ alkoxy group; a $C_2$-$C_6$ alkenyloxy group; a $C_2$-$C_6$ alkynyloxy group; a $C_3$-$C_6$ cycloalkyloxy group; a $C_3$-$C_6$ cycloalkyl $C_1$-$C_6$ alkyloxy group; a $C_1$-$C_6$ haloalkoxy group; a heterocyclic group comprising 3 to 10 carbon atoms and one or more identical or different heteroatoms selected from an oxygen atom, a sulfur atom, and a nitrogen atom [the group may be substituted with 1 to 5 identical or different substituents selected from the Substituent group α, and when the heteroatom in the heterocyclic group is a sulfur atom, the sulfur atom may be oxidized to sulfoxide or sulfone]; a $C_1$-$C_6$ alkyl group substituted with a heterocyclic group comprising 3 to 10 carbon atoms and one or more identical or different heteroatoms selected from an oxygen atom, a sulfur atom, and a nitrogen atom [the group may be substituted with 1 to 5 identical or different substituents selected from the Substituent group α]; a $C_1$-$C_6$ alkoxy $C_1$-$C_6$ alkyl group substituted with a heterocyclic group comprising 3 to 10 carbon atoms and one or more identical or different heteroatoms selected from an oxygen atom, a sulfur atom, and a nitrogen atom [the group may be substituted with 1 to 5 identical or different substituents selected from the Substituent group α]; or a $C_1$-$C_6$ alkoxy $C_1$-$C_6$ alkyl group substituted with a heterocyclic-oxy group in which the heterocyclic group in the heterocyclic-oxy group comprising 3 to 10 carbon atoms and one or more identical or different heteroatoms selected from an oxygen atom, a sulfur atom, and a nitrogen atom [the group may be substituted with 1 to 5 identical or different substituents selected from the Substituent group α];

$R^2$ represents a hydrogen atom; a $C_1$-$C_6$ alkyl group; a $C_2$-$C_6$ alkenyl group; a $C_2$-$C_6$ alkynyl group; a $C_3$-$C_6$ cycloalkyl group; a $C_1$-$C_6$ haloalkyl group; a $C_2$-$C_6$ haloalkenyl group; a $C_2$-$C_6$ haloalkynyl group; a $C_1$-$C_6$ alkoxy $C_1$-$C_6$ alkyl group; a $C_3$-$C_6$ cycloalkyloxy $C_1$-$C_6$ alkyl group; a di($C_1$-$C_6$ alkoxy) $C_1$-$C_6$ alkyl group; a heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α); a phenyl group which may be substituted with one or more substituents selected from the Substituent group α; a phenyl $C_1$-$C_6$ alkyl group which may be substituted with one or more substituents selected from the Substituent group α; a phenyl $C_2$-$C_6$ alkenyl group which may be substituted with one or more substituents selected from the Substituent group α; or a phenyl $C_2$-$C_6$ alkynyl group which may be substituted with one or more substituents selected from the Substituent group α, Y and Z represent an oxygen atom or a sulfur atom, "A" represents any one of the following formula A-1 to A-5,

[Chem. 2]

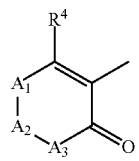

A-1

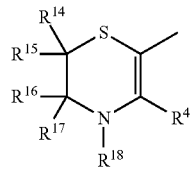

A-2

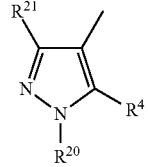

A-3

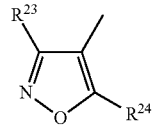

A-4

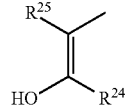

A-5

$R^4$ represents a hydroxyl group; $O^-M^+$ ($M^+$ represents an alkali metal cation or an ammonium cation); an amino group; a halogen atom; a cyano group; an isothiocyanate group; an isocyanate group; a hydroxycarbonyloxy group; a $C_1$-$C_6$ alkoxycarbonyloxy group; a benzyloxycarbonyloxy group which may be substituted with a substituent group selected from Substituent group α; a $C_1$-$C_6$ alkoxy group; a $C_2$-$C_6$ alkenyloxy group; a $C_2$-$C_6$ alkynyloxy group; a $C_3$-$C_6$ cycloalkyloxy group; a cyanomethylene oxy group; a $C_3$-$C_6$ cycloalkyl $C_1$-$C_6$ alkyloxy group; a $C_1$-$C_6$ alkylcarbonyloxy group; a $C_1$-$C_6$ haloalkylcarbonyloxy group; a $C_2$-$C_6$ alkenylcarbonyloxy group; a $C_2$-$C_6$ haloalkenylcarbonyloxy group; a $C_2$-$C_6$ alkynylcarbonyloxy group; a $C_2$-$C_6$ haloalkynylcarbonyloxy group; a $C_1$-$C_6$ alkoxycarbonyl $C_1$-$C_6$ alkoxy group; a phenyloxy group which may be substituted with one or more substituents selected from the Substituent group α; a benzyloxy group which may be substituted with one or more substituents selected from the Substituent group α; a phenylcarbonyloxy group which may be substituted with one or more substituents selected from the Substituent group α; a benzylcarbonyloxy group which may be substituted with one or more substituents selected from the Substituent group α; a phenylcarbonyl $C_1$-$C_6$ alkyloxy group which may be substituted with one or more substituents selected from the Substituent group α; a $C_1$-$C_{10}$ alkylsulfonlyoxy group; a $C_1$-$C_6$ haloalkylsulfonlyoxy group; a phenylsulfonyloxy group which may be substituted with one or more substituents selected from the Substituent group α; a benzylsulfonyloxy group which may be substituted with one or more substituents selected from the Substituent group α; a $C_1$-$C_{10}$ alkylthio group; a $C_1$-$C_{10}$ alkylsulfinyl group; a $C_1$-$C_{10}$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_2$-$C_6$ alkenylthio group; a $C_2$-$C_6$ alkenylsulfinyl group; a $C_2$-$C_6$ alkenylsulfonyl group; a $C_2$-$C_6$ alkynylthio group; a $C_2$-$C_6$ alkynylsulfinyl group; a $C_2$-$C_6$ alkynylsulfonyl group; a phenylthio group which may be substituted with one or more substituents selected from the Substituent group α; a benzylthio group which may be substituted with one or more substituents selected from the Substituent group α; a phenylsulfinyl group which may be substituted with one or more substituents selected from the Substituent group α; a benzylsulfinyl group which may be substituted with one or more substituents selected from the Substituent group α; a phenylsulfonyl group which may be substituted with one or more substituents selected from the Substituent group α; a benzylsulfonyl group which may be substituted with one or more substituents selected from the Substituent group α; a $C_1$-$C_{10}$ alkylamino group; a di($C_1$-$C_{10}$ alkylamino group; a $C_1$-$C_6$ alkoxycarbonylamino group; a $C_1$-$C_6$ alkoxy group substituted with a heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α); a heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α); or a heterocyclic-oxy group in which the heterocyclic group in the heterocyclic-oxy group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α), $A_1$ represents a group represented by the following formula

[Chem. 3]

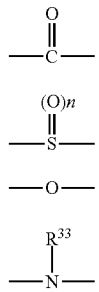

[$X_1$]

[$X_2$]

$A_2$ represents a group represented by the following formula

[Chem. 4]

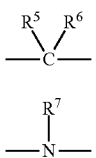

[$X_3$]

-continued

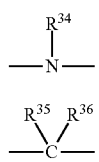

[$X_4$]

[$X_5$]

[$X_6$]

[$X_7$]

$A_3$ represents a group represented by the following formula

[Chem. 5]

[$X_8$]

[$X_9$]

n represents 0, 1, or 2, $R^5$, $R^6$, $R^8$, $R^9$, $R^{35}$ and $R^{36}$ each independently represent a hydrogen atom or a $C_1$-$C_6$ alkyl group, herein, $R^5$ and $R^8$ may be joined together to form a $C_2$-$C_5$ alkylene chain or a $C_2$-$C_5$ alkenylene chain, and may form a ring together with adjacent carbon atoms, and $R^5$ and $R^{35}$ may be joined together to form a $C_1$-$C_5$ alkylene chain to form a ring with adjacent carbon atoms, $R^7$, $R^{33}$, and $R^{34}$ each independently represent a hydrogen atom, a $C_1$-$C_6$ alkyl group, a $C_1$-$C_6$ haloalkyl group, a $C_2$-$C_6$ alkenyl group, a $C_2$-$C_6$ alkynyl group, or a $C_1$-$C_6$ alkoxy group, $R^{14}$, $R^{15}$, $R^{16}$, and $R^{17}$ each independently represent a hydrogen atom, a $C_1$-$C_6$ alkyl group, a $C_1$-$C_6$ alkoxy group, or a benzyl group which may be substituted with one or more substituents selected from the Substituent group α, $R^{18}$ represents a hydrogen atom, a $C_1$-$C_6$ alkyl group, a $C_2$-$C_6$ alkenyl group, a $C_2$-$C_6$ alkynyl group, a cyanomethyl group, or a benzyl group, $R^{20}$ represents a $C_1$-$C_6$ alkyl group, a $C_2$-$C_6$ alkenyl group, a $C_2$-$C_6$ alkynyl group, a $C_3$-$C_6$ cycloalkyl group, or a $C_3$-$C_6$ cycloalkyl $C_1$-$C_6$ alkyl group, $R^{21}$ represents a hydrogen atom, a $C_1$-$C_6$ alkyl group, or a halogen atom, $R^{23}$ represents a $C_1$-$C_6$ alkyl group, a $C_1$-$C_6$ haloalkyl group, a $C_3$-$C_6$ cycloalkyl group, a $C_1$-$C_{10}$ alkylthio group, a $C_1$-$C_{10}$ alkylsulfinyl group, a $C_1$-$C_{10}$ alkylsulfonyl group, a phenylthio group which may be substituted with one or more substituents selected from the Substituent group α, a benzylthio group which may be substituted with one or more substituents selected from the Substituent group α, a phenylsulfinyl group which may be substituted with one or more substituents selected from the Substituent group α, a benzylsulfinyl group which may be substituted with one or more substituents selected from the Substituent group α, a phenylsulfonyl group which may be substituted with one or more substituents selected from the Substituent group α, or a benzylsulfonyl group which may be substituted with one or more substituents selected from the Substituent group α, $R^{24}$ represents a hydrogen atom, a halogen atom, a cyano group, a $C_1$-$C_6$ alkyl group, a $C_3$-$C_6$ cycloalkyl group, or a $C_1$-$C_6$ alkoxycarbonylamino group, $R^{25}$ represents a $C_1$-$C_6$ alkoxycarbonyl group, a cyano group, or a nitro group, $R^{31}$ and $R^{32}$ each independently represent a hydrogen atom; a $C_1$-$C_6$ alkyl group; a phenyl group which may be substituted with one or more substituents selected from the Substituent group α; a benzyl group which may be substituted with one or more substituents selected from the Substituent group α; a $C_1$-$C_6$ alkoxy $C_1$-$C_6$ alkyl group; a $C_1$-$C_6$ alkylcarbonyl group; a $C_1$-$C_{10}$ alkylthio carbonyl group; a $C_1$-$C_6$ alkoxycarbonyl group; a $C_1$-$C_6$ haloalkyl group; a $C_3$-$C_6$ cycloalkyl group; a $C_3$-$C_6$ cycloalkyl $C_1$-$C_6$ alkyl group; a $C_1$-$C_6$ alkylsulfonyl group; a phenylsulfonyl group which may be substituted with one or more substituents selected from the Substituent group α; a benzylsulfonyl group which may be substituted with one or more substituents selected from the Substituent group α; a heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α); or a $C_1$-$C_6$ alkyl group substituted with a heterocyclic group in which the heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α), herein, $R^{31}$ and $R^{32}$ may be joined together to form a 5- to 6-membered ring with adjacent nitrogen atom, and the one or more carbon atoms in the ring may be substituted with a sulfur atom and/or an oxygen atom.

Herein, "Substituent group α" represents a group selected from a group consisting of:

a halogen atom; a hydroxyl group; a $C_1$-$C_6$ alkyl group; a $C_3$-$C_6$ cycloalkyl group; a $C_3$-$C_6$ cycloalkyl $C_1$-$C_6$ alkyl group; a $C_2$-$C_6$ alkenyl group; a $C_2$-$C_6$ alkynyl group; a $C_1$-$C_6$ haloalkyl group; a $C_2$-$C_6$ haloalkenyl group; a $C_2$-$C_6$ haloalkynyl group; a $C_3$-$C_6$ halocycloalkyl group; a $C_3$-$C_6$ halocycloalkyl $C_1$-$C_6$ alkyl group; a $C_1$-$C_6$ alkoxy group; a $C_3$-$C_6$ cycloalkyloxy group; a $C_2$-$C_6$ alkenyloxy group; a $C_2$-$C_6$ alkynyloxy group; a $C_1$-$C_6$ alkylcarbonyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a $C_1$-$C_6$ alkylcarbonylamino group; a mono($C_1$-$C_6$ alkyl)amino group; a di($C_1$-$C_6$ alkyl)amino group; a hydroxy $C_1$-$C_6$ alkyl group; a $C_1$-$C_6$ alkoxy $C_1$-$C_6$ alkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ haloalkylthio $C_1$-$C_6$ alkyl group; a $C_1$-$C_6$ haloalkylsulfinyl $C_1$-$C_6$ alkyl group; a $C_1$-$C_6$ haloalkylsulfonyl $C_1$-$C_6$ alkyl group; a cyano $C_1$-$C_6$ alkyl group; a $C_1$-$C_6$ alkoxy $C_1$-$C_6$ alkoxy group; a $C_3$-$C_6$ cycloalkyl $C_1$-$C_6$ alkyloxy group; a $C_1$-$C_6$ haloalkoxy $C_1$-$C_6$ alkoxy group; a cyano $C_1$-$C_6$ alkoxy group; a $C_1$-$C_6$ acyl group; a $C_1$-$C_6$ alkoxyimino $C_1$-$C_6$ alkyl group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; a nitro group; a cyano group; a phenyl group (the phenyl in the group may be substituted with 1 to 5 identical or different substituents selected from the Substituent group β); a heterocyclic group comprising 2 to 10 carbon atoms and 1 to 5 identical or different heteroatoms selected from an oxygen atom, a sulfur atom, and a nitrogen atom (the group may be substituted with 1 to 5 identical or different substituents selected from the Substituent group β); a heterocyclic oxy group comprising 2 to 10 carbon atoms and 1 to 5 identical or different heteroatoms selected from an oxygen atom, a sulfur atom, and a nitrogen atom (the group may be substituted with 1 to 5 identical or different substituents selected from the Substituent group β); and a $C_3$-$C_6$ allylene group formed with two adjacent substituent groups, wherein 1 to 3 carbon atoms in the alkylene group may be substituted with an atom selected from a group consisting of an oxygen atom, a sulfur atom, a nitrogen atom, and a carbon atom constituting an carbonyl group; and "Substituent group [β" represents a group selected from a group consisting of: a halogen atom, a nitro group, a cyano group, a $C_1$-$C_6$ alkyl group, a $C_1$-$C_6$ haloalkyl group, a $C_1$-$C_6$ alkoxy group, and a $C_1$-$C_6$ haloalkoxy group.].

(2) The triazine derivative or the salt thereof according to (1), wherein A in Formula 1 is A-1.

(3) The triazine derivative or the salt thereof according to (1) or (2), wherein in A-1, $A_1$ is $[X_1]$, $A_2$ is $[X_3]$, and $A_3$ is $[X_9]$.

(4) The triazine derivative or the salt thereof according to (3), wherein $R^5$ and $R^6$ in $[X_1]$ is a hydrogen atom or a $C_1$-$C_6$ alkyl group, $R^8$ and $R^9$ in $[X_3]$ is a hydrogen atom or a $C_1$-$C_6$ alkyl group, and $R^{35}$ and $R^{36}$ in $[X_9]$ is a hydrogen atom or a $C_1$-$C_6$ alkyl group, or $R^5$ and $R^{35}$ may bind to each other via a $C_1$-$C_5$ alkylene chain to form a ring.

(5) The triazine derivative or the salt thereof according to (1), wherein A in Formula 1 is A-3.

(6) The triazine derivative or the salt thereof according to (5), wherein $R^{20}$ in A-3 is a $C_1$-$C_6$ alkyl group, and $R^{21}$ in A-3 is a hydrogen atom or a $C_1$-$C_6$ alkyl group.

(7) The triazine derivative or the salt thereof according to any one of (1) to (6), wherein $R^4$ in A-1 is a hydroxyl group or an $O^-M^+$ ($M^+$ represents an alkali metal cation or an ammonium cation).

(8) The triazine derivative or the salt thereof according to any one of (1) to (7), wherein Y in Formula 1 is an oxygen atom.

(9) The triazine derivative or the salt thereof according to any one of (1) to (8), wherein $R^1$ in Formula 1 is the group selected from the group consisting of a $C_1$-$C_{12}$ alkyl group; a $C_2$-$C_6$ alkenyl group; a $C_2$-$C_6$ alkynyl group; a $C_3$-$C_6$ cycloalkyl group; a $C_3$-$C_6$ cycloalkenyl group; a $C_1$-$C_6$ haloalkyl group; a $C_2$-$C_6$ haloalkenyl group; a $C_1$-$C_6$ alkoxy $C_1$-$C_6$ alkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ alkoxycarbonyl $C_1$-$C_6$ alkyl group; a phenyl group which may be substituted with one or more substituents selected from the Substituent group α; a phenyl $C_1$-$C_6$ alkyl group which may be substituted with one or more substituents selected from the Substituent group α; and a heterocyclic group comprising 3 to 10 carbon atoms and one or more identical or different heteroatoms selected from an oxygen atom, a sulfur atom, and a nitrogen atom [the group may be substituted with 1 to 5 identical or different substituents selected from the Substituent group α, and when the heteroatom in the heterocyclic group is a sulfur atom, the sulfur atom may be oxidized to sulfoxide or sulfone].

(10) The triazine derivative or the salt thereof according to any one of (1) to (9), wherein $R^2$ in Formula 1 is the group selected from the group consisting of a $C_1$-$C_6$ alkyl group; a $C_1$-$C_6$ haloalkyl group; a phenyl group which may be substituted with one or more substituents selected from the Substituent group α; and a heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α).

(11) The triazine derivative or the salt thereof according to (1), in which the groups in Formula 1 are as follows: $R^1$ represents a $C_1$-$C_{12}$ alkyl group; a $C_2$-$C_6$ alkenyl group; a $C_2$-$C_6$ alkynyl group; a $C_3$-$C_6$ cycloalkyl group; a $C_3$-$C_6$ cycloalkenyl group; a $C_3$-$C_6$ cycloalkyl $C_1$-$C_6$ alkyl group; a $C_1$-$C_6$ haloalkyl group; a $C_2$-$C_6$ haloalkenyl group; a $C_2$-$C_6$ haloalkynyl group; a $C_3$-$C_6$ halocycloalkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ allylsulfonyl $C_1$-$C_6$ alkyl group; a $C_1$-$C_6$ alkoxy $C_1$-$C_6$ alkyl group; a $C_1$-$C_6$ alkoxy $C_1$-$C_6$ alkoxy $C_1$-$C_6$ alkyl group; a $C_3$-$C_6$ cycloalkyloxy $C_1$-$C_6$ alkyl group; a phenyloxy $C_1$-$C_6$ alkyl group (the phenyl in the group may be substituted with 1 to 5 identical or different substituents selected from the Substituent group α); a phenylthio $C_1$-$C_6$ alkyl group (the phenyl in the group may be substituted with 1 to 5 identical or different substituents selected from the Substituent group α); a phenylsulfinyl $C_1$-$C_6$ alkyl group (the phenyl in the group may be substituted with 1 to 5 identical or different substituents selected from the Substituent group α); a phenylsulfonyl $C_1$-$C_6$ alkyl group (the phenyl in the group may be substituted with 1 to 5 identical or different substituents selected from the Substituent group α); a phenyl group which may be substituted with one or more substituents selected from the Substituent group α; a phenyl $C_1$-$C_6$ alkyl group which may be substituted with one or more substituents selected from the Substituent group α; a phenyl $C_2$-$C_6$ alkenyl group which may be substituted with one or more substituents selected from the Substituent group α; a phenyl $C_2$-$C_6$ alkynyl group which may be substituted with one or more substituents selected from the Substituent group α; a $C_1$-$C_6$ alkoxyimino $C_1$-$C_6$ alkyl group; a di($C_1$-$C_6$ alkoxy) $C_1$-$C_6$ alkyl group; a $C_1$-$C_6$ alkoxycarbonyl $C_1$-$C_6$ alkyl group; a $C_1$-$C_6$ alkylcarbonyl $C_1$-$C_6$ alkyl group; a $C_1$-$C_6$ alkylcarbonyloxy $C_1$-$C_6$ alkyl group; a $NR^{31}R^{32}$ group; a heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α, and when the heteroatom in the heterocyclic group is a sulfur atom, the sulfur atom may be oxidized to sulfoxide or sulfone); or a $C_1$-$C_6$ alkyl group substituted with a heterocyclic group in which the heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α);

$R^2$ represents a hydrogen atom; a $C_1$-$C_6$ alkyl group; a $C_2$-$C_6$ alkenyl group; a $C_2$-$C_6$ alkynyl group; a $C_3$-$C_6$ cycloalkyl group; a $C_1$-$C_6$ haloalkyl group; a $C_2$-$C_6$ haloalkenyl group; a $C_2$-$C_6$ haloalkynyl group; a heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α); a phenyl group which may be substituted with one or more substituents selected from the Substituent group α; or a phenyl $C_1$-$C_6$ alkyl group which may be substituted with one or more substituents selected from the Substituent group α;

Y and Z represent an oxygen atom or a sulfur atom,
A represents any one of A-1, A-3, and A-5,
$A_1$ is [$X_1$],
$A_2$ is [$X_3$] or [$X_4$], and
$A_3$ is [$X_9$],
in [$X_1$], $R^5$ and $R^6$ each independently represent a hydrogen atom or a $C_1$-$C_6$ alkyl group,
in [$X_3$], $R^8$ and $R^9$ each independently represent a hydrogen atom or a $C_1$-$C_6$ alkyl group,
in [$X_9$], $R^{35}$ and $R^{36}$ each independently represent a hydrogen atom or a $C_1$-$C_6$ alkyl group,
herein, $R^5$ and $R^8$ may be joined together to form a $C_2$-$C_5$ alkylene chain or a $C_2$-$C_5$ alkenylene chain, and may form a ring together with adjacent carbon atoms, and $R^5$ and $R^{35}$ may be joined together to form a $C_1$-$C_5$ alkylene chain to form a ring with adjacent carbon atoms,
in A-3, $R^{20}$ is a $C_1$-$C_6$ alkyl group,
$R^{21}$ is a hydrogen atom or a $C_1$-$C_6$ alkyl group,
in A-5, $R^{24}$ represents a hydrogen atom, a $C_1$-$C_6$ alkyl group, or a $C_3$-$C_6$ cycloalkyl group, $R^{25}$ represents a $C_1$-$C_6$ alkoxycarbonyl group, a cyano group, or a nitro group,
$R^4$ represents a hydroxyl group; $O^-M^+$ ($M^+$ represents an alkali metal cation or an ammonium cation); or a $C_1$-$C_{10}$ alkylsulfonlyoxy group;
$R^{31}$ and $R^{32}$ each independently represent a hydrogen atom; a $C_1$-$C_6$ alkyl group; a phenyl group which may be substituted with one or more substituents selected from the Substituent group α; or a benzyl group which may be substituted with one or more substituents selected from the Substituent group α; herein, $R^{31}$ and $R^{32}$ may be joined together to form a 5- to 6-membered ring with adjacent nitrogen atom, and the one or more carbon atoms in the ring may be substituted with a sulfur atom and/or an oxygen atom,
herein, "Substituent group α" represents a group selected from a group consisting of:
a halogen atom; a $C_1$-$C_6$ alkyl group; a $C_3$-$C_6$ cycloalkyl group; a $C_2$-$C_6$ alkenyl group; a $C_2$-$C_6$ alkynyl group; a $C_1$-$C_6$ haloalkyl group; a $C_2$-$C_6$ haloalkenyl group; a $C_2$-$C_6$ haloalkynyl group; a $C_3$-$C_6$ halocycloalkyl group; a $C_1$-$C_6$ alkoxy group; a $C_3$-$C_6$ cycloalkyloxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a nitro group; a cyano group; a phenyl group (the phenyl in the group may be substituted with 1 to 5 identical or different substituents selected from the Substituent group β); a heterocyclic oxy group comprising 2 to 10 carbon atoms and 1 to 5 heteroatoms that are optionally selected from an oxygen atom, a sulfur atom, and a nitrogen atom (the group may be substituted with 1 to 5 identical or different substituents selected from the Substituent group β); and a $C_3$-$C_6$ alkylene group formed with two adjacent substituent groups, wherein 1 to 3 carbon atoms in the alkylene group may be substituted with an atom selected from a group consisting of an oxygen atom, a sulfur atom, a nitrogen atom, and a carbon atom constituting an carbonyl group.

(12) The triazine derivative or the salt thereof according to (1), in which the groups in Formula 1 are as follows:
$R^1$ is a group selected from a group consisting of a $C_1$-$C_{12}$ alkyl group; a $C_2$-$C_6$ alkenyl group; a $C_2$-$C_6$ alkynyl group; a $C_3$-$C_6$ cycloalkyl group; a $C_3$-$C_6$ cycloalkenyl group; a $C_1$-$C_6$ haloalkyl group; a $C_2$-$C_6$ haloalkenyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ alkoxy $C_1$-$C_6$ alkyl group; a phenyl group which may be substituted with one or more substituents selected from the Substituent group α; a phenyl $C_1$-$C_6$ alkyl group which may be substituted with one or more substituents selected from the Substituent group α; a $C_1$-$C_6$ alkoxyimino $C_1$-$C_6$ alkyl group; a $C_1$-$C_6$ alkoxycarbonyl $C_1$-$C_6$ alkyl group; a $C_1$-$C_6$ alkylcarbonyl $C_1$-$C_6$ alkyl group; a $NR^{31}R^{32}$ group; a heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α, and when the heteroatom in the heterocyclic group is a sulfur atom, the sulfur atom may be oxidized to sulfoxide or sulfone); and, a $C_1$-$C_6$ alkyl group substituted with a heterocyclic group in which the heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α);

$R^{31}$ and $R^{32}$ each independently represent a group selected from a group consisting of a hydrogen atom; a $C_1$-$C_6$ alkyl group; and, a phenyl group which may be substituted with one or more substituents selected from the Substituent group α;

$R^2$ represents a group selected from a group consisting of a $C_1$-$C_6$ alkyl group; a $C_2$-$C_6$ alkenyl group; a $C_2$-$C_6$ alkynyl group; a $C_3$-$C_6$ cycloalkyl group; a $C_1$-$C_6$ haloalkyl group; a heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α); and, a phenyl group which may be substituted with 1 to 5 identical or different substituents selected from the Substituent group α;

Y and Z represent an oxygen atom or a sulfur atom,

A represents any one of A-1, A-3, and A-5, $R^4$ in A-1 represents a hydroxyl group;

$O^-M^+$ ($M^+$ represents an alkali metal cation or an ammonium cation);

or a $C_1$-$C_{10}$ alkylsulfonyloxy group;

in A-1, $A_1$ is [$X_1$], $A_2$ is [$X_3$] or [$X_4$], and $A_3$ is [$X_9$], in [$X_1$], $R^5$ and $R^6$ each independently represent a hydrogen atom or a $C_1$-$C_6$ alkyl group, in [$X_3$], $R^8$ and $R^9$ each independently represent a hydrogen atom or a $C_1$-$C_6$ alkyl group, in [$X_9$], $R^{35}$ and $R^{36}$ each independently represent a hydrogen atom or a $C_1$-$C_6$ alkyl group, herein, $R^5$ and $R^8$ may bind to each other via a $C_2$-$C_5$ alkylene chain or a $C_2$-$C_5$ alkenylene chain to form a ring, and $R^5$ and $R^{35}$ may bind to each other via a $C_1$-$C_5$ alkylene chain to form a ring, in A-3, $R^{20}$ is a $C_1$-$C_6$ alkyl group, $R^{21}$ is a hydrogen atom or a $C_1$-$C_6$ alkyl group, and $R^4$ represents a hydroxyl group; $O^-M^+$ ($M^+$ represents an alkali metal cation or an ammonium cation); or a $C_1$-$C_{10}$ alkylsulfonyloxy group;

"Substituent group α" represents a group selected from a group consisting of: a halogen atom; a $C_1$-$C_6$ alkyl group; a $C_2$-$C_6$ alkenyl group; a $C_2$-$C_6$ alkynyl group; a $C_1$-$C_6$ haloalkyl group; a $C_1$-$C_6$ alkoxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a nitro group; a cyano group; a phenyl group; and a $C_3$-$C_6$ alkylene group formed with two adjacent substituent groups, wherein 1 to 3 carbon atoms in the alkylene group may be substituted with an atom selected from a group consisting of an oxygen atom, a sulfur atom, a nitrogen atom, and a carbon atom constituting an carbonyl group.

(13) The triazine derivative or the salt thereof according to (1), in which the groups in Formula 1 are as follows:

$R^1$ represents a group selected from a group consisting of a $C_1$-$C_{12}$ alkyl group; a $C_2$-$C_6$ alkenyl group; a $C_2$-$C_6$ alkynyl group; a $C_3$-$C_6$ cycloalkyl group; a $C_3$-$C_6$ cycloalkenyl group; a $C_1$-$C_6$ haloalkyl group; a $C_2$-$C_6$ haloalkenyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ alkoxy $C_1$-$C_6$ alkyl group; a phenyl group which may be substituted with one or more substituents selected from the Substituent group α; a phenyl $C_1$-$C_6$ alkyl group; a $C_1$-$C_6$ alkoxyimino $C_1$-$C_6$ alkyl group; a $C_1$-$C_6$ alkoxycarbonyl $C_1$-$C_6$ alkyl group; a $C_1$-$C_6$ alkylcarbonyl $C_1$-$C_6$ alkyl group; a $NR^{31}R^{32}$ group; a heterocyclic group selected from the group consisting of pyridyl group, pyrimidinyl group, pyridazinyl group, thienyl group, isoxazolyl group, pyrazolyl group, morpholinyl group, thiomorpholinyl group, pyrazinyl group, piperidinyl group, and pyperazinyl group (the heterocyclic group may be substituted with 1 to 5 identical or different substituents selected from the Substituent group α, and when the heteroatom in the heterocyclic group is a sulfur atom, the sulfur atom may be oxidized to sulfoxide or sulfone); and, a tetrahydrofuryl-methyl group;

$R^{31}$ and $R^{32}$ each independently represent a group selected from a group consisting of a hydrogen atom; a $C_1$-$C_6$ alkyl group; and a phenyl group;

$R^2$ represents a group selected from a group consisting of a $C_1$-$C_6$ alkyl group; a $C_1$-$C_6$ haloalkyl group; a pyridyl group; and a phenyl group;

Y and Z represent an oxygen atom or a sulfur atom,

A represents any one of A-1 and A-3, $R^4$ in A-1 represents a hydroxyl group; or a $C_1$-$C_{10}$ alkylsulfonlyoxy group, in A-1, $A_1$ is [$X_1$], $A_2$ is [$X_3$] or [$X_4$], and $A_3$ is [$X_9$], in [$X_1$], $R^5$ and $R^6$ are a hydrogen atom or a $C_1$-$C_6$ alkyl group, in [$X_3$], $R^8$ and $R^9$ are a hydrogen atom or a $C_1$-$C_6$ alkyl group, in [$X_9$], $R^{35}$ and $R^{36}$ are a hydrogen atom or a $C_1$-$C_6$ alkyl group, herein, $R^5$ and $R^8$ may be joined together to form a $C_2$-$C_5$ alkylene chain and to form a ring, and $R^5$ and $R^{35}$ may be joined together to form a $C_1$-$C_5$ alkylene chain and to form a ring, in A-3, $R^{20}$ is a $C_1$-$C_6$ alkyl group, $R^{21}$ is a hydrogen atom or a $C_1$-$C_6$ alkyl group, and $R^4$ represents a hydroxyl group or a $C_1$-$C_{10}$ alkylsulfonlyoxy group, and "Substituent group α" represents a group selected from a group consisting of: a halogen atom; a $C_1$-$C_6$ alkyl group; a $C_2$-$C_6$ alkenyl group; a $C_2$-$C_6$ alkynyl group; a $C_1$-$C_6$ haloalkyl group; a $C_1$-$C_6$ alkoxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a nitro group; a cyano group; a phenyl group; and a methylenedioxy group.

(14) An agrochemical composition comprising the triazine derivative or the salt thereof described in any one of (1) to (13), and an agriculturally acceptable carrier.

(15) The agrochemical composition according to (14), in which the agrochemical composition further comprises a surface active agent.

(16) A herbicide comprising the triazine derivative or the salt thereof described in any one of (1) to (13) as an active component.

(17) The herbicide according to (16), in which the herbicide has a herbicidal activity for weeds in a field or a paddy field in which agrohorticultural plants are cultivated.

(18) The herbicide according to (17), in which the agrohorticultural plants are agrohorticultural plants given with resistance by a breeding method or a genetic recombination technique.

(19) A method of eliminating weeds in soils by applying an effective amount of herbicides comprising the triazine derivative or the salt thereof described in any one of (16) to (18).
(20) The method according to (19), in which the soils are a farmland.
(21) The method according to (19), in which the farmland is a field or a paddy field in which agrohorticultural plants are cultivated.
(22) A triazine derivative or a salt thereof represented by following Formula 2:

[Chem. 6]

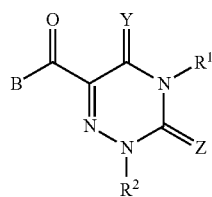

[2]

[in the formula, B represents a hydroxyl group or a $C_1$-$C_6$ alkoxy group and $R^1$, $R^2$, Y, and Z have the same definitions as those described in above Formula 1].
(23) The triazine derivative or the salt thereof according to (22), wherein Y in Formula 2 is an oxygen atom.
(24) The triazine derivative or the salt thereof according to (22) or (23), wherein $R^1$ in Formula 2 represents a group selected from a group consisting of a $C_1$-$C_{12}$ alkyl group; a $C_2$-$C_6$ alkenyl group; a $C_2$-$C_6$ alkynyl group; a $C_3$-$C_6$ cycloalkyl group; a $C_3$-$C_6$ cycloalkenyl group; a $C_1$-$C_6$ haloalkyl group; a $C_2$-$C_6$ haloalkenyl group; a $C_1$-$C_6$ alkoxy $C_1$-$C_6$ alkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ alkoxycarbonyl $C_1$-$C_6$ alkyl group; a phenyl group which may be substituted with one or more substituents selected from the Substituent group α; a phenyl $C_1$-$C_6$ alkyl group which may be substituted with one or more substituents selected from the Substituent group α; and a heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α, and when the heteroatom in the heterocyclic group is a sulfur atom, the sulfur atom may be oxidized to sulfoxide or sulfone).
(25) The triazine derivative or the salt thereof according to any one of (22) to (24), wherein $R^2$ in Formula 2 represents a group selected from a group consisting of a $C_1$-$C_6$ alkyl group; a $C_1$-$C_6$ haloalkyl group; a phenyl group which may be substituted with one or more substituents selected from the Substituent group α; and a heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α).
(26) The triazine derivative or the salt thereof according to (22) or (23), wherein B is a hydroxyl group and $R^2$ is a $C_1$-$C_6$ alkyl group.
(27) The triazine derivative or the salt thereof according to (26), wherein $R^1$ represents a group selected from a group consisting of a phenyl group which may be substituted with one or more substituents selected from the Substituent group α; a phenyl $C_1$-$C_6$ alkyl group which may be substituted with one or more substituents selected from the Substituent group α; a $C_1$-$C_6$ alkoxyimino $C_1$-$C_6$ alkyl group; a $C_1$-$C_6$ alkoxycarbonyl $C_1$-$C_6$ alkyl group; a $C_1$-$C_6$ alkylcarbonyl $C_1$-$C_6$ alkyl group; a $C_1$-$C_6$ alkylcarbonyloxy $C_1$-$C_6$ alkyl group; a $C_1$-$C_6$ alkylidene aminooxy $C_1$-$C_6$ alkyl group; a $NR^{31}R^{32}$ group; and a heterocyclic group comprising 3 to 10 carbon atoms and one or more identical or different heteroatoms selected from an oxygen atom, a sulfur atom, and a nitrogen atom [the group may be substituted with 1 to 5 identical or different substituents selected from the Substituent group α, and when the heteroatom in the heterocyclic group is a sulfur atom, the sulfur atom may be oxidized to sulfoxide or sulfone].
(28) The triazine derivative or the salt thereof according to (26), wherein $R^1$ represents a group selected from a group consisting of a phenyl group which may be substituted with one or more substituents selected from the Substituent group α; a $C_1$-$C_6$ alkoxyimino $C_1$-$C_6$ alkyl group; a $C_1$-$C_6$ alkylcarbonyl $C_1$-$C_6$ alkyl group; a $NR^{31}R^{32}$ group; and a heterocyclic group comprising 3 to 10 carbon atoms and one or more identical or different heteroatoms selected from an oxygen atom, a sulfur atom, and a nitrogen atom [the group may be substituted with 1 to 5 identical or different substituents selected from the Substituent group α, and when the heteroatom in the heterocyclic group is a sulfur atom, the sulfur atom may be oxidized to sulfoxide or sulfone].
(29) The triazine derivative or the salt thereof according to (27) or (28), wherein a heterocyclic group is 5- or 6-membered aromatic heterocyclic group having 1 to 3 nitrogen atoms as a heteroatom.
(30) The triazine derivative or the salt thereof according to any one of (26) to (29), wherein $R^{31}$ and $R^{32}$ each independently represent a hydrogen atom; a $C_1$-$C_6$ alkyl group; a phenyl group which may be substituted with one or more substituents selected from the Substituent group α; a benzyl group which may be substituted with one or more substituents selected from the Substituent group α; a $C_1$-$C_6$ alkylcarbonyl group; a $C_1$-$C_6$ alkoxycarbonyl group; a $C_1$-$C_6$ haloalkyl group; a $C_3$-$C_6$ cycloalkyl group; a $C_3$-$C_6$ cycloalkyl $C_1$-$C_6$ alkyl group; or $R^{31}$ and $R^{32}$ may be joined together to form a 5- to 6-membered ring with adjacent nitrogen atom, and in such case, one or more carbon atom in the ring may be substituted with a sulfur atom and/or an oxygen atom.
(31) The triazine derivative or the salt thereof according to (30), wherein $R^{31}$ and $R^{32}$ each independently represent a hydrogen atom; a $C_1$-$C_6$ alkyl group; or a phenyl group which may be substituted with one or more substituents selected from the Substituent group α.
(32) The triazine derivative or the salt thereof according to any one of (26) to (31), wherein "Substituent group α" represents a group selected from a group consisting of a halogen atom; a $C_1$-$C_6$ alkyl group; a $C_3$-$C_6$ cycloalkyl group; a $C_3$-$C_6$ cycloalkyl $C_1$-$C_6$ alkyl group; a $C_1$-$C_6$ haloalkyl group; a $C_3$-$C_6$ halocycloalkyl group; a $C_3$-$C_6$ halocycloalkyl $C_1$-$C_6$ alkyl group; a $C_1$-$C_6$ alkoxy group; a $C_3$-$C_6$ cycloalkyloxy group; a $C_1$-$C_6$ haloalkoxy group; a $C_1$-$C_6$ alkylthio group; a $C_1$-$C_6$ haloalkylthio group; a $C_1$-$C_6$ alkoxy $C_1$-$C_6$ alkyl group; a $C_1$-$C_6$ alkylthio $C_1$-$C_6$ alkyl group; or a $C_3$-$C_6$ alkylene group formed with two adjacent substituent groups, wherein 1 to 3 carbon atoms in the alkylene group may be substituted with an atom selected from a group consisting of an oxygen atom, a sulfur atom, a nitrogen atom, and a carbon atom constituting an carbonyl group.
(33) The triazine derivative or the salt thereof according to (32), wherein "Substituent group α" represents a group selected from a group consisting of a halogen atom; a $C_1$-$C_6$ alkyl group; a $C_1$-$C_6$ haloalkyl group; a $C_1$-$C_6$ alkoxy group; or a $C_1$-$C_6$ alkylthio group.

(34) The triazine derivative or the salt thereof according to any one of (22) to (33), wherein Y in Formula 2 is an oxygen atom, $R^1$ in Formula 2 represents a group selected from a group consisting of a $C_1$-$C_{12}$ alkyl group; a $C_2$-$C_6$ alkenyl group; a $C_2$-$C_6$ alkynyl group; a $C_3$-$C_6$ cycloalkyl group; a $C_3$-$C_6$ cycloalkenyl group; a $C_1$-$C_6$ haloalkyl group; a $C_2$-$C_6$ haloalkenyl group; a $C_1$-$C_6$ alkoxy $C_1$-$C_6$ alkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ alkoxyimino $C_1$-$C_6$ alkyl group; a $C_1$-$C_6$ alkoxycarbonyl $C_1$-$C_6$ alkyl group; a $C_1$-$C_6$ alkylcarbonyl $C_1$-$C_6$ alkyl group; a phenyl group which may be substituted with one or more substituents selected from the Substituent group α; a phenyl $C_1$-$C_6$ alkyl group which may be substituted with one or more substituents selected from the Substituent group α; and a heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α, and when the heteroatom in the heterocyclic group is a sulfur atom, the sulfur atom may be oxidized to sulfoxide or sulfone); and $R^2$ in Formula 2 represents a group selected from a group consisting of a $C_1$-$C_6$ alkyl group; a $C_1$-$C_6$ haloalkyl group; a phenyl group which may be substituted with one or more substituents selected from the Substituent group α; and a heterocyclic group comprising 3 to 10 carbon atoms and one or more identical or different heteroatoms selected from an oxygen atom, a sulfur atom, and a nitrogen atom (the group may be substituted with 1 to 5 identical or different substituents selected from the Substituent group α).

(35) The triazine derivative or the salt thereof according to any one of (22) to (34), wherein Y in Formula 2 is an oxygen atom, $R^1$ in Formula 2 represents a group selected from a group consisting of a $C_1$-$C_{12}$ alkyl group; a $C_2$-$C_6$ alkenyl group; a $C_2$-$C_6$ alkynyl group; a $C_3$-$C_6$ cycloalkyl group; a $C_3$-$C_6$ cycloalkenyl group; a $C_1$-$C_6$ haloalkyl group; a $C_2$-$C_6$ haloalkenyl group; a $C_1$-$C_6$ alkoxy $C_1$-$C_6$ alkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ alkoxyimino $C_1$-$C_6$ alkyl group; a $C_1$-$C_6$ alkoxycarbonyl $C_1$-$C_6$ alkyl group; a $C_1$-$C_6$ alkylcarbonyl $C_1$-$C_6$ alkyl group; a phenyl group which may be substituted with one or more substituents selected from the Substituent group α; a phenyl $C_1$-$C_6$ alkyl group which may be substituted with one or more substituents selected from the Substituent group α; and a heterocyclic group selected from the group consisting of pyridyl group, pyrimidinyl group, pyrazinyl group, pyridazinyl group, thienyl group, thiazolyl group, isoxazolyl group, pyrazolyl group, morpholinyl group, thiomorpholinyl group, and pyperazinyl group (the group may be substituted with 1 to 5 identical or different substituents selected from the Substituent group α, and when the heteroatom in the heterocyclic group is a sulfur atom, the sulfur atom may be oxidized to sulfoxide or sulfone);

$R^2$ is a group selected from a group consisting of a $C_1$-$C_6$ alkyl group; a $C_1$-$C_6$ haloalkyl group; and a pyridyl group; and, "Substituent group α" represents a group selected from a group consisting of a halogen atom; a $C_1$-$C_6$ alkyl group; a $C_2$-$C_6$ alkenyl group; a $C_2$-$C_6$ alkynyl group; a $C_1$-$C_6$ haloalkyl group; a $C_1$-$C_6$ alkoxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a nitro group; a cyano group; a phenyl group; and a methylenedioxy group.

(36) An agrochemical composition comprising the triazine derivative or the salt thereof described in any one of (22) to (35), and an agriculturally acceptable carrier.

(37) The agrochemical composition according to (36), in which the agrochemical composition further comprises a surface active agent.

(38) A herbicide comprising the triazine derivative or the salt thereof described in any one of (22) to (35) as an active component.

(39) The herbicide according to (38), in which the herbicide has a herbicidal activity for weeds in a field or a paddy field in which agrohorticultural plants are cultivated.

(40) The herbicide according to (39), in which the agrohorticultural plants are agrohorticultural plants given with resistance by a breeding method or a genetic recombination technique.

(41) A method of eliminating weeds in soils by applying an effective amount of herbicides comprising the triazine derivative or the salt thereof described in any one of (22) to (35).

(42) The method according to (41), in which the soils are a farmland.

(43) The method according to (41), in which the farmland is a field or a paddy field in which agrohorticultural plants are cultivated.

Advantageous Effects of Invention

The invention provides the novel triazine derivative represented by Formula 1 or its salt which can effectively control weeds. The triazine derivative of the invention or its salt exhibits an excellent herbicidal effect against various weeds, which cause a problem particularly in an agricultural field over a long period of time from a pre-germination stage to a growing stage, for example, a broad-leaf weed like white pepper, *Amaranthus viridis*, white goosefoot, *Stellaria media*, chamomile, China jute, *Sida spinosa*, sesbania, hogweed, red poppy, morning glory, and cocklebur, annual and perennial weeds of Cyperus microiria family including coco grass, edible galingale, *Kylling a brevifolia* var. *leiolepis*, java galingale, and *Cyperus iria*, and gramineous weeds like barnyard millet, finger grass, foxtail, spear grass, Syrian sorghum nitidum, short awn, and wild oat. In addition, it can control rice paddy weeds including annual weeds like *Echinochloa oryzicola, Cyperus difformis,* and *Monochoria vaginalis* and perennial weeds like *Sagittaria pygmaea, Sagittaria trifolia, Cyperus serotinus, Eleocharis kuroguwai, Scirpus* hotarui, and *Alisma canaliculatum*.

Further, the compound of the invention is highly safe to useful crops and useful plants, in particular, to rice, wheat, barley, corn, grain sorghum, soybean, cotton, sugar beet, etc.

Thus, the invention provides an agrochemical composition having an excellent effect as herbicides.

DESCRIPTION OF EMBODIMENTS

The definitions of the terms used in the present Description are given below.

Halogen atom refers to a fluorine atom, a chlorine atom, a bromine atom, or an iodine atom.

The descriptions like $C_1$-$C_6$ indicate the number of carbon atoms in a substituent group described hereinbelow. For example, $C_1$-$C_6$ means 1 to 6 carbon atoms.

The $C_1$-$C_6$ alkyl group represents, unless specified otherwise, a linear or branched alkyl group having 1 to 6 carbon atoms, and examples thereof include a group like methyl, ethyl, n-propyl, isopropyl, n-butyl, sec-butyl, isobutyl, tert-butyl, n-pentyl, 1-methylbutyl, 2-methylbutyl, 3-methylbutyl, 1-ethylpropyl, 1,1-dimethylpropyl, 1,2-dimethylpropyl, neopentyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl, and 1-ethyl-2-methylpropyl.

The $C_1$-$C_{12}$ alkyl group represents, unless specified otherwise, a linear or branched alkyl group having 1 to 12 carbon atoms, and examples thereof include, in addition to those exemplified above for the $C_1$-$C_6$ alkyl group, a group like heptyl, 1-methylhexyl, 5-methylhexyl, 1,1-dimethylpentyl, 2,2-dimethylpentyl, 4,4-dimethylpentyl, 1-ethylpentyl, 2-ethylpentyl, 1,1,3-trimethylbutyl, 1,2,2-trimethylbutyl, 1,3,3-trimethylbutyl, 2,2,3-trimethylbutyl, 2,3,3-trimethylbutyl, 1-propylbutyl, 1,1,2,2-tetramethylpropyl, octyl, 1-methylheptyl, 3-methylheptyl, 6-methylheptyl, 2-ethylhexyl, 5,5-dimethylhexyl, 2,4,4-trimethylpentyl, 1-ethyl-1-methylpentyl, nonyl, 1-methyloctyl, 2-methyloctyl, 3-methyloctyl, 7-methyloctyl, 1-ethylheptyl, 1,1-dimethylheptyl, 6,6-dimethylheptyl, decyl, 1-methylnonyl, 2-methylnonyl, 6-methylnonyl, 1-ethyloctyl, 1-propylheptyl, n-nonyl, and n-decyl.

The $C_3$-$C_6$ cycloalkyl group represents, unless specified otherwise, a cycloalkyl group having 3 to 6 carbon atoms, and examples thereof include a group like cyclopropyl, cyclobutyl, cyclopentyl, and cyclohexyl.

The $C_3$-$C_6$ cycloalkenyl group represents, unless specified otherwise, a cycloalkenyl group having 3 to 6 carbon atoms, and examples thereof include a group like cyclopentenyl and cyclohexenyl.

The $C_3$-$C_6$ cycloalkyl $C_1$-$C_6$ alkyl group represents, unless specified otherwise, an alkyl group having 1 to 6 carbon atoms substituted with a cycloalkyl having 3 to 6 carbon atoms, wherein the cycloalkyl moiety and alkyl moiety have the same definitions as above, and examples thereof include a group like cyclopropylmethyl, 1-cyclopropylethyl, 2-cyclopropylethyl, 1-cyclopropylpropyl, 2-cyclopropylpropyl, 3-cyclopropylpropyl, cyclobutylmethyl, cyclopentylmethyl, and cyclohexylmethyl.

The $C_3$-$C_6$ cycloalkyl $C_1$-$C_6$ alkyloxy group represents an (alkyl)-O— group (i.e., alkoxy group) having 1 to 6 carbon atoms substituted with a cycloalkyl having 3 to 6 carbon atoms, wherein the cycloalkyl moiety and alkyl moiety have the same definitions as above, and examples thereof include a group like cyclopropylmethoxy, 1-cyclopropylethoxy, 2-cyclopropylethoxy, 1-cyclopropylpropoxy, 2-cyclopropylpropoxy, 3-cyclopropylpropoxy, cyclobutylmethoxy, cyclopentylmethoxy, and cyclohexylmethoxy.

The $C_3$-$C_6$ halocycloalkyl group represents, unless specified otherwise, a cycloalkyl group having 3 to 6 carbon atoms substituted with 1 to 5, or preferably 1 to 3 halogen atoms, wherein the cycloalkyl moiety and the halogen atom have the same definitions as above, and examples thereof include a group like 2,2-difluorocyclopropyl and 2,2-dichlorocyclopropyl.

The $C_3$-$C_6$ halocycloalkyl $C_1$-$C_6$ alkyl group represents, unless specified otherwise, an alkyl group having 1 to 6 carbon atoms substituted with a cycloalkyl group having 3 to 6 carbon atoms substituted with 1 to 5, or preferably 1 to 3 halogen atoms, wherein the cycloalkyl moiety, the alkyl moiety, and the halogen atom have the same definitions as above, and examples thereof include a group like 2,2-difluorocyclopropylmethyl and 2,2-dichlorocyclopropylmethyl.

The amino $C_1$-$C_6$ alkyl group represents, unless specified otherwise, an alkyl group having 1 to 6 carbon atoms substituted with an amino group, wherein the alkyl moiety has the same definition as above, and examples thereof include a group like 2-aminoethyl and 3-aminopropyl.

The nitro $C_1$-$C_6$ alkyl group represents, unless specified otherwise, an alkyl group having 1 to 6 carbon atoms substituted with a nitro group, wherein the alkyl moiety has the same definition as above, and examples thereof include a group like nitromethyl and 2-nitroethyl.

The $C_1$-$C_6$ haloalkyl group represents a linear or branched alkyl group having 1 to 6 carbon atoms substituted with a halogen atom, and examples thereof include a group like fluoromethyl, chloromethyl, bromomethyl, difluoromethyl, dichloromethyl, trifluoromethyl, trichloromethyl, chlorodifluoromethyl, bromodifluoromethyl, 2-fluoroethyl, 1-chloroethyl, 2-chloroethyl, 1-bromoethyl, 2-bromoethyl, 2,2-difluoroethyl, 1,2-dichloroethyl, 2,2-dichloroethyl, 2,2,2-trifluoroethyl, 2,2,2-trichloroethyl, 1,1,2,2-tetrafluoroethyl, pentafluoroethyl, 2-bromo-2-chloroethyl, 2-chloro-1,1,2,2-tetrafluoroethyl, 1-chloro-1,2,2,2-tetrafluoroethyl, 1-chloropropyl, 2-chloropropyl, 3-chloropropyl, 2-bromopropyl, 3-bromopropyl, 2-bromo-1-methylethyl, 3-iodopropyl, 2,3-dichloropropyl, 2,3-dibromopropyl, 3,3,3-trifluoropropyl, 3,3,3-trichloropropyl, 3-bromo-3,3-difluoropropyl, 3,3-dichloro-3-fluoropropyl, 2,2,3,3-tetrafluoropropyl, 1-bromo-3,3,3-trifluoropropyl, 2,2,3,3,3-pentafluoropropyl, 2,2,2-trifluoro-1-trifluoromethylethyl, heptafluoropropyl, 1,2,2,2-tetrafluoro-1-trifluoromethylethyl, 2,3-dichloro-1,1,2,3,3-pentafluoropropyl, 2-chlorobutyl, 3-chlorobutyl, 4-chlorobutyl, 2-chloro-1,1-dimethylethyl, 4-bromobutyl, 3-bromo-2-methylpropyl, 2-bromo-1,1-dimethylethyl, 2,2-dichloro-1,1-dimethylethyl, 2-chloro-1-chloromethyl-2-methylethyl, 4,4,4-trifluorobutyl, 3,3,3-trifluoro-1-methylpropyl, 3,3,3-trifluoro-2-methylpropyl, 2,3,4-trichlorobutyl, 2,2,2-trichloro-1,1-dimethylethyl, 4-chloro-4,4-difluorobutyl, 4,4-dichloro-4-fluorobutyl, 4-bromo-4,4-difluorobutyl, 2,4-dibromo-4,4-difluorobutyl, 3,4-dichloro-3,4,4-trifluorobutyl, 3,3-dichloro-4,4,4-trifluorobutyl, 4-bromo-3,3,4,4-tetrafluorobutyl, 4-bromo-3-chloro-3,4,4-trifluorobutyl, 2,2,3,3,4,4-hexafluorobutyl, 2,2,3,4,4,4-hexafluorobutyl, 2,2,2-trifluoro-1-methyl-1-trifluoromethylethyl, 3,3,3-trifluoro-2-trifluoromethylpropyl, 2,2,3,3,4,4,4-heptafluorobutyl, 2,3,3,3-tetrafluoro-2-trifluoromethylpropyl, 1,1,2,2,3,3,4,4-octafluorobutyl, nonafluorobutyl, 4-chloro-1,1,2,2,3,3,4,4-octafluorobutyl, 5-fluoropentyl, 5-chloropentyl, 5,5-difluoropentyl, 5,5-dichloropentyl, 5,5,5-trifluoropentyl, 6,6,6-trifluorohexyl, and 5,5,6,6,6-pentafluorohexyl.

The $C_2$-$C_6$ alkenyl group represents, unless specified otherwise, a linear or branched alkenyl group having 2 to 6 carbon atoms, and examples thereof include a group like vinyl, 1-propenyl, isopropenyl, 2-propenyl, 1-butenyl, 1-methyl-1-propenyl, 2-butenyl, 1-methyl-2-propenyl, 3-butenyl, 2-methyl-1-propenyl, 2-methyl-2-propenyl, 1,3-butadienyl, 1-pentenyl, 1-ethyl-2-propenyl, 2-pentenyl, 1-methyl-1-butenyl, 3-pentenyl, 1-methyl-2-butenyl, 4-pentenyl, 1-methyl-3-butenyl, 3-methyl-1-butenyl, 1,2-dimethyl-2-propenyl, 1,1-dimethyl-2-propenyl, 2-methyl-2-butenyl, 3-methyl-2-butenyl, 1,2-dimethyl-1-propenyl, 2-methyl-3-butenyl, 3-methyl-3-butenyl, 1,3-pentadienyl, 1-vinyl-2-propenyl, 1-hexenyl, 1-propyl-2-propenyl, 2-hexenyl, 1-methyl-1-pentenyl, 1-ethyl-2-butenyl, 3-hexenyl, 4-hexenyl, 5-hexenyl, 1-methyl-4-pentenyl, 1-ethyl-3-butenyl, 1-(isobutyl)vinyl, 1-ethyl-1-propenyl, 1-ethyl-2-methyl-2-propenyl, 1-(isopropyl)-2-propenyl, 2-methyl-2-pentenyl, 3-methyl-3-pentenyl, 4-methyl-3-pentenyl, 1,3-dimethyl-2-butenyl, 1,1-dimethyl-3-butenyl, 3-methyl-4-pentenyl, 4-methyl-4-pentenyl, 1,2-dimethyl-3-butenyl, 1,3-dimethyl-3-butenyl, 1,1,2-trimethyl-2-propenyl, 1,5-hexadienyl, 1-vinyl-3-butenyl, and 2,4-hexadienyl.

The $C_2$-$C_6$ alkynyl group represents, unless specified otherwise, a linear or branched alkynyl group having 2 to 6 carbon atoms, and examples thereof include a group like ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexynyl, 1-(n-propyl)-2-propynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexynyl, 1-ethyl-3-butynyl, 1-ethyl-1-methyl-2-propynyl, 1-(isopropyl)-2-propynyl, 1,1-dimethyl-2-butynyl, and 2,2-dimethyl-3-butynyl.

The $C_2$-$C_6$ halolalkenyl group represents, unless specified otherwise, a linear or branched alkenyl group having 2 to 6 carbon atoms substituted with 1 to 11 halogen atoms that are the same or different from each other, and examples thereof include 2-chlorovinyl, 2-bromovinyl, 2-iodovinyl, 3-chloro-2-propenyl, 3-bromo-2-propenyl, 1-chloromethylvinyl, 2-bromo-1-methylvinyl, 1-trifluoromethylvinyl, 3,3,3-trichloro-1-propenyl, 3-bromo-3,3-difluoro-1-propenyl, 2,3,3,3-tetrachloro-1-propenyl, 1-trifluoromethyl-2,2-difluorovinyl, 2-chloro-2-propenyl, 3,3-difluoro-2-propenyl, 2,3,3-trichloro-2-propenyl, 4-bromo-3-chloro-3,4,4-trifluoro-1-butenyl, 1-bromomethyl-2-propenyl, 3-chloro-2-butenyl, 4,4,4-trifluoro-2-butenyl, 4-bromo-4,4-difluoro-2-butenyl, 3-bromo-3-butenyl, 3,4,4-trifluoro-3-butenyl, 3,4,4-tribromo-3-butenyl, 3-bromo-2-methyl-2-propenyl, 3,3-difluoro-2-methyl-2-propenyl, 3,3,3-trifluoro-2-methylpropenyl, 3-chloro-4,4,4-trifluoro-2-butenyl, 3,3,3-trifluoro-1-methyl-1-propenyl, 3,4,4-trifluoro-1,3-butadienyl, 3,4-dibromo-1-pentenyl, 4,4-difluoro-3-methyl-3-butenyl, 3,3,4,4,5,5,5-heptafluoro-1-pentenyl, 5,5-difluoro-4-pentenyl, 4,5,5-trifluoro-4-pentenyl, 3,4,4,4-tetrafluoro-3-trifluoromethyl-1-butenyl, 4,4,4-trifluoromethyl-3-methyl-2-butenyl, 3,5,5-trifluoro-2,4-pentadienyl, 4,4,5,5,6,6,6-heptafluoro-2-hexenyl, 3,4,4,5,5,5-hexafluoro-3-trifluoromethyl-1-pentenyl, 4,5,5,5-tetrafluoro-4-trifluoromethyl-2-pentenyl, and 5-bromo-4,5,5-trifluoro-4-trifluoromethyl-2-pentenyl.

The $C_2$-$C_6$ halolalkynyl group represents, unless specified otherwise, a linear or branched alkynyl group having 2 to 6 carbon atoms substituted with 1 to 9 halogen atoms that are the same or different from each other, and examples thereof include 3-chloro-2-propynyl, 3-bromo-2-propynyl, 3-iodo-2-propynyl, 3-chloro-1-propynyl, and 5-chloro-4-pentynyl.

The $C_1$-$C_6$ alkoxy group represents an (alkyl)-O— group having 1 to 6 carbon atoms, wherein the alkyl moiety has the same definition as above, and examples thereof include a group like methoxy, ethoxy, propoxy, isopropoxy, butoxy, pentyloxy, and hexyloxy.

The $C_1$-$C_6$ haloalkoxy group represents a linear or branched alkyl-O— group having 1 to 6 carbon atoms substituted with 1 to 13 halogen atoms that are the same or different from each other, wherein the haloalkyl moiety has the same definition as above, and examples thereof include a group like chloromethoxy, difluoromethoxy, chlorodifluoromethoxy, trifluoromethoxy, and 2,2,2-trifluoroethoxy.

The $C_1$-$C_6$ alkoxy $C_1$-$C_6$ alkyl group represents an alkyl group having 1 to 6 carbon atoms substituted with an alkoxy group having 1 to 6 carbon atoms, wherein the alkyl moiety and alkoxy moiety have the same definitions as above, and examples thereof include a group like methoxymethyl, ethoxymethyl, isopropoxymethyl, pentyloxymethyl, methoxyethyl, and butoxyethyl.

The hydroxy $C_1$-$C_6$ alkyl group represents, unless specified otherwise, an alkyl group having 1 to 6 carbon atoms substituted with a hydroxy group, wherein the alkyl moiety has the same definition as above, and examples thereof include a group like 2-hydroxyethyl and 3-hydroxypropyl.

The $C_1$-$C_6$ alkoxy $C_1$-$C_6$ alkoxy $C_1$-$C_6$ alkyl group represents an alkyl group having 1 to 6 carbon atoms substituted with an alkoxy having 1 to 6 carbon atoms substituted with an alkoxy having 1 to 6 carbon atoms, wherein the alkyl moiety and alkoxy moiety have the same definitions as above, and examples thereof include a group like 2-(2-methoxyethoxy)ethyl and 2-(2-ethoxyethoxy)ethyl.

The phenyl $C_1$-$C_6$ alkoxy $C_1$-$C_6$ alkyl group represents, unless specified otherwise, an alkyl group having 1 to 6 carbon atoms substituted with an alkoxy group having 1 to 6 carbon atoms substituted with a phenyl, wherein the alkyl moiety and alkoxy moiety have the same definitions as above, and examples thereof include a group like benzyloxymethyl and benzyloxyethyl.

The $C_1$-$C_6$ haloalkoxy $C_1$-$C_6$ alkyl group represents an alkyl group having 1 to 6 carbon atoms substituted with a haloalkoxy group having 1 to 6 carbon atoms, wherein the haloalkoxy moiety and alkyl moiety have the same definitions as above, and examples thereof include a group like chloromethoxymethyl, difluoromethoxymethyl, chlorodifluoromethoxymethyl, trifluoromethoxymethyl, and 2,2,2-trifluoroethoxymethyl.

The $C_1$-$C_6$ haloalkoxy $C_1$-$C_6$ alkoxy group represents, unless specified otherwise, an alkoxy group having 1 to 6 carbon atoms substituted with a haloalkoxy group having 1 to 6 carbon atoms, wherein the haloalkoxy moiety and alkoxy moiety have the same definitions as above, and examples thereof include a group like chloromethoxymethoxy, difluoromethoxymethoxy, chlorodifluoromethoxymethoxy, trifluoromethoxymethoxy, and 2,2,2-trifluoroethoxymethoxy.

The $C_3$-$C_6$ cycloalkyloxy group represents, unless specified otherwise, a (cycloalkyl)-O— group having 3 to 6 carbon atoms, wherein the cycloalkyl moiety has the same definition as above, and examples thereof include a group like cyclopropyloxy, cyclobutyloxy, cyclopentyloxy, and cyclohexyloxy.

The $C_3$-$C_6$ cycloalkyloxy $C_1$-$C_6$ alkyl group represents an alkyl group having 1 to 6 carbon atoms substituted with a (cycloalkyl)-O— group having 3 to 6 carbon atoms, wherein the alkyl moiety and cycloalkyl moiety have the same definitions as above, and examples thereof include a group like cyclopropyloxymethyl, cyclobutyloxymethyl, cyclopentyloxymethyl, and cyclohexyloxymethyl.

The $C_3$-$C_6$ cycloalkyl $C_1$-$C_6$ alkyloxy $C_1$-$C_6$ alkyl group represents, unless specified otherwise, an alkyl group having 1 to 6 carbon atoms substituted with an alkoxy group having 1 to 6 carbon atoms substituted with a cycloalkyl group having 3 to 6 carbon atoms, wherein the alkyl moiety, alkoxy moiety, and cycloalkyl moiety have the same definitions as above, and examples thereof include a group like cyclopropylmethyloxymethyl, cyclobutylmethyloxymethyl, cyclopentylmethyloxymethyl, and cyclohexylmethyloxymethyl.

The $(R^{31}R^{32}N\!-\!C\!=\!O)$ $C_1$-$C_6$ alkyl group represents, unless specified otherwise, an alkyl group having 1 to 6 carbon atoms substituted with a $(R^{31}R^{32}N\!-\!OC\!-\!)$ group, wherein the alkyl moiety has the same definition as above, and examples thereof include a group like N,N-dimethylaminocarbonylmethyl, N,N-dimethylaminocarbonylethyl, and N-methyl-N-ethylaminocarbonylmethyl.

The $C_1$-$C_6$ alkoxycarbonyl $C_1$-$C_6$ allyl group represents, unless specified otherwise, an alkyl group having 1 to 6 carbon atoms substituted with an alkoxycarbonyl group having 1 to 6 carbon atoms, wherein the alkoxy moiety and alkyl moiety have the same definitions as above, and examples thereof include a group like 2-methoxy-2-oxoethyl, 2-ethoxy-2-oxoethyl, and 2-tert-butoxy-2-oxoethyl.

The $C_1$-$C_6$ alkoxycarbonyl $C_1$-$C_6$ alkoxy group represents, unless specified otherwise, an alkoxy group having 1 to 6 carbon atoms substituted with an alkoxycarbonyl group having 1 to 6 carbon atoms, wherein the alkoxy moiety and alkyl moiety have the same definitions as above, and examples thereof include a group like a 2-methoxy-2-oxoethoxy group, a 2-ethoxy-2-oxoethoxy group, and a 2-tert-butoxy-2-oxoethoxy group.

The $C_1$-$C_6$ alkylcarbonyl group represents an (alkyl (having 1 to 6 carbon atoms))—C(=O)— group, wherein the alkyl moiety has the same definition as above, and examples thereof include acetyl and propionyl.

The $C_1$-$C_6$ alkylcarbonyl $C_1$-$C_6$ alkyl group represents, unless specified otherwise, an alkyl group having 1 to 6 carbon atoms substituted with an alkylcarbonyl group having 1 to 6 carbon atoms, wherein the alkylcarbonyl moiety and alkyl moiety have the same definitions as above, and examples thereof include a group like 2-oxopropyl, 3-oxopropyl, and 2-oxobutyl.

The $C_1$-$C_6$ alkylcarbonyloxy $C_1$-$C_6$ alkyl group represents, unless specified otherwise, an alkyl group having 1 to 6 carbon atoms substituted with an (alkyl (having 1 to 6 carbon atoms))—C(=O)O— group, wherein the alkyl moiety has the same definition as above, and examples thereof include a group like acetoxymethyl, propionyloxymethyl, isopropionyloxymethyl, and pivaloyloxymethyl.

The $C_1$-$C_6$ alkylidene group represents, unless specified otherwise, a divalent alkylidene group having 1 to 6 carbon atoms, wherein a single carbon carries a divalent charge and the alkyl moiety has the same definition as above, and examples thereof include a group like a methylene group, an ethylidene group, and an isopropylidene group.

The $C_1$-$C_6$ alkylidene aminooxy $C_1$-$C_6$ alkyl group represents, unless specified otherwise, an alkyl group having 1 to 6 carbon atoms substituted with (alkylidene (having 1 to 6 carbon atoms))=N—O—, wherein the alkylidene moiety and alkyl moiety have the same definitions as above, and examples thereof include a group like methyleneaminooxymethyl, 2-(ethylidene aminooxy)ethyl, and 2-(isopropylidene aminooxy)ethyl.

The $C_2$-$C_6$ alkenyloxy group represents, unless specified otherwise, an (alkenyl)-O— group having 2 to 6 carbon atoms, wherein the alkenyl moiety has the same definition as above, and examples thereof include a group like 2-propenyloxy.

The $C_2$-$C_6$ alkynyloxy group represents, unless specified otherwise, an (alkynyl)-O— group having 2 to 6 carbon atoms, wherein the alkynyl moiety has the same definition as above, and examples thereof include 2-propynyloxy.

The phenyloxy $C_1$-$C_6$ alkyl group represents, unless specified otherwise, an alkyl group having 1 to 6 carbon atoms substituted with a (phenyl)-O— group, wherein the alkyl moiety has the same definition as above, and examples thereof include a group like phenoxymethyl, 2-phenoxyethyl, and 3-phenoxypropyl.

The phenylthio $C_1$-$C_6$ alkyl group represents, unless specified otherwise, an alkyl group having 1 to 6 carbon atoms substituted with a (phenyl)-S— group, wherein the alkyl moiety has the same definition as above, and examples thereof include a group like phenylthiomethyl, 2-phenylthioethyl, and 3-phenylthiopropyl.

The phenylsulfinyl $C_1$-$C_6$ alkyl group represents, unless specified otherwise, an alkyl group having 1 to 6 carbon atoms substituted with a (phenyl)-SO— group, wherein the alkyl moiety has the same definition as above, and examples thereof include a group like phenylsulfinylmethyl, 2-phenylsulfinylethyl, and 3-phenylsulfinylpropyl.

The phenylsulfonyl $C_1$-$C_6$ alkyl group represents, unless specified otherwise, an alkyl group having 1 to 6 carbon atoms substituted with a (phenyl)-$SO_2$— group, wherein the alkyl moiety has the same definition as above, and examples thereof include a group like 2-phenylsulfonylethyl, 3-phenylsulfonylpropyl, and 4-phenylsulfonylbutyl.

The $C_1$-$C_6$ alkoxyimino group represents, unless specified otherwise, an (alkoxy)-N=group having 1 to 6 carbon atoms, wherein the alkoxy moiety has the same definition as above, and examples thereof include methoxyimino and ethoxyimino.

The $C_1$-$C_6$ alkoxyimino $C_1$-$C_6$ alkyl group represents an alkyl group having 1 to 6 carbon atoms substituted with an alkoxyimino group having 1 to 6 carbon atoms, wherein the alkoxyimino moiety and alkyl moiety have the same definitions as above, and examples thereof include methoxyiminomethyl and ethoxyiminomethyl.

The phenoxyimino group represents, unless specified otherwise, a (substituted) (phenoxy)-N=group, and examples thereof include phenoxyimino.

The phenoxyimino $C_1$-$C_6$ alkyl group represents an alkyl group having 1 to 6 carbon atoms substituted with a phenoxyimino group, wherein the phenoxyimino moiety and alkyl moiety have the same definitions as above, and examples thereof include phenoxyiminomethyl.

The di($C_1$-$C_6$ alkoxy) $C_1$-$C_6$ alkyl group represents an alkyl group having 1 to 6 carbon atoms di-substituted with an alkoxy group having 1 to 6 carbon atoms, and examples thereof include (2,2-dimethoxy)ethyl, (3,3-dimethoxy)propyl, (2,2-diethoxy)ethyl group, and a (3,3-diethoxy)propyl.

The formyl $C_1$-$C_6$ alkyl group represents an alkyl group having 1 to 6 carbon atoms substituted with a formyl group, wherein the alkyl moiety has the same definition as above, and examples thereof include (2-formyl)ethyl and (3-formyl)propyl.

The $C_1$-$C_6$ allylthio group represents an (alkyl)-S— group having 1 to 6 carbon atoms, wherein the alkyl moiety has the same definition as above, and examples thereof include methylthio, ethylthio, n-propylthio, and isopropylthio.

The $C_1$-$C_{10}$ allylthio group represents an (alkyl)-S— group having 1 to 10 carbon atoms, wherein the alkyl moiety has the same definition as above, and examples thereof include, in addition to those exemplified above for the $C_1$-$C_6$ alkylthio group, n-heptylthio, n-octylthio, n-nonylthio, and n-decylthio.

The $C_1$-$C_6$ alkylsulfinyl group represents an (alkyl)-SO— group having 1 to 6 carbon atoms, wherein the alkyl moiety has the same definition as above, and examples thereof include methylsulfinyl, ethylsulfinyl, n-propylsulfinyl, and isopropylsulfinyl.

The $C_1$-$C_{10}$ alkylsulfinyl group represents an (alkyl)-S— group having 1 to 10 carbon atoms, wherein the alkyl moiety has the same definition as above, and examples thereof include, in addition to those exemplified above for the $C_1$-$C_6$ alkylsulfinyl group, n-heptylsulfinyl, n-octylsulfinyl, n-nonylsulfinyl, and n-decylsulfinyl.

The $C_1$-$C_6$ alkylsulfonyl group represents an (alkyl)-$SO_2$— group having 1 to 6 carbon atoms, wherein the alkyl moiety has the same definition as above, and examples thereof include methylsulfonyl, ethylsulfonyl, n-propylsulfonyl, and isopropylsulfonyl.

The $C_1$-$C_{10}$ alkylsulfonyl group represents an (alkyl)-$SO_2$— group having 1 to 10 carbon atoms, wherein the alkyl moiety has the same definition as above, and examples thereof include, in addition to those exemplified above for the $C_1$-$C_6$ alkylsulfonyl group, n-heptylsulfonyl, n-octylsulfonyl, n-nonylsulfonyl, and n-decylsulfonyl.

The $C_2$-$C_6$ alkenylthio group represents an (alkenyl)-S— group having 2 to 6 carbon atoms, wherein the alkenyl moiety has the same definition as above, and examples thereof include a group like allylthio.

The $C_2$-$C_6$ alkenylsulfinyl group represents an (alkenyl)-SO-group having 2 to 6 carbon atoms, wherein the alkenyl moiety has the same definition as above, and examples thereof include a group like alkylsulfinyl.

The $C_2$-$C_6$ alkenylsulfonyl group represents an (alkenyl)-$SO_2$— group having 2 to 6 carbon atoms, wherein the alkenyl moiety has the same definition as above, and examples thereof include a group like allylsulfonyl.

The $C_2$-$C_6$ alkynylthio group represents an (alkynyl)-S— group having 2 to 6 carbon atoms, wherein the alkynyl moiety has the same definition as above, and examples thereof include a group like 2-propynylthio.

The $C_2$-$C_6$ alkynylsulfinyl group represents an (alkynyl)-SO— group having 2 to 6 carbon atoms, wherein the alkynyl moiety has the same definition as above, and examples thereof include a group like 2-propynylsulfinyl.

The $C_2$-$C_6$ alkenylsulfonyl group represents an (alkynyl)-$SO_2$— group having 2 to 6 carbon atoms, wherein the alkynyl moiety has the same definition as above, and examples thereof include a group like 2-propynylsulfonyl.

The $C_1$-$C_{10}$ alkylsulfonyloxy group represents an (alkyl) $SO_2$—O— group having 1 to 10 carbon atoms, wherein the alkyl moiety has the same definition as above, and examples thereof include methylsulfonyloxy and ethylsulfonyloxy.

The $C_1$-$C_6$ alkylthio $C_1$-$C_6$ alkyl group represents an alkyl group having 1 to 6 carbon atoms substituted with an alkylthio group having 1 to 6 carbon atoms, wherein the alkyl moiety and alkylthio moiety have the same definitions as above, and examples thereof include methylthiomethyl and ethylthiomethyl.

The $C_1$-$C_6$ alkylsulfinyl $C_1$-$C_6$ alkyl group represents an alkyl group having 1 to 6 carbon atoms substituted with an alkylsulfinyl group having 1 to 6 carbon atoms, wherein the alkyl moiety and alkylsulfinyl moiety have the same definitions as above, and examples thereof include methylsulfinylmethyl and ethylsulfinylmethyl.

The $C_1$-$C_6$ alkylsulfonyl $C_1$-$C_6$ alkyl group represents an alkyl group having 1 to 6 carbon atoms substituted with an alkylsulfonyl group having 1 to 6 carbon atoms, wherein the alkyl moiety and alkylsulfonyl moiety have the same definitions as above, and examples thereof include methylsulfonylmethyl and ethylsulfonylmethyl.

The $C_1$-$C_6$ alkoxy $C_1$-$C_6$ alkoxy group represents an alkoxy group having 1 to 6 carbon atoms substituted with an alkoxy having 1 to 6 carbon atoms, wherein the alkoxy moiety has the same definition as above, and examples thereof include a group like methoxymethoxy, ethoxymethoxy, 2-methoxyethoxy, and 2-ethoxyethoxy.

The $C_1$-$C_6$ haloalkylthio $C_1$-$C_6$ alkyl group represents, unless specified otherwise, an alkyl group having 1 to 6 carbon atoms substituted with a (haloalkyl)-S— group having 1 to 6 carbon atoms, wherein the alkyl moiety and haloalkyl moiety have the same definitions as above, and examples thereof include a group like difluoromethylthiomethyl and trifluoromethylthiomethyl.

The $C_1$-$C_6$ haloalkylsulfinyl $C_1$-$C_6$ alkyl group represents, unless specified otherwise, an alkyl group having 1 to 6 carbon atoms substituted with a (haloalkyl)-SO— group having 1 to 6 carbon atoms, wherein the alkyl moiety and haloalkyl moiety have the same definitions as above, and examples thereof include a group like difluoromethylsulfinylmethyl and trifluoromethylsulfinylmethyl.

The $C_1$-$C_6$ haloalkylsulfonyl $C_1$-$C_6$ alkyl group represents, unless specified otherwise, an alkyl group having 1 to 6 carbon atoms substituted with a (haloalkyl)-$SO_2$— group having 1 to 6 carbon atoms, wherein the alkyl moiety and haloalkyl moiety have the same definitions as above, and examples thereof include a group like difluoromethylsulfonylmethyl and trifluoromethylsulfonylmethyl.

The $C_1$-$C_6$ alkylthio $C_1$-$C_6$ alkoxy $C_1$-$C_6$ alkyl group represents, unless specified otherwise, an alkyl group having 1 to 6 carbon atoms substituted with an alkoxy group having 1 to 6 carbon atoms substituted with an alkylthio group having 1 to 6 carbon atoms, wherein the alkylthio moiety, alkoxy moiety, and alkyl moiety have the same definitions as above, and examples thereof include a group like 2-methylthioethoxymethyl and 2-ethylthioethoxymethyl.

The $C_1$-$C_6$ alkylsulfinyl $C_1$-$C_6$ alkoxy $C_1$-$C_6$ alkyl group represents, unless specified otherwise, an alkyl group having 1 to 6 carbon atoms substituted with an alkoxy group having 1 to 6 carbon atoms substituted with an alkylsulfinyl group having 1 to 6 carbon atoms, wherein the alkylsulfinyl moiety, alkoxy moiety, and alkyl moiety have the same definitions as above, and examples thereof include a group like 2-methylsulfinyl ethoxymethyl and 2-ethylsulfinyl ethoxymethyl.

The $C_1$-$C_6$ alkylsulfonyl $C_1$-$C_6$ alkoxy $C_1$-$C_6$ alkyl group represents, unless specified otherwise, an alkyl group having 1 to 6 carbon atoms substituted with an alkoxy group having 1 to 6 carbon atoms substituted with an alkylsulfonyl group having 1 to 6 carbon atoms, wherein the alkylsulfonyl moiety, alkoxy moiety, and alkyl moiety have the same definitions as above, and examples thereof include a group like 2-methylsulfonylethoxymethyl and 2-ethylsulfonylethoxymethyl.

The $C_1$-$C_6$ acyl group represents an acyl group derived from $C_1$-$C_6$ carboxylic acid, and examples thereof include an acetyl group and a propionyl group.

The $C_1$-$C_6$ alkylcarbonyl group represents an (alkyl (having 1 to 6 carbon atoms))—C(=O)— group, wherein the alkyl moiety has the same definition as above, and examples thereof include an acetyl group and a propionyl group.

The $C_1$-$C_6$ alkylcarbonyloxy group represents an (alkyl (having 1 to 6 carbon atoms))—C(=O)—O— group, wherein the alkyl moiety has the same definition as above, and examples thereof include acetoxy and propionyloxy.

The $C_1$-$C_6$ haloalkylcarbonyloxy group represents a (haloalkyl (having 1 to 6 carbon atoms))—C(=O)—O— group, wherein the haloalkyl moiety has the same definition as above, and examples thereof include a group like chloromethylcarbonyloxy, difluoromethylcarbonyloxy, chlorodifluoromethylcarbonyloxy, trifluoromethylcarbonyloxy, and 2,2,2-trifluoroethylcarbonyloxy.

The $C_2$-$C_6$ alkenylcarbonyloxy group represents an (alkenyl (having 2 to 6 carbon atoms))—C(=O)—O— group, wherein the alkenyl moiety has the same definition as above, and examples thereof include a group like 1-propenylcarbonyloxy, 2-propenylcarbonyloxy, 1-butenylcarbonyloxy, and 1-methyl-1-propenylcarbonyloxy.

The $C_2$-$C_6$ halolalkenylcarbonyloxy group represents a (haloalkenyl (having 2 to 6 carbon atoms))—C(=O)—O— group, wherein the haloalkenyl moiety has the same definition as above, and examples thereof include a group like 3-chloro-2-propenylcarbonyloxy and 3-bromo-2-propenylcarbonyloxy.

The $C_2$-$C_6$ alkynylcarbonyloxy group represents an (alkenyl (having 2 to 6 carbon atoms))—C(=O)—O— group, wherein the alkynyl moiety has the same definition as above, and examples thereof include a group like 1-propynylcarbonyloxy and 2-propynylcarbonyloxy.

The $C_2$-$C_6$ haloalkynylcarbonyloxy group represents a (haloalkynyl (having 2 to 6 carbon atoms))—C(=O)—O— group, wherein the haloalkynyl moiety has the same definition as above, and examples thereof include a group like 3-chloro-1-propynylcarbonyloxy and 3,3,3-trifluoro-1-propynylcarbonyloxy.

The $C_2$-$C_6$ alkylidene amino group represents an alkyl (having 1 to 5 carbon atoms)-CH=N— group, wherein the alkyl moiety has the same definition as above, and examples thereof include a group like ethylideneamino and propylideneamino.

The di($C_1$-$C_{10}$ alkyl)amino $C_1$-$C_6$ alkylidene amino group represents an amino group substituted with an alkylidene group having 1 to 6 carbon atoms substituted with an amino group di-substituted with an alkyl group having 1 to 10 carbon atoms, wherein the alkyl moiety has the same definition as above, and examples thereof include a group like a dimethylamino methylidene amino group and a diethylamino methylidene amino group.

The $C_1$-$C_{10}$ alkylamino group represents an (alkyl)-NH— group having 1 to 10 carbon atoms, wherein the alkyl moiety has the same definition as above, and examples thereof include methylamino and ethylamino.

The di($C_1$-$C_{10}$ alkyl)amino group represents an (alkyl)$_2$N— group, wherein the alkyl moiety has the same definition as above, and examples thereof include dimethylamino, diethylamino, methylethylamino, dipropylamino, and dibutylamino.

The mono($C_1$-$C_6$ alkyl)amino group represents an (alkyl)-NH— group having 1 to 6 carbon atoms, wherein the alkyl moiety has the same definition as above, and examples thereof include a group like methylamino and ethylamino.

The di($C_1$-$C_6$ alkyl)amino group represents an (alkyl (having 1 to 6 carbon atoms))$_2$N— group, wherein the alkyl moiety has the same definition as above, and examples thereof include a group like dimethylamino, diethylamino, methylethylamino, dipropylamino, and dibutylamino.

The $C_1$-$C_6$ alkylamino $C_1$-$C_6$ alkyl group represents an alkyl group having 1 to 6 carbon atoms substituted with an alkylamino group having 1 to 6 carbon atoms, wherein the alkyl moiety has the same definition as above, and examples thereof include N-methylaminomethyl and N-methylaminoethyl.

The di($C_1$-$C_6$ alkyl)amino $C_1$-$C_6$ alkyl group represents an alkyl group having 1 to 6 carbon atoms substituted with an (alkyl (having 1 to 6 carbon atoms))$_2$N— group, wherein the alkyl moiety has the same definition as above, and examples thereof include N,N-dimethylaminomethyl and N,N-dimethylaminoethyl.

The $C_1$-$C_6$ alkoxycarbonyl amino group represents an amino group substituted with an (alkoxy (having 1 to 6 carbon atoms))—C(=O)— group, wherein the alkoxy moiety has the same definition as above, and examples thereof include methoxycarbonyl amino and ethoxycarbonyl amino.

The $C_1$-$C_6$ alkylcarbonyl amino group represents, unless specified otherwise, an amino group substituted with an alkylacarbonyl group having 1 to 6 carbon atoms, wherein the alkylcarbonyl moiety has the same definition as above, and examples thereof include a group like formamide, acetamide, and propionamide.

The $C_1$-$C_6$ alkoxycarbonyl group represents an (alkyl (having 1 to 6 carbon atoms))—O—C(=O)— group, wherein the alkyl moiety has the same definition as above, and examples thereof include methoxycarbonyl, ethoxycarbonyl, n-propoxycarbonyl, and isopropoxycarbonyl.

The $C_1$-$C_{10}$ alkylthiocarbonyl group represents an (alkyl (having 1 to 10 carbon atoms))—S—C(=O)— group, wherein the alkyl moiety has the same definition as above, and examples thereof include methylthiocarbonyl and ethylthiocarbonyl.

The $C_1$-$C_6$ alkoxycarbonyloxy group represents an oxy group substituted with an (alkoxy (having 1 to 6 carbon atoms))—C(=O)— group, wherein the alkoxycarbonyl moiety has the same definition as above, and examples thereof include methoxycarbonyloxy and ethoxycarbonyloxy.

The $C_1$-$C_6$ haloalkylcarbonyl group represents a (haloalkyl (having 1 to 6 carbon atoms))—C(=O)— group, wherein the haloalkyl moiety has the same definition as above, and examples thereof include chloroacetyl, trifluoroacetyl, pentafluoropropionyl, and difluoromethylthio.

The $C_1$-$C_6$ haloalkylthio group represents a (haloalkyl (having 1 to 6 carbon atoms))—S— group, wherein the haloalkyl moiety has the same definition as above, and examples thereof include difluoromethylthio and trifluoromethylthio.

The $C_1$-$C_6$ halalkylsulfinyl group represents a (haloalkyl (having 1 to 6 carbon atoms))—SO— group, wherein the haloalkyl moiety has the same definition as above, and examples thereof include trifluoromethylsulfinyl and difluoromethylsulfinyl.

The $C_1$-$C_6$ haloalkylsulfonyl group represents a (haloalkyl (having 1 to 6 carbon atoms))—SO$_2$— group, wherein the haloalkyl moiety has the same definition as above, and examples thereof include chloromethylsulfonyl, difluoromethylsulfonyl, and trifluoromethylsulfonyl.

The $C_1$-$C_6$ haloalkylsulfonyloxy group represents a (haloalkyl (having 1 to 6 carbon atoms))—SO$_2$—O— group, wherein the haloalkyl moiety has the same definition as above, and examples thereof include chloromethylsulfonyloxy and trifluoromethylsulfonyloxy.

The mono($C_1$-$C_6$ alkyl)aminocarbonyl group represents an (alkyl (having 1 to 6 carbon atoms))—NH—C(=O)— group, wherein the alkyl moiety has the same definition as above, and examples thereof include methylaminocarbonyl and ethylaminocarbonyl.

The di($C_1$-$C_6$ alkyl)aminocarbonyl group represents an (alkyl (having 1 to 6 carbon atoms))$_2$N—C(=O)— group, wherein the alkyl moiety has the same definition as above, and examples thereof include a group like dimethylaminocarbonyl, diethylaminocarbonyl, methylethylaminocarbonyl, dipropylaminocarbonyl, and dibutylaminocarbonyl.

The cyano $C_1$-$C_6$ alkyl group represents a cyano alkyl group having 1 to 6 carbon atoms, wherein the alkyl moiety has the same definition as above, and examples thereof include cyanomethyl and cyanoethyl.

The cyano $C_1$-$C_6$ alkoxy group represents an alkoxy group having 1 to 6 carbon atoms substituted with a cyano group, wherein the alkoxy moiety has the same definition as above, and examples thereof include a group like 2-cyanoethoxy and 3-cyanopropoxy.

The cyano $C_1$-$C_6$ alkoxy $C_1$-$C_6$ alkyl group represents, unless specified otherwise, an alkyl group having 1 to 6 carbon atoms substituted with an alkoxy group having 1 to 6 carbon atoms substituted with a cyano group, wherein the alkoxy moiety and alkyl moiety have the same definitions as above, and examples thereof include a group like 2-cyanoethoxymethyl and 3-cyanopropoxymethyl.

The phenyl $C_1$-$C_6$ alkyl group represents an alkyl group having 1 to 6 carbon atoms substituted with a phenyl group, wherein the alkyl moiety has the same definition as above, and examples thereof include benzyl, phenethyl, and phenylpropyl.

The phenyl $C_2$-$C_6$ alkenyl group represents an alkenyl group having 2 to 6 carbon atoms substituted with a phenyl group, wherein the alkenyl moiety has the same definition as above, and examples thereof include styryl and cinnamyl.

The phenyl $C_2$-$C_6$ alkynyl group represents an alkynyl group having 2 to 6 carbon atoms substituted with a phenyl group, wherein the alkynyl moiety has the same definition as above, and examples thereof include (2-phenyl)ethynyl and 2-(3-phenyl)ethynyl.

The phenylcarbonyloxy group represents a (phenyl)-C(=O)—O— group and examples thereof include a phenylcarbonyloxy group.

The phenylcarbonyl $C_1$-$C_6$ alkyloxy group represents an alkoxy group having 1 to 6 carbon atoms substituted with a (phenyl)-C(=O) group and examples thereof include phenylcarbonylmethoxy.

The phenylthio group represents a phenyl-S— group.

The phenylsulfinyl group represents a phenyl-SO— group.

The phenylsulfonyl group represents a phenyl-SO$_2$— group.

The phenylsulfonyloxy group represents a phenyl-SO$_2$—O— group.

The benzylthio group represents a benzyl-S— group.

The benzylsulfinyl group represents a benzyl-SO— group.

The benzylsulfonyl group represents a benzyl-SO$_2$— group.

The benzylsulfonyloxy group represents a benzyl-SO$_2$—O— group.

As a group constituting a $C_3$-$C_6$ alkylene group, 1 to 3 carbon atoms in the alkylene group may be substituted with an atom selected from a group consisting of an oxygen atom, a sulfur atom, a nitrogen atom, and a carbon atom constituting a carbonyl group, and the $C_3$-$C_6$ alkylene group is a linear or branched divalent alkylene group having 3 to 6 carbon atoms, and 1 to 3 carbon atoms in the alkylene group may be substituted with an atom or a group of atoms selected from a group consisting of an oxygen atom, a sulfur atom, a nitrogen atom, and a carbon atom constituting a carbonyl group, and examples thereof include a trimethylene group, a propylene group, a butylene group, a methylenedioxy group, and an ethylenedioxy group. Preferred examples of the alkylene group include a $C_1$-$C_3$ alkylenedioxy group.

Examples of the heterocyclic group having 3 to 10 carbon atoms and one or more heteroatoms that are the same or different from each other and selected from an oxygen atom, a sulfur atom, and a nitrogen atom include furan, thiophene, pyrrole, pyrazole, imidazole, pyridine, pyrimidine, pyrazine, pyridazine, pyrrolidine, piperidine, piperazine, morpholine, thiomorpholine, benzofuran, benzothiophene, indole, benzoxazole, benzothiazole, benzimidazole, isoxazole, isoxazoline, oxazole, oxazoline, isothiazole, isothiazoline, thiazole, thetrahydrofuran, and thiazoline. Preferred examples of the heterocyclic group include pyridine, pyrimidine, pyrazine, thiophene, pyrazole, isoxazole, morpholine, thiomorpholine (sulfur atom of thiomorpholine may be bonded with one or two oxygen atoms), piperidine, pyridazine, piperazine, and tetrahydrofuran. More preferred examples of the heterocyclic group include pyridine, pyrimidine, pyrazine, thiophene, pyrazole, isoxazole, morpholine, thiomorpholine (sulfur atom of thiomorpholine may be bonded with one or two oxygen atoms), and piperidine.

The heterocyclic oxy group having 3 to 10 carbon atoms and one or more heteroatoms that are the same or different from each other and optionally selected from an oxygen atom, a sulfur atom, and a nitrogen atom represents, unless specified otherwise, a group in which the oxygen atom is substituted with a heterocycle having the same definition as above, and examples thereof include (tetrahydrofuran-2-yl)oxy, (4,5-dihydroisoxazol-5-yl)oxy, (isoxazol-5-yl)oxy, and a (thiophen-2-yl)oxy group.

The $C_1$-$C_6$ alkyl group substituted with a heterocyclic group having 3 to 10 carbon atoms and one or more heteroatoms that are the same or different from each other and selected from an oxygen atom, a sulfur atom, and a nitrogen atom represents an alkyl group having 1 to 6 carbon atoms substituted with a heterocycle wherein the alkyl moiety and heterocyclic moiety have the same definitions as above, and examples thereof include (2-furan)methyl, (3-furan)methyl, (2-thiophene)methyl, and (3-thiophene)methyl.

The $C_1$-$C_6$ alkyl group substituted with a heterocyclic oxy group having 3 to 10 carbon atoms and one or more heteroatoms that are the same or different from each other and selected from an oxygen atom, a sulfur atom, and a nitrogen atom represents an alkyl group having 1 to 6 carbon atoms substituted with a heterocyclic oxy group wherein the alkyl moiety and heterocyclic moiety have the same definitions as above, and examples thereof include (tetrahydrofuran-2-yl)oxymethyl, (4,5-dihydroisoxazol-5-yl)oxymethyl, (isoxazol-5-yl)oxymethyl, and (thiophen-2-yl)oxymethyl.

The $C_1$-$C_6$ alkoxy $C_1$-$C_6$ alkyl group substituted with a heterocyclic oxy group having 3 to 10 carbon atoms and one or more heteroatoms that are the same or different from each other and selected from an oxygen atom, a sulfur atom, and a nitrogen atom represents an alkyl group having 1 to 6 carbon atoms substituted with an alkoxy group having 1 to 6 carbon atoms substituted with a heterocyclic oxy group wherein the alkyl moiety, alkoxy moiety, and heterocyclic moiety have the same definitions as above, and examples thereof include (tetrahydrofuran-2-yl)oxymethoxymethyl, (4,5-dihydroisoxazol-5-yl)oxyethoxymethyl, (isoxazol-5-yl)oxymethoxymethyl, and (thiophen-2-yl)oxyethoxymethyl.

The $C_1$-$C_6$ alkoxy $C_1$-$C_6$ alkyl group substituted with a heterocyclic group having 3 to 10 carbon atoms and one or more heteroatoms that are the same or different from each other and selected from an oxygen atom, a sulfur atom, and a nitrogen atom represents an alkyl group having 1 to 6 carbon atoms substituted with an alkoxy group having 1 to 6 carbon atoms substituted with a heterocyclic group wherein the alkyl moiety, alkoxy moiety, and heterocyclic moiety have the same definitions as above, and examples thereof include tetrahydrofurfuryloxyethyl and tetrahydrofurfuryloxymethyl.

The $C_1$-$C_6$ alkoxy group substituted with a heterocyclic group having 3 to 10 carbon atoms and one or more heteroatoms that are the same or different from each other and selected from an oxygen atom, a sulfur atom, and a nitrogen atom represents an alkoxy group having 1 to 6 carbon atoms substituted with a heterocyclic group wherein the heterocyclic moiety and alkoxy moiety have the same definitions as above, and examples thereof include a 6-methyl-2-pyridinemethoxy group and a tetrahydrofurfuryloxy group.

Alkali metal includes sodium, potassium, and the like.

Next, specific examples of the compound of the invention represented by Formula 1 are described in Table 1 to Table 43. However, the invention is not limited to those compounds.

In the present Description, the following descriptions included in the tables indicate the corresponding group, respectively, as shown below.

For example, Me represents a methyl group, Et represents an ethyl group, Pr-n represents a n-propyl group, Pr-i represents an isopropyl group, Pr-c represents a cyclopropyl group, Bu-n represents a n-butyl group, Bu-s represents a secondary butyl group, Bu-i represents an isobutyl group, Bu-t represents a tertiary butyl group, Bu-c represents a cyclobutyl group, Pen-n represents a n-pentyl group, Pen-c represents a cyclopentyl group, Hex-n represents a n-hexyl group, Hex-c represents a cyclohexyl group, Ac represents an acetyl group, Ph represents a phenyl group, Bn represents a benzyl group, Ts represents a p-toluene sulfonyl group, pyridyl represents a pyridyl group, and pyrimidinyl represents a pyrimidinyl group. Further, Ph(2-OMe) represents a 2-methoxyphenyl group, $CH_2Ph(2\text{-OMe})$ represents a 2-methoxybenzyl group, and $Ph(3,4\text{-}Cl_2)$ represents a 3,4-dichlorophenyl group.

TABLE 1

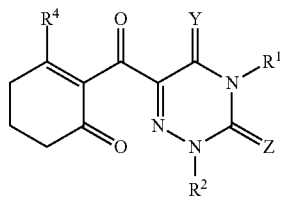

| Compound No. | $R^1$ | $R^2$ | Y | Z | $R^4$ |
|---|---|---|---|---|---|
| I-1 | Me | Me | O | O | OH |
| I-2 | Et | Me | O | O | OH |
| I-3 | Pr-n | Me | O | O | OH |
| I-4 | Pr-i | Me | O | O | OH |
| I-5 | Bu-n | Me | O | O | OH |
| I-6 | Bu-i | Me | O | O | OH |
| I-7 | Bu-s | Me | O | O | OH |
| I-8 | Bu-t | Me | O | O | OH |
| I-9 | Hex-n | Me | O | O | OH |
| I-10 | $CH_2CF_3$ | Me | O | O | OH |
| I-11 | $CH_2CH=CH_2$ | Me | O | O | OH |
| I-12 | $CH_2C(Me)=CH_2$ | Me | O | O | OH |
| I-13 | $CH_2CH_2CH=CMe_2$ | Me | O | O | OH |
| I-14 | $CH_2C\equiv CH$ | Me | O | O | OH |
| I-15 | $CH_2C\equiv CCH_3$ | Me | O | O | OH |
| I-16 | Pr-c | Me | O | O | OH |
| I-17 | Bu-c | Me | O | O | OH |
| I-18 | Pen-c | Me | O | O | OH |
| I-19 | Hex-c | Me | O | O | OH |
| I-20 | $CH_2Pr\text{-}c$ | Me | O | O | OH |
| I-21 | $CH_2Bu\text{-}c$ | Me | O | O | OH |
| I-22 | $CH_2Pen\text{-}c$ | Me | O | O | OH |
| I-23 | $CH_2Hex\text{-}c$ | Me | O | O | OH |
| I-24 | $CH_2CH=CCl_2$ | Me | O | O | OH |
| I-25 | $CH_2CCl=CHCl$ | Me | O | O | OH |
| I-26 | $CH_2CH_2CH=CCl_2$ | Me | O | O | OH |
| I-27 | $CH_2CH_2C(Me)=CF_2$ | Me | O | O | OH |
| I-28 | $CH_2CH_2CH_2CH_2C(Me)=CF_2$ | Me | O | O | OH |
| I-29 | $CH_2CH=CF_2$ | Me | O | O | OH |
| I-30 | $CH_2CH_2OMe$ | Me | O | O | OH |
| I-31 | $CH_2CH_2OEt$ | Me | O | O | OH |
| I-32 | $CH(Me)CH_2OMe$ | Me | O | O | OH |
| I-33 | $CH_2CH_2OCH_2CH_2OMe$ | Me | O | O | OH |
| I-34 | $CH_2CH_2OPr\text{-}n$ | Me | O | O | OH |
| I-35 | $CH_2CH_2OPr\text{-}i$ | Me | O | O | OH |
| I-36 | $CH_2CH_2OPr\text{-}c$ | Me | O | O | OH |
| I-37 | $CH_2CH_2OBu\text{-}c$ | Me | O | O | OH |
| I-38 | $CH_2CH_2OPen\text{-}c$ | Me | O | O | OH |
| I-39 | $CH_2CH_2OHex\text{-}c$ | Me | O | O | OH |
| I-40 | $CH_2CH_2OCH_2CF_3$ | Me | O | O | OH |
| I-41 | $CH_2CH_2CH_2OMe$ | Me | O | O | OH |

TABLE 2

| Compound No. | $R^1$ | $R^2$ | Y | Z | $R^4$ |
|---|---|---|---|---|---|
| I-42 | $CH=CHMe$ | Me | O | O | OH |
| I-43 | $CH_2SMe$ | Me | O | O | OH |
| I-44 | $CH_2SPr\text{-}n$ | Me | O | O | OH |
| I-45 | $CH_2CH_2SMe$ | Me | O | O | OH |
| I-46 | $CH_2SOMe$ | Me | O | O | OH |
| I-47 | $CH_2SO_2Me$ | Me | O | O | OH |
| I-48 | $CH_2CH_2CH_2SMe$ | Me | O | O | OH |
| I-49 | $CH_2CH_2CH_2SO_2Me$ | Me | O | O | OH |
| I-50 | Ph | Me | O | O | OH |
| I-51 | Ph(2-Cl) | Me | O | O | OH |
| I-52 | Ph(3-Cl) | Me | O | O | OH |
| I-53 | Ph(4-Cl) | Me | O | O | OH |
| I-54 | Ph(2-F) | Me | O | O | OH |
| I-55 | Ph(3-F) | Me | O | O | OH |
| I-56 | Ph(4-F) | Me | O | O | OH |
| I-57 | Ph(2-Me) | Me | O | O | OH |
| I-58 | Ph(3-Me) | Me | O | O | OH |
| I-59 | Ph(4-Me) | Me | O | O | OH |
| I-60 | Ph(2-OMe) | Me | O | O | OH |
| I-61 | Ph(3-OMe) | Me | O | O | OH |
| I-62 | Ph(4-OMe) | Me | O | O | OH |
| I-63 | Ph(2-$CF_3$) | Me | O | O | OH |
| I-64 | Ph(3-$CF_3$) | Me | O | O | OH |
| I-65 | Ph(4-$CF_3$) | Me | O | O | OH |
| I-66 | Ph(2-$NO_2$) | Me | O | O | OH |
| I-67 | Ph(3-$NO_2$) | Me | O | O | OH |
| I-68 | Ph(4-$NO_2$) | Me | O | O | OH |
| I-69 | Ph(2-$OCF_3$) | Me | O | O | OH |
| I-70 | Ph(3-$OCF_3$) | Me | O | O | OH |
| I-71 | Ph(4-$OCF_3$) | Me | O | O | OH |
| I-72 | Ph(2-CN) | Me | O | O | OH |
| I-73 | Ph(3-CN) | Me | O | O | OH |
| I-74 | Ph(4-CN) | Me | O | O | OH |
| I-75 | Ph(3,4-$F_2$) | Me | O | O | OH |
| I-76 | Ph(3,5-$F_2$) | Me | O | O | OH |
| I-77 | Ph(2,3-$F_2$) | Me | O | O | OH |
| I-78 | Ph(2,4-$F_2$) | Me | O | O | OH |
| I-79 | Ph(2,5-$F_2$) | Me | O | O | OH |
| I-80 | Ph(2,6-$F_2$) | Me | O | O | OH |
| I-81 | Ph(3,4-$Cl_2$) | Me | O | O | OH |
| I-82 | Ph(3,5-$Cl_2$) | Me | O | O | OH |
| I-83 | Ph(2,3-$Cl_2$) | Me | O | O | OH |
| I-84 | Ph(2,4-$Cl_2$) | Me | O | O | OH |
| I-85 | Ph(2,5-$Cl_2$) | Me | O | O | OH |

TABLE 3

| Compound No. | $R^1$ | $R^2$ | Y | Z | $R^4$ |
|---|---|---|---|---|---|
| I-86 | Ph(2,6-$Cl_2$) | Me | O | O | OH |
| I-87 | Ph(3,4-$Me_2$) | Me | O | O | OH |
| I-88 | Ph(3,5-$Me_2$) | Me | O | O | OH |
| I-89 | Ph(2,3-$Me_2$) | Me | O | O | OH |
| I-90 | Ph(2,4-$Me_2$) | Me | O | O | OH |
| I-91 | Ph(2,5-$Me_2$) | Me | O | O | OH |
| I-92 | Ph(2,6-$Me_2$) | Me | O | O | OH |
| I-93 | Ph(3,4-$OMe_2$) | Me | O | O | OH |
| I-94 | Ph(3,5-$OMe_2$) | Me | O | O | OH |
| I-95 | Ph(2,3-$OMe_2$) | Me | O | O | OH |
| I-96 | Ph(2,4-$OMe_2$) | Me | O | O | OH |
| I-97 | Ph(2,5-$OMe_2$) | Me | O | O | OH |
| I-98 | Ph(2,6-$OMe_2$) | Me | O | O | OH |
| I-99 | Ph(3-F-4-OMe) | Me | O | O | OH |
| I-100 | Ph(3-F-5-OMe) | Me | O | O | OH |
| I-101 | Ph(2-F-3-OMe) | Me | O | O | OH |
| I-102 | Ph(2-F-4-OMe) | Me | O | O | OH |
| I-103 | Ph(2-F-5-OMe) | Me | O | O | OH |
| I-104 | Ph(2-F-6-OMe) | Me | O | O | OH |
| I-105 | Ph(3-F-4-Me) | Me | O | O | OH |
| I-106 | Ph(3-F-5-Me) | Me | O | O | OH |
| I-107 | Ph(2-F-3-Me) | Me | O | O | OH |
| I-108 | Ph(2-F-4-Me) | Me | O | O | OH |
| I-109 | Ph(2-F-5-Me) | Me | O | O | OH |
| I-110 | Ph(2-F-6-Me) | Me | O | O | OH |

TABLE 3-continued

| Compound No. | R¹ | R² | Y | Z | R⁴ |
|---|---|---|---|---|---|
| I-111 | Ph(3-OMe-4-F) | Me | O | O | OH |
| I-112 | Ph(2-OMe-3-F) | Me | O | O | OH |
| I-113 | Ph(2-OMe-4-F) | Me | O | O | OH |
| I-114 | Ph(2-OMe-5-F) | Me | O | O | OH |
| I-115 | Ph(3-Me-4-F) | Me | O | O | OH |
| I-116 | Ph(2-Me-3-F) | Me | O | O | OH |
| I-117 | Ph(2-Me-4-F) | Me | O | O | OH |
| I-118 | Ph(2-Me-5-F) | Me | O | O | OH |
| I-119 | Ph(3-Cl-4-OMe) | Me | O | O | OH |
| I-120 | Ph(3-Cl-5-OMe) | Me | O | O | OH |
| I-121 | Ph(2-Cl-3-OMe) | Me | O | O | OH |
| I-122 | Ph(2-Cl-4-OMe) | Me | O | O | OH |
| I-123 | Ph(2-Cl-5-OMe) | Me | O | O | OH |
| I-124 | Ph(2-Cl-6-OMe) | Me | O | O | OH |
| I-125 | Ph(3-Cl-4-Me) | Me | O | O | OH |
| I-126 | Ph(3-Cl-5-Me) | Me | O | O | OH |
| I-127 | Ph(2-Cl-3-Me) | Me | O | O | OH |
| I-128 | Ph(2-Cl-4-Me) | Me | O | O | OH |
| I-129 | Ph(2-Cl-5-Me) | Me | O | O | OH |

TABLE 4

| Compound No. | R¹ | R² | Y | Z | R⁴ |
|---|---|---|---|---|---|
| I-130 | Ph(2-Cl-6-Me) | Me | O | O | OH |
| I-131 | Ph(3-OMe-4-Cl) | Me | O | O | OH |
| I-132 | Ph(2-OMe-3-Cl) | Me | O | O | OH |
| I-133 | Ph(2-OMe-4-Cl) | Me | O | O | OH |
| I-134 | Ph(2-OMe-5-Cl) | Me | O | O | OH |
| I-135 | Ph(3-Me-4-Cl) | Me | O | O | OH |
| I-136 | Ph(2-Me-3-Cl) | Me | O | O | OH |
| I-137 | Ph(2-Me-4-Cl) | Me | O | O | OH |
| I-138 | Ph(2-Me-5-Cl) | Me | O | O | OH |
| I-139 | Ph(3-F-4-Cl) | Me | O | O | OH |
| I-140 | Ph(3-F-5-Cl) | Me | O | O | OH |
| I-141 | Ph(2-F-3-Cl) | Me | O | O | OH |
| I-142 | Ph(2-F-4-Cl) | Me | O | O | OH |
| I-143 | Ph(2-F-5-Cl) | Me | O | O | OH |
| I-144 | Ph(2-F-6-Cl) | Me | O | O | OH |
| I-145 | Ph(3-Cl-4-F) | Me | O | O | OH |
| I-146 | Ph(2-Cl-3-F) | Me | O | O | OH |
| I-147 | Ph(2-Cl-4-F) | Me | O | O | OH |
| I-148 | Ph(2-Cl-5-F) | Me | O | O | OH |
| I-149 | Ph(3-Me-4-OMe) | Me | O | O | OH |
| I-150 | Ph(3-Me-5-OMe) | Me | O | O | OH |
| I-151 | Ph(2-Me-3-OMe) | Me | O | O | OH |
| I-152 | Ph(2-Me-4-OMe) | Me | O | O | OH |
| I-153 | Ph(2-Me-5-OMe) | Me | O | O | OH |
| I-154 | Ph(2-Me-6-OMe) | Me | O | O | OH |
| I-155 | Ph(3-OMe-4-Me) | Me | O | O | OH |
| I-156 | Ph(2-OMe-3-Me) | Me | O | O | OH |
| I-157 | Ph(2-OMe-4-Me) | Me | O | O | OH |
| I-158 | Ph(2-OMe-5-Me) | Me | O | O | OH |
| I-159 | Ph(3-CN-4-OMe) | Me | O | O | OH |
| I-160 | Ph(3-OMe-4-CN) | Me | O | O | OH |
| I-161 | Ph(3-Me-4-CN) | Me | O | O | OH |
| I-162 | Ph(3-CN-4-Me) | Me | O | O | OH |
| I-163 | Ph(3-NO$_2$-4-OMe) | Me | O | O | OH |
| I-164 | Ph(3-OMe-4-NO$_2$) | Me | O | O | OH |
| I-165 | Ph(3-Me-4-NO$_2$) | Me | O | O | OH |
| I-166 | Ph(3-NO$_2$-4-Me) | Me | O | O | OH |
| I-167 | Ph(3,5-F$_2$-4-OMe) | Me | O | O | OH |
| I-168 | Ph(3,5-F$_2$-4-Me) | Me | O | O | OH |
| I-169 | Ph(3,4,5-(OMe)$_3$) | Me | O | O | OH |

TABLE 5

| Compound No. | R¹ | R² | Y | Z | R⁴ |
|---|---|---|---|---|---|
| I-170 | 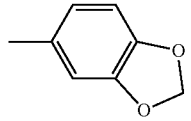 | Me | O | O | OH |
| I-171 | 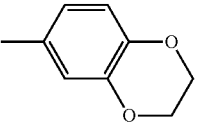 | Me | O | O | OH |
| I-172 | 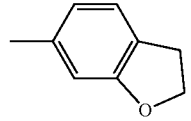 | Me | O | O | OH |
| I-173 | 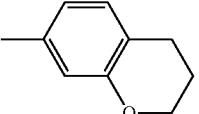 | Me | O | O | OH |
| I-174 | 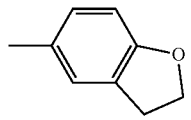 | Me | O | O | OH |
| I-175 | 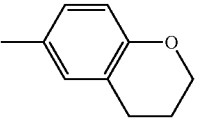 | Me | O | O | OH |
| I-176 | 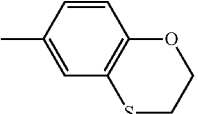 | Me | O | O | OH |
| I-177 | 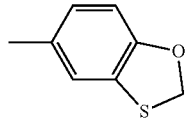 | Me | O | O | OH |
| I-178 | 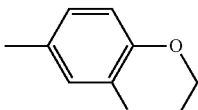 | Me | O | O | OH |
| I-179 | 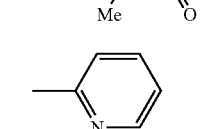 | Me | O | O | OH |
| I-180 | 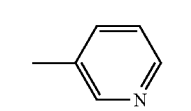 | Me | O | O | OH |
| I-181 | 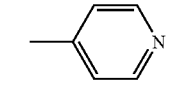 | Me | O | O | OH |

TABLE 5-continued

| Compound No. | R¹ | R² | Y | Z | R⁴ |
|---|---|---|---|---|---|
| I-182 | 2-methyl-5-methylpyridinyl | Me | O | O | OH |
| I-183 | 2-methyl-5-methoxypyridinyl | Me | O | O | OH |
| I-184 | 2-methyl-5-fluoropyridinyl | Me | O | O | OH |

TABLE 6

| Compound No. | R¹ | R² | Y | Z | R⁴ |
|---|---|---|---|---|---|
| I-185 | 2-methyl-5-chloropyridinyl | Me | O | O | OH |
| I-186 | 2-methyl-5-bromopyridinyl | Me | O | O | OH |
| I-187 | 2-methyl-5-trifluoromethylpyridinyl | Me | O | O | OH |
| I-188 | 3-methylisoxazol-5-yl | Me | O | O | OH |
| I-189 | 5-methylisoxazol-3-yl | Me | O | O | OH |
| I-190 | 5-methyl-4,5-dihydroisoxazolyl | Me | O | O | OH |
| I-191 | 3-methyl-4,5-dihydroisoxazol-5-yl | Me | O | O | OH |
| I-192 | 3-methyl-4,5-dihydroisoxazolyl | Me | O | O | OH |
| I-193 | 5-methyl-4,5-dihydroisoxazol-3-yl | Me | O | O | OH |
| I-194 | 2-methylthiazolyl | Me | O | O | OH |

TABLE 6-continued

| Compound No. | R¹ | R² | Y | Z | R⁴ |
|---|---|---|---|---|---|
| I-195 | 2,5-dimethylthiazolyl | Me | O | O | OH |
| I-196 | 2,4-dimethylthiazolyl | Me | O | O | OH |
| I-197 | 2,4,5-trimethylthiazolyl | Me | O | O | OH |
| I-198 | 2-thienyl | Me | O | O | OH |
| I-199 | 3-thienyl | Me | O | O | OH |
| I-200 | 5-methylthien-2-yl | Me | O | O | OH |

TABLE 7

| Compound No. | R¹ | R² | Y | Z | R⁴ |
|---|---|---|---|---|---|
| I-201 | 4-methyl-2-methylthienyl | Me | O | O | OH |
| I-202 | morpholinyl | Me | O | O | OH |
| I-203 | thiomorpholinyl | Me | O | O | OH |
| I-204 | thiomorpholinyl-SO₂ | Me | O | O | OH |
| I-205 | CH₂Ph | Me | O | O | OH |
| I-206 | CH₂CH₂Ph | Me | O | O | OH |
| I-207 | CH₂CH₂CH₂Ph | Me | O | O | OH |
| I-208 | CH₂CH=CHPh | Me | O | O | OH |
| I-209 | CH₂C≡CPh | Me | O | O | OH |
| I-210 | CH₂CH=NOMe | Me | O | O | OH |
| I-211 | CH₂CH=NOEt | Me | O | O | OH |
| I-212 | CH₂CH=NOPr-n | Me | O | O | OH |
| I-213 | CH₂CH=NOPh | Me | O | O | OH |
| I-214 | CH₂CH(OMe)₂ | Me | O | O | OH |
| I-215 | CH₂CHO | Me | O | O | OH |
| I-216 | NH₂ | Me | O | O | OH |
| I-217 | NHMe | Me | O | O | OH |
| I-218 | NHEt | Me | O | O | OH |
| I-219 | NHPr-n | Me | O | O | OH |
| I-220 | NHPr-i | Me | O | O | OH |
| I-221 | NHBu-n | Me | O | O | OH |
| I-222 | NHBu-i | Me | O | O | OH |
| I-223 | NHBu-s | Me | O | O | OH |

TABLE 7-continued

| Compound No. | R¹ | R² | Y | Z | R⁴ |
|---|---|---|---|---|---|
| I-224 | NHCH₂Pr-c | Me | O | O | OH |
| I-225 | NHPen-n | Me | O | O | OH |
| I-226 | NHHex-n | Me | O | O | OH |
| I-227 | NHCH₂CH₂CH₂Cl | Me | O | O | OH |
| I-228 | NHCH₂CH₂CH₂F | Me | O | O | OH |
| I-229 | NHCH₂CH₂OMe | Me | O | O | OH |
| I-230 | NMe₂ | Me | O | O | OH |
| I-231 | NEt₂ | Me | O | O | OH |
| I-232 | N(Pr-n)₂ | Me | O | O | OH |
| I-233 | N(Bu-n)₂ | Me | O | O | OH |
| I-234 | N(Me)Et | Me | O | O | OH |
| I-235 | N(Me)CH₂CH₂OMe | Me | O | O | OH |
| I-236 | NHPh | Me | O | O | OH |
| I-237 | NHCH₂Ph | Me | O | O | OH |
| I-238 | N=CMe₂ | Me | O | O | OH |
| I-239 | N=CEt₂ | Me | O | O | OH |

TABLE 8

| Compound No. | R¹ | R² | Y | Z | R⁴ |
|---|---|---|---|---|---|
| I-240 | N=CHNMe₂ | Me | O | O | OH |
| I-241 | NHC(=O)Me | Me | O | O | OH |
| I-242 | N[C(=O)Me]₂ | Me | O | O | OH |
| I-243 | NHC(=O)OMe | Me | O | O | OH |
| I-244 | N[C(=O)OMe]₂ | Me | O | O | OH |
| I-245 | NHSO₂Me | Me | O | O | OH |
| I-246 | NHSO₂Ph | Me | O | O | OH |
| I-247 | NHSO₂CH₂Ph | Me | O | O | OH |
| I-248 | OMe | Me | O | O | OH |
| I-249 | OEt | Me | O | O | OH |
| I-250 | OPr-n | Me | O | O | OH |
| I-251 | OPr-i | Me | O | O | OH |
| I-252 | OCH₂Pr-c | Me | O | O | OH |
| I-253 | OCH₂Cl | Me | O | O | OH |
| I-254 | OCHCl₂ | Me | O | O | OH |
| I-255 | OCCl₃ | Me | O | O | OH |
| I-256 | OCH₂F | Me | O | O | OH |
| I-257 | OCHF₂ | Me | O | O | OH |
| I-258 | OCF₃ | Me | O | O | OH |
| I-259 | Ph | Et | O | O | OH |
| I-260 | Ph | Pr-i | O | O | OH |
| I-261 | Ph | CHF₂ | O | O | OH |
| I-262 | Ph | Ph | O | O | OH |
| I-263 | Ph | Me | O | S | OH |
| I-264 | Ph | Me | S | S | OH |
| I-265 | Me | Me | O | S | OH |
| I-266 | Me | Me | S | S | OH |
| I-267 | Ph | Me | O | O | SPh |
| I-268 | Ph(4-OEt) | Me | O | O | OH |
| I-269 | Ph(2-Ph) | Me | O | O | OH |
| I-270 | Ph(3-Ph) | Me | O | O | OH |
| I-271 | Ph(4-Ph) | Me | O | O | OH |
| I-272 | 1-Me-5-Me-3-CF₃-pyrazolyl | Me | O | O | OH |
| I-273 | 2-Me-4,6-diOMe-pyrimidinyl | Me | O | O | OH |
| I-274 | Me | 2-pyridyl | O | O | OH |

TABLE 8-continued

| Compound No. | R¹ | R² | Y | Z | R⁴ |
|---|---|---|---|---|---|
| I-275 | Et | 2-Me-pyridyl | O | O | OH |
| I-276 | 2-Cl-3-Me-pyridyl | Me | O | O | OH |

TABLE 9

| Compound No. | R¹ | R² | Y | Z | R⁴ |
|---|---|---|---|---|---|
| I-277 | 2-Me-3-Me-pyridyl | Me | O | O | OH |
| I-278 | 3-Me-5-Me-pyridyl | Me | O | O | OH |
| I-279 | 2-Me-6-Me-pyridyl | Me | O | O | OH |
| I-280 | 2-Cl-5-Me-pyridyl | Me | O | O | OH |
| I-281 | 4-Me-2-Br-pyridyl | Me | O | O | OH |
| I-282 | Ph(2-Me-4-Br) | Me | O | O | OH |
| I-283 | Ph(2-Me-4-I) | Me | O | O | OH |
| I-284 | Ph(2-Me-5-CF₃) | Me | O | O | OH |
| I-285 | Ph(2-Me-6-OCF₃) | Me | O | O | OH |
| I-286 | Ph(2-Pr-i) | Me | O | O | OH |
| I-287 | 2-OMe-5-Me-pyridyl | Me | O | O | OH |
| I-288 | Ph(2-Et) | Me | O | O | OH |
| I-289 | 2-Me-5-Me-pyridyl | Me | O | O | OH |
| I-290 | 2-Me-5-OMe-pyridyl | Me | O | O | OH |
| I-291 | 2-Me-5-Me-pyridyl | Me | O | S | OH |

TABLE 9-continued

| Compound No. | R¹ | R² | Y | Z | R⁴ |
|---|---|---|---|---|---|
| I-292 | 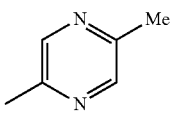 2,5-dimethylpyrazinyl | Me | O | O | OH |
| I-293 | 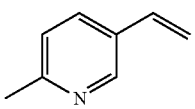 6-methyl-3-vinylpyridinyl | Me | O | O | OH |
| I-294 | CH₂COOBu-t | Me | O | O | OH |
| I-295 | (C₇H₁₄)CH₃ | Me | O | O | OH |
| I-296 | (C₉H₁₈)CH₃ | Me | O | O | OH |
| I-297 | Ph(2-F, 4-Cl, 5-OMe) | Me | O | O | OH |
| I-298 | Ph(2,3,4-(OMe)₃ | Me | O | O | OH |
| I-299 | Ph(3,5-Cl₂-4-OMe) | Me | O | O | OH |
| I-300 | Ph(3,5-Cl₂-4-SMe) | Me | O | O | OH |
| I-301 | Ph(3,5-Cl₂-4-SO₂Me) | Me | O | O | OH |
| I-302 | Ph(3,4,5-F₃) | Me | O | O | OH |
| I-303 | 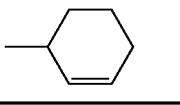 cyclohexenyl | Me | O | O | OH |

TABLE 10

| Compound No. | R¹ | R² | Y | Z | R⁴ |
|---|---|---|---|---|---|
| I-304 | 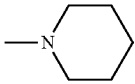 N-methylpiperidinyl | Me | O | O | OH |
| I-305 | 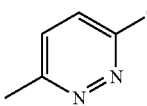 6-methyl-3-hydroxypyridazinyl | Me | O | O | OH |
| I-306 | Bu-n | 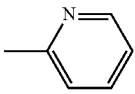 2-methylpyridinyl | O | O | OH |
| I-307 | CH₂CH(CH₃)₂ | 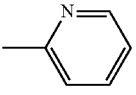 2-methylpyridinyl | O | O | OH |
| I-308 | Ph | Pen-n | O | O | OH |
| I-309 | H | Me | O | O | OH |
| I-310 | CH₂C≡CF | Me | O | O | OH |
| I-311 | 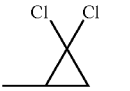 2,2-dichlorocyclopropyl | Me | O | O | OH |
| I-312 |  2,2-dichloro-3-ethylcyclopropyl | Me | O | O | OH |
| I-313 | CH₂NH₂ | Me | O | O | OH |
| I-314 | CH₂NO₂ | Me | O | O | OH |
| I-315 | CH₂NHCH₃ | Me | O | O | OH |
| I-316 | CH₂N(CH₃)₂ | Me | O | O | OH |
| I-317 | CH₂SCH₂CF₃ | Me | O | O | OH |
| I-318 | CH₂SOCH₂CF₃ | Me | O | O | OH |
| I-319 | CH₂SO₂CH₂CF₃ | Me | O | O | OH |
| I-320 | CH₂OH | Me | O | O | OH |
| I-321 | CH₂OBn | Me | O | O | OH |
| I-322 | CH₂OCH₂Pr-c | Me | O | O | OH |
| I-323 | CH₂OPh | Me | O | O | OH |
| I-324 | CH₂SPh | Me | O | O | OH |
| I-325 | CH₂SOPh | Me | O | O | OH |
| I-326 | CH₂SO₂Ph | Me | O | O | OH |
| I-327 | CH₂CON(CH₃)₂ | Me | O | O | OH |
| I-328 | CH₂COCH₃ | Me | O | O | OH |
| I-329 | CH₂OCOCH₃ | Me | O | O | OH |
| I-330 | CH₂ON=CHCH₃ | Me | O | O | OH |
| I-331 | C₂H₄OC₂H₄SCH₃ | Me | O | O | OH |
| I-332 | C₂H₄OC₂H₄SOCH₃ | Me | O | O | OH |
| I-333 | C₂H₄OC₂H₄SO₂CH₃ | Me | O | O | OH |
| I-334 | CH₂OCH₂CN | Me | O | O | OH |
| I-335 | CH₂CN | Me | O | O | OH |
| I-336 | OCH₂CH=CH₂ | Me | O | O | OH |
| I-337 | OCH₂C≡CH | Me | O | O | OH |
| I-338 | OPr-c | Me | O | O | OH |

TABLE 11

| Compound No. | R¹ | R² | Y | Z | R⁴ |
|---|---|---|---|---|---|
| I-339 | 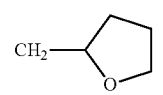 CH₂-(tetrahydrofuran-2-yl) | Me | O | O | OH |
| I-340 | 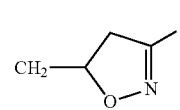 CH₂-(3-methyl-4,5-dihydroisoxazol-5-yl) | Me | O | O | OH |
| I-341 |  CH₂-(3-methylisoxazol-5-yl) | Me | O | O | OH |
| I-342 | 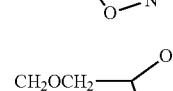 CH₂OCH₂-(tetrahydrofuran-2-yl) | Me | O | O | OH |

TABLE 11-continued

| Compound No. | R¹ | R² | Y | Z | R⁴ |
|---|---|---|---|---|---|
| I-343 | CH₂CH₂OCH₂CH₂O-(2-pyridyl) | Me | O | O | OH |
| I-344 | Ph | H | O | O | OH |
| I-345 | Ph | CH₂CH=CH₂ | O | O | OH |
| I-346 | Ph | CH₂C≡CH | O | O | OH |
| I-347 | Ph | Pr-c | O | O | OH |
| I-348 | Ph | CH₂CH=CF₂ | O | O | OH |
| I-349 | Ph | CH₂C≡CF | O | O | OH |
| I-350 | Ph | C₂H₄OCH₃ | O | O | OH |
| I-351 | Ph | C₂H₄OC₂H₅ | O | O | OH |
| I-352 | Ph | CH(Me)OEt | O | O | OH |
| I-353 | Ph | CH₂OPr-c | O | O | OH |
| I-354 | Ph | CH(OCH₃)₂ | O | O | OH |
| I-355 | Ph | CH₂Ph | O | O | OH |
| I-356 | Ph | CH=CH-Ph | O | O | OH |
| I-357 | Ph | C≡C-Ph | O | O | OH |
| I-358 | Ph | Me | O | O | NH₂ |
| I-359 | Ph | Me | O | O | Cl |
| I-360 | Ph | Me | O | O | CN |
| I-361 | Ph | Me | O | O | NCS |
| I-362 | Ph | Me | O | O | NCO |
| I-363 | Ph | Me | O | O | OCO2H |
| I-364 | Ph | Me | O | O | OCO₂CH₃ |
| I-365 | Ph | Me | O | O | OCO₂CH₂Ph |
| I-366 | Ph | Me | O | O | OMe |
| I-367 | Ph | Me | O | O | OEt |
| I-368 | Ph | Me | O | O | OPr |
| I-369 | Ph | Me | O | O | OCH₂CH=CH₂ |
| I-370 | Ph | Me | O | O | OCH₂C≡CH |
| I-371 | Ph | Me | O | O | OPr-c |
| I-372 | Ph | Me | O | O | OBu-c |
| I-373 | Ph | Me | O | O | OPen-c |

TABLE 12

| Compound No. | R¹ | R² | Y | Z | R⁴ |
|---|---|---|---|---|---|
| I-374 | Ph | Me | O | O | OHex-c |
| I-375 | Ph | Me | O | O | OCH₂CN |
| I-376 | Ph | Me | O | O | OCH₂Pr-c |
| I-377 | Ph | Me | O | O | OCOCH₃ |
| I-378 | Ph | Me | O | O | OCOCCl₂ |
| I-379 | Ph | Me | O | O | OCOCH=CH₂ |
| I-380 | Ph | Me | O | O | OCOCH=CF₂ |
| I-381 | Ph | Me | O | O | OCOCH₂C≡CH |
| I-382 | Ph | Me | O | O | OCOCH₂C≡CF |
| I-383 | Ph | Me | O | O | OCH₂CO₂CH₂ |
| I-384 | Ph | Me | O | O | OPh |
| I-385 | Ph | Me | O | O | OCH₂Ph |
| I-386 | Ph | Me | O | O | OCOPh |
| I-387 | Ph | Me | O | O | OCOCH₂Ph |
| I-388 | Ph | Me | O | O | OCH₂COPh |
| I-389 | Ph | Me | O | O | OSO₂CH₂CF₃ |
| I-390 | Ph | Me | O | O | OSO₂CH₂Ph |
| I-391 | Ph | Me | O | O | SCH₃ |
| I-392 | Ph | Me | O | O | SOCH₃ |
| I-393 | Ph | Me | O | O | SO₂CH₃ |
| I-394 | Ph | Me | O | O | SCH₂CF₃ |
| I-395 | Ph | Me | O | O | SOCH₂CF₃ |
| I-396 | Ph | Me | O | O | SO₂CH₂CF₃ |
| I-397 | Ph | Me | O | O | SCH₂CH=CH₂ |
| I-398 | Ph | Me | O | O | SOCH₂CH=CH₂ |
| I-399 | Ph | Me | O | O | SO₂CH₂CH=CH₂ |
| I-400 | Ph | Me | O | O | SCH₂CH=CH |
| I-401 | Ph | Me | O | O | SOCH₂CH=CH |
| I-402 | Ph | Me | O | O | SO₂CH₂CH=CH |
| I-403 | Ph | Me | O | O | SCH₂Ph |
| I-404 | Ph | Me | O | O | SOPh |
| I-405 | Ph | Me | O | O | SOCH₂Ph |
| I-406 | Ph | Me | O | O | SO₂Ph |
| I-407 | Ph | Me | O | O | SO₂CH₂Ph |
| I-408 | Ph | Me | O | O | NHCH₃ |
| I-409 | Ph | Me | O | O | N(CH₃)₂ |
| I-410 | Ph | Me | O | O | NHCOCH₃ |
| I-411 | Ph | Me | O | O | OCH₂CH₂-(2-pyridyl) |
| I-412 | Ph | Me | O | O | 1-methyl-1,2,4-triazol-3-yl |

TABLE 13

| Compound No. | R¹ | R² | Y | Z | R⁴ |
|---|---|---|---|---|---|
| I-413 | Ph | Me | O | O | 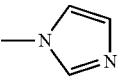 N-methylimidazole |
| I-414 | Ph | Me | O | O | N-methyltetrazole |
| I-415 | Ph | Me | O | O | N-methylpyrazole |
| I-416 | Ph | Me | O | O | 2-pyridyloxy |
| I-417 | (4-Pr-c)Ph | Me | O | O | OH |
| I-418 | (4-CH₂Pr-c)Ph | Me | O | O | OH |
| I-419 | (4-CH₂=CHCH₂)Ph | Me | O | O | OH |
| I-420 | (4-CH≡CCH₂)Ph | Me | O | O | OH |
| I-421 | (4-CH₂CH=CF₂)Ph | Me | O | O | OH |
| I-422 | (4-CH₂CH=CF)Ph | Me | O | O | OH |
| I-423 | 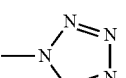 4-(2,2-dichlorocyclopropyl)phenyl | Me | O | O | OH |
| I-424 | 4-((2,2-dichlorocyclopropyl)methyl)phenyl | Me | O | O | OH |
| I-425 | 4-(cyclopropyloxy)phenyl | Me | O | O | OH |
| I-426 | 4-(allyloxy)phenyl | Me | O | O | OH |
| I-427 | 4-(propargyloxy)phenyl | Me | O | O | OH |
| I-428 | 4-(acetyloxy)phenyl | Me | O | O | OH |
| I-429 | (4-OCHF₂)Ph | Me | O | O | OH |
| I-430 | (4-SMe)Ph | Me | O | O | OH |
| I-431 | (4-SOMe)Ph | Me | O | O | OH |
| I-432 | (4-SO₂Me)Ph | Me | O | O | OH |
| I-433 | (4-SCF₃)Ph | Me | O | O | OH |
| I-434 | (4-SOCF₃)Ph | Me | O | O | OH |
| I-435 | (4-SO₂CF₃)Ph | Me | O | O | OH |
| I-436 | 4-aminophenyl | Me | O | O | OH |
| I-437 | 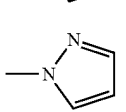 6-methyl-5-(N-acetylamino)pyridin-2-yl | Me | O | O | OH |

TABLE 14

| Compound No. | R¹ | R² | Y | Z | R⁴ |
|---|---|---|---|---|---|
| I-438 | 4-(NHMe)phenyl | Me | O | O | OH |
| I-439 | 4-(NMe₂)phenyl | Me | O | O | OH |
| I-440 | 4-(CH₂OH)phenyl | Me | O | O | OH |
| I-441 | 4-(CH₂OMe)phenyl | Me | O | O | OH |
| I-442 | 4-(CH₂SMe)phenyl | Me | O | O | OH |
| I-443 | 4-(CH₂SOMe)phenyl | Me | O | O | OH |
| I-444 | 4-(CH₂SO₂Me)phenyl | Me | O | O | OH |
| I-445 | 4-(CH₂SCF₃)phenyl | Me | O | O | OH |
| I-446 | 4-(CH₂SOCF₃)phenyl | Me | O | O | OH |
| I-447 | 4-(CH₂SO₂CF₃)phenyl | Me | O | O | OH |
| I-448 | 4-(CH₂CN)phenyl | Me | O | O | OH |
| I-449 | 4-(OCH₂OMe)phenyl | Me | O | O | OH |

TABLE 14-continued

| Compound No. | R¹ | R² | Y | Z | R⁴ |
|---|---|---|---|---|---|
| I-450 | (6-methyl-pyridin-3-yl)oxymethyl-cyclopropane group | Me | O | O | OH |
| I-451 | 4-(methoxymethoxy)phenyl | Me | O | O | OH |
| I-452 | 4-(cyanomethoxy)phenyl | Me | O | O | OH |
| I-453 | 4-acetylphenyl | Me | O | O | OH |
| I-454 | 4-((methoxyimino)methyl)phenyl | Me | O | O | OH |
| I-455 | 4-carboxyphenyl | Me | O | O | OH |

TABLE 15

| Compound No. | R¹ | R² | Y | Z | R⁴ |
|---|---|---|---|---|---|
| I-456 | 4-(methoxycarbonyl)phenyl | Me | O | O | OH |
| I-457 | 4-carbamoylphenyl | Me | O | O | OH |
| I-458 | 4-(methylcarbamoyl)phenyl | Me | O | O | OH |
| I-459 | 4-(dimethylcarbamoyl)phenyl | Me | O | O | OH |
| I-460 | 4-(pyridin-2-yl)phenyl | Me | O | O | OH |
| I-461 | 4-(pyridin-2-yloxy)phenyl | Me | O | O | OH |

TABLE 15-continued

| Compound No. | R¹ | R² | Y | Z | R⁴ |
|---|---|---|---|---|---|
| I-462 | 5-ethyl-2-methylpyridin-yl | Me | O | O | OH |
| I-463 | 5-ethynyl-2-methylpyridin-yl | Me | O | O | OH |
| I-464 | 3,4,5-trimethoxyphenyl | Me | O | S | OH |
| I-465 | Ph(3,4,5-Cl) | Me | O | O | OH |
| I-466 | N(Me)Ph | Me | O | O | OH |
| I-467 | 2,4,6-trimethylpyrimidin-5-yl | Me | O | O | OH |
| I-468 | CH₂CO(Bu-t) | Me | O | O | OH |
| I-469 | Ph(2,3,5,6-F₄) | Me | O | O | OH |
| I-470 | Ph[(3,5-(CF₃)₂] | Me | O | O | OH |
| I-471 | CH₂C(Me)=NOMe | Me | O | O | OH |
| I-472 | Ph(2,4,6-Me₃) | Me | O | O | OH |
| I-473 | Ph(2,3,4,5,6-F₅) | Me | O | O | OH |
| I-474 | N(Et)Ph | Me | O | O | OH |
| I-475 | N(Pr-i)Ph | Me | O | O | OH |
| I-476 | N(Me)Ph(4-F) | Me | O | O | OH |
| I-477 | Ph | CH₂CF₃ | O | O | OH |
| I-478 | CH₂C(Me)=NOEt | Me | O | O | OH |
| I-479 | CH₂C(Me)=NO(Pr-i) | Me | O | O | OH |
| I-480 | Ph(4-F) | Me | O | S | OH |

TABLE 16

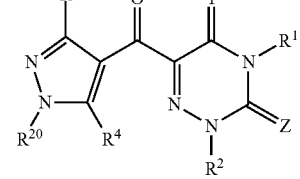

| Compound No. | R¹ | R² | Y | Z | R²⁰ | R²¹ | R⁴ |
|---|---|---|---|---|---|---|---|
| II-1 | Me | Me | O | O | Me | H | OH |
| II-2 | Et | Me | O | O | Me | Me | OH |
| II-3 | Pr-n | Me | O | O | Me | H | OH |
| II-4 | Pr-i | Me | O | O | Me | H | OH |
| II-5 | Bu-n | Me | O | O | Me | H | OH |
| II-6 | Bu-i | Me | O | O | Me | H | OH |
| II-7 | Bu-s | Me | O | O | Me | Me | OH |
| II-8 | Bu-t | Me | O | O | Me | H | OSO₂Pr |
| II-9 | Hex-n | Me | O | O | Me | H | OH |
| II-10 | CH₂CF₃ | Me | O | O | Me | H | OH |
| II-11 | CH₂CH=CH₂ | Me | O | O | Et | H | OH |

TABLE 16-continued

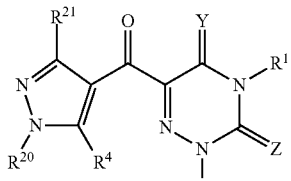

| Compound No. | R¹ | R² | Y | Z | R²⁰ | R²¹ | R⁴ |
|---|---|---|---|---|---|---|---|
| II-12 | CH$_2$C(Me)=CH$_2$ | Me | O | O | Me | H | OH |
| II-13 | CH$_2$CH$_2$CH=CMe$_2$ | Me | O | O | Me | H | OH |
| II-14 | CH$_2$C≡CH | Me | O | O | Me | Me | OH |
| II-15 | CH$_2$C≡CCH$_3$ | Me | O | O | Me | H | OSO$_2$Ph |
| II-16 | Pr-c | Me | O | O | Me | H | OH |
| II-17 | Bu-c | Me | O | O | i-Pr | H | OH |
| II-18 | Pen-c | Me | O | O | Me | H | OH |
| II-19 | Hex-c | Me | O | O | Et | H | OH |
| II-20 | CH$_2$Pr-c | Me | O | O | Me | H | OH |
| II-21 | CH$_2$Bu-c | Me | O | O | Me | H | OH |
| II-22 | CH$_2$Pen-c | Me | O | O | Me | Me | OH |
| II-23 | CH$_2$Hex-c | Me | O | O | Me | H | OH |
| II-24 | CH$_2$CH=CCl$_2$ | Me | O | O | Me | H | OSO$_2$Pr |
| II-25 | CH$_2$CCl=CHCl | Me | O | O | Me | H | OH |
| II-26 | CH$_2$CH$_2$CH=CCl$_2$ | Me | O | O | Et | H | OH |
| II-27 | CH$_2$CH$_2$C(Me)=CF$_2$ | Me | O | O | Me | H | OH |
| II-28 | CH$_2$CH$_2$CH$_2$CH$_2$C(Me)=CF$_2$ | Me | O | O | Me | H | OH |
| II-29 | CH$_2$CH=CF$_2$ | Me | O | O | Me | Me | OH |
| II-30 | CH$_2$CH$_2$OMe | Me | O | O | Me | H | OH |
| II-31 | CH$_2$CH$_2$OEt | Me | O | O | Me | H | OH |
| II-32 | CH(Me)CH$_2$OMe | Me | O | O | Pr-i | H | OH |
| II-33 | CH$_2$CH$_2$OCH$_2$CH$_2$OMe | Me | O | O | Me | H | OH |
| II-34 | CH$_2$CH$_2$OPr-n | Me | O | O | Et | H | OH |
| II-35 | CH$_2$CH$_2$OPr-i | Me | O | O | Me | H | OH |
| II-36 | CH$_2$CH$_2$OPr-c | Me | O | O | Me | Me | OH |
| II-37 | CH$_2$CH$_2$OBu-c | Me | O | O | Me | H | OH |
| II-38 | CH$_2$CH$_2$OPen-c | Me | O | O | Me | H | OH |
| II-39 | CH$_2$CH$_2$OHex-c | Me | O | O | Me | H | OH |

TABLE 17

| Compound No. | R¹ | R² | Y | Z | R²⁰ | R²¹ | R⁴ |
|---|---|---|---|---|---|---|---|
| II-40 | CH$_2$CH$_2$OCH$_2$CF$_3$ | Me | O | O | Et | Me | OH |
| II-41 | CH$_2$CH$_2$CH$_2$OMe | Me | O | O | Me | H | OH |
| II-42 | CH=CHMe | Me | O | O | Me | H | OSO$_2$Ph |
| II-43 | CH$_2$SMe | Me | O | O | Me | H | OH |
| II-44 | CH$_2$SPr-n | Me | O | O | Me | H | OH |
| II-45 | CH$_2$CH$_2$SMe | Me | O | O | Pr-i | H | OH |
| II-46 | CH$_2$CH$_2$SOMe | Me | O | O | Me | H | OH |
| II-47 | CH$_2$CH$_2$SO$_2$Me | Me | O | O | Me | Me | OH |
| II-48 | CH$_2$CH$_2$CH$_2$SMe | Me | O | O | Et | H | OH |
| II-49 | CH$_2$CH$_2$CH$_2$SO$_2$Me | Me | O | O | Me | H | OH |
| II-50 | Ph | Me | O | O | Me | H | OH |
| II-51 | Ph(2-Cl) | Me | O | O | Me | H | OH |
| II-52 | Ph(3-Cl) | Me | O | O | Me | H | OH |
| II-53 | Ph(4-Cl) | Me | O | O | Me | H | OSO$_2$Pr |
| II-54 | Ph(2-F) | Me | O | O | Pr-i | H | OH |
| II-55 | Ph(3-F) | Me | O | O | Me | H | OH |
| II-56 | Ph(4-F) | Me | O | O | Me | H | OH |
| II-57 | Ph(2-Me) | Me | O | O | Me | Me | OH |
| II-58 | Ph(3-Me) | Me | O | O | Me | H | OH |
| II-59 | Ph(4-Me) | Me | O | O | Et | H | OH |
| II-60 | Ph(2-OMe) | Me | O | O | Me | H | OH |
| II-61 | Ph(3-OMe) | Me | O | O | Me | H | OH |
| II-62 | Ph(4-OMe) | Me | O | O | Me | H | OH |
| II-63 | Ph(2-CF$_3$) | Me | O | O | Me | H | OH |
| II-64 | Ph(3-CF$_3$) | Me | O | O | Pr-i | H | OSO$_2$Ph |
| II-65 | Ph(4-CF$_3$) | Me | O | O | Me | H | OH |

TABLE 17-continued

| Compound No. | R¹ | R² | Y | Z | R²⁰ | R²¹ | R⁴ |
|---|---|---|---|---|---|---|---|
| II-66 | Ph(2-NO$_2$) | Me | O | O | Me | H | OH |
| II-67 | Ph(3-NO$_2$) | Me | O | O | Me | H | OH |
| II-68 | Ph(4-NO$_2$) | Me | O | O | Me | Me | OH |
| II-69 | Ph(2-OCF$_3$) | Me | O | O | Me | H | OH |
| II-70 | Ph(3-OCF$_3$) | Me | O | O | Et | H | OH |
| II-71 | Ph(4-OCF$_3$) | Me | O | O | Me | H | OH |
| II-72 | Ph(2-CN) | Me | O | O | Me | H | OH |
| II-73 | Ph(3-CN) | Me | O | O | Me | H | OH |
| II-74 | Ph(4-CN) | Me | O | O | Me | H | OH |
| II-75 | Ph(3,4-F$_2$) | Me | O | O | Pr-i | H | OH |
| II-76 | Ph(3,5-F$_2$) | Me | O | O | Me | H | OH |
| II-77 | Ph(2,3-F$_2$) | Me | O | O | Me | Me | OSO$_2$Pr |
| II-78 | Ph(2,4-F$_2$) | Me | O | O | Me | H | OH |
| II-79 | Ph(2,5-F$_2$) | Me | O | O | Me | H | OH |

TABLE 18

| Compound No. | R¹ | R² | Y | Z | R²⁰ | R²¹ | R⁴ |
|---|---|---|---|---|---|---|---|
| II-80 | Ph(2,6-F$_2$) | Me | O | O | Et | Me | OH |
| II-81 | Ph(3,4-Cl$_2$) | Me | O | O | Me | H | OH |
| II-82 | Ph(3,5-Cl$_2$) | Me | O | O | Me | H | OH |
| II-83 | Ph(2,3-Cl$_2$) | Me | O | O | Me | H | OH |
| II-84 | Ph(2,4-Cl$_2$) | Me | O | O | Me | H | OH |
| II-85 | Ph(2,5-Cl$_2$) | Me | O | O | Pr-i | H | OH |
| II-86 | Ph(2,6-Cl$_2$) | Me | O | O | Me | H | OH |
| II-87 | Ph(3,4-Me$_2$) | Me | O | O | Me | H | OH |
| II-88 | Ph(3,5-Me$_2$) | Me | O | O | Me | H | OH |
| II-89 | Ph(2,3-Me$_2$) | Me | O | O | Me | Me | OH |
| II-90 | Ph(2,4-Me$_2$) | Me | O | O | Me | H | OH |
| II-91 | Ph(2,5-Me$_2$) | Me | O | O | Me | H | OH |
| II-92 | Ph(2,6-Me$_2$) | Me | O | O | Me | H | OH |
| II-93 | Ph(3,4-(OMe)$_2$) | Me | O | O | Me | H | OH |
| II-94 | Ph(3,5-(OMe)$_2$) | Me | O | O | Me | H | OH |
| II-95 | Ph(2,3-(OMe)$_2$) | Me | O | O | Me | H | OH |
| II-96 | Ph(2,4-(OMe)$_2$) | Me | O | O | Pr-i | H | OH |
| II-97 | Ph(2,5-(OMe)$_2$) | Me | O | O | Me | H | OSO$_2$Ph |
| II-98 | Ph(2,6-(OMe)$_2$) | Me | O | O | Me | H | OH |
| II-99 | Ph(3-F-4-OMe) | Me | O | O | Me | Me | OH |
| II-100 | Ph(3-F-5-OMe) | Me | O | O | Me | H | OH |
| II-101 | Ph(2-F-3-OMe) | Me | O | O | Me | H | OH |
| II-102 | Ph(2-F-4-OMe) | Me | O | O | Me | H | OH |
| II-103 | Ph(2-F-5-OMe) | Me | O | O | Me | H | OH |
| II-104 | Ph(2-F-6-OMe) | Me | O | O | Me | H | OH |
| II-105 | Ph(3-F-4-Me) | Me | O | O | Me | H | OSO$_2$Pr |
| II-106 | Ph(3-F-5-Me) | Me | O | O | Me | H | OH |
| II-107 | Ph(2-F-3-Me) | Me | O | O | Me | H | OH |
| II-108 | Ph(2-F-4-Me) | Me | O | O | Me | H | OH |
| II-109 | Ph(2-F-5-Me) | Me | O | O | Me | Me | OH |
| II-110 | Ph(2-F-6-Me) | Me | O | O | Me | H | OH |
| II-111 | Ph(3-OMe-4-F) | Me | O | O | Me | H | OH |
| II-112 | Ph(2-OMe-3-F) | Me | O | O | Pr-i | H | OSO$_2$Ph(4-Me) |
| II-113 | Ph(2-OMe-4-F) | Me | O | O | Me | H | OH |
| II-114 | Ph(2-OMe-5-F) | Me | O | O | Me | H | OH |
| II-115 | Ph(3-Me-4-F) | Me | O | O | Me | H | OH |
| II-116 | Ph(2-Me-3-F) | Me | O | O | Me | H | OH |
| II-117 | Ph(2-Me-4-F) | Me | O | O | Me | H | OH |
| II-118 | Ph(2-Me-5-F) | Me | O | O | Me | H | OH |
| II-119 | Ph(3-Cl-4-OMe) | Me | O | O | Me | Me | OH |
| II-120 | Ph(3-Cl-5-OMe) | Me | O | O | Me | H | OH |

TABLE 19

| Compound No. | R¹ | R² | Y | Z | R²⁰ | R²¹ | R⁴ |
|---|---|---|---|---|---|---|---|
| II-121 | Ph(2-Cl-3-OMe) | Me | O | O | Me | H | OH |
| II-122 | Ph(2-Cl-4-OMe) | Me | O | O | Me | H | OSO$_2$Ph(4-Me) |

TABLE 19-continued

| Compound No. | R¹ | R² | Y | Z | R²⁰ | R²¹ | R⁴ |
|---|---|---|---|---|---|---|---|
| II-123 | Ph(2-Cl-5-OMe) | Me | O | O | Pr-i | H | OH |
| II-124 | Ph(2-Cl-6-OMe) | Me | O | O | Me | H | OH |
| II-125 | Ph(3-Cl-4-Me) | Me | O | O | Me | H | OH |
| II-126 | Ph(3-Cl-5-Me) | Me | O | O | Me | Me | OH |
| II-127 | Ph(2-Cl-3-Me) | Me | O | O | Me | H | OH |
| II-128 | Ph(2-Cl-4-Me) | Me | O | O | Me | H | OH |
| II-129 | Ph(2-Cl-5-Me) | Me | O | O | Me | H | OH |
| II-130 | Ph(2-Cl-6-Me) | Me | O | O | Me | H | OH |
| II-131 | Ph(3-OMe-4-Cl) | Me | O | O | Me | H | OH |
| II-132 | Ph(2-OMe-3-Cl) | Me | O | O | Me | H | OSO₂Ph |
| II-133 | Ph(2-OMe-4-Cl) | Me | O | O | Pr-i | H | OH |
| II-134 | Ph(2-OMe-5-Cl) | Me | O | O | Me | H | OH |
| II-135 | Ph(3-Me-4-Cl) | Me | O | O | Me | Me | OH |
| II-136 | Ph(2-Me-3-Cl) | Me | O | O | Me | H | OH |
| II-137 | Ph(2-Me-4-Cl) | Me | O | O | Me | H | OH |
| II-138 | Ph(2-Me-5-Cl) | Me | O | O | Me | H | OH |
| II-139 | Ph(3-F-4-Cl) | Me | O | O | Me | H | OSO₂Ph(4-Me) |
| II-140 | Ph(3-F-5-Cl) | Me | O | O | Me | H | OH |
| II-141 | Ph(2-F-3-Cl) | Me | O | O | Me | H | OH |
| II-142 | Ph(2-F-4-Cl) | Me | O | O | Me | H | OH |
| II-143 | Ph(2-F-5-Cl) | Me | O | O | Me | H | OH |
| II-144 | Ph(2-F-6-Cl) | Me | O | O | Me | H | OH |
| II-145 | Ph(3-Cl-4-F) | Me | O | O | Me | H | OH |
| II-146 | Ph(2-Cl-3-F) | Me | O | O | Me | Me | OH |
| II-147 | Ph(2-Cl-4-F) | Me | O | O | Me | H | OH |
| II-148 | Ph(2-Cl-5-F) | Me | O | O | Pr-i | H | OH |
| II-149 | Ph(3-Me-4-OMe) | Me | O | O | Me | H | OH |
| II-150 | Ph(3-Me-5-OMe) | Me | O | O | Me | H | OH |
| II-151 | Ph(2-Me-3-OMe) | Me | O | O | Me | H | OSO₂Ph(4-Me) |
| II-152 | Ph(2-Me-4-OMe) | Me | O | O | Me | H | OH |
| II-153 | Ph(2-Me-5-OMe) | Me | O | O | Me | H | OH |
| II-154 | Ph(2-Me-6-OMe) | Me | O | O | Me | H | OH |
| II-155 | Ph(3-OMe-4-Me) | Me | O | O | Me | Me | OH |
| II-156 | Ph(2-OMe-3-Me) | Me | O | O | Me | H | OH |
| II-157 | Ph(2-OMe-4-Me) | Me | O | O | Me | H | OH |
| II-158 | Ph(2-OMe-5-Me) | Me | O | O | Me | Me | OH |
| II-159 | Ph(3-CN-4-OMe) | Me | O | O | Me | H | OH |
| II-160 | Ph(3-OMe-4-CN) | Me | O | O | Me | H | OH |
| II-161 | Ph(3-Me-4-CN) | Me | O | O | Pr-i | H | OSO₂Ph(4-Me) |

TABLE 20

| Compound No. | R¹ | R² | Y | Z | R²⁰ | R²¹ | R⁴ |
|---|---|---|---|---|---|---|---|
| II-162 | Ph(3-CN-4-Me) | Me | O | O | Me | H | OH |
| II-163 | Ph(3-NO₂-4-OMe) | Me | O | O | Me | H | OH |
| II-164 | Ph(3-OMe-4-NO₂) | Me | O | O | Me | H | OH |
| II-165 | Ph(3-Me-4-NO₂) | Me | O | O | Me | H | OH |
| II-166 | Ph(3-NO₂-4-Me) | Me | O | O | Me | H | OH |
| II-167 | Ph(3,5-F₂-5-OMe) | Me | O | O | Me | H | OH |
| II-168 | Ph(3,5-F₂-5-Me) | Me | O | O | Me | Me | OH |
| II-169 | Ph(3,4,5-(OMe)₃) | Me | O | O | Me | H | OH |
| II-170 | 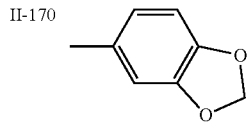 | Me | O | O | Me | H | OH |
| II-171 | 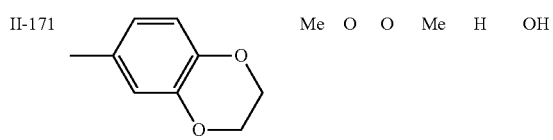 | Me | O | O | Me | H | OH |

TABLE 20-continued

| Compound No. | R¹ | R² | Y | Z | R²⁰ | R²¹ | R⁴ |
|---|---|---|---|---|---|---|---|
| II-172 | | Me | O | O | Pr-i | H | OSO₂Ph(4-Me) |
| II-173 | | Me | O | O | Me | H | OH |
| II-174 | | Me | O | O | Me | H | OH |
| II-175 | | Me | O | O | Me | H | OH |
| II-176 | | Me | O | O | Me | H | OH |
| II-177 | | Me | O | O | Me | H | OH |
| II-178 | | Me | O | O | Me | H | OH |
| II-179 | | Me | O | O | Me | H | OH |
| II-180 | | Me | O | O | Me | H | OH |

TABLE 21

| Compound No. | R¹ | R² | Y | Z | R²⁰ | R²¹ | R⁴ |
|---|---|---|---|---|---|---|---|
| II-181 | | Me | O | O | Me | H | OH |

TABLE 21-continued

| Compound No. | R¹ | R² | Y | Z | R²⁰ | R²¹ | R⁴ |
|---|---|---|---|---|---|---|---|
| II-182 | 2-methyl-5-methylpyridin-yl | Me | O | O | Me | H | OH |
| II-183 | 2-methyl-5-methoxypyridin-yl | Me | O | O | Me | H | OH |
| II-184 | 2-methyl-5-fluoropyridin-yl | Me | O | O | Pr-i | H | OH |
| II-185 | 2-methyl-5-chloropyridin-yl | Me | O | O | Me | Me | OH |
| II-186 | 2-methyl-5-bromopyridin-yl | Me | O | O | Me | H | OH |
| II-187 | 2-methyl-5-trifluoromethylpyridin-yl | Me | O | O | Me | H | OH |
| II-188 | 3-methylisoxazol-5-yl | Me | O | O | Me | H | OH |
| II-189 | 3-methylisoxazol-5-yl | Me | O | O | Me | H | OSO₂Ph (4-Me) |
| II-190 | 4,5-dihydroisoxazol-5-yl | Me | O | O | Me | H | OH |
| II-191 | 3-methyl-4,5-dihydroisoxazol-5-yl | Me | O | O | Me | H | OH |
| II-192 | 3-methyl-4,5-dihydroisoxazol-yl | Me | O | O | Me | H | OH |
| II-193 | 3,5-dimethyl-4,5-dihydroisoxazol-yl | Me | O | O | Me | H | OH |
| II-194 | thiazol-2-yl | Me | O | O | Me | H | OH |

TABLE 22

| Compound No. | R¹ | R² | Y | Z | R²⁰ | R²¹ | R⁴ |
|---|---|---|---|---|---|---|---|
| II-195 | 2-methyl-4-methylthiazol-yl | Me | O | O | Me | H | OH |
| II-196 | 2-methyl-5-methylthiazol-yl | Me | O | O | Me | H | OH |
| II-197 | 2-methyl-4,5-dimethylthiazol-yl | Me | O | O | Me | H | OH |
| II-198 | 2-methylthien-yl | Me | O | O | Me | H | OH |
| II-199 | 3-methylthien-yl | Me | O | O | Pr-i | Me | OH |
| II-200 | 2,5-dimethylthien-yl | Me | O | O | Me | H | OH |
| II-201 | 2,4-dimethylthien-yl | Me | O | O | Me | H | OH |
| II-202 | morpholin-4-yl | Me | O | O | Me | H | OH |
| II-203 | thiomorpholin-4-yl | Me | O | O | Me | H | OH |
| II-204 | thiomorpholin-4-yl-1,1-dioxide | Me | O | O | Me | Me | OH |
| II-205 | CH₂Ph | Me | O | O | Me | H | OH |
| II-206 | CH₂CH₂Ph | Me | O | O | Me | H | OH |
| II-207 | CH₂CH₂CH₂Ph | Me | O | O | Me | H | OH |
| II-208 | CH₂CH=CHPh | Me | O | O | Me | H | OH |
| II-209 | CH₂C≡CPh | Me | O | O | Me | H | OH |
| II-210 | CH₂CH=NOMe | Me | O | O | Me | H | OH |
| II-211 | CH₂CH=NOEt | Me | O | O | Me | H | OH |
| II-212 | CH₂CH=NOPr-n | Me | O | O | Me | H | OH |
| II-213 | CH₂CH=NOPh | Me | O | O | Me | Me | OH |
| II-214 | CH₂CH(OMe)₂ | Me | O | O | Me | H | OH |
| II-215 | CH₂CHO | Me | O | O | Et | H | OH |
| II-216 | NH₂ | Me | O | O | Me | H | OH |
| II-217 | NHMe | Me | O | O | Me | H | OH |
| II-218 | NHEt | Me | O | O | Me | H | OH |

TABLE 23

| Compound No. | R¹ | R² | Y | Z | R²⁰ | R²¹ | R⁴ |
|---|---|---|---|---|---|---|---|
| II-219 | NHPr-n | Me | O | O | Me | H | OSO₂Ph(4-Me) |
| II-220 | NHPr-i | Me | O | O | Me | H | OH |
| II-221 | NHBu-n | Me | O | O | Pr-i | H | OH |
| II-222 | NHBu-i | Me | O | O | Me | H | OH |
| II-223 | NHBu-s | Me | O | O | Me | Me | OH |
| II-224 | NHCH₂Pr-c | Me | O | O | Me | H | OH |
| II-225 | NHPen-n | Me | O | O | Me | H | OH |
| II-226 | NHHex-n | Me | O | O | Me | H | OH |
| II-227 | NHCH₂CH₂CH₂Cl | Me | O | O | Me | H | OH |
| II-228 | NHCH₂CH₂CH₂F | Me | O | O | Me | H | OH |
| II-229 | NHCH₂CH₂OMe | Me | O | O | Me | H | OH |
| II-230 | NMe₂ | Me | O | O | Me | H | OH |
| II-231 | NEt₂ | Me | O | O | Me | H | OH |
| II-232 | N(Pr-n)₂ | Me | O | O | Me | H | OH |
| II-233 | N(Bu-n)₂ | Me | O | O | Me | H | OH |
| II-234 | N(Me)Et | Me | O | O | Me | Me | OH |
| II-235 | N(Me)CH₂CH₂OMe | Me | O | O | Et | H | OH |
| II-236 | NHPh | Me | O | O | Me | H | OH |
| II-237 | NHCH₂Ph | Me | O | O | Me | H | OH |
| II-238 | N=CMe₂ | Me | O | O | Me | H | OH |
| II-239 | N=CEt₂ | Me | O | O | Me | H | OSO₂Ph(4-Me) |
| II-240 | N=CHNMe₂ | Me | O | O | Me | H | OH |
| II-241 | NHC(=O)Me | Me | O | O | Me | H | OH |
| II-242 | N[C(=O)Me]₂ | Me | O | O | Me | H | OH |
| II-243 | NHC(=O)OMe | Me | O | O | Pr-i | H | OH |
| II-244 | N[C(=O)OMe]₂ | Me | O | O | Me | H | OH |
| II-245 | NHSO₂Me | Me | O | O | Me | H | OH |
| II-246 | NHSO₂Ph | Me | O | O | Me | Me | OH |
| II-247 | NHSO₂CH₂Ph | Me | O | O | Me | H | OH |
| II-248 | OMe | Me | O | O | Et | H | OH |
| II-249 | OEt | Me | O | O | Me | H | OH |
| II-250 | OPr-n | Me | O | O | Me | H | OH |
| II-251 | OPr-i | Me | O | O | Me | H | OH |
| II-252 | OCH₂Pr-c | Me | O | O | Me | H | OH |
| II-253 | OCH₂Cl | Me | O | O | Me | H | OH |
| II-254 | OCHCl₂ | Me | O | O | Me | H | OH |
| II-255 | OCCl₃ | Me | O | O | Me | Me | OH |
| II-256 | OCH₂F | Me | O | O | Me | H | OH |
| II-257 | OCHF₂ | Me | O | O | Me | H | OH |
| II-258 | OCF₃ | Me | O | O | Me | H | OSO₂Ph(4-Me) |
| II-259 | Ph | Et | O | O | Et | H | OH |
| II-260 | Ph | Pr-i | O | O | Me | H | OH |
| II-261 | Ph | CHF₂ | O | O | Me | H | OH |

TABLE 24

| Compound No. | R¹ | R² | Y | Z | R²⁰ | R²¹ | R⁴ |
|---|---|---|---|---|---|---|---|
| II-262 | Ph | Ph | O | O | Me | H | OH |
| II-263 | Ph | Me | O | S | Me | Me | OH |
| II-264 | Ph | Me | S | S | Me | H | OH |
| II-265 | Me | Me | O | S | Me | H | OH |
| II-266 | Me | Me | S | S | Me | H | OH |
| II-267 | Ph | Me | O | O | Pr-i | H | OSO₂Pr |
| II-268 | Ph(4-OEt) | Me | O | O | Me | H | OH |
| II-269 | Ph(2-Ph) | Me | O | O | Me | H | OH |
| II-270 | Ph(3-Ph) | Me | O | O | Me | H | OH |
| II-271 | Ph(4-Ph) | Me | O | O | Me | H | OH |
| II-272 | 1,5-dimethyl-3-(trifluoromethyl)pyrazol-4-yl | Me | O | O | Me | Me | OH |

TABLE 24-continued

| Compound No. | R¹ | R² | Y | Z | R²⁰ | R²¹ | R⁴ |
|---|---|---|---|---|---|---|---|
| II-273 | 2-methyl-4,6-dimethoxypyrimidinyl | Me | O | O | Et | H | OSO$_2$Ph(4-Me) |
| II-274 | Me | 2-methylpyridinyl | O | O | Me | H | OH |
| II-275 | Et | 2-methylpyridinyl | O | O | Me | H | OH |
| II-276 | H | Me | O | O | Me | H | OH |
| II-277 | CH$_2$C≡CF | Me | O | O | Me | H | OH |
| II-278 | 2,2-dichlorocyclopropyl | Me | O | O | Me | H | OH |
| II-279 | (2,2-dichlorocyclopropyl)methyl | Me | O | O | Me | H | OH |
| II-280 | CH$_2$NH$_2$ | Me | O | O | Me | H | OH |
| II-281 | CH$_2$NO$_2$ | Me | O | O | Me | H | OH |
| II-282 | CH$_2$NHCH$_3$ | Me | O | O | Me | H | OH |
| II-283 | CH$_2$N(CH$_3$)$_2$ | Me | O | O | Me | H | OH |
| II-284 | CH$_2$SCH$_2$CF$_3$ | Me | O | O | Me | H | OH |
| II-285 | CH$_2$SOCH$_2$CF$_3$ | Me | O | O | Me | H | OH |
| II-286 | CH$_2$SO$_2$CH$_2$CF$_3$ | Me | O | O | Me | H | OH |
| II-287 | CH$_2$OH | Me | O | O | Me | H | OH |
| II-288 | CH$_2$OBn | Me | O | O | Me | H | OH |
| II-289 | CH$_2$OCH$_2$Pr-c | Me | O | O | Me | H | OH |

TABLE 25

| Compound No. | R¹ | R² | Y | Z | R²⁰ | R²¹ | R⁴ |
|---|---|---|---|---|---|---|---|
| II-290 | CH$_2$OPh | Me | O | O | Me | H | OH |
| II-291 | CH$_2$SPh | Me | O | O | Me | H | OH |
| II-292 | CH$_2$SOPh | Me | O | O | Me | H | OH |
| II-293 | CH$_2$SO$_2$Ph | Me | O | O | Me | H | OH |
| II-294 | CH$_2$CON(CH$_3$)$_2$ | Me | O | O | Me | H | OH |
| II-295 | CH$_2$COCH$_3$ | Me | O | O | Me | H | OH |
| II-296 | CH$_2$OCOCH$_3$ | Me | O | O | Me | H | OH |
| II-297 | CH$_2$ON=CHCH$_3$ | Me | O | O | Me | H | OH |
| II-298 | C$_2$H$_4$OC$_2$H$_4$SCH$_3$ | Me | O | O | Me | H | OH |
| II-299 | C$_2$H$_4$OC$_2$H$_4$SOCH$_3$ | Me | O | O | Me | H | OH |
| II-300 | C$_2$H$_4$OC$_2$H$_4$SO$_2$CH$_3$ | Me | O | O | Me | H | OH |
| II-301 | CH$_2$OCH$_2$CN | Me | O | O | Me | H | OH |
| II-302 | CH$_2$CN | Me | O | O | Me | H | OH |
| II-303 | OCH$_2$CH=CH$_2$ | Me | O | O | Me | H | OH |
| II-304 | OCH$_2$C≡CH | Me | O | O | Me | H | OH |
| II-305 | OPr-c | Me | O | O | Me | H | OH |
| II-306 | CH$_2$-(tetrahydrofuran-2-yl) | Me | O | O | Me | H | OH |
| II-307 | CH$_2$-(3-methyl-4,5-dihydroisoxazol-5-yl) | Me | O | O | Me | H | OH |

TABLE 25-continued

| Compound No. | R¹ | R² | Y | Z | R²⁰ | R²¹ | R⁴ |
|---|---|---|---|---|---|---|---|
| II-308 | 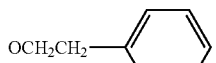 | Me | O | O | Me | H | OH |
| II-309 | CH₂OCH₂-(tetrahydrofuran) | Me | O | O | Me | H | OH |
| II-310 | CH₂CH₂OCH₂O-(pyridine) | Me | O | O | Me | H | OH |
| II-311 | Ph | H | O | O | Me | H | OH |
| II-312 | Ph | CH₂CH=CH₂ | O | O | Me | H | OH |
| II-313 | Ph | CH₂C≡CH | O | O | Me | H | OH |
| II-314 | Ph | Pr-c | O | O | Me | H | OH |
| II-315 | Ph | CH₂CH=CF₂ | O | O | Me | H | OH |
| II-316 | Ph | CH₂C≡CF | O | O | Me | H | OH |
| II-317 | Ph | C₂H₄OCH₃ | O | O | Me | H | OH |
| II-318 | Ph | C₂H₄OC₂H₅ | O | O | Me | H | OH |
| II-319 | Ph | CH(Me)OEt | O | O | Me | H | OH |
| II-320 | Ph | CH₂OPr-c | O | O | Me | H | OH |
| II-321 | Ph | CH(OCH₃)₂ | O | O | Me | H | OH |
| II-322 | Ph | CH₂Ph | O | O | Me | H | OH |

TABLE 26

| Compound No. | R¹ | R² | Y | Z | R²⁰ | R²¹ | R⁴ |
|---|---|---|---|---|---|---|---|
| II-323 | Ph | (E)-CH=CH-Ph | O | O | Me | H | OH |
| II-324 | Ph | C≡C-Ph | O | O | Me | H | OH |
| II-325 | Ph | Me | O | O | Me | H | NH₂ |
| II-326 | Ph | Me | O | O | Me | H | Cl |
| II-327 | Ph | Me | O | O | Me | H | CN |
| II-328 | Ph | Me | O | O | Me | H | NCS |
| II-329 | Ph | Me | O | O | Me | H | NCO |
| II-330 | Ph | Me | O | O | Me | H | OCO₂H |
| II-331 | Ph | Me | O | O | Me | H | OCO₂CH₃ |
| II-332 | Ph | Me | O | O | Me | H | OCO₂CH₂Ph |
| II-333 | Ph | Me | O | O | Me | H | OMe |
| II-334 | Ph | Me | O | O | Me | H | OEt |
| II-335 | Ph | Me | O | O | Me | H | OPr |
| II-336 | Ph | Me | O | O | Me | H | OCH₂CH=CH₂ |
| II-337 | Ph | Me | O | O | Me | H | OCH₂C≡CH |
| II-338 | Ph | Me | O | O | Me | H | OPr-c |
| II-339 | Ph | Me | O | O | Me | H | OBu-c |
| II-340 | Ph | Me | O | O | Me | H | OPen-c |
| II-341 | Ph | Me | O | O | Me | H | OHex-c |
| II-342 | Ph | Me | O | O | Me | H | OCH₂CN |
| II-343 | Ph | Me | O | O | Me | H | OCH₂Pr-c |
| II-344 | Ph | Me | O | O | Me | H | OCOCH₃ |
| II-345 | Ph | Me | O | O | Me | H | OCOCCl₃ |
| II-346 | Ph | Me | O | O | Me | H | OCOCH=CH₂ |
| II-347 | Ph | Me | O | O | Me | H | OCOCH=CF₂ |
| II-348 | Ph | Me | O | O | Me | H | OCOCH₂C≡CH |
| II-349 | Ph | Me | O | O | Me | H | OCOCH₂C≡CF |
| II-350 | Ph | Me | O | O | Me | H | OCH₂CO₂CH₃ |
| II-351 | Ph | Me | O | O | Me | H | OPh |
| II-352 | Ph | Me | O | O | Me | H | OCH₂Ph |
| II-353 | Ph | Me | O | O | Me | H | OCOPh |
| II-354 | Ph | Me | O | O | Me | H | OCOCH₂Ph |
| II-355 | Ph | Me | O | O | Me | H | OCH₂COPh |
| II-356 | Ph | Me | O | O | Me | H | OSO₂CH₂CF₃ |
| II-357 | Ph | Me | O | O | Me | H | OSO₂CH₂Ph |
| II-358 | Ph | Me | O | O | Me | H | SCH₃ |
| II-359 | Ph | Me | O | O | Me | H | SOCH₃ |
| II-360 | Ph | Me | O | O | Me | H | SO₂CH₃ |
| II-361 | Ph | Me | O | O | Me | H | SCH₂CF₃ |
| II-362 | Ph | Me | O | O | Me | H | SOCH₂CF₃ |
| II-363 | Ph | Me | O | O | Me | H | SO₂CH₂CF₃ |

TABLE 27

| Compound No. | R¹ | R² | Y | Z | R²⁰ | R²¹ | R⁴ |
|---|---|---|---|---|---|---|---|
| II-364 | Ph | Me | O | O | Me | H | SCH₂CH=CH₂ |
| II-365 | Ph | Me | O | O | Me | H | SOCH₂CH=CH₂ |
| II-366 | Ph | Me | O | O | Me | H | SO₂CH₂CH=CH₂ |
| II-367 | Ph | Me | O | O | Me | H | SCH₂CH=CH |
| II-368 | Ph | Me | O | O | Me | H | SOCH₂CH=CH |
| II-369 | Ph | Me | O | O | Me | H | SO₂CH₂CH=CH |
| II-370 | Ph | Me | O | O | Me | H | SCH₂Ph |
| II-371 | Ph | Me | O | O | Me | H | SOPh |
| II-372 | Ph | Me | O | O | Me | H | SOCH₂Ph |
| II-373 | Ph | Me | O | O | Me | H | SO₂Ph |
| II-374 | Ph | Me | O | O | Me | H | SO₂CH₂Ph |
| II-375 | Ph | Me | O | O | Me | H | NHCH₃ |
| II-376 | Ph | Me | O | O | Me | H | N(CH₃)₂ |
| II-377 | Ph | Me | O | O | Me | H | NHCOCH₃ |
| II-378 | Ph | Me | O | O | Me | H | OCH₂CH₂-(2-pyridyl) |
| II-379 | Ph | Me | O | O | Me | H | 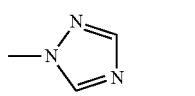 (1,2,4-triazol-1-yl) |

TABLE 27-continued

| Compound No. | R¹ | R² | Y | Z | R²⁰ | R²¹ | R⁴ |
|---|---|---|---|---|---|---|---|
| II-380 | Ph | Me | O | O | Me | H | (1-imidazolyl) |
| II-381 | Ph | Me | O | O | Me | H | (1-tetrazolyl) |
| II-382 | Ph | Me | O | O | Me | H | (1-pyrazolyl) |
| II-383 | Ph | Me | O | O | Me | H | (2-pyridyloxy) |

TABLE 28

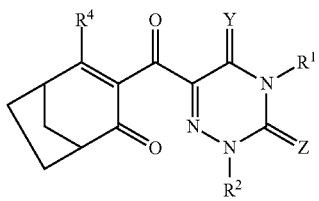

| Compound No. | R¹ | R² | Y | Z | R⁴ |
|---|---|---|---|---|---|
| III-1 | Me | Me | O | O | OH |
| III-2 | Et | Me | O | O | OH |
| III-3 | Pr-n | Me | O | O | OH |
| III-4 | Pr-i | Me | O | O | OH |
| III-5 | Bu-n | Me | O | O | OH |
| III-6 | Bu-i | Me | O | O | OH |
| III-7 | Bu-s | Me | O | O | OH |
| III-8 | Bu-t | Me | O | O | OH |
| III-9 | Hex-n | Me | O | O | OH |
| III-10 | $CH_2CF_3$ | Me | O | O | OH |
| III-11 | $CH_2CH=CH_2$ | Me | O | O | OH |
| III-12 | $CH_2C(Me)=CH_2$ | Me | O | O | OH |
| III-13 | $CH_2CH_2CH=CMe_2$ | Me | O | O | OH |
| III-14 | $CH_2C\equiv CH$ | Me | O | O | OH |
| III-15 | $CH_2C\equiv CCH_3$ | Me | O | O | OH |
| III-16 | Pr-c | Me | O | O | OH |
| III-17 | Bu-c | Me | O | O | OH |
| III-18 | Pen-c | Me | O | O | OH |
| III-19 | Hex-c | Me | O | O | OH |
| III-20 | $CH_2Pr\text{-}c$ | Me | O | O | OH |
| III-21 | $CH_2Bu\text{-}c$ | Me | O | O | OH |
| III-22 | $CH_2Pen\text{-}c$ | Me | O | O | OH |
| III-23 | $CH_2Hex\text{-}c$ | Me | O | O | OH |
| III-24 | $CH_2CH=CCl_2$ | Me | O | O | OH |
| III-25 | $CH_2CCl=CHCl$ | Me | O | O | OH |
| III-26 | $CH_2CH_2CH=CCl_2$ | Me | O | O | OH |
| III-27 | $CH_2CH_2C(Me)=CF_2$ | Me | O | O | OH |
| III-28 | $CH_2CH_2CH_2CH_2C(Me)=CF_2$ | Me | O | O | OH |
| III-29 | $CH_2CH=CF_2$ | Me | O | O | OH |
| III-30 | $CH_2CH_2OMe$ | Me | O | O | OH |
| III-31 | $CH_2CH_2OEt$ | Me | O | O | OH |
| III-32 | $CH(Me)CH_2OMe$ | Me | O | O | OH |
| III-33 | $CH_2CH_2OCH_2CH_2OMe$ | Me | O | O | OH |
| III-34 | $CH_2CH_2OPr\text{-}n$ | Me | O | O | OH |
| III-35 | $CH_2CH_2OPr\text{-}i$ | Me | O | O | OH |
| III-36 | $CH_2CH_2OPr\text{-}c$ | Me | O | O | OH |
| III-37 | $CH_2CH_2OBu\text{-}c$ | Me | O | O | OH |
| III-38 | $CH_2CH_2OPen\text{-}c$ | Me | O | O | OH |

TABLE 29

| Compound No. | R¹ | R² | Y | Z | R⁴ |
|---|---|---|---|---|---|
| III-39 | $CH_2CH_2OHex\text{-}c$ | Me | O | O | OH |
| III-40 | $CH_2CH_2OCH_2CF_3$ | Me | O | O | OH |
| III-41 | $CH_2CH_2CH_2OMe$ | Me | O | O | OH |
| III-42 | $CH=CHMe$ | Me | O | O | OH |
| III-43 | $CH_2SMe$ | Me | O | O | OH |
| III-44 | $CH_2SPr\text{-}n$ | Me | O | O | OH |
| III-45 | $CH_2CH_2SMe$ | Me | O | O | OH |
| III-46 | $CH_2CH_2SOMe$ | Me | O | O | OH |
| III-47 | $CH_2CH_2SO_2Me$ | Me | O | O | OH |
| III-48 | $CH_2CH_2CH_2SMe$ | Me | O | O | OH |
| III-49 | $CH_2CH_2CH_2SO_2Me$ | Me | O | O | OH |
| III-50 | Ph | Me | O | O | OH |
| III-51 | Ph(2-Cl) | Me | O | O | OH |
| III-52 | Ph(3-Cl) | Me | O | O | OH |
| III-53 | Ph(4-Cl) | Me | O | O | OH |
| III-54 | Ph(2-F) | Me | O | O | OH |
| III-55 | Ph(3-F) | Me | O | O | OH |
| III-56 | Ph(4-F) | Me | O | O | OH |
| III-57 | Ph(2-Me) | Me | O | O | OH |
| III-58 | Ph(3-Me) | Me | O | O | OH |
| III-59 | Ph(4-Me) | Me | O | O | OH |
| III-60 | Ph(2-OMe) | Me | O | O | OH |
| III-61 | Ph(3-OMe) | Me | O | O | OH |
| III-62 | Ph(4-OMe) | Me | O | O | OH |
| III-63 | Ph(2-$CF_3$) | Me | O | O | OH |
| III-64 | Ph(3-$CF_3$) | Me | O | O | OH |
| III-65 | Ph(4-$CF_3$) | Me | O | O | OH |
| III-66 | Ph(2-$NO_2$) | Me | O | O | OH |
| III-67 | Ph(3-$NO_2$) | Me | O | O | OH |
| III-68 | Ph(4-$NO_2$) | Me | O | O | OH |
| III-69 | Ph(2-$OCF_3$) | Me | O | O | OH |
| III-70 | Ph(3-$OCF_3$) | Me | O | O | OH |
| III-71 | Ph(4-$OCF_3$) | Me | O | O | OH |
| III-72 | Ph(2-CN) | Me | O | O | OH |
| III-73 | Ph(3-CN) | Me | O | O | OH |
| III-74 | Ph(4-CN) | Me | O | O | OH |
| III-75 | Ph(3,4-$F_2$) | Me | O | O | OH |
| III-76 | Ph(3,5-$F_2$) | Me | O | O | OH |
| III-77 | Ph(2,3-$F_2$) | Me | O | O | OH |
| III-78 | Ph(2,4-$F_2$) | Me | O | O | OH |

TABLE 30

| Compound No. | R¹ | R² | Y | Z | R⁴ |
|---|---|---|---|---|---|
| III-79 | Ph(2,5-$F_2$) | Me | O | O | OH |
| III-80 | Ph(2,6-$F_2$) | Me | O | O | OH |
| III-81 | Ph(3,4-$Cl_2$) | Me | O | O | OH |
| III-82 | Ph(3,5-$Cl_2$) | Me | O | O | OH |
| III-83 | Ph(2,3-$Cl_2$) | Me | O | O | OH |
| III-84 | Ph(2,4-$Cl_2$) | Me | O | O | OH |
| III-85 | Ph(2,5-$Cl_2$) | Me | O | O | OH |
| III-86 | Ph(2,6-$Cl_2$) | Me | O | O | OH |
| III-87 | Ph(3,4-$Me_2$) | Me | O | O | OH |
| III-88 | Ph(3,5-$Me_2$) | Me | O | O | OH |
| III-89 | Ph(2,3-$Me_2$) | Me | O | O | OH |
| III-90 | Ph(2,4-$Me_2$) | Me | O | O | OH |
| III-91 | Ph(2,5-$Me_2$) | Me | O | O | OH |
| III-92 | Ph(2,6-$Me_2$) | Me | O | O | OH |
| III-93 | Ph(3,4-$(OMe)_2$) | Me | O | O | OH |
| III-94 | Ph(3,5-$(OMe)_2$) | Me | O | O | OH |
| III-95 | Ph(2,3-$(OMe)_2$) | Me | O | O | OH |
| III-96 | Ph(2,4-$(OMe)_2$) | Me | O | O | OH |
| III-97 | Ph(2,5-$(OMe)_2$) | Me | O | O | OH |
| III-98 | Ph(2,6-$(OMe)_2$) | Me | O | O | OH |
| III-99 | Ph(3-F-4-Me) | Me | O | O | OH |
| III-100 | Ph(3-F-5-OMe) | Me | O | O | OH |
| III-101 | Ph(2-F-3-OMe) | Me | O | O | OH |
| III-102 | Ph(2-F-4-OMe) | Me | O | O | OH |
| III-103 | Ph(2-F-5-OMe) | Me | O | O | OH |
| III-104 | Ph(2-F-6-OMe) | Me | O | O | OH |
| III-105 | Ph(3-F-4-Me) | Me | O | O | OH |
| III-106 | Ph(3-F-5-Me) | Me | O | O | OH |
| III-107 | Ph(2-F-3-Me) | Me | O | O | OH |

TABLE 30-continued

| Compound No. | R¹ | R² | Y | Z | R⁴ |
|---|---|---|---|---|---|
| III-108 | Ph(2-F-4-Me) | Me | O | O | OH |
| III-109 | Ph(2-F-5-Me) | Me | O | O | OH |
| III-110 | Ph(2-F-6-Me) | Me | O | O | OH |
| III-111 | Ph(3-OMe-4-F) | Me | O | O | OH |
| III-112 | Ph(2-OMe-3-F) | Me | O | O | OH |
| III-113 | Ph(2-OMe-4-F) | Me | O | O | OH |
| III-114 | Ph(2-OMe-5-F) | Me | O | O | OH |
| III-115 | Ph(3-Me-4-F) | Me | O | O | OH |
| III-116 | Ph(2-Me-3-F) | Me | O | O | OH |
| III-117 | Ph(2-Me-4-F) | Me | O | O | OH |

TABLE 31

| Compound No. | R¹ | R² | Y | Z | R⁴ |
|---|---|---|---|---|---|
| III-118 | Ph(2-Me-5-F) | Me | O | O | OH |
| III-119 | Ph(3-Cl-4-OMe) | Me | O | O | OH |
| III-120 | Ph(3-Cl-5-OMe) | Me | O | O | OH |
| III-121 | Ph(2-Cl-3-OMe) | Me | O | O | OH |
| III-122 | Ph(2-Cl-4-OMe) | Me | O | O | OH |
| III-123 | Ph(2-Cl-5-OMe) | Me | O | O | OH |
| III-124 | Ph(2-Cl-6-OMe) | Me | O | O | OH |
| III-125 | Ph(3-Cl-4-Me) | Me | O | O | OH |
| III-126 | Ph(3-Cl-5-Me) | Me | O | O | OH |
| III-127 | Ph(2-Cl-3-Me) | Me | O | O | OH |
| III-128 | Ph(2-Cl-4-Me) | Me | O | O | OH |
| III-129 | Ph(2-Cl-5-Me) | Me | O | O | OH |
| III-130 | Ph(2-Cl-6-Me) | Me | O | O | OH |
| III-131 | Ph(3-OMe-4-Cl) | Me | O | O | OH |
| III-132 | Ph(2-OMe-3-Cl) | Me | O | O | OH |
| III-133 | Ph(2-OMe-4-Cl) | Me | O | O | OH |
| III-134 | Ph(2-OMe-5-Cl) | Me | O | O | OH |
| III-135 | Ph(3-Me-4-Cl) | Me | O | O | OH |
| III-136 | Ph(2-Me-3-Cl) | Me | O | O | OH |
| III-137 | Ph(2-Me-4-Cl) | Me | O | O | OH |
| III-138 | Ph(2-Me-5-Cl) | Me | O | O | OH |
| III-139 | Ph(3-F-4-Cl) | Me | O | O | OH |
| III-140 | Ph(3-F-5-Cl) | Me | O | O | OH |
| III-141 | Ph(2-F-3-Cl) | Me | O | O | OH |
| III-142 | Ph(2-F-4-Cl) | Me | O | O | OH |
| III-143 | Ph(2-F-5-Cl) | Me | O | O | OH |
| III-144 | Ph(2-F-6-Cl) | Me | O | O | OH |
| III-145 | Ph(3-Cl-4-F) | Me | O | O | OH |
| III-146 | Ph(2-Cl-3-F) | Me | O | O | OH |
| III-147 | Ph(2-Cl-4-F) | Me | O | O | OH |
| III-148 | Ph(2-Cl-5-F) | Me | O | O | OH |
| III-149 | Ph(3-Me-4-OMe) | Me | O | O | OH |
| III-150 | Ph(3-Me-5-OMe) | Me | O | O | OH |
| III-151 | Ph(2-Me-3-OMe) | Me | O | O | OH |
| III-152 | Ph(2-Me-4-OMe) | Me | O | O | OH |
| III-153 | Ph(2-Me-5-OMe) | Me | O | O | OH |
| III-154 | Ph(2-Me-6-OMe) | Me | O | O | OH |
| III-155 | Ph(3-OMe-4-Me) | Me | O | O | OH |
| III-156 | Ph(2-OMe-3-Me) | Me | O | O | OH |

TABLE 32

| Compound No. | R¹ | R² | Y | Z | R⁴ |
|---|---|---|---|---|---|
| III-157 | Ph(2-OMe-4-Me) | Me | O | O | OH |
| III-158 | Ph(2-OMe-5-Me) | Me | O | O | OH |
| III-159 | Ph(3-CN-4-OMe) | Me | O | O | OH |
| III-160 | Ph(3-OMe-4-CN) | Me | O | O | OH |
| III-161 | Ph(3-Me-4-CN) | Me | O | O | OH |
| III-162 | Ph(3-CN-4-Me) | Me | O | O | OH |
| III-163 | Ph(3-NO₂-4-OMe) | Me | O | O | OH |
| III-164 | Ph(3-OMe-4-NO₂) | Me | O | O | OH |
| III-165 | Ph(3-Me-4-NO₂) | Me | O | O | OH |
| III-166 | Ph(3-NO₂-4-Me) | Me | O | O | OH |
| III-167 | Ph(3,5-F₂-5-OMe) | Me | O | O | OH |
| III-168 | Ph(3,5-F₂-5-Me) | Me | O | O | OH |

TABLE 32-continued

| Compound No. | R¹ | R² | Y | Z | R⁴ |
|---|---|---|---|---|---|
| III-169 | Ph(3,4,5-(OMe)₃) | Me | O | O | OH |
| III-170 | 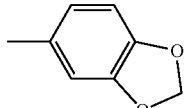 | Me | O | O | OH |
| III-171 | 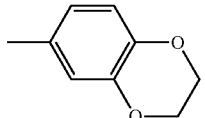 | Me | O | O | OH |
| III-172 | 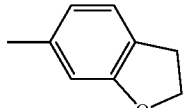 | Me | O | O | OH |
| III-173 | 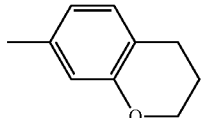 | Me | O | O | OH |
| III-174 | 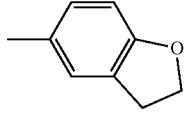 | Me | O | O | OH |
| III-175 | 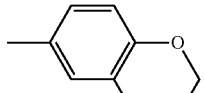 | Me | O | O | OH |
| III-176 | 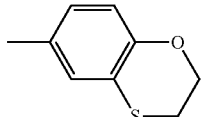 | Me | O | O | OH |
| III-177 | 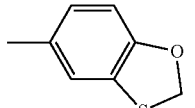 | Me | O | O | OH |
| III-178 | 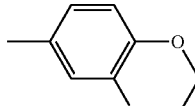 | Me | O | O | OH |

TABLE 33

| Compound No. | R¹ | R² | Y | Z | R⁴ |
|---|---|---|---|---|---|
| III-179 | 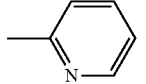 | Me | O | O | OH |

TABLE 33-continued

| Compound No. | R¹ | R² | Y | Z | R⁴ |
|---|---|---|---|---|---|
| III-180 | 3-pyridyl | Me | O | O | OH |
| III-181 | 4-pyridyl | Me | O | O | OH |
| III-182 | 5-Me-2-pyridyl | Me | O | O | OH |
| III-183 | 5-OMe-2-pyridyl | Me | O | O | OH |
| III-184 | 5-F-2-pyridyl | Me | O | O | OH |
| III-185 | 5-Cl-2-pyridyl | Me | O | O | OH |
| III-186 | 5-Br-2-pyridyl | Me | O | O | OH |
| III-187 | 5-CF₃-2-pyridyl | Me | O | O | OH |
| III-188 | 3-Me-isoxazol-5-yl | Me | O | O | OH |
| III-189 | 5-Me-isoxazol-3-yl | Me | O | O | OH |
| III-190 | 4,5-dihydroisoxazol-3-yl | Me | O | O | OH |
| III-191 | 5-Me-4,5-dihydroisoxazol-3-yl | Me | O | O | OH |
| III-192 | 3-Me-4,5-dihydroisoxazol-5-yl | Me | O | O | OH |

TABLE 34

| Compound No. | R¹ | R² | Y | Z | R⁴ |
|---|---|---|---|---|---|
| III-193 | 3,5-diMe-4,5-dihydroisoxazol-5-yl | Me | O | O | OH |
| III-194 | 2-thiazolyl | Me | O | O | OH |
| III-195 | 4-Me-2-thiazolyl | Me | O | O | OH |
| III-196 | 5-Me-2-thiazolyl | Me | O | O | OH |
| III-197 | 4,5-diMe-2-thiazolyl | Me | O | O | OH |
| III-198 | 2-thienyl | Me | O | O | OH |
| III-199 | 3-thienyl | Me | O | O | OH |
| III-200 | 5-Me-2-thienyl | Me | O | O | OH |
| III-201 | 3,5-diMe-2-thienyl | Me | O | O | OH |
| III-202 | morpholino | Me | O | O | OH |
| III-203 | thiomorpholino | Me | O | O | OH |
| III-204 | thiomorpholino-1,1-dioxide | Me | O | O | OH |
| III-205 | CH₂Ph | Me | O | O | OH |
| III-206 | CH₂CH₂Ph | Me | O | O | OH |
| III-207 | CH₂CH₂CH₂Ph | Me | O | O | OH |
| III-208 | CH₂CH═CHPh | Me | O | O | OH |
| III-209 | CH₂C≡CPh | Me | O | O | OH |
| III-210 | CH₂CH═NOMe | Me | O | O | OH |
| III-211 | CH₂CH═NOEt | Me | O | O | OH |

TABLE 35

| Compound No. | R¹ | R² | Y | Z | R⁴ |
|---|---|---|---|---|---|
| III-212 | CH₂CH=NOPr-n | Me | O | O | OH |
| III-213 | CH₂CH=NOPh | Me | O | O | OH |
| III-214 | CH₂CH(OMe)₂ | Me | O | O | OH |
| III-215 | CH₂CHO | Me | O | O | OH |
| III-216 | NH₂ | Me | O | O | OH |
| III-217 | NHMe | Me | O | O | OH |
| III-218 | NHEt | Me | O | O | OH |
| III-219 | NHPr-n | Me | O | O | OH |
| III-220 | NHPr-i | Me | O | O | OH |
| III-221 | NHBu-n | Me | O | O | OH |
| III-222 | NHBu-i | Me | O | O | OH |
| III-223 | NHBu-s | Me | O | O | OH |
| III-224 | NHCH₂Pr-c | Me | O | O | OH |
| III-225 | NHPen-n | Me | O | O | OH |
| III-226 | NHHex-n | Me | O | O | OH |
| III-227 | NHCH₂CH₂CH₂Cl | Me | O | O | OH |
| III-228 | NHCH₂CH₂CH₂F | Me | O | O | OH |
| III-229 | NHCH₂CH₂OMe | Me | O | O | OH |
| III-230 | NMe₂ | Me | O | O | OH |
| III-231 | NEt₂ | Me | O | O | OH |
| III-232 | N(Pr-n)₂ | Me | O | O | OH |
| III-233 | N(Bu-n)₂ | Me | O | O | OH |
| III-234 | N(Me)Et | Me | O | O | OH |
| III-235 | N(Me)CH₂CH₂OMe | Me | O | O | OH |
| III-236 | NHPh | Me | O | O | OH |
| III-237 | NHCH₂Ph | Me | O | O | OH |
| III-238 | N=CMe₂ | Me | O | O | OH |
| III-239 | N=CEt₂ | Me | O | O | OH |
| III-240 | N=CHNMe₂ | Me | O | O | OH |
| III-241 | NHC(=O)Me | Me | O | O | OH |
| III-242 | N[C(=O)Me]₂ | Me | O | O | OH |
| III-243 | NHC(=O)OMe | Me | O | O | OH |
| III-244 | N[C(=O)OMe]₂ | Me | O | O | OH |
| III-245 | NHSO₂Me | Me | O | O | OH |
| III-246 | NHSO₂Ph | Me | O | O | OH |
| III-247 | NHSO₂CH₂Ph | Me | O | O | OH |
| III-248 | OMe | Me | O | O | OH |
| III-249 | OEt | Me | O | O | OH |
| III-250 | OPr-n | Me | O | O | OH |
| III-251 | OPr-i | Me | O | O | OH |
| III-252 | OCH₂Pr-c | Me | O | O | OH |
| III-253 | OCH₂Cl | Me | O | O | OH |
| III-254 | OCHCl₂ | Me | O | O | OH |

TABLE 36

| Compound No. | R¹ | R² | Y | Z | R⁴ |
|---|---|---|---|---|---|
| III-255 | OCCl₃ | Me | O | O | OH |
| III-256 | OCH₂F | Me | O | O | OH |
| III-257 | OCHF₂ | Me | O | O | OH |
| III-258 | OCF₃ | Me | O | O | OH |
| III-259 | Ph | Et | O | O | OH |
| III-260 | Ph | Pr-i | O | O | OH |
| III-261 | Ph | CHF₂ | O | O | OH |
| III-262 | Ph | Ph | O | O | OH |
| III-263 | Ph | Me | O | S | OH |
| III-264 | Ph | Me | S | S | OH |
| III-265 | Me | Me | O | S | OH |
| III-266 | Me | Me | S | S | OH |
| III-267 | Ph | Me | O | O | SPh |
| III-268 | Ph(4-OEt) | Me | O | O | OH |
| III-269 | Ph(2-Ph) | Me | O | O | OH |
| III-270 | Ph(3-Ph) | Me | O | O | OH |
| III-271 | Ph(4-Ph) | Me | O | O | OH |
| III-272 | 1-Me-3-CF₃-pyrazol-5-yl | Me | O | O | OH |
| III-273 | 4,6-dimethoxy-pyrimidin-2-yl | Me | O | O | OH |
| III-274 | Me | 6-methylpyridin-2-yl | O | O | OH |
| III-275 | Et | 6-methylpyridin-2-yl | O | O | OH |
| III-276 | H | Me | O | O | OH |
| III-277 | CH₂C≡CF | Me | O | O | OH |
| III-278 | 2,2-dichlorocyclopropyl | Me | O | O | OH |
| III-279 | 2,2-dichloro-3-ethylcyclopropyl | Me | O | O | OH |
| III-280 | CH₂NH₂ | Me | O | O | OH |
| III-281 | CH₂NO₂ | Me | O | O | OH |
| III-282 | CH₂NHCH₃ | Me | O | O | OH |
| III-283 | CH₂N(CH₃)₂ | Me | O | O | OH |
| III-284 | CH₂SCH₂CF₃ | Me | O | O | OH |
| III-285 | CH₂SOCH₂CF₃ | Me | O | O | OH |
| III-286 | CH₂SO₂CH₂CF₃ | Me | O | O | OH |
| III-287 | CH₂OH | Me | O | O | OH |
| III-288 | CH₂OBn | Me | O | O | OH |
| III-289 | CH₂OCH₂Pr-c | Me | O | O | OH |

TABLE 37

| Compound No. | R¹ | R² | Y | Z | R⁴ |
|---|---|---|---|---|---|
| III-290 | CH₂OPh | Me | O | O | OH |
| III-291 | CH₂SPh | Me | O | O | OH |
| III-292 | CH₂SOPh | Me | O | O | OH |
| III-293 | CH₂SO₂Ph | Me | O | O | OH |
| III-294 | CH₂CON(CH₃)₂ | Me | O | O | OH |
| III-295 | CH₂COCH₃ | Me | O | O | OH |
| III-296 | CH₂OCOCH₃ | Me | O | O | OH |
| III-297 | CH₂ON=CHCH₃ | Me | O | O | OH |
| III-298 | C₂H₄OC₂H₄SCH₃ | Me | O | O | OH |
| III-299 | C₂H₄OC₂H₄SOCH₃ | Me | O | O | OH |

TABLE 37-continued

| Compound No. | R¹ | R² | Y | Z | R⁴ |
|---|---|---|---|---|---|
| III-300 | $C_2H_4OC_2H_4SO_2CH_3$ | Me | O | O | OH |
| III-301 | $CH_2OCH_2CN$ | Me | O | O | OH |
| III-302 | $CH_2CN$ | Me | O | O | OH |
| III-303 | $OCH_2CH=CH_2$ | Me | O | O | OH |
| III-304 | $OCH_2C\equiv CH$ | Me | O | O | OH |
| III-305 | OPr-c | Me | O | O | OH |
| III-306 | $CH_2$-(tetrahydrofuran-2-yl) | Me | O | O | OH |
| III-307 | $CH_2$-(3-methylisoxazolin-5-yl) | Me | O | O | OH |
| III-308 | $CH_2$-(3-methylisoxazol-5-yl) | Me | O | O | OH |
| III-309 | $CH_2OCH_2$-(tetrahydrofuran-2-yl) | Me | O | O | OH |
| III-310 | $CH_2CH_2OCH_2CH_2O$-(pyridin-2-yl) | Me | O | O | OH |
| III-311 | Ph | H | O | O | OH |
| III-312 | Ph | $CH_2CH=CH_2$ | O | O | OH |
| III-313 | Ph | $CH_2C\equiv CH$ | O | O | OH |
| III-314 | Ph | Pr-c | O | O | OH |
| III-315 | Ph | $CH_2CH=CF_2$ | O | O | OH |
| III-316 | Ph | $CH_2C\equiv CF$ | O | O | OH |
| III-317 | Ph | $C_2H_4OCH_3$ | O | O | OH |
| III-318 | Ph | $C_2H_4OC_2H_5$ | O | O | OH |
| III-319 | Ph | CH(Me)OEt | O | O | OH |
| III-320 | Ph | $CH_2OPr$-c | O | O | OH |
| III-321 | Ph | $CH(OCH_3)_2$ | O | O | OH |
| III-322 | Ph | $CH_2Ph$ | O | O | OH |
| III-323 | Ph | $-CH=CH-Ph$ | O | O | OH |

TABLE 38

| Compound No. | R¹ | R² | Y | Z | R⁴ |
|---|---|---|---|---|---|
| III-324 | Ph | $-C\equiv C-Ph$ | O | O | OH |
| III-325 | Ph | Me | O | O | $NH_2$ |
| III-326 | Ph | Me | O | O | Cl |
| III-327 | Ph | Me | O | O | CN |
| III-328 | Ph | Me | O | O | NCS |
| III-329 | Ph | Me | O | O | NCO |
| III-330 | Ph | Me | O | O | $OCO_2H$ |
| III-331 | Ph | Me | O | O | $OCO_2CH_3$ |
| III-332 | Ph | Me | O | O | $OCO_2CH_2Ph$ |
| III-333 | Ph | Me | O | O | OMe |
| III-334 | Ph | Me | O | O | OEt |
| III-335 | Ph | Me | O | O | OPr |
| III-336 | Ph | Me | O | O | $OCH_2CH=CH_2$ |
| III-337 | Ph | Me | O | O | $OCH_2C\equiv CH$ |
| III-338 | Ph | Me | O | O | OPr-c |
| III-339 | Ph | Me | O | O | OBu-c |
| III-340 | Ph | Me | O | O | OPen-c |
| III-341 | Ph | Me | O | O | OHex-c |
| III-342 | Ph | Me | O | O | $OCH_2CN$ |
| III-343 | Ph | Me | O | O | $OCH_2Pr$-c |
| III-344 | Ph | Me | O | O | $OCOCH_3$ |
| III-345 | Ph | Me | O | O | $OCOCCl_3$ |
| III-346 | Ph | Me | O | O | $OCOCH=CH_2$ |
| III-347 | Ph | Me | O | O | $OCOCH=CF_2$ |
| III-348 | Ph | Me | O | O | $OCOCH_2C\equiv CH$ |
| III-349 | Ph | Me | O | O | $OCOCH_2C\equiv CF$ |
| III-350 | Ph | Me | O | O | $OCH_2CO_2CH_3$ |
| III-351 | Ph | Me | O | O | OPh |
| III-352 | Ph | Me | O | O | $OCH_2Ph$ |

TABLE 38-continued

| Compound No. | R¹ | R² | Y | Z | R⁴ |
|---|---|---|---|---|---|
| III-353 | Ph | Me | O | O | OCOPh |
| III-354 | Ph | Me | O | O | OCOCH₂Ph |
| III-355 | Ph | Me | O | O | OCH₂COPh |
| III-356 | Ph | Me | O | O | OSO₂CH₂CF₃ |
| III-357 | Ph | Me | O | O | OSO₂CH₂Ph |
| III-358 | Ph | Me | O | O | SCH₃ |
| III-359 | Ph | Me | O | O | SOCH₃ |
| III-360 | Ph | Me | O | O | SO₂CH₃ |
| III-361 | Ph | Me | O | O | SCH₂CF₃ |
| III-362 | Ph | Me | O | O | SOCH₂CF₃ |
| III-363 | Ph | Me | O | O | SO₂CH₂CF₃ |
| III-364 | Ph | Me | O | O | SCH₂CH=CH₂ |
| III-365 | Ph | Me | O | O | SOCH₂CH=CH₂ |
| III-366 | Ph | Me | O | O | SO₂CH₂CH=CH₂ |

TABLE 39

| Compound No. | R¹ | R² | Y | Z | R⁴ |
|---|---|---|---|---|---|
| III-367 | Ph | Me | O | O | SCH₂CH≡CH |
| III-368 | Ph | Me | O | O | SOCH₂CH≡CH |
| III-369 | Ph | Me | O | O | SO₂CH₂CH≡CH |
| III-370 | Ph | Me | O | O | SCH₂Ph |
| III-371 | Ph | Me | O | O | SOPh |
| III-372 | Ph | Me | O | O | SOCH₂Ph |
| III-373 | Ph | Me | O | O | SO₂Ph |
| III-374 | Ph | Me | O | O | SO₂CH₂Ph |
| III-375 | Ph | Me | O | O | NHCH₃ |
| III-376 | Ph | Me | O | O | N(CH₃)₂ |
| III-377 | Ph | Me | O | O | NHCOCH₃ |
| III-378 | Ph | Me | O | O | OCH₂CH₂-(2-pyridyl) |
| III-379 | Ph | Me | O | O | 1,2,4-triazol-1-yl |
| III-380 | Ph | Me | O | O | imidazol-1-yl |
| III-381 | Ph | Me | O | O | tetrazol-1-yl |
| III-382 | Ph | Me | O | O | pyrazol-1-yl |

TABLE 39-continued

| Compound No. | R¹ | R² | Y | Z | R⁴ |
|---|---|---|---|---|---|
| III-383 | Ph | Me | O | O | O-(2-pyridyl) |

TABLE 40

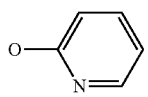

| Compound No. | R¹ | A₁ | A₂ | A₃ |
|---|---|---|---|---|
| VI-1 | Ph | C(CH₃)₂ | CO | C(CH₃)₂ |
| VI-2 | Ph | CHCH₃ | CH₂ | CH₂ |
| VI-3 | Ph | CH₂ | CHCH₃ | CH₂ |
| VI-4 | Ph | CHCH₃ | CHCH₃ | CHCH₃ |
| VI-5 | Ph | C(CH₃)₂ | CH₂ | CH₂ |
| VI-6 | Ph | CH₂ | C(CH₃)₂ | CH₂ |
| VI-7 | Ph | CHCH₃ | CH₂ | C(CH₃)₂ |
| VI-8 | Ph | CHCH₃ | CH₂ | CHCH₃ |
| VI-9 | Ph | CHCH₃ | CHCH₃ | CH₂ |
| VI-10 | Ph | NCH₃ | CO | CH₂ |
| VI-11 | Ph | C(CH₃)₂ | C(CH₃)₂ | C(CH₃)₂ |
| VI-12 | Ph | C(CH₃)₂ | S | C(CH₃)₂ |
| VI-13 | Ph | C(CH₃)₂ | SO | C(CH₃)₂ |
| VI-14 | Ph | C(CH₃)₂ | SO₂ | C(CH₃)₂ |
| VI-15 | Ph | C(CH₃)₂ | O | C(CH₃)₂ |
| VI-16 | Ph | C(CH₃)₂ | NCH₃ | C(CH₃)₂ |
| VI-17 | Me | C(CH₃)₂ | CO | C(CH₃)₂ |
| VI-18 | Me | CHCH₃ | CH₂ | CH₂ |
| VI-19 | Me | CH₂ | CHCH₃ | CH₂ |
| VI-20 | Me | CHCH₃ | CHCH₃ | CHCH₃ |
| VI-21 | Me | C(CH₃)₂ | CH₂ | CH₂ |
| VI-22 | Me | CH₂ | C(CH₃)₂ | CH₂ |
| VI-23 | Me | CHCH₃ | CH₂ | C(CH₃)₂ |
| VI-24 | Me | CHCH₃ | CH₂ | CHCH₃ |
| VI-25 | Me | CHCH₃ | CHCH₃ | CH₂ |
| VI-26 | Me | NCH₃ | CO | CH₂ |
| VI-27 | Me | C(CH₃)₂ | C(CH₃)₂ | C(CH₃)₂ |
| VI-28 | Me | C(CH₃)₂ | S | C(CH₃)₂ |
| VI-29 | Me | C(CH₃)₂ | SO | C(CH₃)₂ |
| VI-30 | Me | C(CH₃)₂ | SO₂ | C(CH₃)₂ |
| VI-31 | Me | C(CH₃)₂ | O | C(CH₃)₂ |
| VI-32 | Me | C(CH₃)₂ | NCH₃ | C(CH₃)₂ |
| VI-33 | 5-Me-pyridin-2-yl | C(CH₃)₂ | CO | C(CH₃)₂ |
| VI-34 | 5-Me-pyridin-2-yl | CHCH₃ | CH₂ | CH₂ |

TABLE 41

| Compound No. | R¹ | A₁ | A₂ | A₃ |
|---|---|---|---|---|
| VI-35 | 6-Me-pyridin-3-yl | CH₂ | CHCH₃ | CH₂ |
| VI-36 | 6-Me-pyridin-3-yl | CHCH₃ | CHCH₃ | CHCH₃ |
| VI-37 | 6-Me-pyridin-3-yl | C(CH₃)₂ | CH₂ | CH₂ |
| VI-38 | 6-Me-pyridin-3-yl | CH₂ | C(CH₃)₂ | CH₂ |
| VI-39 | 6-Me-pyridin-3-yl | CHCH₃ | CH₂ | C(CH₃)₂ |
| VI-40 | 6-Me-pyridin-3-yl | CHCH₃ | CH₂ | CHCH₃ |
| VI-41 | 6-Me-pyridin-3-yl | CHCH₃ | CHCH₃ | CH₂ |
| VI-42 | 6-Me-pyridin-3-yl | NCH₃ | CO | CH₂ |
| VI-43 | 6-Me-pyridin-3-yl | C(CH₃)₂ | C(CH₃)₂ | C(CH₃)₂ |
| VI-44 | 6-Me-pyridin-3-yl | C(CH₃)₂ | S | C(CH₃)₂ |
| VI-45 | 6-Me-pyridin-3-yl | C(CH₃)₂ | SO | C(CH₃)₂ |
| VI-46 | 6-Me-pyridin-3-yl | C(CH₃)₂ | SO₂ | C(CH₃)₂ |
| VI-47 | 6-Me-pyridin-3-yl | C(CH₃)₂ | O | C(CH₃)₂ |
| VI-48 | 6-Me-pyridin-3-yl | C(CH₃)₂ | NCH₃ | C(CH₃)₂ |

TABLE 41-continued

| Compound No. | R¹ | A₁ | A₂ | A₃ |
|---|---|---|---|---|
| VI-49 | Ph(4-OMe) | C(CH₃)₂ | CO | C(CH₃)₂ |
| VI-50 | Ph(4-OMe) | CHCH₃ | CH₂ | CH₂ |
| VI-51 | Ph(4-OMe) | CH₂ | CHCH₃ | CH₂ |
| VI-52 | Ph(4-OMe) | CHCH₃ | CHCH₃ | CHCH₃ |
| VI-53 | Ph(4-OMe) | C(CH₃)₂ | CH₂ | CH₂ |
| VI-54 | Ph(4-OMe) | CH₂ | C(CH₃)₂ | CH₂ |
| VI-55 | Ph(4-OMe) | CHCH₃ | CH₂ | C(CH₃)₂ |
| VI-56 | Ph(4-OMe) | CHCH₃ | CH₂ | CHCH₃ |
| VI-57 | Ph(4-OMe) | CHCH₃ | CHCH₃ | CH₂ |

TABLE 42

| Compound No. | R¹ | A₁ | A₂ | A₃ |
|---|---|---|---|---|
| VI-58 | Ph(4-OMe) | NCH₃ | CO | CH₂ |
| VI-59 | Ph(4-OMe) | C(CH₃)₂ | C(CH₃)₂ | C(CH₃)₂ |
| VI-60 | Ph(4-OMe) | C(CH₃)₂ | S | C(CH₃)₂ |
| VI-61 | Ph(4-OMe) | C(CH₃)₂ | SO | C(CH₃)₂ |
| VI-62 | Ph(4-OMe) | C(CH₃)₂ | SO₂ | C(CH₃)₂ |
| VI-63 | Ph(4-OMe) | C(CH₃)₂ | O | C(CH₃)₂ |
| VI-64 | Ph(4-OMe) | C(CH₃)₂ | NCH₃ | C(CH₃)₂ |
| VI-65 | Ph(2,4-Me₂) | C(CH₃)₂ | CO | C(CH₃)₂ |
| VI-66 | Ph(2,4-Me₂) | CHCH₃ | CH₂ | CH₂ |
| VI-67 | Ph(2,4-Me₂) | CH₂ | CHCH₃ | CH₂ |
| VI-68 | Ph(2,4-Me₂) | CHCH₃ | CHCH₃ | CHCH₃ |
| VI-69 | Ph(2,4-Me₂) | C(CH₃)₂ | CH₂ | CH₂ |
| VI-70 | Ph(2,4-Me₂) | CH₂ | C(CH₃)₂ | CH₂ |
| VI-71 | Ph(2,4-Me₂) | CHCH₃ | CH₂ | C(CH₃)₂ |
| VI-72 | Ph(2,4-Me₂) | CHCH₃ | CH₂ | CHCH₃ |
| VI-73 | Ph(2,4-Me₂) | CHCH₃ | CHCH₃ | CH₂ |
| VI-74 | Ph(2,4-Me₂) | NCH₃ | CO | CH₂ |
| VI-75 | Ph(2,4-Me₂) | C(CH₃)₂ | C(CH₃)₂ | C(CH₃)₂ |
| VI-76 | Ph(2,4-Me₂) | C(CH₃)₂ | S | C(CH₃)₂ |
| VI-77 | Ph(2,4-Me₂) | C(CH₃)₂ | SO | C(CH₃)₂ |
| VI-78 | Ph(2,4-Me₂) | C(CH₃)₂ | SO₂ | C(CH₃)₂ |
| VI-79 | Ph(2,4-Me₂) | C(CH₃)₂ | O | C(CH₃)₂ |
| VI-80 | Ph(2,4-Me₂) | C(CH₃)₂ | NCH₃ | C(CH₃)₂ |
| VI-81 | 3,5-diMe-isoxazol-yl | C(CH₃)₂ | CO | C(CH₃)₂ |
| VI-82 | 3,5-diMe-isoxazol-yl | CHCH₃ | CH₂ | CH₂ |
| VI-83 | 3,5-diMe-isoxazol-yl | CH₂ | CHCH₃ | CH₂ |
| VI-84 | 3,5-diMe-isoxazol-yl | CHCH₃ | CHCH₃ | CHCH₃ |
| VI-85 | 3,5-diMe-isoxazol-yl | C(CH₃)₂ | CH₂ | CH₂ |
| VI-86 | 3,5-diMe-isoxazol-yl | CH₂ | C(CH₃)₂ | CH₂ |

TABLE 42-continued

| Compound No. | R¹ | A₁ | A₂ | A₃ |
|---|---|---|---|---|
| VI-87 | 3-methylisoxazol-5-yl (Me on 5) | CHCH₃ | CH₂ | C(CH₃)₂ |
| VI-88 | 3-methylisoxazol-5-yl (Me on 5) | CHCH₃ | CH₂ | CHCH₃ |

TABLE 43

| Compound No. | R¹ | A₁ | A₂ | A₃ |
|---|---|---|---|---|
| VI-89 | 3-methylisoxazol-5-yl | CHCH₃ | CHCH₃ | CH₂ |
| VI-90 | 3-methylisoxazol-5-yl | NCH₃ | CO | CH₂ |
| VI-91 | 3-methylisoxazol-5-yl | C(CH₃)₂ | C(CH₃)₂ | C(CH₃)₂ |
| VI-92 | 3-methylisoxazol-5-yl | C(CH₃)₂ | S | C(CH₃)₂ |
| VI-93 | 3-methylisoxazol-5-yl | C(CH₃)₂ | SO | C(CH₃)₂ |
| VI-94 | 3-methylisoxazol-5-yl | C(CH₃)₂ | SO₂ | C(CH₃)₂ |
| VI-95 | 3-methylisoxazol-5-yl | C(CH₃)₂ | O | C(CH₃)₂ |
| VI-96 | 3-methylisoxazol-5-yl | C(CH₃)₂ | NCH₃ | C(CH₃)₂ |
| VI-97 | Ph(3,4,5-(OMe)₃) | C(CH₃)₂ | CO | C(CH₃)₂ |

Preferred examples of the triazine derivative represented by Formula 1 of the invention or salt thereof include the followings.

A in Formula 1 is preferably A-1, A-3, or A-5, and more preferably A-1 or A-3.

In A-1, $A_1$ is preferably $[X_1]$, $A_2$ is preferably $[X_3]$ or $[X_4]$, and $A_3$ is preferably $[X_9]$.

In $[X_1]$, $R^5$ and $R^6$ are preferably a hydrogen atom or a $C_1$-$C_6$ alkyl group. In $[X_3]$, $R^8$ and $R^9$ are preferably a hydrogen atom or a $C_1$-$C_6$ alkyl group. In $[X_9]$, $R^{35}$ and $R^{36}$ are preferably a hydrogen atom or a $C_1$-$C_6$ alkyl group. Further, according to the preferred example of the invention, $R^5$ in $[X_1]$ and $R^{35}$ in $[X_9]$ bind to each other via a $C_1$-$C_5$ alkylene chain, preferably an ethylene chain, to form a ring.

In A-3, $R^{20}$ is preferably a $C_1$-$C_6$ alkyl group and $R^{21}$ is preferably a hydrogen atom or a $C_1$-$C_6$ alkyl group.

In A-1 and A-3, $R^4$ is preferably a hydroxyl group, an $O^-M^+$ ($M^+$ represents an alkali metal cation or an ammonium cation), or a $C_1$-$C_{10}$ alkylsulfonyloxy group.

In Formula 1, Y is preferably an oxygen atom.

In Formula 1, $R^1$ is preferably a group selected from a group consisting of a $C_1$-$C_{12}$ alkyl group; a $C_2$-$C_6$ alkenyl group; a $C_2$-$C_6$ alkynyl group; a $C_3$-$C_6$ cycloalkyl group; a $C_3$-$C_6$ cycloalkenyl group; a $C_1$-$C_6$ haloalkyl group; a $C_2$-$C_6$ halolalkenyl group; a $C_1$-$C_6$ alkoxy $C_1$-$C_6$ alkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ alkoxycarbonyl $C_1$-$C_6$ alkyl group; a phenyl group which may be substituted with a substituent group selected from Substituent group α; a phenyl $C_1$-$C_6$ alkyl group which may be substituted with a substituent group selected from Substituent group α; and a heterocyclic group having 3 to 10 carbon atoms and one or more heteroatoms that are the same or different from each other and selected from an oxygen atom, a sulfur atom, and a nitrogen atom (the group may be substituted with one substituent group selected from Substituent group α or 2 to 5 substituent groups that are the same or different from each other and selected from Substituent group α, and when the heterocyclic group contains a sulfur atom, it may be oxidized to be present as sulfoxide or sulfone).

In Formula 1, $R^2$ is preferably a group selected from a group consisting of a $C_1$-$C_6$ alkyl group; a $C_1$-$C_6$ haloalkyl group; a phenyl group which may be substituted with a substituent group selected from Substituent group α; and a heterocyclic group having 3 to 10 carbon atoms and one or more heteroatoms that are the same or different from each other and selected from an oxygen atom, a sulfur atom, and a nitrogen atom (the group may be substituted with one substituent group selected from Substituent group α or 2 to 5 substituent groups that are the same or different from each other and selected from Substituent group α).

The triazine derivative compounds represented by Formula 1, i.e., the compounds of the invention, and their salts can be produced according to various methods. Representative examples of the production method are given below, but the invention is not limited to them.

<Production Method 1>

The compound represented by following Formula 1a, which is one of the compounds of the invention, can be produced according to the method with the reaction scheme shown below.

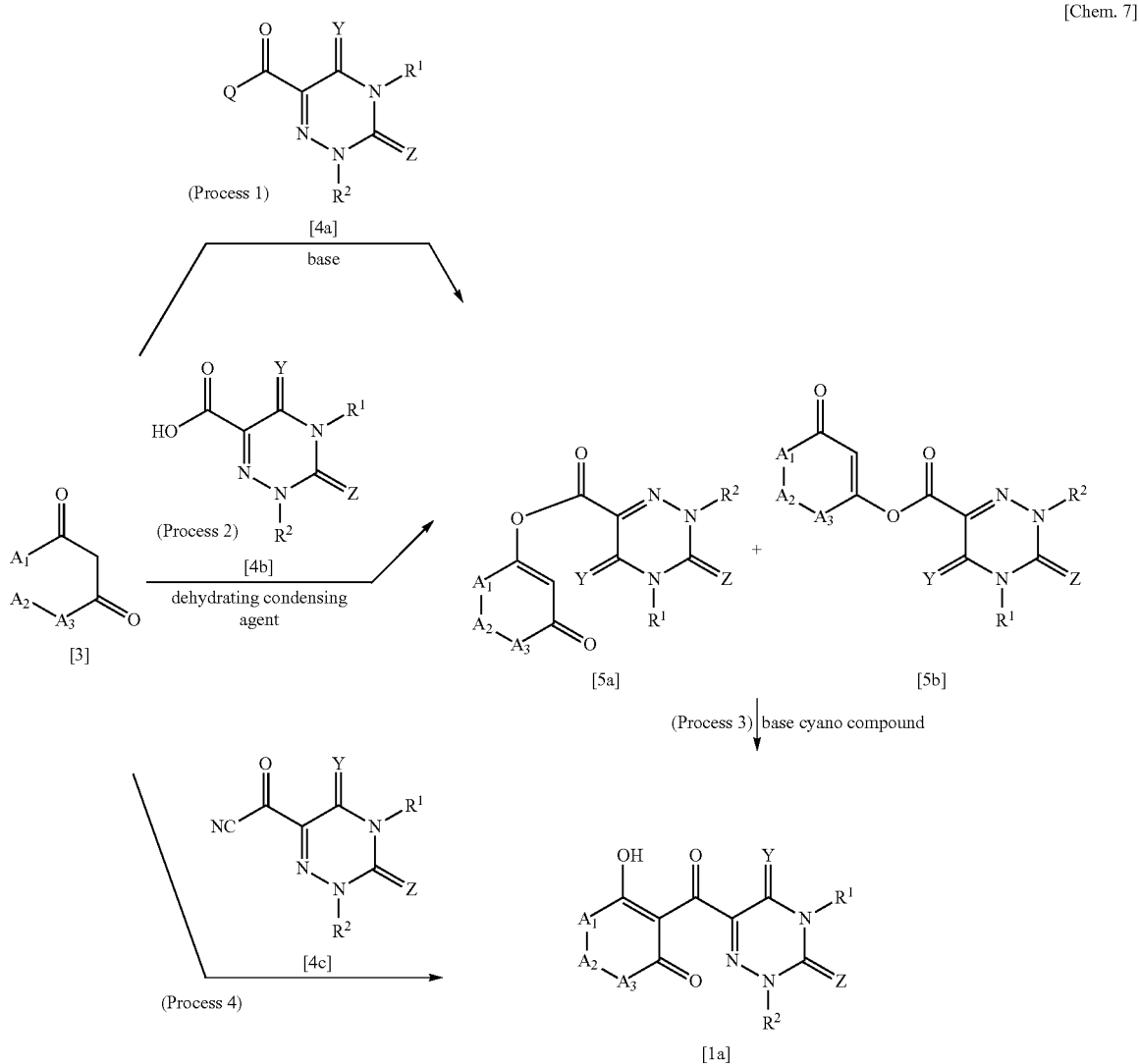

[Chem. 7]

(in the formula, $R^1$, $R^2$, $A_1$, $A_2$, $A_3$, Y and Z have the same definitions as above and Q represents a leaving group like a halogen atom, an alkylcarbonyloxy group, an alkoxycarbonyloxy group, a haloalkylcarbonyloxy group, a haloalkoxycarbonyloxy group, a benzoyloxy group, a pyridyl group, and an imidazolyl group).

(Process 1)

By reacting the compound of Formula 3 and the compound of Formula 4a in a solvent in the presence of a base, the enolester compound of Formula 5a and/or Formula 5b can be produced.

Herein, the use amount of Formula 4a can be appropriately selected from the range of 0.5 to 10 mol per 1 mol of Formula 3. Preferably, it is from 1.0 to 1.2 mol.

Examples of the base which can be used for the present process include organic amines like triethylamine, pyridine, 4-dimethylaminopyridine, N,N-dimethylaniline, and 1,8-diazabicyclo[5.4.0]undec-7-ene (DBU); metal carbonates like sodium carbonate, potassium carbonate, magnesium carbonate, and calcium carbonate; metal hydrogen carbonates like sodium hydrogen carbonate and potassium hydrogen carbonate; metal carboxylate salts represented by metal acetate salts like sodium acetate, potassium acetate, calcium acetate, and magnesium acetate; metal alkoxides like sodium methoxide, sodium ethoxide, sodium tertiary butoxide, potassium methoxide, and potassium tertiary butoxide; metal hydroxides like sodium hydroxide, potassium hydroxide, calcium hydroxide, and magnesium hydroxide, and; metal hydrides like lithium hydride, sodium hydride, potassium hydride, and calcium hydride. The use amount of the base is appropriately selected from the range of 0.5 to 10 mol per 1 mol of Formula 3. Preferably, it is from 1.0 to 1.2 mol.

The solvent that can be used for the present process can be any solvent if it does not inhibit the progress of the reaction. Solvents including nitriles like acetonitrile; ethers like diethyl ether, diisopropyl ether, tetrahydrofuran, dioxane, monoglyme, and diglyme; halogenated hydrocarbons like dichloroethane, chloroform, carbon tetrachloride, and tetrachloroethane; aromatic hydrocarbons like benzene, chlorobenzene, nitrobenzene, and toluene; amides like N,N-dimethylformamide and N,N-dimethylacetamide; imidazolinones like 1,3-dimethyl-2-imidazolinone, and; sulfur compounds like dimethyl sulfoxide can be used. Further, their mixture solvent can be also used.

The reaction temperature may be selected from the range of from −20° C. to the boiling point of an inert solvent used. Preferably, the reaction is carried out in the range of from 0° C. to 100° C. By using a phase transfer catalyst like quaternary ammonium salt, the reaction can be carried out in a two-phase system.

The reaction time varies depending on the reaction temperature, the reaction substrates, the reaction amount, etc. In general, it is from 10 minutes to 48 hours.

After the completion of the reaction, the compound of Formula 5a and/or Formula 5b, which is the target compound of the reaction, can be collected from the reaction system by general method, and if necessary, purified by a process like column chromatography and recrystallization.

(Process 2)

Compound of Formula 5a and/or Formula 5b can be also produced by reacting the compound of Formula 3 and the compound of Formula 4b with a dehydrating condensing agent in a solvent, in the presence or absence of a base.

The use amount of Formula 4b that is used for the present process can be appropriately selected from the range of 0.5 to 10 mol per 1 mol of Formula 3. Preferably, it is from 1.0 to 1.2 mol.

Examples of the dehydrating condensing agent include dicyclohexyl carbodiimide (DCC), N-(3-dimethylaminopropyl)-N'-ethylcarbodiimide (EDC or WSC), N,N-carbonyldiimidazole, 2-chloro-1,3-dimethylimidazolium chloride, and 2-chloro-1-pyridinium iodide.

Examples of the base and the solvent which can be used for the present process include those described above for Process 1.

The reaction temperature may be selected from the range of from −20° C. to the boiling point of an inert solvent used. Preferably, the reaction is carried out in the range of from 0° C. to 100° C.

The reaction time varies depending on the reaction temperature, the reaction substrates, the reaction amount, etc. In general, it is from 10 minutes to 48 hours.

The compound of Formula 5a and/or Formula 5b, which is the target compound of the reaction, can be separated and purified in the same manner as Process 1.

(Process 3)

Compound of Formula 1a can be produced by reacting the compound of Formula 5a and/or Formula 5b produced by Process 1 or Process 2 with a cyano compound in the presence of a base.

Examples of the base which can be used for the present process include those described above for Process 1. The use amount of the base can be appropriately selected from the range of 0.5 to 10 mol per 1 mol of Formula 5a and Formula 5b. Preferably, it is from 1.0 to 1.2 mol.

Examples of the cyano compound which can be used for the present process include potassium cyanide, sodium cyanide, acetone cyanohydrin, hydrogen cyanide, and a polymer supported with hydrogen cyanide. The use amount of the cyano compound can be appropriately selected from the range of 0.01 to 1.0 mol per 1 mol of Formula 5a and Formula 5b. Preferably, it is from 0.05 to 0.2 mol.

For the present process, a small amount of a phase transfer catalyst like crown ether can be also used.

Examples of the solvent which can be used for the present process include those described above for Process 1. The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

Further, according to the present process, compound of Formula 1a can be produced while using Formula 5a and/or Formula 5b produced by Process 1 or Process 2 without any separation.

(Process 4)

Compound of Formula 1a can be also produced by reacting the compound of Formula 3 and the compound of Formula 4c in the presence of a base or a Lewis acid.

The use amount of Formula 4c that is used for the present process can be appropriately selected from the range of 0.5 to 10 mol per 1 mol of Formula 3. Preferably, it is from 1.0 to 1.2 mol.

Examples of the Lewis acid include zinc chloride and aluminum chloride.

Examples of the base which can be used for the present process include those described above for Process 1. The use amount of the base that can be used for the present process can be appropriately selected from the range of 0.5 to 10 mol per 1 mol of Formula 3. Preferably, it is from 1.0 to 1.2 mol.

Examples of the solvent which can be used for the present process include those described above for Process 1.

The reaction temperature is selected from the range of from −20° C. to the boiling point of an inert solvent used. Preferably, the reaction is carried out in the range of from 0° C. to 100° C.

The reaction time varies depending on the reaction temperature, the reaction substrates, the reaction amount, etc. In general, it is from 10 minutes to 48 hours.

After the completion of the reaction, compound of Formula 1a, which is produced according to Process 3 or Process 4, can be collected from the reaction system by general method, and if necessary, purified by a process like column chromatography and recrystallization.

<Production Method 2>

With regard to Formula 1a produced by Production method 1, the hydroxyl group in the cyclohexane ring can be converted to other substituent group according to the method with the following reaction scheme.

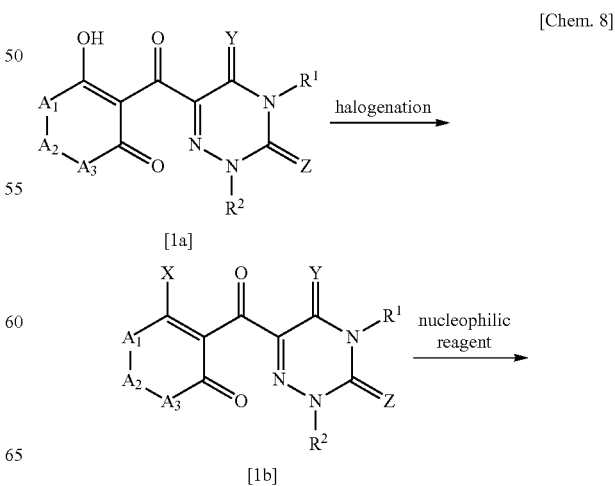

[Chem. 8]

-continued

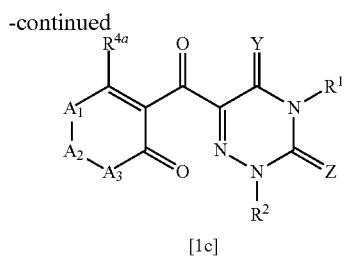

[1c]

(in the formula, $R^1$, $R^2$, $A_1$, $A_2$, $A_3$, Y and Z each have the same definitions as above, $R^{4a}$ represents an amino group, a cyano group, an isothiocyanate group, an isocyanate group, a hydroxycarbonyloxy group, a $C_1$-$C_6$ alkoxycarbonyloxy group, a benzyloxycarbonyloxy group which may be substituted with a substituent group selected from Substituent group α, a $C_1$-$C_6$ alkoxy group, a $C_2$-$C_6$ alkenyloxy group, a $C_2$-$C_6$ alkynyloxy group, a $C_3$-$C_6$ cycloalkyloxy group, a cyanomethyleneoxy group, a $C_3$-$C_6$ cycloalkyl $C_1$-$C_6$ alkyloxy group, a $C_1$-$C_6$ alkylcarbonyloxy group, a $C_1$-$C_6$ haloalkylcarbonyloxy group, a $C_2$-$C_6$ alkenylcarbonyloxy group, a $C_2$-$C_6$ halolalkenylcarbonyloxy group, a $C_2$-$C_6$ alkynylcarbonyloxy group, a $C_2$-$C_6$ halolalkynylcarbonyloxy group, a $C_1$-$C_6$ alkoxycarbonyl $C_1$-$C_6$ alkoxy group, a phenyloxy group which may be substituted with a substituent group selected from Substituent group α, a benzyloxy group which may be substituted with a substituent group selected from Substituent group α, a phenylcarbonyloxy group which may be substituted with a substituent group selected from Substituent group α, a benzylcarbonyloxy group which may be substituted with a substituent group selected from Substituent group α, a phenylcarbonyl $C_1$-$C_6$ alkyloxy group which may be substituted with a substituent group selected from Substituent group α, a $C_1$-$C_{10}$ alkylsulfonyloxy group, a phenylsulfonyloxy group which may be substituted with a substituent group selected from Substituent group α, a benzylsulfonyloxy group which may be substituted with a substituent group selected from Substituent group α, a $C_1$-$C_{10}$ alkylthio group, a $C_1$-$C_{10}$ alkylsulfinyl group, a $C_1$-$C_{10}$ alkylsulfonyl group, a $C_1$-$C_6$ haloalkylthio group, a $C_1$-$C_6$ haloalkylsulfinyl group, a $C_1$-$C_6$ haloalkylsulfonyl group, a $C_2$-$C_6$ alkenylthio group, a $C_2$-$C_6$ alkenylsulfinyl group, a $C_2$-$C_6$ alkenylsulfonyl group, a $C_2$-$C_6$ alkynylthio group, a $C_2$-$C_6$ alkynylsulfinyl group, a $C_2$-$C_6$ alkynylsulfonyl group, a phenylthio group which may be substituted with a substituent group selected from Substituent group α, a benzylthio group which may be substituted with a substituent group selected from Substituent group α, a phenylsulfinyl group which may be substituted with a substituent group selected from Substituent group α, a benzylsulfinyl group which may be substituted with a substituent group selected from Substituent group α, a phenylsulfonyl group which may be substituted with a substituent group selected from Substituent group α, a benzylsulfonyl group which may be substituted with a substituent group selected from Substituent group α, a $C_1$-$C_{10}$ alkylamino group, a di($C_1$-$C_{10}$ alkylamino group, a $C_1$-$C_6$ alkoxycarbonyl amino group, a $C_1$-$C_6$ alkoxy group substituted with a heterocyclic group having 3 to 10 carbon atoms and one or more heteroatoms that are the same or different from each other and selected from an oxygen atom, a sulfur atom, and a nitrogen atom [the group may be substituted with one substituent group selected from Substituent group α or 2 to 5 substituent groups that are the same or different from each other and selected from Substituent group α], a heterocyclic group having 3 to 10 carbon atoms and one or more heteroatoms that are the same or different from each other and selected from an oxygen atom, a sulfur atom, and a nitrogen atom [the group may be substituted with one substituent group selected from Substituent group α or 2 to 5 substituent groups that are the same or different from each other and selected from Substituent group α], or a heterocyclic oxy group having 3 to 10 carbon atoms and one or more heteroatoms that are the same or different from each other and selected from an oxygen atom, a sulfur atom, and a nitrogen atom [the group may be substituted with one substituent group selected from Substituent group α or 2 to 5 substituent groups that are the same or different from each other and selected from Substituent group α], and X represents a halogen atom).

Specifically, the compound of Formula 1b can be produced by reacting the compound of Formula 1a and a halogenating agent, and Formula 1c can be produced by reacting the compound of Formula 1b and a nucleophilic reagent in the presence of a base.

Examples of the halogenating agent that can be used for preparation of the compound of Formula 1b from the compound of Formula 1a include thionyl chloride, thionyl bromide, phosphorus oxy chloride, phosphorus oxy bromide, phenyltrimethyl ammonium tribromide, and Meldrum's acid tribromide. The use amount of the halogenating agent can be appropriately selected from the range of 0.5 to 10 mol per 1 mol of Formula 1a. Preferably, it is from 1.0 to 1.2 mol.

Examples of the solvent which can be used for the present process include those described above for Process 1 of Production method 1.

The reaction temperature may be selected from the range of from −20° C. to the boiling point of an inert solvent used. Preferably, the reaction is carried out in the range of from 0° C. to 100° C.

The reaction time varies depending on the reaction temperature, the reaction substrates, the reaction amount, etc. In general, it is from 10 minutes to 48 hours.

Examples of the nucleophilic reagent for the process for obtaining Formula 1c from Formula 1b, which is a compound represented by the formula $R^{4a}$—H, include alcohols like methanol, ethanol, and benzyl alcohol; mercaptans like methyl mercaptan and ethyl mercaptan; amities like ammonia, methyl amine, and ethyl amine; phenols like p-cresol and phenol; thiophenols like p-chlorothiophenol; a $C_1$-$C_6$ alkyl acids like acetic acid, and benzoic acids. The use amount of the nucleophilic reagent can be appropriately selected from the range of 0.5 to 10 mol per 1 mol of Formula 1b. Preferably, it is from 1.0 to 1.2 mol.

Examples of the base which can be used for the present process include those described above for Process 1 of Production method 1.

Examples of the solvent which can be used for the present process include those described above for Process 1 of Production method 1.

The reaction temperature is selected from the range of from −20° C. to the boiling point of an inert solvent used. Preferably, the reaction is carried out in the range of from 0° C. to 100° C.

The reaction time varies depending on the reaction temperature, the reaction substrates, the reaction amount, etc. In general, it is from 10 minutes to 48 hours.

After the completion of the reaction, the compound of Formula 1c, which is produced according to this method, can be collected from the reaction system by general method, and if necessary, purified by a process like column chromatography and recrystallization.

<Production Method 3>

Compound of Formula 1c can be also produced by the method with the following reaction scheme.

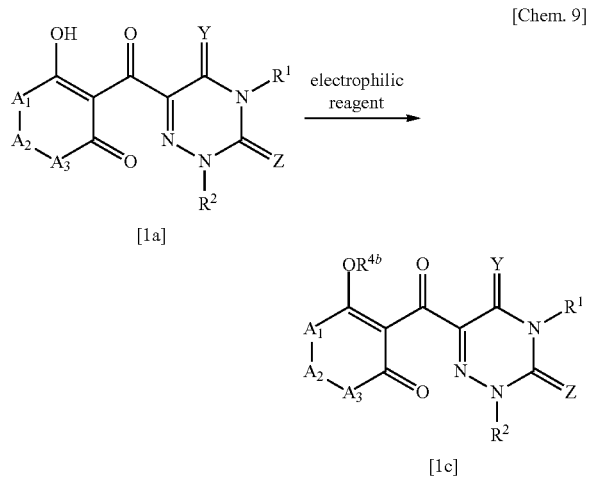

(in the formula, $R^1$, $R^2$, $A_1$, $A_2$, $A_3$, Y and Z each have the same definitions as above, $R^{4a}$ represents a hydroxycarbonyl group, a $C_1$-$C_6$ alkoxycarbonyl group, a benzyloxycarbonyl group which may be substituted with a substituent group selected from Substituent group α, a $C_1$-$C_6$ alkyl group, a $C_2$-$C_6$ alkenyl group, a $C_2$-$C_6$ alkynyl group, a $C_3$-$C_6$ cycloalkyl group, a cyanomethylene group, a $C_3$-$C_6$ cycloalkyl $C_1$-$C_6$ alkyl group, a $C_1$-$C_6$ alkylcarbonyl group, a $C_1$-$C_{10}$ alkylthiocarbonyl group, a $C_1$-$C_6$ haloalkylcarbonyl group, a $C_2$-$C_6$ alkenylcarbonyl group, a $C_2$-$C_6$ halolalkenylcarbonyl group, a $C_2$-$C_6$ alkynylcarbonyl group, a $C_2$-$C_6$ halolalkynylcarbonyl group, a $C_1$-$C_6$ alkoxycarbonyl $C_1$-$C_6$ alkyl group, a $C_1$-$C_{10}$ alkylsulfonyl group, a phenyl group which may be substituted with a substituent group selected from Substituent group α, a benzyl group which may be substituted with a substituent group selected from Substituent group α, a phenylcarbonyl group which may be substituted with a substituent group selected from Substituent group α, a benzylcarbonyl group which may be substituted with a substituent group selected from Substituent group α, a phenylsulfonyl group which may be substituted with a substituent group selected from Substituent group α, a phenylcarbonyl $C_1$-$C_6$ alkyl group which may be substituted with a substituent group selected from Substituent group α, or a heterocyclic group having 3 to 10 carbon atoms and one or more heteroatoms that are the same or different from each other and selected from an oxygen atom, a sulfur atom, and a nitrogen atom [the group may be substituted with one substituent group selected from Substituent group α or 2 to 5 substituent groups that are the same or different from each other and selected from Substituent group α]).

Specifically, the compound of Formula 1c can be produced by reacting the compound of Formula 1a and an electrophilic reagent in a solvent in the presence or absence of a base.

The electrophilic reagent indicates a compound represented by the formula $R^{4b}$—$L_a$ ($L_a$ represents a leaving group), and examples thereof include $C_1$-$C_6$ alkyl halide like methyl iodide and propyl chloride; benzyl halide like benzyl bromide; $C_1$-$C_6$ alkylcarbonyl halide like acetyl chloride and propionyl chloride; benzoyl halide like benzoyl chloride; $C_2$-$C_6$ alkenylcarbonyl halide like methacryl chloride and crotonyl chloride; $C_2$-$C_6$ alkynylcarbonyl halide like 4-pentynoyl chloride; $C_1$-$C_6$ alkyl sulfonyl halide like methane sulfonyl chloride and ethane sulfonyl chloride; benzene sulfonyl halide like benzene sulfonyl chloride and p-toluene sulfonyl chloride; and di $C_1$-$C_6$ alkyl sulfate ester like dimethyl sulfate and diethyl sulfate. The use amount of the electrophilic reagent can be appropriately selected from the range of 0.1 to 10 mol per 1 mol of Formula 1a. Preferably, it is from 1.0 to 1.2 mol.

Examples of the base which can be used for the present process include those described above for Process 1 of Production method 1. The use amount of the base can be appropriately selected from the range of 0.1 to 10 mol per 1 mol of Formula 1a. Preferably, it is from 1.0 to 1.2 mol.

Examples of the solvent which can be used for the present process include those described above for Process 1 of Production method 1.

The reaction temperature is selected from the range of from −20° C. to the boiling point of an inert solvent used. Preferably, the reaction is carried out in the range of from 0° C. to 100° C.

The reaction time varies depending on the reaction temperature, the reaction substrates, the reaction amount, etc. In general, it is from 10 minutes to 48 hours.

After the completion of the reaction, the compound of Formula 1c, which is a target compound of this process, can be collected from the reaction system by general method, and if necessary, purified by a process like column chromatography and recrystallization.

Formula 1c of the invention has many tautomers shown below, and they are all included in the invention.

-continued

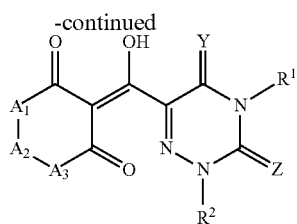

<Production Method 4>

Compound of Formula 1d can be also produced by the method with the following reaction scheme.

[Chem. 11]

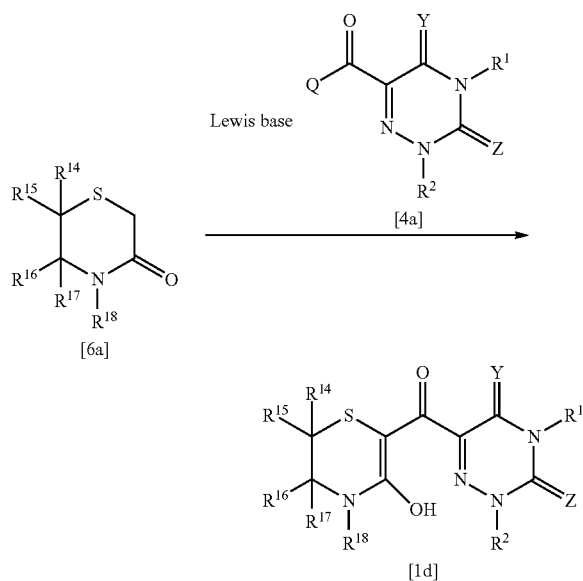

(in the formula, $R^1$, $R^2$, $R^{14}$, $R^{15}$, $R^{16}$, $R^{17}$, $R^{18}$, Y and Z each have the same definitions as above and Q represents a leaving group like a halogen atom, alkylcarbonyloxy group, an alkoxycarbonyloxy group, a haloalkylcarbonyloxy group, a haloalkoxycarbonyloxy group, a benzoyloxy group, a pyridyl group, and an imidazolyl group, as described above).

Specifically, compound of Formula 1d can be produced by reacting the compound of Formula 6a and the compound of Formula 4a in a solvent, in the presence of a Lewis acid.

The use amount of Formula 4a can be appropriately selected from the range of 0.5 to 10 mol per 1 mol of Formula 6a. Preferably, it is from 1.0 to 1.2 mol.

Examples of the Lewis acid that can be used include organo lithium compounds like methyl lithium, ethyl lithium, n-butyl lithium, sec-butyl lithium, tert-butyl lithium, and benzyl lithium; Grignard's reagent like methyl magnesium iodide and ethyl magnesium bromide; metal compounds like lithium, potassium and sodium; organo copper compounds produced from Grignard's reagent or organometallic compound and monovalent copper salt; alkali metal amides like lithium diisopropyl amide (LDA), and; organic amines like triethylamine, pyridine, 4-dimethylaminopyridine, N,N-dimethylaniline, and 1,8-diazabicyclo[5.4.0]undec-7-ene (DBU). n-Butyl lithium and lithium diisopropyl amide (LDA) are particularly preferable. The use amount of Lewis acid can be appropriately selected from the range of 0.5 to 10 mol per 1 mol of Formula 5a. Preferably, it is from 1.0 to 1.2 mol.

Examples of the solvent which can be used for the present process include those described above for Process 1 of Production method 1. Diethyl ether and tetrahydrofuran are particularly preferable. The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

After the completion of the reaction, the compound of Formula 1d, i.e., the target compound of this reaction, can be collected from the reaction system by general method, and if necessary, purified by a process like column chromatography and recrystallization.

Formula 1d of the invention has many tautomers shown below, and they are all included in the invention.

[Chem. 12]

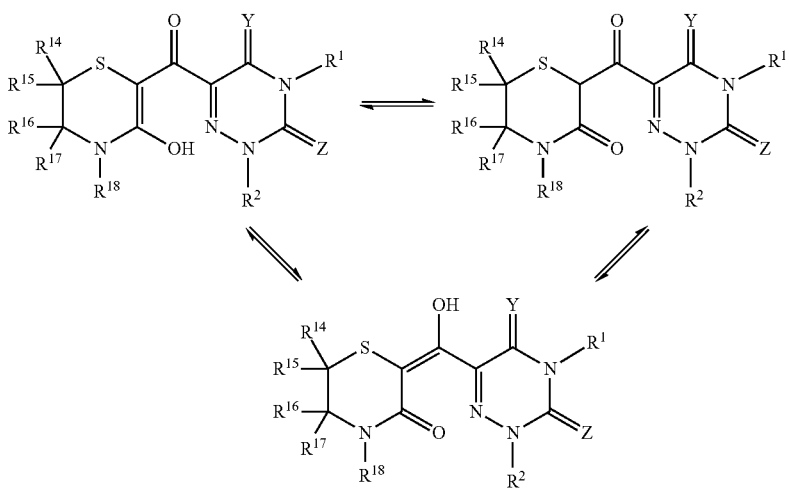

<Production Method 5>

Compound of Formula 1e can be also produced by the method with the following reaction scheme.

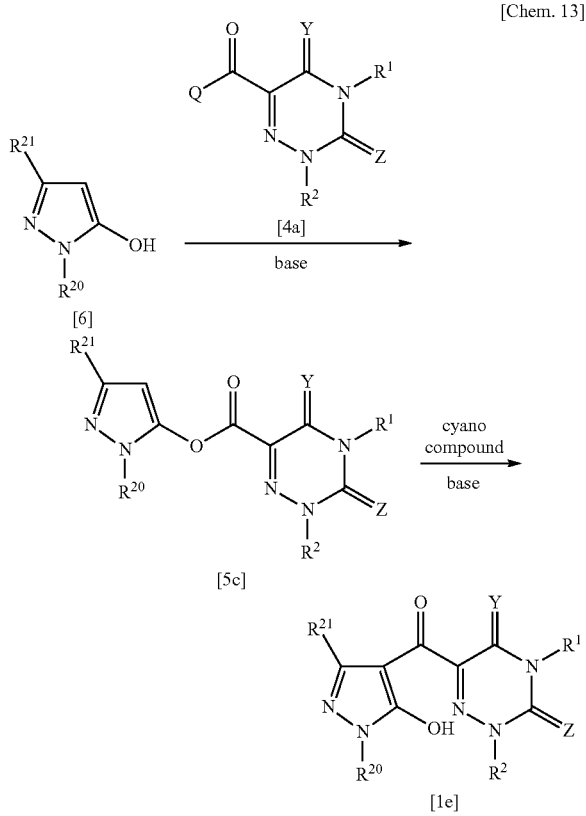

[Chem. 13]

(in the formula, $R^1$, $R^2$, $R^{20}$, $R^{21}$, Y and Z each have the same definitions as above and Q represents a leaving group like a halogen atom, alkylcarbonyloxy group, an alkoxycarbonyloxy group, a haloalkylcarbonyloxy group, a haloalkoxycarbonyloxy group, a benzoyloxy group, a pyridyl group, and an imidazolyl group, as described above).

Specifically, the compound of Formula 5c can be produced by reacting the compound of Formula 6 and the compound of Formula 4a in a solvent in the presence of a base, and the compound of Formula 1e can be produced by reacting the compound of Formula 5c and a cyano compound in the presence of a base.

In the above reaction, use amount of Formula 4a for preparing Formula 5c from Formula 6 can be appropriately selected from the range of 0.1 to 10 mol per 1 mol of Formula 6. Preferably, it is from 1.0 to 1.2 mol.

Examples of the base and solvent that can be used include those described above for Process 1 of Production method 1. The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

Examples of the cyano compound which can be used for the reaction above for obtaining Formula 1e from Formula 5c include potassium cyanide, sodium cyanide, acetone cyanohydrin, hydrogen cyanide, and a polymer supported with hydrogen cyanide. The use amount of the cyano compound can be appropriately selected from the range of 0.01 to 1.0 mol per 1 mol of Formula 6. Preferably, it is 0.05 to 0.2 mol.

Examples of the base that can be used include those described above for Process 1 of Production method 1. The use amount of the base can be appropriately selected from the range of 0.1 to 1.0 mol per 1 mol of Formula 6. Preferably, it is 1.0 to 1.2 mol.

Examples of the solvent which can be used for the present process include those described above for Process 1 of Production method 1.

The reaction temperature is selected from the range of from −20° C. to the boiling point of an inert solvent used. Preferably, the reaction is carried out in the range of from 0° C. to 100° C.

The reaction time varies depending on the reaction temperature, the reaction substrates, the reaction amount, etc. In general, it is from 10 minutes to 48 hours.

After the completion of the reaction, the compound of Formula 1e, i.e., the target compound of this reaction, can be collected from the reaction system by general method, and if necessary, purified by a process like column chromatography and recrystallization.

Formula 1e of the invention has many tautomers shown below, and they are all included in the invention.

[Chem. 14]

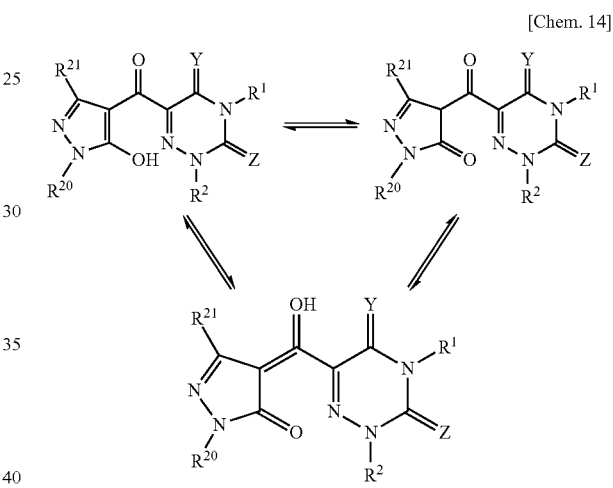

<Production Method 6>

Compound of Formula 1g in which the substituent group in the pyrazole ring is modified can be also produced from the compound of Formula 1e by the method with the following reaction scheme.

[Chem. 15]

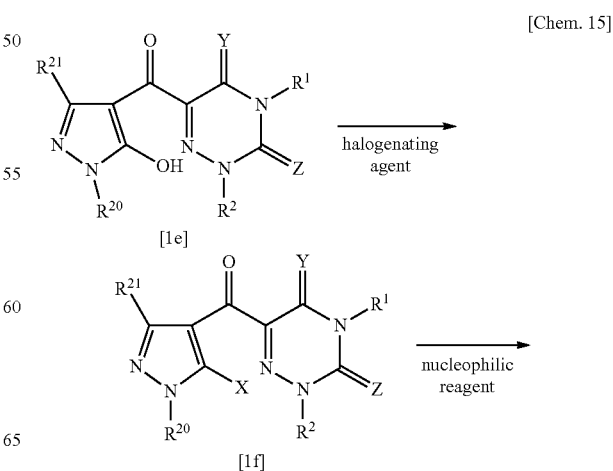

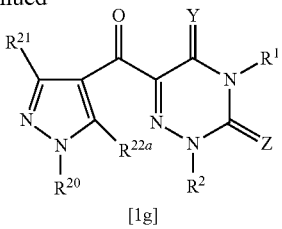

[1g]

(in the formula, $R^1$, $R^2$, $R^{20}$, $R^{21}$, Y and Z each have the same definitions as above, $R^{22a}$ represents an amino group, a cyano group, an isothiocyanate group, an isocyanate group, a hydroxycarbonyloxy group, a $C_1$-$C_6$ alkoxycarbonyloxy group, a benzyloxycarbonyloxy group which may be substituted with a substituent group selected from Substituent group α, a $C_1$-$C_6$ alkoxy group, a $C_2$-$C_6$ alkenyloxy group, a $C_2$-$C_6$ alkynyloxy group, a $C_3$-$C_6$ cycloalkyloxy group, a cyanomethyleneoxy group, a $C_3$-$C_6$ cycloalkyl $C_1$-$C_6$ alkyloxy group, a $C_1$-$C_6$ alkylcarbonyloxy group, a $C_1$-$C_6$ haloalkylcarbonyloxy group, a $C_2$-$C_6$ alkenylcarbonyloxy group, a $C_2$-$C_6$ haloalkenylcarbonyloxy group, a $C_2$-$C_6$ alkynylcarbonyloxy group, a $C_2$-$C_6$ haloalkynylcarbonyloxy group, a $C_1$-$C_6$ alkoxycarbonyl $C_1$-$C_6$ alkoxy group, a phenyloxy group which may be substituted with a substituent group selected from Substituent group α, a benzyloxy group which may be substituted with a substituent group selected from Substituent group α, a phenylcarbonyloxy group which may be substituted with a substituent group selected from Substituent group α, a benzylcarbonyloxy group which may be substituted with a substituent group selected from Substituent group α, a phenylcarbonyl $C_1$-$C_6$ alkyloxy group which may be substituted with a substituent group selected from Substituent group α, a $C_1$-$C_{10}$ alkylsulfonyloxy group, a phenylsulfonyloxy group which may be substituted with a substituent group selected from Substituent group α, a benzylsulfonyloxy group which may be substituted with a substituent group selected from Substituent group α, a $C_1$-$C_{10}$ alkylthio group, a $C_1$-$C_{10}$ alkylsulfinyl group, a $C_1$-$C_{10}$ alkylsulfonyl group, a $C_1$-$C_6$ haloalkylthio group, a $C_1$-$C_6$ haloalkylsulfinyl group, a $C_1$-$C_6$ haloalkylsulfonyl group, a $C_2$-$C_6$ alkenylthio group, a $C_2$-$C_6$ alkenylsulfinyl group, a $C_2$-$C_6$ alkenylsulfonyl group, a $C_2$-$C_6$ alkynylthio group, a $C_2$-$C_6$ alkynylsulfinyl group, a $C_2$-$C_6$ alkynylsulfonyl group, a phenylthio group which may be substituted with a substituent group selected from Substituent group α, a benzylthio group which may be substituted with a substituent group selected from Substituent group α, a phenylsulfinyl group which may be substituted with a substituent group selected from Substituent group α, a benzylsulfinyl group which may be substituted with a substituent group selected from Substituent group α, a phenylsulfonyl group which may be substituted with a substituent group selected from Substituent group α, a benzylsulfonyl group which may be substituted with a substituent group selected from Substituent group α, a $C_1$-$C_{10}$ alkylamino group, a di($C_1$-$C_{10}$ alkyl)amino group, a $C_1$-$C_6$ alkoxycarbonyl amino group, a $C_1$-$C_6$ alkoxy group substituted with a heterocyclic group having 3 to 10 carbon atoms and one or more heteroatoms that are the same or different from each other and selected from an oxygen atom, a sulfur atom, and a nitrogen atom [the group may be substituted with one substituent group selected from Substituent group α or 2 to 5 substituent groups that are the same or different from each other and selected from Substituent group α], a heterocyclic group having 3 to 10 carbon atoms and one or more heteroatoms that are the same or different from each other and selected from an oxygen atom, a sulfur atom, and a nitrogen atom [the group may be substituted with one substituent group selected from Substituent group α or 2 to 5 substituent groups that are the same or different from each other and selected from Substituent group α], or a heterocyclic oxy group having 3 to 10 carbon atoms and one or more heteroatoms that are the same or different from each other and selected from an oxygen atom, a sulfur atom, and a nitrogen atom [the group may be substituted with one substituent group selected from Substituent group α or 2 to 5 substituent groups that are the same or different from each other and selected from Substituent group α], and X represents a halogen atom).

Specifically, the compound of Formula 1f can be produced by reacting the compound of Formula 1e and a halogenating agent and Formula 1g can be produced by reacting it with a nucleophilic reagent.

Examples of the halogenating agent that can be used for the process of producing the compound of Formula 1f from the compound of Formula 1e include thionyl chloride, thionyl bromide, phosphorus oxychloride, phosphorus oxybromide, phenyltrimethyl ammonium tribromide, and Meldrum's acid tribromide.

The use amount of the halogenating agent can be appropriately selected from the range of 0.1 to 10 mol per 1 mol of Formula 1e. Preferably, it is from 1.0 to 1.2 mol.

Examples of the solvent which can be used for the present process include those described above for Process 1 of Production method 1. The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

The nucleophilic reagent for the process for obtaining Formula 1g from Formula 1f is, for example, a compound represented by the formula $R^{22a}$—H, and examples thereof include alcohols like methanol, ethanol, and benzyl alcohol; mercaptans like methyl mercaptan and ethyl mercaptan; amines like ammonia, methyl amine, and ethyl amine; phenols like p-cresol and phenol; thiophenols like p-chlorothiophenol; $C_1$-$C_6$ alkyl acids like acetic acid, and benzoic acids. The use amount of the nucleophilic reagent can be appropriately selected from the range of 0.1 to 10 mol per 1 mol of Formula 1f. Preferably, it is from 1.0 to 1.2 mol.

Examples of the solvent which can be used for the present process include those described above for Process 1 of Production method 1.

The reaction temperature is selected from the range of from −20° C. to the boiling point of an inert solvent used. Preferably, the reaction is carried out in the range of from 0° C. to 100° C.

The reaction time varies depending on the reaction temperature, the reaction substrates, the reaction amount, etc. In general, it is from 10 minutes to 48 hours.

After the completion of the reaction, the compound of Formula 1g, i.e., the target compound of this reaction, can be collected from the reaction system by general method, and if necessary, purified by a process like column chromatography and recrystallization.

<Production Method 7>

Compound of Formula 1g can be also produced by the method with the following reaction scheme.

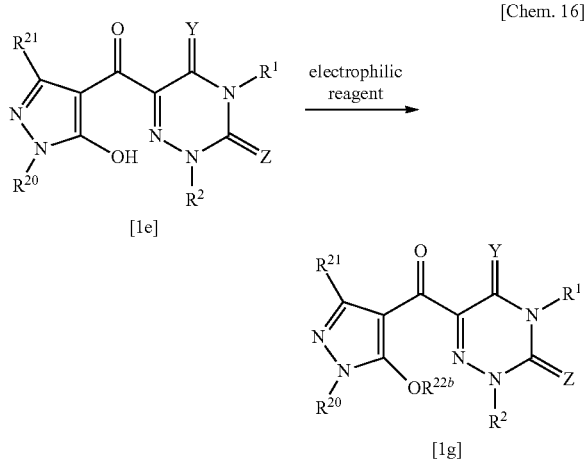

[1e]

[1g]

(in the formula, $R^1$, $R^2$, $R^{20}$, $R^{21}$, Y and Z each have the same definitions as above, $R^{22b}$ represents a hydroxycarbonyl group, a $C_1$-$C_6$ alkoxycarbonyl group, a benzyloxycarbonyl group which may be substituted with a substituent group selected from Substituent group α, a $C_1$-$C_6$ alkyl group, a $C_2$-$C_6$ alkenyl group, a $C_2$-$C_6$ alkynyl group, a $C_3$-$C_6$ cycloalkyl group, a cyanomethylene group, a $C_3$-$C_6$ cycloalkyl $C_1$-$C_6$ alkyl group, a $C_1$-$C_6$ alkylcarbonyl group, a $C_1$-$C_{10}$ alkylthiocarbonyl group, a $C_1$-$C_6$ haloalkylcarbonyl group, a $C_2$-$C_6$ alkenylcarbonyl group, a $C_2$-$C_6$ halolalkenylcarbonyl group, a $C_2$-$C_6$ alkynylcarbonyl group, a $C_2$-$C_6$ halolalkynylcarbonyl group, a $C_1$-$C_6$ alkoxycarbonyl $C_1$-$C_6$ alkyl group, a $C_1$-$C_{10}$ allylsulfonyl group, a phenyl group which may be substituted with a substituent group selected from Substituent group α, a benzyl group which may be substituted with a substituent group selected from Substituent group α, a phenylcarbonyl group which may be substituted with a substituent group selected from Substituent group α, a benzylcarbonyl group which may be substituted with a substituent group selected from Substituent group α, a phenylsulfonyl group which may be substituted with a substituent group selected from Substituent group α, a phenylcarbonyl $C_1$-$C_6$ alkyl group which may be substituted with a substituent group selected from Substituent group α, or a heterocyclic group having 3 to 10 carbon atoms and one or more heteroatoms that are the same or different from each other and selected from an oxygen atom, a sulfur atom, and a nitrogen atom [the group may be substituted with one substituent group selected from Substituent group α or 2 to 5 substituent groups that are the same or different from each other and selected from Substituent group α]).

Specifically, the compound of Formula 1g can be produced by reacting the compound of Formula 1e and an electrophilic reagent in a solvent, in the presence or absence of a base.

The electrophilic reagent that can be used indicates a compound represented by the formula $R^{22b}$-$L_a$ ($L_a$ represents a leaving group), and examples thereof include $C_1$-$C_6$ alkyl halide like methyl iodide and propyl chloride; benzyl halide like benzyl bromide; $C_1$-$C_6$ alkylcarbonyl halide like acetyl chloride and propionyl chloride; benzoyl halide like benzoyl chloride; $C_2$-$C_6$ alkenylcarbonyl halide like methacryl chloride and crotonyl chloride; $C_2$-$C_6$ alkynylcarbonyl halide like 4-pentinoyl chloride; $C_1$-$C_6$ alkyl sulfonyl halide methane sulfonyl chloride and ethane sulfonyl chloride; benzene sulfonyl halide like benzene sulfonyl chloride and p-toluene sulfonyl chloride; and di $C_1$-$C_6$ alkyl sulfate ester like dimethyl sulfate and diethyl sulfate. The use amount of the electrophilic reagent can be appropriately selected from the range of 0.1 to 10 mol per 1 mol of Formula 1e. Preferably, it is from 1.0 to 1.2 mol.

Examples of the base and the solvent which can be used for the present process include those described above for Process 1 of Production method 1.

The use amount of the base can be appropriately selected from the range of 0.1 to 10 mol per 1 mol of Formula 1e. Preferably, it is from 1.0 to 1.2 mol.

The reaction temperature is selected from the range of from −20° C. to the boiling point of an inert solvent used. Preferably, the reaction is carried out in the range of from 0° C. to 100° C.

The reaction time varies depending on the reaction temperature, the reaction substrates, the reaction amount, etc. In general, it is from 10 minutes to 48 hours.

After the completion of the reaction, the compound of Formula 1g, i.e., the target compound of this reaction, can be collected from the reaction system by general method, and if necessary, purified by a process like column chromatography and recrystallization.

<Production Method 8>

Compound of Formula 1h can be also produced by the method with the following reaction scheme.

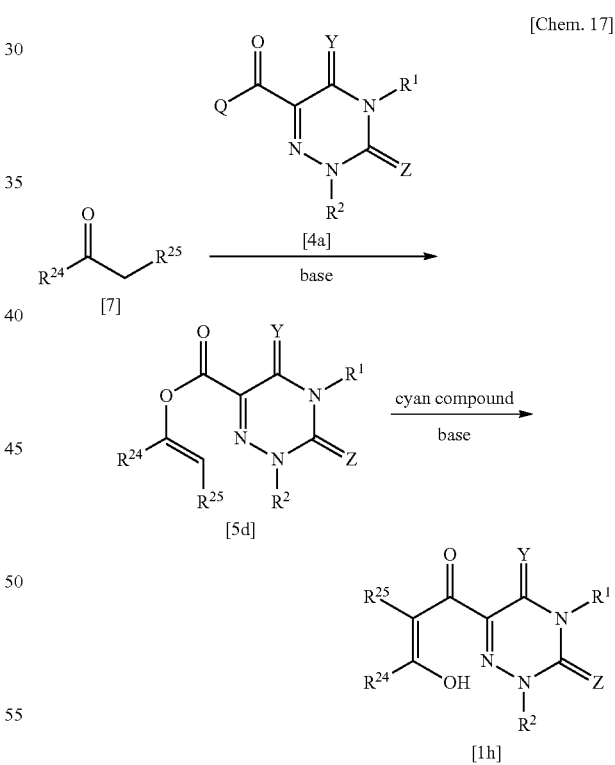

(in the formula, $R^1$, $R^2$, $R^{24}$, $R^{25}$, Y and Z each have the same definitions as above and Q represents a leaving group like a halogen atom, alkylcarbonyloxy group, an alkoxycarbonyloxy group, a haloalkylcarbonyloxy group, a haloalkoxycarbonyloxy group, a benzoyloxy group, a pyridyl group, and an imidazolyl group, as described above).

Specifically, the compound of Formula 5d can be produced by reacting the compound of Formula 7 and the compound of Formula 4a in a solvent, in the presence of a base, and the compound of Formula 1h can be produced by reacting the compound of Formula 5d and a cyano compound in the presence of a base.

In the above reaction, use amount of Formula 4a for preparing Formula 5d from Formula 7 can be appropriately selected from the range of 0.1 to 10 mol per 1 mol of Formula 7. Preferably, it is from 1.0 to 1.2 mol.

Examples of the base that can be used include those described above for Process 1 of Production method 1. Use amount of the base can be appropriately selected from the range of 0.1 to 10 mol per 1 mol of Formula 7. Preferably, it is from 1.0 to 1.2 mol.

Examples of the solvent that can be used include those described above for Process 1 of Production method 1.

Examples of the cyano compound which can be used for the reaction above for obtaining Formula 1h from Formula 5d include potassium cyanide, sodium cyanide, acetone cyanohydrin, hydrogen cyanide, and a polymer supported with hydrogen cyanide. The use amount of the cyano compound can be appropriately selected from the range of 0.01 to 1.0 mol per 1 mol of Formula 5d. Preferably, it is 0.05 to 0.2 mol.

Examples of the base that can be used include those described above for Process 1 of Production method 1. The use amount of the base can be appropriately selected from the range of 0.1 to 1.0 mol per 1 mol of Formula 5d. Preferably, it is 1.0 to 1.2 mol.

[Chem. 18]

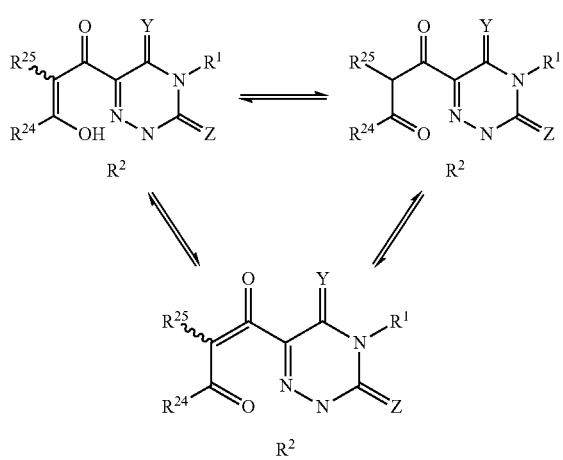

<Production Method 9>

Compound of Formula 11 can be produced by the method with the following reaction scheme.

[Chem. 19]

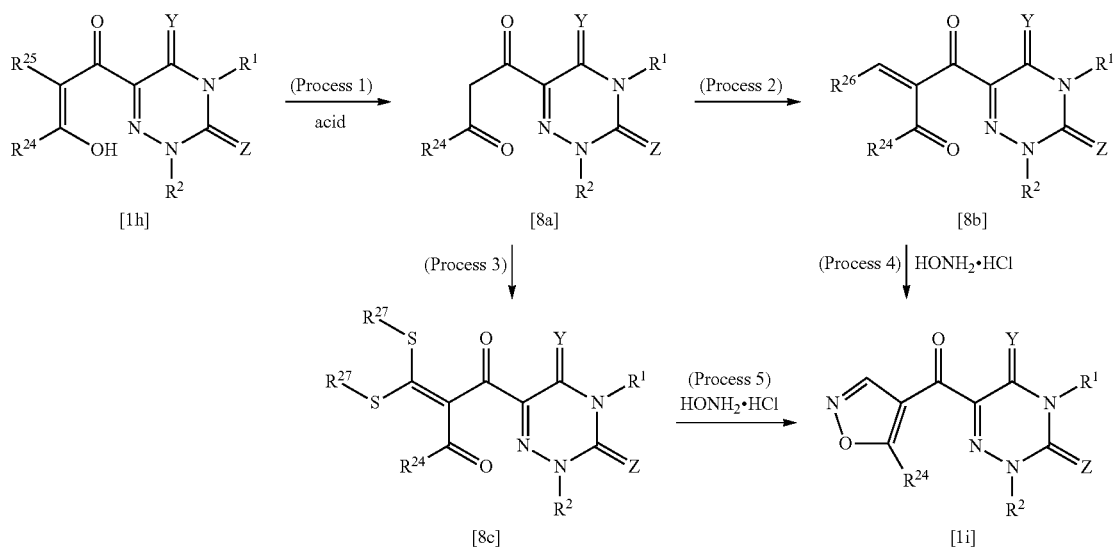

Examples of the solvent that can be used include those described above for Process 1 of Production method 1.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

After the completion of the reaction, the compound of Formula 1h, i.e., the target compound of this reaction, can be collected from the reaction system by general method, and if necessary, purified by a process like column chromatography and recrystallization.

Formula 1h of the invention has many tautomers shown below, and they are all included in the invention.

(in the formula, $R^1$, $R^2$, $R^{24}$, Y and Z each have the same definitions as above, $R^{25}$ represents a $C_1$-$C_6$ alkoxycarbonyl group, $R^{26}$ represents an alkoxy group, a haloalkoxy group, a cycloalkoxy group, or a dimethylamino group, and $R^{27}$ represents an alkyl group or a benzyl group).

(Process 1)

In this process, Formula 8a can be prepared by reacting Formula 1h and acid with or without using a solvent.

Examples of the acid that can be used for the present process include sulfonic acids like p-toluene sulfonic acid. Use amount of the acid can be appropriately selected from the range of 0.1 to 10 mol per 1 mol of Formula 1h. Preferably, it is from 1.0 to 1.2 mol.

Examples of the solvent that can be used include those described above for Process 1 of Production method 1.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

(Process 2)

By reacting Formula 8a and an ortho formic acid ester compound in N,N-dimethylacetamide dimethyl acetal compound or acetic anhydride, Formula 8b can be obtained. Use amount of N,N-dimethylacetamide dimethyl acetal and ortho formic acid ester can be appropriately selected from the range of 0.1 to 10 mol per 1 mol of Formula 8a. Preferably, it is from 1.0 to 3.0 mol.

The reaction temperature is selected from the range of from −20° C. to the boiling point of an inert solvent used. Preferably, the reaction is carried out in the range of from 0° C. to 150° C. The reaction time varies depending on the reaction temperature, the reaction substrates, the reaction amount, etc. In general, it is from 10 minutes to 48 hours.

(Process 3)

Formula 8c can be obtained by reacting Formula 8a and carbon disulfide, and without isolation, adding with alkyl halide like methyl iodide or benzyl halide like benzyl bromide. Use amount of carbon disulfide can be appropriately selected from the range of 0.1 to 10 mol per 1 mol of Formula 8a. Preferably, it is from 1.0 to 1.2 mol. Use amount of the halide can be appropriately selected from the range of 0.1 to 10 mol per 1 mol of Formula 8a. Preferably, it is 2.0 to 2.4 mol. Examples of the solvent that can be used for the present process include those described above for Process 1 of Production method 1.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

(Process 4 & Process 5)

Formula 1i can be obtained by reacting Formula 8b or Formula 8c obtained from Process 2 or Process 3 above and hydroxylamine chloride in a solvent.

Use amount of hydroxylamine chloride can be appropriately selected from the range of 0.1 to 10 mol per 1 mol of Formula 8b or Formula 8c. Preferably, it is from 1.0 to 1.2 mol.

Examples of the solvent that can be used for the present process include those described above for Process 1 of Production method 1.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

After the completion of the reaction, the compound of Formula 11, i.e., the target compound of this reaction, can be collected from the reaction system by general method, and if necessary, purified by a process like column chromatography and recrystallization.

Hereinbelow, a method of producing synthetic intermediates of the compounds of the invention is given.

<Production Method 10>

Compound of Formula 3b can be produced by the method with the following reaction scheme.

[Chem. 20]
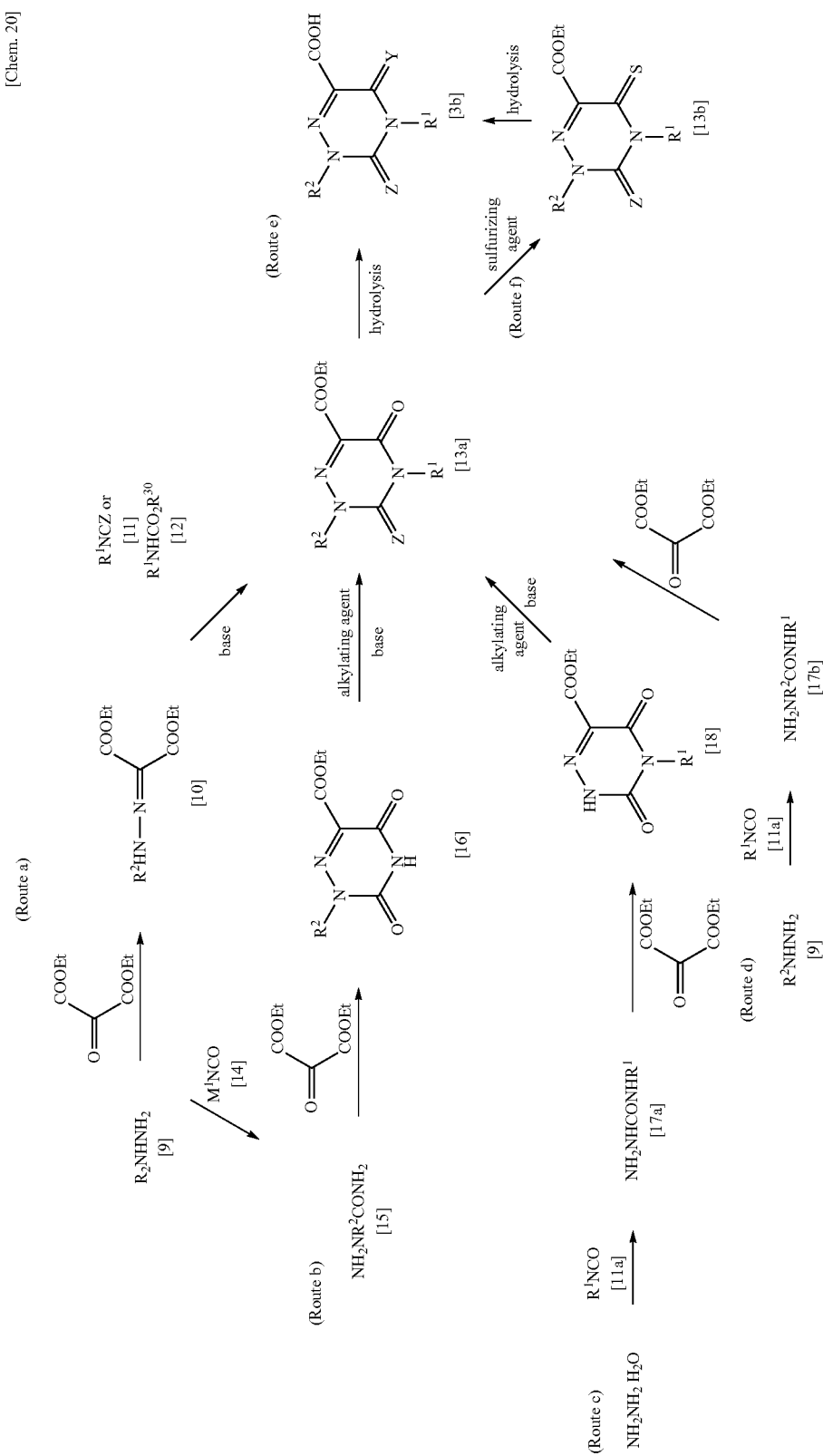

(in the formula, $R^1$, $R^2$, Y and Z each have the same definitions as above, $R^{30}$ represents a phenyl group or an alkyl group, and $M^1$ represents sodium, potassium or trimethylsilyl).

(Route a)

Specifically, compound of Formula 10 can be obtained by reacting the compound of Formula 9 and diethyl ketomalonate. In addition, compound of Formula 13a can be obtained by reacting the compound of Formula 10 and the compound of Formula 11 or the compound of Formula 12 in the presence of a base.

Use amount of diethyl ketomalonate for the process of producing Formula 10 from Formula 9 can be appropriately selected from the range of 1.0 to 1.5 mol per 1 mol of Formula 9. Preferably, it is from 1.0 to 1.2 mol.

Examples of the solvent that can be used for the present process include those described above for Process 1 of Production method 1.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

Use amount of the compound of Formula 11 or the compound of Formula 12 for the process of producing Formula 13a from Formula 10 can be appropriately selected from the range of 1.0 to 1.5 mol per 1 mol of Formula 10. Preferably, it is from 1.0 to 1.2 mol.

Examples of the base that can be used for the present process include those described above for Process 1 of Production method 1. Use amount of the base can be appropriately selected from the range of 0.1 to 10 mol per 1 mol of Formula 10. Preferably, it is from 1.0 to 1.2 mol.

Examples of the solvent that can be used for the present process include those described above for Process 1 of Production method 1.

The reaction temperature is selected from the range of from −20° C. to the boiling point of an inert solvent used. Preferably, the reaction is carried out in the range of from 0° C. to 100° C.

The reaction time varies depending on the reaction temperature, the reaction substrates, the reaction amount, etc. In general, it is from 10 minutes to 48 hours.

(Route b)

Specifically, compound of Formula 15 can be obtained by reacting the compound of Formula 9 and the compound of Formula 14. In addition, compound of Formula 16 can be obtained by reacting the compound of Formula 15 and diethyl ketomalonate. In addition, compound of Formula 13a can be obtained by reacting the compound of Formula 16 and an alkylating agent in the presence of a base.

Use amount of the compound of Formula 14 for the process of producing Formula 15 from Formula 9 can be appropriately selected from the range of 1.0 to 1.5 mol per 1 mol of Formula 9. Preferably, it is from 1.0 to 1.2 mol.

Examples of the solvent that can be used for the present process include those described above for Process 1 of Production method 1.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

Use amount of diethyl ketomalonate for the process of producing Formula 16 from Formula 15 can be appropriately selected from the range of 1.0 to 1.5 mol per 1 mol of Formula 15. Preferably, it is from 1.0 to 1.2 mol.

Examples of the solvent that can be used for the present process include those described above for Process 1 of Production method 1.

The reaction temperature is selected from the range of from −20° C. to the boiling point of an inert solvent used. Preferably, the reaction is carried out in the range of from 0° C. to 100° C.

The reaction time varies depending on the reaction temperature, the reaction substrates, the reaction amount, etc. In general, it is from 10 minutes to 48 hours.

Use amount of the alkylating agent for the process of producing Formula 13a from Formula 16 can be appropriately selected from the range of 1.0 to 3.0 mol per 1 mol of Formula 16. Preferably, it is from 1.0 to 1.5 mol.

Examples of the alkylating agent that can be used include alkyl sulfates like dimethyl sulfate and diethyl sulfate; alkyl halides like methyl iodide, ethyl iodide, benzyl chloride, benzyl bromide, propargyl bromide, ethyl bromoacetate, and chloroacetonitrile, and; sulfonic acid esters like ethoxyethyl p-toluene sulfonate and cyclopentylmethane sulfonate.

Examples of the base that can be used for the present process include those described above for Process 1 of Production method 1. Use amount of the base can be appropriately selected from the range of 0.1 to 10 mol per 1 mol of Formula 16. Preferably, it is from 1.0 to 1.2 mol.

Examples of the solvent that can be used for the present process include those described above for Process 1 of Production method 1.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

(Route c)

Specifically, compound of Formula 17a can be obtained by reacting the compound of Formula 11a and hydrazine hydrate. In addition, compound of Formula 18 can be obtained by reacting the compound of Formula 17 and diethyl ketomalonate. In addition, compound of Formula 13a can be obtained by reacting the compound of Formula 18 and an alkylating agent in the presence of a base.

Use amount of hydrazine hydrate for the process of producing Formula 17a from Formula 11a can be appropriately selected from the range of 1.0 to 1.5 mol per 1 mol of Formula 9. Preferably, it is from 1.0 to 1.2 mol.

Examples of the solvent that can be used for the present process include those described above for Process 1 of Production method 1.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

Use amount of diethyl ketomalonate for the process of producing Formula 18 from Formula 17a can be appropriately selected from the range of 1.0 to 1.5 mol per 1 mol of Formula 17a. Preferably, it is from 1.0 to 1.2 mol.

Examples of the solvent that can be used for the present process include those described above for Process 1 of Production method 1.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

Use amount of the alkylating agent for the process of producing Formula 13a from Formula 18 can be appropriately selected from the range of 1.0 to 3.0 mol per 1 mol of Formula 18. Preferably, it is from 1.0 to 1.5 mol.

Examples of the alkylating agent that can be used include alkyl sulfates like dimethyl sulfate and diethyl sulfate; alkyl halides like methyl iodide, ethyl iodide, benzyl chloride, benzyl bromide, propargyl bromide, ethyl bromoacetate, and chloroacetonitrile, and; sulfonic acid esters like ethoxyethyl p-toluene sulfonate and cyclopentylmethane sulfonate.

Examples of the base that can be used for the present process include those described above for Process 1 of Production method 1. Use amount of the base can be appropriately selected from the range of 0.1 to 10 mol per 1 mol of Formula 18. Preferably, it is from 1.0 to 1.2 mol.

Examples of the solvent that can be used for the present process include those described above for Process 1 of Production method 1.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

(Route d)

Specifically, compound of Formula 17b can be obtained by reacting the compound of Formula 11a and the compound of Formula 9. In addition, compound of Formula 13a can be obtained by reacting the compound of Formula 17b and diethyl ketomalonate, using an acid or a base depending on the condition.

Use amount of the compound of Formula 9 for the process of producing Formula 17b from Formula 11a can be appropriately selected from the range of 1.0 to 1.5 mol per 1 mol of Formula 9. Preferably, it is from 1.0 to 1.2 mol.

Examples of the acid that can be used include organic acids represented by organic sulfonic acid like p-toluene sulfonic acid, methane sulfonic acid, and benzene sulfonic acid; hydrogen halide acids represented by hydrochloric acid and hydrogen bromic acid, and; inorganic acids like sulfuric acid and phosphoric acid. These acids can be used either singly or in combination of two or more.

Examples of the base that can be used for the present process include those described above for Process 1 of Production method 1.

Examples of the solvent that can be used for the present process include those described above for Process 1 of Production method 1.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

Use amount of diethyl ketomalonate for the process of producing Formula 13a from Formula 17b can be appropriately selected from the range of 1.0 to 1.5 mol per 1 mol of Formula 17b. Preferably, it is from 1.0 to 1.2 mol.

Examples of the solvent that can be used for the present process include those described above for Process 1 of Production method 1.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

Examples of the acid include organic acids like p-toluene sulfonic acid.

Examples of the base include organic bases like triethylamine and 1,8-diazabicyclo[5.4.0]undec-7-ene (DBU) and inorganic bases like sodium hydride, sodium methoxide, and sodium ethoxide.

After the completion of the reaction, the compound of Formula 13a, i.e., the target compound of this reaction, can be collected from the reaction system by general method, and if necessary, purified by a process like column chromatography and recrystallization.

(Route e)

Specifically, compound of Formula 3b can be obtained by hydrolyzing the compound of Formula 13a.

With regard to the process of obtaining the compound of Formula 3b from the compound of Formula 13a, the production can be carried out by hydrolysis in water, organic solvent, or a mixture solvent in the presence of an acid or a base.

Examples of the base that can be used include those described above for Process 1 of Production method 1.

Use amount of the base can be appropriately selected from the range of 0.01 to 100 mol per 1 mol of Formula 13a. Preferably, it is 0.1 to 10 mol.

Examples of the acid that can be used include inorganic acids like hydrochloric acid, hydrobromic acid, and sulfuric acid, and organic acids like acetic acid and trifluoroacetic acid.

Use amount of the acid can be appropriately selected from the range of 1 mol to excess amount per 1 mol of Formula 13a. Preferably, it is from 1 to 100 mol.

Examples of the organic solvent that can be used include a mixture solvent of water and an organic solvent. Examples of the organic solvent include alcohols like methanol and ethanol, ether like tetrahydrofuran, ketones like acetone and methyl isobutyl ketone, amides like N,N-dimethyl formamide and N,N-dimethyl acetamide, sulfur compounds like dimethyl sulfoxide and sulfolane, acetonitrile, and their mixture.

Use amount of the solvent is 0.01 to 100 L per 1 mol of Formula 13a. Preferably, it is 0.1 to 10 L.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

(Route f)

Specifically, compound of Formula 13b can be obtained by reacting the compound of Formula 13a and a sulfurizing agent. In addition, the compound of Formula 3b can be obtained by hydrolyzing the compound of Formula 13b.

Use amount of the compound of the sulfurizing agent for the process of producing Formula 13b from Formula 13a can be appropriately selected from the range of 1.0 to 8.0 mol per 1 mol of Formula 13a. Preferably, it is from 1.0 to 4.0 mol.

Examples of the sulfurizing agent that can be used include diphosphorus pentoxide and 2,4-bis(4-methoxyphenyl)-1,3,2,4-dithiadiphosphetane-2,4-disulfide.

Use amount of the compound of the sulfurizing agent can be appropriately selected from the range of 1.0 to 8.0 mol per 1 mol of Formula 13a. Preferably, it is 0.1 to 4.0 mol.

Examples of the solvent that can be used include those described above for Process 1 of Production method 1.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

With regard to the process of obtaining the compound of Formula 3b from the compound of Formula 13b, the production can be carried out by hydrolysis in water, organic solvent, or a mixture solvent in the presence of an acid or a base.

Examples of the base that can be used include those described above for Process 1 of Production method 1.

Use amount of the base can be appropriately selected from the range of 0.01 to 100 mol per 1 mol of Formula 13b. Preferably, it is 0.1 to 10 mol.

Examples of the acid that can be used include inorganic acids like hydrochloric acid, hydrobromic acid, and sulfuric acid, and organic acids like acetic acid and trifluoroacetic acid.

Use amount of the acid can be appropriately selected from the range of 1 mol to excess amount per 1 mol of Formula 13b. Preferably, it is from 1 to 100 mol.

Examples of the organic solvent that can be used include a mixture solvent of water and an organic solvent. Examples of the organic solvent include alcohols like methanol and ethanol, ether like tetrahydrofuran, ketones like acetone and methyl isobutyl ketone, amides like N,N-dimethyl formamide and N,N-dimethyl acetamide, sulfur compounds like dimethyl sulfoxide and sulfolane, acetonitrile, and their mixture.

Use amount of the solvent is 0.01 to 100 L per 1 mol of Formula 13b. Preferably, it is 0.1 to 10 L.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

After the completion of the reaction, the compound of Formula 3b, i.e., the target compound of this reaction, can be collected from the reaction system by general method, and if necessary, purified by a process like column chromatography and recrystallization.

<Intermediate Synthesis Method 1>

Compound of Formula 3a can be produced according to the method with the following reaction scheme.

[Chem. 21]

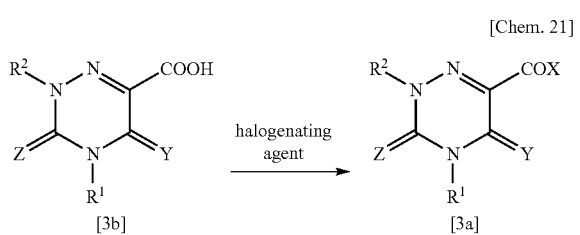

(in the formula, $R^1$, $R^2$, Y and Z each have the same definitions as above and X represents a chlorine or a bromine).

Specifically, Formula 3a can be produced by reacting Formula 3b and an appropriate halogenating agent with or without a solvent.

Examples of the halogenating agent that can be used include oxalyl chloride and thionyl chloride.

Use amount of the halogenating agent can be appropriately selected from the range of 0.01 to 20 mol per 1 mol of Formula 3b. Preferably, it is from 1 to 10 mol.

Examples of the solvent include halogenated hydrocarbons like dichloromethane and chloroform, ethers like diethyl ether and tetrahydrofuran, and aromatic hydrocarbons like benzene and toluene.

Use amount of the solvent is 0.01 to 100 L per 1 mol of Formula 3b. Preferably, it is 0.1 to 10 L.

The reaction temperature is selected from the range of from −20° C. to the boiling point of an inert solvent used. Preferably, the reaction is carried out in the range of from 0° C. to 100° C. The reaction time varies depending on the reaction temperature, the reaction substrates, the reaction amount, etc. In general, it is from 10 minutes to 48 hours.

After the completion of the reaction, the compound of Formula 3a, i.e., the target compound of this reaction, can be collected from the reaction system by general method, and if necessary, purified by a process like column chromatography and recrystallization.

Examples of the production intermediates [13a] and [3b], that can be described for the Production method 10, are shown in Table 44 to Table 67.

TABLE 44

| Compound No. | $R^1$ | $R^2$ | Y | Z |
|---|---|---|---|---|
| IV-1 | Me | Me | O | O |
| IV-2 | Et | Me | O | O |
| IV-3 | Pr-n | Me | O | O |
| IV-4 | Pr-i | Me | O | O |
| IV-5 | Bu-n | Me | O | O |
| IV-6 | Bu-i | Me | O | O |
| IV-7 | Bu-s | Me | O | O |
| IV-8 | Bu-t | Me | O | O |
| IV-9 | Hex-n | Me | O | O |
| IV-10 | $CH_2CF_3$ | Me | O | O |
| IV-11 | $CH_2CH=CH_2$ | Me | O | O |
| IV-12 | $CH_2C(Me)=CH_2$ | Me | O | O |
| IV-13 | $CH_2CH_2CH=CMe_2$ | Me | O | O |
| IV-14 | $CH_2C≡CH$ | Me | O | O |
| IV-15 | $CH_2C≡CCH_3$ | Me | O | O |
| IV-16 | Pr-c | Me | O | O |
| IV-17 | Bu-c | Me | O | O |
| IV-18 | Pen-c | Me | O | O |
| IV-19 | Hex-c | Me | O | O |
| IV-20 | $CH_2Pr-c$ | Me | O | O |
| IV-21 | $CH_2Bu-c$ | Me | O | O |
| IV-22 | $CH_2Pen-c$ | Me | O | O |
| IV-23 | $CH_2Hex-c$ | Me | O | O |
| IV-24 | $CH_2CH=CCl_2$ | Me | O | O |
| IV-25 | $CH_2CCl=CHCl$ | Me | O | O |
| IV-26 | $CH_2CH_2CH=CCl_2$ | Me | O | O |
| IV-27 | $CH_2CH_2C(Me)=CF_2$ | Me | O | O |
| IV-28 | $CH_2CH_2CH_2CH_2C(Me)=CF_2$ | Me | O | O |
| IV-29 | $CH_2CH=CF_2$ | Me | O | O |
| IV-30 | $CH_2CH_2OMe$ | Me | O | O |
| IV-31 | $CH_2CH_2OEt$ | Me | O | O |
| IV-32 | $CH(Me)CH_2OMe$ | Me | O | O |
| IV-33 | $CH_2CH_2OCH_2CH_2OMe$ | Me | O | O |
| IV-34 | $CH_2CH_2OPr-n$ | Me | O | O |
| IV-35 | $CH_2CH_2OPr-i$ | Me | O | O |
| IV-36 | $CH_2CH_2OPr-c$ | Me | O | O |

TABLE 45

| Compound No. | R¹ | R² | Y | Z |
|---|---|---|---|---|
| IV-37 | CH$_2$CH$_2$OBu-c | Me | O | O |
| IV-38 | CH$_2$CH$_2$OPen-c | Me | O | O |
| IV-39 | CH$_2$CH$_2$OHex-c | Me | O | O |
| IV-40 | CH$_2$CH$_2$OCH$_2$CF$_3$ | Me | O | O |
| IV-41 | CH$_2$CH$_2$CH$_2$OMe | Me | O | O |
| IV-42 | CH=CHMe | Me | O | O |
| IV-43 | CH$_2$SMe | Me | O | O |
| IV-44 | CH$_2$SPr-n | Me | O | O |
| IV-45 | CH$_2$CH$_2$SMe | Me | O | O |
| IV-46 | CH$_2$SOMe | Me | O | O |
| IV-47 | CH$_2$SO$_2$Me | Me | O | O |
| IV-48 | CH$_2$CH$_2$CH$_2$SMe | Me | O | O |
| IV-49 | CH$_2$CH$_2$CH$_2$SO$_2$Me | Me | O | O |
| IV-50 | Ph | Me | O | O |
| IV-51 | Ph(2-Cl) | Me | O | O |
| IV-52 | Ph(3-Cl) | Me | O | O |
| IV-53 | Ph(4-Cl) | Me | O | O |
| IV-54 | Ph(2-F) | Me | O | O |
| IV-55 | Ph(3-F) | Me | O | O |
| IV-56 | Ph(4-F) | Me | O | O |
| IV-57 | Ph(2-Me) | Me | O | O |
| IV-58 | Ph(3-Me) | Me | O | O |
| IV-59 | Ph(4-Me) | Me | O | O |
| IV-60 | Ph(2-OMe) | Me | O | O |
| IV-61 | Ph(3-OMe) | Me | O | O |
| IV-62 | Ph(4-OMe) | Me | O | O |
| IV-63 | Ph(2-CF$_3$) | Me | O | O |
| IV-64 | Ph(3-CF$_3$) | Me | O | O |
| IV-65 | Ph(4-CF$_3$) | Me | O | O |
| IV-66 | Ph(2-NO$_2$) | Me | O | O |
| IV-67 | Ph(3-NO$_2$) | Me | O | O |
| IV-68 | Ph(4-NO$_2$) | Me | O | O |
| IV-69 | Ph(2-OCF$_3$) | Me | O | O |
| IV-70 | Ph(3-OCF$_3$) | Me | O | O |
| IV-71 | Ph(4-OCF$_3$) | Me | O | O |
| IV-72 | Ph(2-CN) | Me | O | O |
| IV-73 | Ph(3-CN) | Me | O | O |
| IV-74 | Ph(4-CN) | Me | O | O |
| IV-75 | Ph(3,4-F$_2$) | Me | O | O |

TABLE 46

| Compound No. | R¹ | R² | Y | Z |
|---|---|---|---|---|
| IV-76 | Ph(3,5-F$_2$) | Me | O | O |
| IV-77 | Ph(2,3-F$_2$) | Me | O | O |
| IV-78 | Ph(2,4-F$_2$) | Me | O | O |
| IV-79 | Ph(2,5-F$_2$) | Me | O | O |
| IV-80 | Ph(2,6-F$_2$) | Me | O | O |
| IV-81 | Ph(3,4-Cl$_2$) | Me | O | O |
| IV-82 | Ph(3,5-Cl$_2$) | Me | O | O |
| IV-83 | Ph(2,3-Cl$_2$) | Me | O | O |
| IV-84 | Ph(2,4-Cl$_2$) | Me | O | O |
| IV-85 | Ph(2,5-Cl$_2$) | Me | O | O |
| IV-86 | Ph(2,6-Cl$_2$) | Me | O | O |
| IV-87 | Ph(3,4-Me$_2$) | Me | O | O |
| IV-88 | Ph(3,5-Me$_2$) | Me | O | O |
| IV-89 | Ph(2,3-Me$_2$) | Me | O | O |
| IV-90 | Ph(2,4-Me$_2$) | Me | O | O |
| IV-91 | Ph(2,5-Me$_2$) | Me | O | O |
| IV-92 | Ph(2,6-Me$_2$) | Me | O | O |
| IV-93 | Ph(3,4-(OMe)$_2$) | Me | O | O |
| IV-94 | Ph(3,5-(OMe)$_2$) | Me | O | O |
| IV-95 | Ph(2,3-(OMe)$_2$) | Me | O | O |
| IV-96 | Ph(2,4-(OMe)$_2$) | Me | O | O |
| IV-97 | Ph(2,5-(OMe)$_2$) | Me | O | O |
| IV-98 | Ph(2,6-(OMe)$_2$) | Me | O | O |
| IV-99 | Ph(2-F-4-OMe) | Me | O | O |
| IV-100 | Ph(3-F-5-OMe) | Me | O | O |
| IV-101 | Ph(2-F-3-OMe) | Me | O | O |
| IV-102 | Ph(2-F-4-OMe) | Me | O | O |
| IV-103 | Ph(2-F-5-OMe) | Me | O | O |
| IV-104 | Ph(2-F-6-OMe) | Me | O | O |
| IV-105 | Ph(3-F-4-Me) | Me | O | O |
| IV-106 | Ph(3-F-5-Me) | Me | O | O |
| IV-107 | Ph(2-F-3-Me) | Me | O | O |
| IV-108 | Ph(2-F-4-Me) | Me | O | O |
| IV-109 | Ph(2-F-5-Me) | Me | O | O |
| IV-110 | Ph(2-F-6-Me) | Me | O | O |
| IV-111 | Ph(3-OMe-4-F) | Me | O | O |
| IV-112 | Ph(2-OMe-3-F) | Me | O | O |
| IV-113 | Ph(2-OMe-4-F) | Me | O | O |
| IV-114 | Ph(2-OMe-5-F) | Me | O | O |

TABLE 47

| Compound No. | R¹ | R² | Y | Z |
|---|---|---|---|---|
| IV-115 | Ph(3-Me-4-F) | Me | O | O |
| IV-116 | Ph(2-Me-3-F) | Me | O | O |
| IV-117 | Ph(2-Me-4-F) | Me | O | O |
| IV-118 | Ph(2-Me-5-F) | Me | O | O |
| IV-119 | Ph(3-Cl-4-OMe) | Me | O | O |
| IV-120 | Ph(3-Cl-5-OMe) | Me | O | O |
| IV-121 | Ph(2-Cl-3-OMe) | Me | O | O |
| IV-122 | Ph(2-Cl-4-OMe) | Me | O | O |
| IV-123 | Ph(2-Cl-5-OMe) | Me | O | O |
| IV-124 | Ph(2-Cl-6-OMe) | Me | O | O |
| IV-125 | Ph(3-Cl-4-Me) | Me | O | O |
| IV-126 | Ph(3-Cl-5-Me) | Me | O | O |
| IV-127 | Ph(2-Cl-3-Me) | Me | O | O |
| IV-128 | Ph(2-Cl-4-Me) | Me | O | O |
| IV-129 | Ph(2-Cl-5-Me) | Me | O | O |
| IV-130 | Ph(2-Cl-6-Me) | Me | O | O |
| IV-131 | Ph(3-OMe-4-Cl) | Me | O | O |
| IV-132 | Ph(2-OMe-3-Cl) | Me | O | O |
| IV-133 | Ph(2-OMe-4-Cl) | Me | O | O |
| IV-134 | Ph(2-OMe-5-Cl) | Me | O | O |
| IV-135 | Ph(3-Me-4-Cl) | Me | O | O |
| IV-136 | Ph(2-Me-3-Cl) | Me | O | O |
| IV-137 | Ph(2-Me-4-Cl) | Me | O | O |
| IV-138 | Ph(2-Me-5-Cl) | Me | O | O |
| IV-139 | Ph(3-F-4-Cl) | Me | O | O |
| IV-140 | Ph(3-F-5-Cl) | Me | O | O |
| IV-141 | Ph(2-F-3-Cl) | Me | O | O |
| IV-142 | Ph(2-F-4-Cl) | Me | O | O |
| IV-143 | Ph(2-F-5-Cl) | Me | O | O |
| IV-144 | Ph(2-F-6-Cl) | Me | O | O |
| IV-145 | Ph(3-Cl-4-F) | Me | O | O |
| IV-146 | Ph(2-Cl-3-F) | Me | O | O |
| IV-147 | Ph(2-Cl-4-F) | Me | O | O |
| IV-148 | Ph(2-Cl-5-F) | Me | O | O |
| IV-149 | Ph(3-Me-4-OMe) | Me | O | O |
| IV-150 | Ph(3-Me-5-OMe) | Me | O | O |
| IV-151 | Ph(2-Me-3-OMe) | Me | O | O |
| IV-152 | Ph(2-Me-4-OMe) | Me | O | O |
| IV-153 | Ph(2-Me-5-OMe) | Me | O | O |

TABLE 48

| Compound No. | R¹ | R² | Y | Z |
|---|---|---|---|---|
| IV-154 | Ph(2-Me-6-OMe) | Me | O | O |
| IV-155 | Ph(3-OMe-4-Me) | Me | O | O |
| IV-156 | Ph(2-OMe-3-Me) | Me | O | O |
| IV-157 | Ph(2-OMe-4-Me) | Me | O | O |
| IV-158 | Ph(2-OMe-5-Me) | Me | O | O |
| IV-159 | Ph(3-CN-4-OMe) | Me | O | O |
| IV-160 | Ph(3-OMe-4-CN) | Me | O | O |
| IV-161 | Ph(3-Me-4-CN) | Me | O | O |
| IV-162 | Ph(3-CN-4-Me) | Me | O | O |
| IV-163 | Ph(3-NO$_2$-4-OMe) | Me | O | O |
| IV-164 | Ph(3-OMe-4-NO$_2$) | Me | O | O |
| IV-165 | Ph(3-Me-4-NO$_2$) | Me | O | O |
| IV-166 | Ph(3-NO$_2$-4-Me) | Me | O | O |
| IV-167 | Ph(3,5-F$_2$-5-OMe) | Me | O | O |
| IV-168 | Ph(3,5-F$_2$-5-Me) | Me | O | O |
| IV-169 | Ph(3,4,5-(OMe)$_3$) | Me | O | O |

TABLE 48-continued

| Compound No. | R¹ | R² | Y | Z |
|---|---|---|---|---|
| IV-170 | 6-methylbenzo[d][1,3]dioxole | Me | O | O |
| IV-171 | 7-methyl-2,3-dihydrobenzo[b][1,4]dioxine | Me | O | O |
| IV-172 | 6-methyl-2,3-dihydrobenzofuran | Me | O | O |
| IV-173 | 6-methylchroman | Me | O | O |
| IV-174 | 5-methyl-2,3-dihydrobenzofuran | Me | O | O |
| IV-175 | 6-methylchroman (isomer) | Me | O | O |
| IV-176 | 6-methyl-2,3-dihydrobenzo[b][1,4]oxathiine | Me | O | O |
| IV-177 | 6-methylbenzo[d][1,3]oxathiole | Me | O | O |

TABLE 49

| Compound No. | R¹ | R² | Y | Z |
|---|---|---|---|---|
| IV-178 | 6-methyl-4-methyl-2H-benzo[b][1,4]oxazin-3(4H)-one | Me | O | O |
| IV-179 | 2-methylpyridine | Me | O | O |
| IV-180 | 3-methylpyridine | Me | O | O |
| IV-181 | 4-methylpyridine | Me | O | O |
| IV-182 | 2,5-dimethylpyridine | Me | O | O |
| IV-183 | 5-methoxy-2-methylpyridine | Me | O | O |
| IV-184 | 5-fluoro-2-methylpyridine | Me | O | O |
| IV-185 | 5-chloro-2-methylpyridine | Me | O | O |
| IV-186 | 5-bromo-2-methylpyridine | Me | O | O |
| IV-187 | 2-methyl-5-(trifluoromethyl)pyridine | Me | O | O |
| IV-188 | 3,5-dimethylisoxazole | Me | O | O |
| IV-189 | 3,5-dimethylisoxazole (isomer) | Me | O | O |
| IV-190 | 5-methyl-4,5-dihydroisoxazole | Me | O | O |
| IV-191 | 3,5-dimethyl-4,5-dihydroisoxazole | Me | O | O |

TABLE 50

| Compound No. | R¹ | R² | Y | Z |
|---|---|---|---|---|
| IV-192 | 3-methyl-4,5-dihydroisoxazole | Me | O | O |

TABLE 50-continued

| Compound No. | R¹ | R² | Y | Z |
|---|---|---|---|---|
| IV-193 | 3-methyl-5-methyl-isoxazoline | Me | O | O |
| IV-194 | 2-methylthiazole | Me | O | O |
| IV-195 | 2,5-dimethylthiazole | Me | O | O |
| IV-196 | 2,4-dimethylthiazole | Me | O | O |
| IV-197 | 2,4,5-trimethylthiazole | Me | O | O |
| IV-198 | 2-thienyl | Me | O | O |
| IV-199 | 3-thienyl | Me | O | O |
| IV-200 | 5-methyl-2-thienyl | Me | O | O |
| IV-201 | 2,5-dimethyl-3-thienyl | Me | O | O |
| IV-202 | morpholino | Me | O | O |
| IV-203 | thiomorpholino | Me | O | O |
| IV-204 | 1,1-dioxo-thiomorpholino | Me | O | O |

TABLE 51

| Compound No. | R¹ | R² | Y | Z |
|---|---|---|---|---|
| IV-205 | CH₂Ph | Me | O | O |
| IV-206 | CH₂CH₂Ph | Me | O | O |
| IV-207 | CH₂CH₂CH₂Ph | Me | O | O |
| IV-208 | CH₂CH=CHPh | Me | O | O |
| IV-209 | CH₂C≡CPh | Me | O | O |
| IV-210 | CH₂CH=NOMe | Me | O | O |
| IV-211 | CH₂CH=NOEt | Me | O | O |
| IV-212 | CH₂CH=NOPr-n | Me | O | O |

TABLE 51-continued

| Compound No. | R¹ | R² | Y | Z |
|---|---|---|---|---|
| IV-213 | CH₂CH=NOPh | Me | O | O |
| IV-214 | CH₂CH(OMe)₂ | Me | O | O |
| IV-215 | CH₂CHO | Me | O | O |
| IV-216 | NH₂ | Me | O | O |
| IV-217 | NHMe | Me | O | O |
| IV-218 | NHEt | Me | O | O |
| IV-219 | NHPr-n | Me | O | O |
| IV-220 | NHPr-i | Me | O | O |
| IV-221 | NHBu-n | Me | O | O |
| IV-222 | NHBu-i | Me | O | O |
| IV-223 | NHBu-s | Me | O | O |
| IV-224 | NHCH₂Pr-c | Me | O | O |
| IV-225 | NHPen-n | Me | O | O |
| IV-226 | NHHex-n | Me | O | O |
| IV-227 | NHCH₂CH₂CH₂Cl | Me | O | O |
| IV-228 | NHCH₂CH₂CH₂F | Me | O | O |
| IV-229 | NHCH₂CH₂OMe | Me | O | O |
| IV-230 | NMe₂ | Me | O | O |
| IV-231 | NEt₂ | Me | O | O |
| IV-232 | N(Pr-n)₂ | Me | O | O |
| IV-233 | N(Bu-n)₂ | Me | O | O |
| IV-234 | N(Me)Et | Me | O | O |
| IV-235 | N(Me)CH₂CH₂OMe | Me | O | O |
| IV-236 | NHPh | Me | O | O |
| IV-237 | NHCH₂Ph | Me | O | O |
| IV-238 | N=CMe₂ | Me | O | O |
| IV-239 | N=CEt₂ | Me | O | O |
| IV-240 | N=CHNMe₂ | Me | O | O |
| IV-241 | NHC(=O)Me | Me | O | O |
| IV-242 | N[C(=O)Me]₂ | Me | O | O |
| IV-243 | NHC(=O)OMe | Me | O | O |
| IV-244 | N[C(=O)OMe]₂ | Me | O | O |
| IV-245 | NHSO₂Me | Me | O | O |

TABLE 52

| Compound No. | R¹ | R² | Y | Z |
|---|---|---|---|---|
| IV-246 | NHSO₂Ph | Me | O | O |
| IV-247 | NHSO₂CH₂Ph | Me | O | O |
| IV-248 | OMe | Me | O | O |
| IV-249 | OEt | Me | O | O |
| IV-250 | OPr-n | Me | O | O |
| IV-251 | OPr-i | Me | O | O |
| IV-252 | OCH2Pr-c | Me | O | O |
| IV-253 | OCH₂Cl | Me | O | O |
| IV-254 | OCHCl₂ | Me | O | O |
| IV-255 | OCCl₃ | Me | O | O |
| IV-256 | OCH₂F | Me | O | O |
| IV-257 | OCHF₂ | Me | O | O |
| IV-258 | OCF₃ | Me | O | O |
| IV-259 | Ph | Et | O | O |
| IV-260 | Ph | Pr-i | O | O |
| IV-261 | Ph | CHF₂ | O | O |
| IV-262 | Ph | Ph | O | O |
| IV-263 | Ph | Me | O | S |
| IV-264 | Ph | Me | S | S |
| IV-265 | Me | Me | O | S |
| IV-266 | Me | Me | S | S |
| IV-267 | Ph | Me | O | O |
| IV-268 | Ph(4-OEt) | Me | O | O |
| IV-269 | Ph(2-Ph) | Me | O | O |
| IV-270 | Ph(3-Ph) | Me | O | O |
| IV-271 | Ph(4-Ph) | Me | O | O |
| IV-272 | 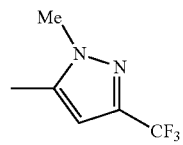 1,5-dimethyl-3-(trifluoromethyl)-pyrazol-1-yl | Me | O | O |

TABLE 52-continued

| Compound No. | R¹ | R² | Y | Z |
|---|---|---|---|---|
| IV-273 | 2-methyl-4,6-dimethoxypyrimidin-yl | Me | O | O |
| IV-274 | Me | 6-methylpyridin-2-yl | O | O |
| IV-275 | Et | 6-methylpyridin-2-yl | O | O |
| IV-276 | 2-chloro-3-methylpyridin-yl | Me | O | O |

TABLE 53

| Compound No. | R¹ | R² | Y | Z |
|---|---|---|---|---|
| IV-277 | 2-methyl-3-methylpyridin-yl | Me | O | O |
| IV-278 | 3,5-dimethylpyridin-yl | Me | O | O |
| IV-279 | 2,6-dimethylpyridin-yl | Me | O | O |
| IV-280 | 6-chloro-3-methylpyridin-yl | Me | O | O |
| IV-281 | 6-bromo-4-methylpyridin-yl | Me | O | O |
| IV-282 | Ph(2-Me-4-Br) | Me | O | O |
| IV-283 | Ph(2-Me-4-I) | Me | O | O |
| IV-284 | Ph(2-Me-4-CF₃) | Me | O | O |
| IV-285 | Ph(2-Me-4-OCF₃) | Me | O | O |
| IV-286 | Ph(2-Pr-i) | Me | O | O |
| IV-287 | 2-chloro-3-methylpyridin-yl | Me | O | O |
| IV-288 | Ph(2-Et) | Me | O | O |

TABLE 53-continued

| Compound No. | R¹ | R² | Y | Z |
|---|---|---|---|---|
| IV-289 | 2-methyl-3-methylpyridin-yl | Me | O | O |
| IV-290 | 3,5-dimethylpyridin-yl | Me | O | O |
| IV-291 | 2,6-dimethylpyridin-yl | Me | O | S |
| IV-292 | 6-chloro-3-methylpyridin-yl | Me | O | O |
| IV-293 | 6-bromo-4-methylpyridin-yl | Me | O | O |
| IV-294 | CH₂COOBu-t | Me | O | O |
| IV-295 | (C₇H₁₄)CH₃ | Me | O | O |
| IV-296 | (C₉H₁₈)CH₃ | Me | O | O |
| IV-297 | Ph(2-F, 4-Cl, 5-OMe) | Me | O | O |
| IV-298 | Ph(2,3,4-(OMe)₃) | Me | O | O |
| IV-299 | Ph(3,5-Cl₂-4-OMe) | Me | O | O |
| IV-300 | Ph(3,5-Cl₂-4-SMe) | Me | O | O |

TABLE 54

| Compound No. | R¹ | R² | Y | Z |
|---|---|---|---|---|
| IV-301 | Ph(3,5-Cl₂-4-SO₂Me) | Me | O | O |
| IV-302 | Ph(3,4,5-F₃) | Me | O | O |
| IV-303 | cyclohexenyl | Me | O | O |
| IV-304 | N-methylpiperidinyl | Me | O | O |
| IV-305 | 3-hydroxy-6-methylpyridazin-yl | Me | O | O |
| IV-306 | Bu-n | 6-methylpyridin-2-yl | O | O |
| IV-307 | CH₂CH(CH₃)₂ | 6-methylpyridin-2-yl | O | O |
| IV-308 | Ph | Pen-n | O | O |
| IV-309 | H | Me | O | O |
| IV-310 | CH₂C≡CF | Me | O | O |

TABLE 54-continued

| Compound No. | R¹ | R² | Y | Z |
|---|---|---|---|---|
| IV-311 | (Cl,Cl-cyclopropyl) | Me | O | O |
| IV-312 | (Et, Cl, Cl-cyclopropyl) | Me | O | O |
| IV-313 | $CH_2NH_2$ | Me | O | O |
| IV-314 | $CH_2NO_2$ | Me | O | O |
| IV-315 | $CH_2NHCH_3$ | Me | O | O |
| IV-316 | $CH_2N(CH_3)_2$ | Me | O | O |
| IV-317 | $CH_2SCH_2CF_3$ | Me | O | O |
| IV-318 | $CH_2SOCH_2CF_3$ | Me | O | O |
| IV-319 | $CH_2SO_2CH_2CF_3$ | Me | O | O |
| IV-320 | $CH_2OH$ | Me | O | O |
| IV-321 | $CH_2OBn$ | Me | O | O |
| IV-322 | $CH_2OCH_2Pr\text{-}c$ | Me | O | O |
| IV-323 | $CH_2OPh$ | Me | O | O |
| IV-324 | $CH_2SPh$ | Me | O | O |
| IV-325 | $CH_2SOPh$ | Me | O | O |
| IV-326 | $CH_2SO_2Ph$ | Me | O | O |
| IV-327 | $CH_2CON(CH_3)_2$ | Me | O | O |
| IV-328 | $CH_2COCH_3$ | Me | O | O |
| IV-329 | $CH_2OCOCH_3$ | Me | O | O |

TABLE 55

| Compound No. | R¹ | R² | Y | Z |
|---|---|---|---|---|
| IV-330 | $CH_2ON=CHCH_3$ | Me | O | O |
| IV-331 | $C_2H_4OC_2H_4SCH_3$ | Me | O | O |
| IV-332 | $C_2H_4OC_2H_4SOCH_3$ | Me | O | O |
| IV-333 | $C_2H_4OC_2H_4SO_2CH_3$ | Me | O | O |
| IV-334 | $CH_2OCH_2CN$ | Me | O | O |
| IV-335 | $CH_2CN$ | Me | O | O |
| IV-336 | $OCH_2CH=CH_2$ | Me | O | O |
| IV-337 | $OCH_2C\equiv CH$ | Me | O | O |
| IV-338 | $OPr\text{-}c$ | Me | O | O |
| IV-339 | $CH_2$-(tetrahydrofuran-2-yl) | Me | O | O |
| IV-340 | $CH_2$-(3-Me-isoxazolin-5-yl) | Me | O | O |
| IV-341 | $CH_2$-(3-Me-isoxazol-5-yl) | Me | O | O |
| IV-342 | $CH_2OCH_2$-(tetrahydrofuran-2-yl) | Me | O | O |
| IV-343 | $CH_2CH_2OCH_2CH_2O$-(pyridin-2-yl) | Me | O | O |
| IV-344 | Ph | H | O | O |
| IV-345 | Ph | $CH_2CH=CH_2$ | O | O |
| IV-346 | Ph | $CH_2C\equiv CH$ | O | O |
| IV-347 | Ph | Pr-c | O | O |
| IV-348 | Ph | $CH_2CH=CF_2$ | O | O |
| IV-349 | Ph | $CH_2C=CF$ | O | O |
| IV-350 | Ph | $C_2H_4OCH_3$ | O | O |
| IV-351 | Ph | $C_2H_4OC_2H_5$ | O | O |
| IV-352 | Ph | $CH(Me)OEt$ | O | O |
| IV-353 | Ph | $CH_2OPr\text{-}c$ | O | O |
| IV-354 | Ph | $CH(OCH_3)_2$ | O | O |
| IV-355 | Ph | $CH_2Ph$ | O | O |
| IV-356 | Ph | $CH=CH-Ph$ | O | O |
| IV-357 | Ph | $C\equiv C-Ph$ | O | O |

TABLE 56

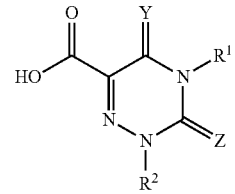

| Compound No. | R¹ | R² | Y | Z |
|---|---|---|---|---|
| V-1 | Me | Me | O | O |
| V-2 | Et | Me | O | O |
| V-3 | Pr-n | Me | O | O |
| V-4 | Pr-i | Me | O | O |
| V-5 | Bu-n | Me | O | O |
| V-6 | Bu-i | Me | O | O |
| V-7 | Bu-s | Me | O | O |
| V-8 | Bu-t | Me | O | O |
| V-9 | Hex-n | Me | O | O |
| V-10 | $CH_2CF_3$ | Me | O | O |
| V-11 | $CH_2CH=CH_2$ | Me | O | O |
| V-12 | $CH_2C(Me)=CH_2$ | Me | O | O |
| V-13 | $CH_2CH_2CH=CMe_2$ | Me | O | O |
| V-14 | $CH_2C\equiv CH$ | Me | O | O |
| V-15 | $CH_2C\equiv CCH_3$ | Me | O | O |
| V-16 | Pr-c | Me | O | O |
| V-17 | Bu-c | Me | O | O |
| V-18 | Pen-c | Me | O | O |
| V-19 | Hex-c | Me | O | O |
| V-20 | $CH_2Pr\text{-}c$ | Me | O | O |
| V-21 | $CH_2Bu\text{-}c$ | Me | O | O |
| V-22 | $CH_2Pen\text{-}c$ | Me | O | O |
| V-23 | $CH_2Hex\text{-}c$ | Me | O | O |
| V-24 | $CH_2CH=CCl_2$ | Me | O | O |
| V-25 | $CH_2CCl=CHCl$ | Me | O | O |
| V-26 | $CH_2CH_2CH=CCl_2$ | Me | O | O |
| V-27 | $CH_2CH_2C(Me)=CF_2$ | Me | O | O |
| V-28 | $CH_2CH_2CH_2CH_2C(Me)=CF_2$ | Me | O | O |
| V-29 | $CH_2CH=CF_2$ | Me | O | O |
| V-30 | $CH_2CH_2OMe$ | Me | O | O |
| V-31 | $CH_2CH_2OEt$ | Me | O | O |
| V-32 | $CH(Me)CH_2OMe$ | Me | O | O |
| V-33 | $CH_2CH_2OCH_2CH_2OMe$ | Me | O | O |
| V-34 | $CH_2CH_2OPr\text{-}n$ | Me | O | O |
| V-35 | $CH_2CH_2OPr\text{-}i$ | Me | O | O |
| V-36 | $CH_2CH_2OPr\text{-}c$ | Me | O | O |
| V-37 | $CH_2CH_2OBu\text{-}c$ | Me | O | O |
| V-38 | $CH_2CH_2OPen\text{-}c$ | Me | O | O |

TABLE 57

| Compound No. | R¹ | R² | Y | Z |
|---|---|---|---|---|
| V-39 | $CH_2CH_2OHex\text{-}c$ | Me | O | O |
| V-40 | $CH_2CH_2OCH_2CF_3$ | Me | O | O |
| V-41 | $CH_2CH_2CH_2OMe$ | Me | O | O |

TABLE 57-continued

| Compound No. | R¹ | R² | Y | Z |
|---|---|---|---|---|
| V-42 | CH=CHMe | Me | O | O |
| V-43 | CH$_2$SMe | Me | O | O |
| V-44 | CH$_2$SPr-n | Me | O | O |
| V-45 | CH$_2$CH$_2$SMe | Me | O | O |
| V-46 | CH$_2$SOMe | Me | O | O |
| V-47 | CH$_2$SO$_2$Me | Me | O | O |
| V-48 | CH$_2$CH$_2$CH$_2$SMe | Me | O | O |
| V-49 | CH$_2$CH$_2$CH$_2$SO$_2$Me | Me | O | O |
| V-50 | Ph | Me | O | O |
| V-51 | Ph(2-Cl) | Me | O | O |
| V-52 | Ph(3-Cl) | Me | O | O |
| V-53 | Ph(4-Cl) | Me | O | O |
| V-54 | Ph(2-F) | Me | O | O |
| V-55 | Ph(3-F) | Me | O | O |
| V-56 | Ph(4-F) | Me | O | O |
| V-57 | Ph(2-Me) | Me | O | O |
| V-58 | Ph(3-Me) | Me | O | O |
| V-59 | Ph(4-Me) | Me | O | O |
| V-60 | Ph(2-OMe) | Me | O | O |
| V-61 | Ph(3-OMe) | Me | O | O |
| V-62 | Ph(4-OMe) | Me | O | O |
| V-63 | Ph(2-CF$_3$) | Me | O | O |
| V-64 | Ph(3-CF$_3$) | Me | O | O |
| V-65 | Ph(4-CF$_3$) | Me | O | O |
| V-66 | Ph(2-NO$_2$) | Me | O | O |
| V-67 | Ph(3-NO$_2$) | Me | O | O |
| V-68 | Ph(4-NO$_2$) | Me | O | O |
| V-69 | Ph(2-OCF$_3$) | Me | O | O |
| V-70 | Ph(3-OCF$_3$) | Me | O | O |
| V-71 | Ph(4-OCF$_3$) | Me | O | O |
| V-72 | Ph(2-CN) | Me | O | O |
| V-73 | Ph(3-CN) | Me | O | O |
| V-74 | Ph(4-CN) | Me | O | O |
| V-75 | Ph(3,4-F$_2$) | Me | O | O |
| V-76 | Ph(3,5-F$_2$) | Me | O | O |
| V-77 | Ph(2,3-F$_2$) | Me | O | O |
| V-78 | Ph(2,4-F$_2$) | Me | O | O |

TABLE 58

| Compound No. | R¹ | R² | Y | Z |
|---|---|---|---|---|
| V-79 | Ph(2,5-F$_2$) | Me | O | O |
| V-80 | Ph(2,6-F$_2$) | Me | O | O |
| V-81 | Ph(3,4-Cl$_2$) | Me | O | O |
| V-82 | Ph(3,5-Cl$_2$) | Me | O | O |
| V-83 | Ph(2,3-Cl$_2$) | Me | O | O |
| V-84 | Ph(2,4-Cl$_2$) | Me | O | O |
| V-85 | Ph(2,5-Cl$_2$) | Me | O | O |
| V-86 | Ph(2,6-Cl$_2$) | Me | O | O |
| V-87 | Ph(3,4-Me$_2$) | Me | O | O |
| V-88 | Ph(3,5-Me$_2$) | Me | O | O |
| V-89 | Ph(2,3-Me$_2$) | Me | O | O |
| V-90 | Ph(2,4-Me$_2$) | Me | O | O |
| V-91 | Ph(2,5-Me$_2$) | Me | O | O |
| V-92 | Ph(2,6-Me$_2$) | Me | O | O |
| V-93 | Ph(3,4-(OMe)$_2$) | Me | O | O |
| V-94 | Ph(3,5-(OMe)$_2$) | Me | O | O |
| V-95 | Ph(2,3-(OMe)$_2$) | Me | O | O |
| V-96 | Ph(2,4-(OMe)$_2$) | Me | O | O |
| V-97 | Ph(2,5-(OMe)$_2$) | Me | O | O |
| V-98 | Ph(2,6-(OMe)$_2$) | Me | O | O |
| V-99 | Ph(3-F-4-OMe) | Me | O | O |
| V-100 | Ph(3-F-5-OMe) | Me | O | O |
| V-101 | Ph(2-F-3-OMe) | Me | O | O |
| V-102 | Ph(2-F-4-OMe) | Me | O | O |
| V-103 | Ph(2-F-5-OMe) | Me | O | O |
| V-104 | Ph(2-F-6-OMe) | Me | O | O |
| V-105 | Ph(3-F-4-Me) | Me | O | O |
| V-106 | Ph(3-F-5-Me) | Me | O | O |
| V-107 | Ph(2-F-3-Me) | Me | O | O |
| V-108 | Ph(2-F-4-Me) | Me | O | O |
| V-109 | Ph(2-F-5-Me) | Me | O | O |

TABLE 58-continued

| Compound No. | R¹ | R² | Y | Z |
|---|---|---|---|---|
| V-110 | Ph(2-F-6-Me) | Me | O | O |
| V-111 | Ph(3-OMe-4-F) | Me | O | O |
| V-112 | Ph(2-OMe-3-F) | Me | O | O |
| V-113 | Ph(2-OMe-4-F) | Me | O | O |
| V-114 | Ph(2-OMe-5-F) | Me | O | O |
| V-115 | Ph(3-Me-4-F) | Me | O | O |
| V-116 | Ph(2-Me-3-F) | Me | O | O |
| V-117 | Ph(2-Me-4-F) | Me | O | O |

TABLE 59

| Compound No. | R¹ | R² | Y | Z |
|---|---|---|---|---|
| V-118 | Ph(2-Me-5-F) | Me | O | O |
| V-119 | Ph(3-Cl-4-OMe) | Me | O | O |
| V-120 | Ph(3-Cl-5-OMe) | Me | O | O |
| V-121 | Ph(2-Cl-3-OMe) | Me | O | O |
| V-122 | Ph(2-Cl-4-OMe) | Me | O | O |
| V-123 | Ph(2-Cl-5-OMe) | Me | O | O |
| V-124 | Ph(2-Cl-6-OMe) | Me | O | O |
| V-125 | Ph(3-Cl-4-Me) | Me | O | O |
| V-126 | Ph(3-Cl-5-Me) | Me | O | O |
| V-127 | Ph(2-Cl-3-Me) | Me | O | O |
| V-128 | Ph(2-Cl-4-Me) | Me | O | O |
| V-129 | Ph(2-Cl-5-Me) | Me | O | O |
| V-130 | Ph(2-Cl-6-Me) | Me | O | O |
| V-131 | Ph(3-OMe-4-Cl) | Me | O | O |
| V-132 | Ph(2-OMe-3-Cl) | Me | O | O |
| V-133 | Ph(2-OMe-4-Cl) | Me | O | O |
| V-134 | Ph(2-OMe-5-Cl) | Me | O | O |
| V-135 | Ph(3-Me-4-Cl) | Me | O | O |
| V-136 | Ph(2-Me-3-Cl) | Me | O | O |
| V-137 | Ph(2-Me-4-Cl) | Me | O | O |
| V-138 | Ph(2-Me-5-Cl) | Me | O | O |
| V-139 | Ph(3-F-4-Cl) | Me | O | O |
| V-140 | Ph(3-F-5-Cl) | Me | O | O |
| V-141 | Ph(2-F-3-Cl) | Me | O | O |
| V-142 | Ph(2-F-4-Cl) | Me | O | O |
| V-143 | Ph(2-F-5-Cl) | Me | O | O |
| V-144 | Ph(2-F-6-Cl) | Me | O | O |
| V-145 | Ph(3-Cl-4-F) | Me | O | O |
| V-146 | Ph(2-Cl-3-F) | Me | O | O |
| V-147 | Ph(2-Cl-4-F) | Me | O | O |
| V-148 | Ph(2-Cl-5-F) | Me | O | O |
| V-149 | Ph(3-Me-4-OMe) | Me | O | O |
| V-150 | Ph(3-Me-5-OMe) | Me | O | O |
| V-151 | Ph(2-Me-3-OMe) | Me | O | O |
| V-152 | Ph(2-Me-4-OMe) | Me | O | O |
| V-153 | Ph(2-Me-5-OMe) | Me | O | O |
| V-154 | Ph(2-Me-6-OMe) | Me | O | O |
| V-155 | Ph(3-OMe-4-Me) | Me | O | O |
| V-156 | Ph(2-OMe-3-Me) | Me | O | O |

TABLE 60

| Compound No. | R¹ | R² | Y | Z |
|---|---|---|---|---|
| V-157 | Ph(2-OMe-4-Me) | Me | O | O |
| V-158 | Ph(2-OMe-5-Me) | Me | O | O |
| V-159 | Ph(3-CN-4-OMe) | Me | O | O |
| V-160 | Ph(3-OMe-4-CN) | Me | O | O |
| V-161 | Ph(3-Me-4-CN) | Me | O | O |
| V-162 | Ph(3-CN-4-Me) | Me | O | O |
| V-163 | Ph(3-NO$_2$-4-OMe) | Me | O | O |
| V-164 | Ph(3-OMe-4-NO$_2$) | Me | O | O |
| V-165 | Ph(3-Me-4-NO$_2$) | Me | O | O |
| V-166 | Ph(3-NO$_2$-4-Me) | Me | O | O |
| V-167 | Ph(3,5-F$_2$-4-OMe) | Me | O | O |
| V-168 | Ph(3,5-F$_2$-4-Me) | Me | O | O |
| V-169 | Ph(3,4,5-(OMe)$_3$) | Me | O | O |

TABLE 60-continued

| Compound No. | R¹ | R² | Y | Z |
|---|---|---|---|---|
| V-170 | (6-methyl-1,3-benzodioxole) | Me | O | O |
| V-171 | (7-methyl-2,3-dihydro-1,4-benzodioxine) | Me | O | O |
| V-172 | (6-methyl-2,3-dihydrobenzofuran) | Me | O | O |
| V-173 | (7-methylchroman) | Me | O | O |
| V-174 | (5-methyl-2,3-dihydrobenzofuran) | Me | O | O |
| V-175 | (6-methylchroman) | Me | O | O |
| V-176 | (6-methyl-2,3-dihydro-1,4-benzoxathiine) | Me | O | O |
| V-177 | (6-methyl-1,3-benzoxathiole) | Me | O | O |
| V-178 | (6-methyl-4-methyl-3-oxo-3,4-dihydro-2H-1,4-benzoxazine) | Me | O | O |

TABLE 61

| Compound No. | R¹ | R² | Y | Z |
|---|---|---|---|---|
| V-179 | (2-methylpyridine) | Me | O | O |
| V-180 | (3-methylpyridine) | Me | O | O |
| V-181 | (4-methylpyridine) | Me | O | O |
| V-182 | (2-methyl-5-methylpyridine) | Me | O | O |
| V-183 | (2-methyl-5-methoxypyridine) | Me | O | O |
| V-184 | (2-methyl-5-fluoropyridine) | Me | O | O |
| V-185 | (2-methyl-5-chloropyridine) | Me | O | O |
| V-186 | (2-methyl-5-bromopyridine) | Me | O | O |
| V-187 | (2-methyl-5-trifluoromethylpyridine) | Me | O | O |
| V-188 | (3,5-dimethylisoxazole) | Me | O | O |
| V-189 | (3-methyl-5-methylisoxazole) | Me | O | O |
| V-190 | (5-methyl-4,5-dihydroisoxazole) | Me | O | O |
| V-191 | (3,5-dimethyl-4,5-dihydroisoxazole) | Me | O | O |
| V-192 | (3-methyl-4,5-dihydroisoxazole) | Me | O | O |

TABLE 62

| Compound No. | R¹ | R² | Y | Z |
|---|---|---|---|---|
| V-193 | 3-methyl-5-methyl-isoxazoline | Me | O | O |
| V-194 | 2-thiazolyl | Me | O | O |
| V-195 | 2-methyl-4-methyl-thiazolyl | Me | O | O |
| V-196 | 2-methyl-5-methyl-thiazolyl | Me | O | O |
| V-197 | 2,4,5-trimethyl-thiazolyl | Me | O | O |
| V-198 | 2-thienyl | Me | O | O |
| V-199 | 3-thienyl | Me | O | O |
| V-200 | 2,5-dimethyl-thienyl | Me | O | O |
| V-201 | 3,5-dimethyl-thienyl | Me | O | O |
| V-202 | morpholinyl | Me | O | O |
| V-203 | thiomorpholinyl | Me | O | O |
| V-204 | 1,1-dioxo-thiomorpholinyl | Me | O | O |
| V-205 | CH$_2$Ph | Me | O | O |
| V-206 | CH$_2$CH$_2$Ph | Me | O | O |
| V-207 | CH$_2$CH$_2$CH$_2$Ph | Me | O | O |
| V-208 | CH$_2$CH=CHPh | Me | O | O |
| V-209 | CH$_2$C≡CPh | Me | O | O |
| V-210 | CH$_2$CH=NOMe | Me | O | O |

TABLE 63

| Compound No. | R¹ | R² | Y | Z |
|---|---|---|---|---|
| V-211 | CH$_2$CH=NOEt | Me | O | O |
| V-212 | CH$_2$CH=NOPr-n | Me | O | O |
| V-213 | CH$_2$CH=NOPh | Me | O | O |
| V-214 | CH$_2$CH(OMe)$_2$ | Me | O | O |
| V-215 | CH$_2$CHO | Me | O | O |
| V-216 | NH$_2$ | Me | O | O |
| V-217 | NHMe | Me | O | O |
| V-218 | NHEt | Me | O | O |
| V-219 | NHPr-n | Me | O | O |
| V-220 | NHPr-i | Me | O | O |
| V-221 | NHBu-n | Me | O | O |
| V-222 | NHBu-i | Me | O | O |
| V-223 | NHBu-s | Me | O | O |
| V-224 | NHCH$_2$Pr-c | Me | O | O |
| V-225 | NHPen-n | Me | O | O |
| V-226 | NHHex-n | Me | O | O |
| V-227 | NHCH$_2$CH$_2$CH$_2$Cl | Me | O | O |
| V-228 | NHCH$_2$CH$_2$CH$_2$F | Me | O | O |
| V-229 | NHCH$_2$CH$_2$OMe | Me | O | O |
| V-230 | NMe$_2$ | Me | O | O |
| V-231 | NEt$_2$ | Me | O | O |
| V-232 | N(Pr-n)$_2$ | Me | O | O |
| V-233 | N(Bu-n)$_2$ | Me | O | O |
| V-234 | N(Me)Et | Me | O | O |
| V-235 | N(Me)CH$_2$CH$_2$OMe | Me | O | O |
| V-236 | NHPh | Me | O | O |
| V-237 | NHCH$_2$Ph | Me | O | O |
| V-238 | N=CMe$_2$ | Me | O | O |
| V-239 | N=CEt$_2$ | Me | O | O |
| V-240 | N=CHNMe$_2$ | Me | O | O |
| V-241 | NHC(=O)Me | Me | O | O |
| V-242 | N[C(=O)Me]$_2$ | Me | O | O |
| V-243 | NHC(=O)OMe | Me | O | O |
| V-244 | N[C(=O)OMe]$_2$ | Me | O | O |
| V-245 | NHSO$_2$Me | Me | O | O |
| V-246 | NHSO$_2$Ph | Me | O | O |
| V-247 | NHSO$_2$CH$_2$Ph | Me | O | O |
| V-248 | OMe | Me | O | O |
| V-249 | OEt | Me | O | O |
| V-250 | OPr-n | Me | O | O |
| V-251 | OPr-i | Me | O | O |
| V-252 | OCH$_2$Pr-c | Me | O | O |
| V-253 | OCH$_2$Cl | Me | O | O |
| V-254 | OCHCl$_2$ | Me | O | O |

TABLE 64

| Compound No. | R¹ | R² | Y | Z |
|---|---|---|---|---|
| V-255 | OCCl$_3$ | Me | O | O |
| V-256 | OCH$_2$F | Me | O | O |
| V-257 | OCHF$_2$ | Me | O | O |
| V-258 | OCF$_3$ | Me | O | O |
| V-259 | Ph | Et | O | O |
| V-260 | Ph | Pr-i | O | O |
| V-261 | Ph | CHF$_2$ | O | O |
| V-262 | Ph | Ph | O | O |
| V-263 | Ph | Me | O | S |
| V-264 | Ph | Me | S | S |
| V-265 | Me | Me | O | S |
| V-266 | Me | Me | S | S |
| V-267 | Ph | Me | O | O |
| V-268 | Ph(4-OEt) | Me | O | O |
| V-269 | Ph(2-Ph) | Me | O | O |
| V-270 | Ph(3-Ph) | Me | O | O |
| V-271 | Ph(4-Ph) | Me | O | O |
| V-272 | 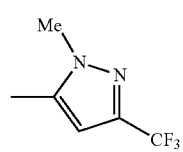 | Me | O | O |

TABLE 64-continued

| Compound No. | R¹ | R² | Y | Z |
|---|---|---|---|---|
| V-273 | 2-methyl-4,6-dimethoxypyrimidin-5-yl | Me | O | O |
| V-274 | Me | 6-methylpyridin-2-yl | O | O |
| V-275 | Et | 6-methylpyridin-2-yl | O | O |
| V-276 | 2-chloro-3-methylpyridin-? | Me | O | O |
| V-277 | 2,3-dimethylpyridin-? | Me | O | O |
| V-278 | 3,5-dimethylpyridin-? | Me | O | O |
| V-279 | 2,6-dimethylpyridin-? | Me | O | O |

TABLE 65

| Compound No. | R¹ | R² | Y | Z |
|---|---|---|---|---|
| V-280 | 6-chloro-3-methylpyridin-? | Me | O | O |
| V-281 | 2-bromo-4-methylpyridin-? | Me | O | O |
| V-282 | Ph(2-Me-4-Br) | Me | O | O |
| V-283 | Ph(2-Me-5-I) | Me | O | O |
| V-284 | Ph(2-Me-5-CF₃) | Me | O | O |
| V-285 | Ph(2-Me-6-OCF₃) | Me | O | O |
| V-286 | Ph(2-Pr-i) | Me | O | O |
| V-287 | 2-methoxy-5-methylpyridin-? | Me | O | O |
| V-288 | Ph(2-Et) | Me | O | O |

TABLE 65-continued

| Compound No. | R¹ | R² | Y | Z |
|---|---|---|---|---|
| V-289 | 2,5-dimethylpyridin-? | Me | O | O |
| V-290 | 5-methoxy-2-methylpyridin-? | Me | O | O |
| V-291 | 2,5-dimethylpyridin-? | Me | O | S |
| V-292 | 2,5-dimethylpyrazin-? | Me | O | O |
| V-293 | 2-methyl-5-vinylpyridin-? | Me | O | O |
| V-294 | CH₂COOBu-t | Me | O | O |
| V-295 | (C₇H₁₄)CH₃ | Me | O | O |
| V-296 | (C₉H₁₈)CH₃ | Me | O | O |
| V-297 | Ph(2-F, 4-Cl, 5-OMe) | Me | O | O |
| V-298 | Ph(2,3,4-(OMe)₃) | Me | O | O |
| V-299 | Ph(3,5-Cl₂-4-OMe) | Me | O | O |
| V-300 | Ph(3,5-Cl₂-4-SMe) | Me | O | O |
| V-301 | Ph(3,5-Cl₂-4-SO₂Me) | Me | O | O |
| V-302 | Ph(3,4,5-F₃) | Me | O | O |
| V-303 | 4-methylcyclohex-3-en-1-yl | Me | O | O |

TABLE 66

| Compound No. | R¹ | R² | Y | Z |
|---|---|---|---|---|
| V-304 | 1-methylpiperidin-? | Me | O | O |
| V-305 | 3-hydroxy-6-methylpyridazin-? | Me | O | O |
| V-306 | Bu-n | 6-methylpyridin-2-yl | O | O |
| V-307 | CH₂CH(CH₃)₂ | 6-methylpyridin-2-yl | O | O |
| V-308 | Ph | Pen-n | O | O |
| V-309 | H | Me | O | O |
| V-310 | CH₂C≡CF | Me | O | O |

TABLE 66-continued

| Compound No. | R$^1$ | R$^2$ | Y | Z |
|---|---|---|---|---|
| V-311 | (2,2-dichlorocyclopropyl) | Me | O | O |
| V-312 | (2,2-dichloro-3-ethylcyclopropyl) | Me | O | O |
| V-313 | CH$_2$NH$_2$ | Me | O | O |
| V-314 | CH$_2$NO$_2$ | Me | O | O |
| V-315 | CH$_2$NHCH$_3$ | Me | O | O |
| V-316 | CH$_2$N(CH$_3$)$_2$ | Me | O | O |
| V-317 | CH$_2$SCH$_2$CF$_3$ | Me | O | O |
| V-318 | CH$_2$SOCH$_2$CF$_3$ | Me | O | O |
| V-319 | CH$_2$SO$_2$CH$_2$CF$_3$ | Me | O | O |
| V-320 | CH$_2$OH | Me | O | O |
| V-321 | CH$_2$OBn | Me | O | O |
| V-322 | CH$_2$OCH$_2$Pr-c | Me | O | O |
| V-323 | CH$_2$OPh | Me | O | O |
| V-324 | CH$_2$SPh | Me | O | O |
| V-325 | CH$_2$SOPh | Me | O | O |
| V-326 | CH$_2$SO$_2$Ph | Me | O | O |
| V-327 | CH$_2$CON(CH$_3$)$_2$ | Me | O | O |
| V-328 | CH$_2$COCH$_3$ | Me | O | O |
| V-329 | CH$_2$OCOCH$_3$ | Me | O | O |
| V-330 | CH$_2$ON=CHCH$_3$ | Me | O | O |
| V-331 | C$_2$H$_4$OC$_2$H$_4$SCH$_3$ | Me | O | O |
| V-332 | C$_2$H$_4$OC$_2$H$_4$SOCH$_3$ | Me | O | O |
| V-333 | C$_2$H$_4$OC$_2$H$_4$SO$_2$CH$_3$ | Me | O | O |

TABLE 67

| Compound No. | R$^1$ | R$^2$ | Y | Z |
|---|---|---|---|---|
| V-334 | CH$_2$OCH$_2$CN | Me | O | O |
| V-335 | CH$_2$CN | Me | O | O |
| V-336 | OCH$_2$CH=CH$_2$ | Me | O | O |
| V-337 | OCH$_2$C≡CH | Me | O | O |
| V-338 | OPr-c | Me | O | O |
| V-339 | CH$_2$-(tetrahydrofuran-2-yl) | Me | O | O |
| V-340 | CH$_2$-(3-methyl-4,5-dihydroisoxazol-5-yl) | Me | O | O |
| V-341 | CH$_2$-(3-methyl-4,5-dihydroisoxazol-5-yl) | Me | O | O |
| V-342 | CH$_2$OCH$_2$-(tetrahydrofuran-2-yl) | Me | O | O |
| V-343 | CH$_2$CH$_2$OCH$_2$CH$_2$O-(pyridin-2-yl) | Me | O | O |
| V-344 | Ph | H | O | O |
| V-345 | Ph | CH$_2$CH=CH$_2$ | O | O |
| V-346 | Ph | CH$_2$C≡CH | O | O |
| V-347 | Ph | Pr-c | O | O |
| V-348 | Ph | CH$_2$CH=CF$_2$ | O | O |
| V-349 | Ph | CH$_2$C≡CF | O | O |
| V-350 | Ph | C$_2$H$_4$OCH$_3$ | O | O |
| V-351 | Ph | C$_2$H$_4$OC$_2$H$_5$ | O | O |
| V-352 | Ph | CH(Me)OEt | O | O |
| V-353 | Ph | CH$_2$OPr-c | O | O |
| V-354 | Ph | CH(OCH$_3$)$_2$ | O | O |
| V-355 | Ph | CH$_2$Ph | O | O |
| V-356 | Ph | CH=CH—Ph | O | O |
| V-357 | Ph | C≡C—Ph | O | O |
| V-358 | Ph(3,4,5-Cl) | Me | O | O |
| V-359 | N(Me)Ph | Me | O | O |
| V-360 | (2,4,6-trimethylpyrimidin-5-yl) | Me | O | O |
| V-361 | (6-methyl-5-pyridin-3-yl) | Me | O | O |
| V-362 | CH$_2$CO(Bu-t) | Me | O | O |
| V-363 | Ph(2,3,5,6-F$_4$) | Me | O | O |
| V-364 | Ph[(3,5-(CF$_3$)$_2$] | Me | O | O |
| V-365 | CH$_2$C(Me)=NOMe | Me | O | O |
| V-366 | Ph(2,4,6-Me$_3$) | Me | O | O |
| V-367 | Ph(2,3,4,5,6-F$_5$) | Me | O | O |
| V-368 | N(Et)Ph | Me | O | O |
| V-369 | N(Pr-i)Ph | Me | O | O |
| V-370 | N(Me)Ph(4-F) | Me | O | O |
| V-371 | CH$_2$C(Me)=NOEt | Me | O | O |

Compounds of the invention have an excellent herbicidal activity and some of them show excellent selectivity between crops and weeds and are useful as an agrochemical composition for farmland, especially as herbicides. In other words, the compounds of the invention have a herbicidal activity for various weeds during foliage treatment, soil treatment, seed dressing treatment, soil blending treatment, soil treatment before sowing, treatment at the time of sowing, soil treatment after sowing, soil covering and blending treatment at the time of sowing, and soil treatment before and after sowing for no-tillage farming of a field for cultivating agrohorticultural plants.

Hereinbelow, examples of the weeds are given, but the invention is not limited to them;

weeds of Onagraceae family: *Oenothera erythrosepala, Oenothera laciniata;* weeds of Ranunculaceae family: *Ranunculus muricatus, Ranunculus sardous;* weeds of Polygonaceae family: *Polygonum convolvulus, Polygonum lapathifolium, Polygonum pensylvanicum, Polygonum persicaria, Rumex crispus, Rumex obtusifolius, Poligonum cuspidatum, Polygonum pensylvanicum, Persicaria longiseta, Persicaria lapathifolia, Persicaria nepalensis;* weeds of Portulacaceae family: *Portulaca oleracea;* weeds of Caryophyllaceae family: *Stellaria media, Cerastium glomeratum, Stellaria alsine, Spergula arvensis, Stellaria aquatica;* weeds of Chenopodiaceae family: *Chenopodium album, Kochia scoparia, Chenopodium album, Chenopodium ficifolium;* weeds of Amaranthaceae family: *Amaranthus retroflexus, Amaranthus hybridus, Amaranthus palmeri, Amaranthus spinosus, Amaranthus rudis, Amaranthus albus, Amaranthus viridus, Amaranthus lividus;* weeds of Brassicaceae family: *Raphanus raphanistrum, Sinapis arvensis, Capsella bursa-pastoris, Lepidium virginicum, Thlaspi arvense, Descurarinia sophia, Rorippa indica, Rorippa islandica, Sisymnrium officinale, Cardamine flexuosa, Nasturtium officinale, Draba nemorosa;* weeds of Fabaceae family: *Sesbania exaltata, Cassia obtusifolia, Desmodium tortuosum, Trifolium repens, Vicia sativa, Medicago lupulina, Vicia hirsuta; Kummerowia striata, Medicago polymorpha, Vicia angustifolia, Aeschynomene indica;* weeds of Malvaceae family: *Abutilon theophrasti, Sida spinosa;* weeds of Violet family: *Viola arvensis, Viola tricolor;* weeds of Rubiaceae family: *Galium aparine;* weeds of Convolvulaceae family: *Ipomoea hederacea, Ipomoea purpurea, Ipomoea hederacea var integriuscula, Ipomoea lacunosa, Convolvulus arvensis, Ipomoea indica, Ipomoea coccinea, Ipomoea triloba;* weeds of Lamiaceae family: *Lamium purpureum, Lamium amplexicaule, Stachys arvensis;* weeds of Solanaceae family: *Datura stramonium, Solanum nigrum, Physalis angulata, Solanum americanum, Solanum carolinense;* weeds of Scrophulariaceae family: *Veronica persica, Veronica arvensis, Veronica hederaefolia;* weeds of Asteraceae family: *Xanthium pensylvanicum, Helianthus annuus, Matricaria chamomilla, Matricaria perforata or inodora, Chrysanthemum segetum, Matricaria matricarioides, Ambrosia artemisiifolia, Ambrosia trifida, Erigeron canadensis, Artemisia princeps, Solidago altissima, Taraxacum officinale, Anthemis cotula, Breea setosa, Sonchus oleraceus, Helianthus tuberosus, Cirsium arvense, Bidens frondosa, Bidens pilosa, Centurea cyanus, Cirsium vulgare, Lactuca scariola, Rudbeckia hirta, Rudbeckia laciniata, Rudbeckia laciniata var. hortensis Bailey, Senecio vulgais, Silybum marianum, Sonchus asper, Sonchus arvensis, Salsola kali, Bidens frondosa, Eclipta ptostrata, Bidense tipartita, Senecio madagascariensis, Coreopsis lanceolata, Rudbeckia laciniata;* weeds of Boraginaceae family: *Myosotis arvensis;* weeds of Asclepiadaceae family: *Asclepias syriaca;* weeds of Euphorbiaceae family: *Euphorbia helioscopia, Euphorbia maculata, Acalypha australis;* weeds of Geraniaceae family: *Geranium carolinianum;* weeds of Oxalidaceae family: *Oxalis corymbosa;* weeds of Cucurbitaceae family: *Sicyos angulatus;* weeds of Poaceae family: *Echinochloa crus-galli, Setaria viridis, Setaria faberi, Digitaria sanguinalis, Eleusine indica, Poa annus, Alopecurus myosuroides, Avena fatua, Sorghum halepense, Agropyron repens, Bromus tectorum, Cynodone dactylon, Panicum dichotomiflorum, Panicum texanum, Sorghum vulgare, Alopecurus geniculatus, Lolium multiflorum, Lolium rigidum, Setaria glauca, Beckmannia syzigachne;* weeds of Commelinaceae family: *Commelina communis;* weeds of Equisetaceae family: *Equisetum arvense;* weeds of Papaveraceae family: *Papaver rhoeas;* weeds of Cyperaceae family: *Cyperus iria, Cyperus rotundus, Cyperus esculentus.*

Compounds of the invention do not exhibit any phytotoxicity which causes a problem in major crops like *Zea mays, Triticum aestivum, Hordeum vulgare, Oryza sativa, Sorghum bicolor, Glycine* max, *Gossypium* spp., *Beta vulgaris, Arachis hypogaea, Helianthus annuus, Brassica napus*, buck wheat, sugar cane, and tobacco, and horticultural crops like flowers and vegetables.

Further, the compounds of the invention are useful for effective elimination of various weeds which cause a trouble in no-tillage farming of soybean, corn, and wheat, and they do not exhibit any problematic phytotoxicity to crops.

According to many treatment methods like soil treatment before cultivation; soil treatment after cultivation but before or after sowing; soil treatment after harrowing but before or after sowing, or treatment before or after transplanting a seedling; treatment at the time of transplanting a seedling; desalination treatment after transplanting a seedling; and foliage treatment, the compounds of the invention can exhibit an herbicidal activity for many problematic weeds in paddy field that are described below.

Hereinbelow, examples of the weeds are given, but the invention is not limited to them:

weeds of Poaceae family: *Echinochloa oryzicola; Echinochloa crus-galli, Leptochloa chinensis, Isachne globosa, Paspalum distichum, Leersia sayanuka, Leersia oryzoides;* weeds of Scrophulariaceae family: *Lindernia procumbens, Lindernia dubia, Dopatrium junceum, Gratiola japonica, Lindernia angustifolia, Limnophila sessiliflora;* weeds of Lythraceae family: *Rotala indica, Ammannia multiflora;* weeds of Elatinaceae family: Elatine triandra;

weeds of Cyperaceae family: *Cyperus difformis, Scirpus hotarui, Eleocharis acicularis, Cyperus serotinus, Eleocharis kuroguwai, Fimbristylis miliacea, Cyperus flaccidus, Cyperus globosus, Scirpus juncoides, Scirpus wallichii, Scirpus nipponicus, Fimbristylis autumnalis, Scirpus tabernaemontani, Scirpus juncoides Rocxb., Scirpus lineolatus Franch. et Savat., Cyperus orthostachyus Franch. et Savat., Cyperus orthostachyus Franch. et Savat., Eleocharis congesta D. Don, Scirpus planiculmis Fr. Schm.;* weeds of Pontederiaceae family: *Monochoria vaginalis, Monochoria korsakowii, Heteranthera limosa;* weeds of Alismataceae family: *Sagittaria pygmaea, Sagittaria trifolia, Alisma canaliculatum, Sagittaria aginashi;* weeds of Potamogetonaceae family: *Potamogeton distinctus;* weeds of Eruocaulaceae family: *Eriocaulon cinereum;* weeds of Apiacease family: *Oenanthe javanica;* weeds of Asteracease family: *Eclipta prostrata, Bidens tripartita;* weeds of Commelinaceae family: *Murdannia keisak;* weeds of Characease family: *Chara braunii;* weeds of Lemnacease family: *Spirodela polyrhiza;*

Hepaticae: *Ricciocarpus natans;*

Zygnemataceae: *Spirogyra arcla.*

Further, the compounds of the invention show no phytoxicity to paddy rice according to any cultivation method including direct sowing or transplanting of paddy rice followed by cultivation.

Further, the compounds of the invention can be used for controlling a wide spectrum of weeds thriving in a lot for industrial facilities like a slope of a levee, a riverbed, a shoulder and a slope of a road, a railway site, park spaces, grand, a parking lot, an airport, a factory and a storage facility, a non-crop land like fallow fields, and vacant lots in city, which needs the weed control, or an orchard, a pasture land, a grass land, a forest land, etc.

Moreover, according to foliage treatment, water-surface application, etc., the compounds of the invention can exhibit a herbicidal activity for water weeds which occur in river, waterway, canal, reservoir, etc., wherein the water weeds include Pontederiaceae family: *Eichhomia crassipes*; Salvinia natans family: *Azolla imbricata, Azolla japonica, Salvinia natanas*; Araceae family: *Pistia stratiotes*; Haloragaceae family: *Myriophyllum brasilensa, Myriophyllum verticillatum; Myriophyllum spicatum; Myriophyllum matogrossense*; Azollaceae family: *Azolla cristata*; Scrophulariaceae family: *Veronica anagallis-aquatica*; Amaranthaceae family: *Alternanthera philoxeroides; Gymnocoronis spilanthoides*; Poaceate family: *Spartina anglica*; Apiaceae family: *Hydrocotyle ranunculoides*; Hydrocharitaceae family: *Hydrilla verticillata, Egeria densa*; Cabpmbaceae family: *Cabomba caroliniana*; and Lemnaceae family: *Wolffia globosa*.

The agrohorticultural plants described in the invention include crops like corn, rice, wheat, barley, rye, sorghum, cotton, soybean, peanuts, buck wheat, sugar beet, rapeseed, sun flower, sugar cane, and tobacco; vegetable like vegetables of *Solanaceae* (eggplant, tomato, bell pepper, pepper, potato, etc.), vegetables of *Cucurbitaceae* (cucumber, pumpkin, zucchini, water melon, melon, etc.), vegetables of *Cruciferae* (daikon, turnip, horseradish, kohlrabi, Chinese cabbage, cabbage, mustard, broccoli, cauliflower, etc.), vegetables of *Compositae* (burdock, crown daisy, artichoke, lettuce, etc.), vegetables of *Liliaceae* (scallion, onion, garlic, asparagus, etc.), vegetables of *Apiaceae* (carrot, parsley, celery, parsnip, etc.), vegetables of *Chenopodiaceae* (spinach, leaf beet, etc.), vegetables of *Lamiaceae* (beefsteak plant, mint, basil, etc.), vegetables like strawberry, sweet potato, yam, and taro; kernel fruits (apple, western pear, Japanese pear, Chinese quince, quince, etc.), stone fruits (peach, plum, nectarine, Japanese apricot, cherry, apricot, prune, etc.), mandarins (tangerine, orange, lemon, lime, grape fruits, etc.), nuts (chestnut, walnut, hazelnut, almond, pistachio, cashewnut, macadamia nut, etc.), berries (blueberry, cranberry, blackberry, raspberry, etc.), fruits like grape, persimmon, olive, loquat, banana, coffee, date, coconut, and oil nut; trees other than fruit tree like tea, mulberry, roadside trees (ash tree, birch, American flowering dogwood, eucalyptus, gingko, lilac, maple tree, oak tree, poplar tree, redbud tree, liquidambar, sycamore, zelkova, Japanese arborvitae, Japanese fir, hemlock spruce, juniper, pine tree, spruce, yew, elm, a horse chestnut, etc.), coral, Buddist pine, cedar, Japanese cypress, croton, spindle tree, *Photinia glabra*, etc.; grasses like turf (turf, gold turf, etc.), Bermuda grasses (*Cynodon dactylon*, etc.), bentgrasses (creeping bentgrass, *Agrostis alba* L., *Agrostis capillaries*, etc.), bluegrasses (Kentucky bluegrass, *Poa trivialis* L., etc.), fescues (tall fescue, chewings fescue, *Festuca rabra* L., etc.), rye grasses (*Lolium temulentum* L., *Lolium perenne* L., etc.), orchard grass, timothy, etc.; oil crops like oil coconut, *Jatropha curcas*, etc.; flowers (rose, carnation, mum, prairie gentian, common gypsophila, gerbera, marigold, salvia, petunia, verbena, tulip, Chinese aster, *Gentiana scabra* var. buergeri, lily, pansy, cyclamen, orchid, lily of the valley, lavender, stock, cauliflower, primula, poincetia, gladiolus, cattleya, daisy, verbena, cymbidium, begonia, etc.); a foliage plant, etc., but the invention is not limited thereto.

The agrohorticultural plant described in the invention includes a plant given with resistance to HPPD inhibitor like Isoxaflutole, ALS inhibitor like Imazetaphyr and tifensulfuron methyl, EPSP synthase inhibitor like glifosate, glutamine synthase inhibitor like glufosinate, acetyl CoA carboxylase inhibitor like sethoxydim, PPO inhibitor like flumioxazin, and herbicides like bromoxinil, dicamba and 2,4-D according to classic breeding method or genetic recombination method.

Examples of the "agrohorticultural plant" given with resistance according to classic breeding include rapeseed, wheat, sun flower, rice, and corn that are resistant to imidazoloinone-based ALS inhibitor like Imazetaphyr, and they are already commercially available in the name of Clearfield <Trade Name>.

Similarly, there is soybean resistant to sulfonylurea-based ALS inhibitor like tifensulfuron metil as produced by classic breeding method, and it is already commercially available in the trade name of STS Soybean. Similarly, examples of the "agrohorticultural plant" given with resistance to an acetyl CoA carboxylase inhibitor like trione-oxime based or aryloxyphenoxy propionic acid-based herbicides according to classic breeding include SR Corn. The horticultural plant given with resistance to acetyl CoA carboxylase is described in Proceedings of the National Academy of Sciences of the United States of America (Proc. Natl. Acad. Sci. USA), Vol 87, pages 7175 to 7179 (1990), etc. Further, a mutant acetyl CoA carboxylase which is resistant to acetyl CoA carboxylase inhibitor is reported in Weed Science Vol. 53, pages 728 to 746 (2005), and by introducing a mutant gene of acetyl CoA carboxylase to a plant by genetic recombination technique or by introducing mutation for giving resistance to acetyl CoA carboxylase of crops, a plant which is resistant to an acetyl CoA carboxylase inhibitor can be produced. Further, by having site-specific amino acid substitution mutation on a gene of crops based on introduction of a nucleic acid with base substitution mutation to a plant cell as represented by chimeraplasty technique (Gura T. 1999. Repairing the Genome's Spelling Mistakes. Science 285: 316-318), a plant which is resistant to acetyl CoA carboxylase inhibitor/herbicides can be produced.

Examples of the "agrohorticultural plant" given with resistance according to genetic recombination technique include corn, soybean, cotton, rapeseed, and sugar beet that are resistant to glyfosate, and they are already commercially available in the name of RoundupReady <trade name>, AgrisureGT, etc. Similarly, there are corn, soybean, cotton, and rapeseed varieties that are produced to be resistant to glufosinate by genetic recombination technique, and they are already commercially available in the name of LibertyLink <trade name>, etc. Similarly, cotton having resistance to bromoxinil is also made available by genetic recombination technique and is already commercially available in the trade name of BXN.

The "agrohorticultural plant" includes a plant which is engineered by genetic recombination technique to synthesize a selective toxin like *Baciullus* spp., for example.

Examples of the insecticidal toxin expressed in a genetically engineered plant include an insecticidal protein originating from *Bacillus cereus* or *Bacillus popilliae*; δ-endotoxin originating from *Bacillus thuringiensis* like Cry1Ab, Cry1Ac, Cry1F, Cry1Fa2, Cry2Ab, Cry3A, Cry3Bb1, and Cry9C, and insecticidal proteins like VIP1, VIP2, VIP3, and VIP3A; insecticidal proteins originating from a nematode; animal-produced toxins like scorpion toxin, spider toxin, bee toxin, and insect specific neurotoxin; filamentous fungus toxin; plant lectin; agglutinin; protease like trypsin inhibitor, serine protease, patatin, cistatin, and papain inhibitor; ribosome inactivating proteins (RIP) like lysine, corn-RIP, abrin, saporin, and briodin; enzymes for steroid metabolism like 3-hydroxysteroid oxidase, ecdisteroid-UDP-glycosyl transferase, and cholesterol oxidase; ecdysone inhibitor; HMG-CoA reductase; ion channel inhibitors like sodium channel inhibitor and potassium channel inhibitor; juvenile hormone esterase; natriuretic hormone receptor; stilbene synthase; bibenzyl synthase; chitinase; and glucanase.

Examples of the toxins expressed in a genetically engineered plant include a hybrid toxin, a partially deleted toxin, and a modified toxin of an insecticidal protein like δ-endotoxin including Cry1Ab, Cry1Ac, Cry1F, Cry1Fa2, Cry2Ab, Cry3A, Cry3Bb1, and Cry9C, and insecticidal proteins including VIP1, VIP2, VIP3, and VIP3A. The hybrid toxin is produced by new combination of domains having different proteins based on recombination technique. Examples of the partially deleted toxin include Cry1Ab in which part of amino acid sequence is deleted. In the modified toxin, one or more amino acids of a natural type toxin are replaced with other amino acids.

Examples of the toxins and recombinant plants capable of producing the toxins are described in EP-A-0374753, WO93/07278, WO95/34656, EP-A-0427529, EP-A-451878, and WO03/052073, and the like.

The toxins contained in such recombinant plant can provide a plant with a resistance to harmful insects of Coleoptera, harmful insects of Diptera, and harmful insects of Lepidoptera.

A genetically engineered plant which contains one or more pesticidal harmful insect-resistant gene and expresses one or more toxins is known, and some are already commercially available. Examples of the genetically engineered plant include YieldGard <trade name> (corn variety which expresses Cry1Ab toxin), YieldGard Rootworm <trade name> (corn variety which expresses Cry3Bb1 toxin), YieldGard Plus <trade name> (corn variety which expresses Cry1Ab and Cry3Bb1 toxin), Herculex I<trade name> (corn variety which expresses phosphinotricine N-acetyl transferase (PAT) to give resistance to Cry1Fa2 toxin and glufosinate), NuCOTN33B<trade name> (cotton variety which expresses Cry1Ac toxin), Bollgard I<trade name> (cotton variety which expresses Cry1Ac toxin), Bollgard II<trade name> (cotton variety which expresses Cry1Ac and Cry2Ab toxin), VIPCOT <trade name> (cotton variety which expresses VIP toxin), NewLeaf <trade name> (potato variety which expresses Cry3A toxin), NatureGard <trade name> Agrisure <trade name> GT Advantage (GA21 glyfosate resistant trait), Agrisure <trade name> CB Advantage (Btl1 Corn Borer (CB) trait), and Protecta <trade name>.

The “agrohorticultural plant” includes a plant which is genetically engineered to have an ability of producing an anti-pathogenic substance having selective activity.

Examples of the anti-pathogenic substance include PR proteins (PRPs, described in EP-A-0392225); ion channel inhibitors like sodium channel inhibitor and calcium channel inhibitor (KP1, KP4, KP6 toxin that are produced by virus are known); stilbene synthase; bibenzyl synthase; chitinase; glucanase; and a substance produced by a microorganism like peptide antibiotics, antibiotics having heterocycle, and a protein factor related to resistance to plant disease (referred to as “plant disease resistant gene”, and described in WO03/000906). Such anti-pathogenic substances and plants genetically engineered to produce the substances are described in EP-A-0392225, WO95/33818, and EP-A-0353191, etc.

The “agrohorticultural plant” includes a plant which is given with useful traits like a trait of having modified oil components or a trait for producing enhanced amount of amino acid according to genetic recombination technique. Examples thereof include VISTIVE <trade name> (low-linolenic soybean having reduced linolen content) or high-lysine (high oil) corn (corn having enhanced amount of lysine or oil).

Further, there is also a stack variety in which multiple traits of classic herbicidal trait or herbicides-resistant gene, pesticidal insect-resistant gene, anti-pathogenic substance-producing gene, and useful traits like a trait of having modified oil components or a trait for producing enhanced amount of amino acid are combined.

The agrochemical composition of the invention contains the triazine derivative of the invention or a salt thereof, and an agriculturally acceptable carrier. The agrochemical composition of the invention may contain additive components that may be normally employed for agrochemical formulations, as needed.

Examples of the additive components include carriers such as solid carrier and liquid carrier, surface active agent, binder, tackifier, thickener, coloring agent, spreader, sticker, antifreezing agent, anticaking agent, collapsing agent, decomposition inhibitor and the like.

If necessary, an antiseptic agent, a piece of plant (soybean powder, tobacco powder, walnut powder, wheat powder, wood powder, hulls, wheat hulls, outer hulls, sawdust, pulp flock, corn stalk, nut shell, fruit core chips, etc.) and the like may also be employed as additive components.

These additive components may be used alone or in combination of two or more kinds.

The above additive components will be described.

Examples of the solid carrier include natural minerals such as quartz, clay, kaolinite, pyrophyllite, sericite, talc, bentonite, acid clay, attapulgite, zeolite and diatomite; inorganic salts such as calcium carbonate, ammonium sulfate, sodium sulfate and potassium chloride; organic solid carriers such as synthetic silicic acid, synthetic silicate, starch, cellulose and plant powder; plastic carriers such as polyethylene, polypropylene and polyvinylidene chloride; and the like. These may be used alone or in combination of two or more kinds.

Examples of the liquid carrier include alcohols classified broadly into monohydric alcohols such as methanol, ethanol, propanol, isopropanol and butanol, and polyhydric alcohols such as ethylene glycol, diethylene glycol, propylene glycol, hexylene glycol, polyethylene glycol, polypropylene glycol and glycerin; polyhydric alcohol derivatives such as propylene based glycol ether; ketones such as acetone, methylethyl ketone, methylisobutyl ketone, diisobutyl ketone, and cyclohexanone; ethers such as ethyl ether, dioxane, cellosolve, dipropyl ether and tetrahydrofuran; aliphatic hydrocarbons such as n-paraffin, naphthene, isoparaffin, kerosene and mineral oil; aromatic hydrocarbons such as benzene, toluene, xylene, solvent naphtha and alkylnaphthalene; halogenated hydrocarbons such as dichloroethane, chloroform and carbon tetrachloride; esters such as ethyl acetate, diisopropyl phthalate, dibutyl phthalate, dioctyl phthalate and dimethyl adipate; lactones such as γ-butyrolactone; amides such as N,N-dimethylformamide, N,N-diethylformamide, N,N-dimethyllacetamide and N-alkyl pyrrolidinone; nitriles such as acetonitrile; sulfur compounds such as dimethylsulfoxide; vegetable oils such as soybean oil, canola oil, cottonseed oil and castor oil; water; and the like. These may be use alone or in combination of two or more kinds.

The surface active agent is not particularly limited, but preferred are those either turning into a gel in water or exhibiting swelling property. Examples thereof include non-ionic surface active agents such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkylphenyl ether, polyoxyethylene dialkylphenyl ether, polyoxyethylene alkylphenyl ether formaldehyde condensate, polyoxyethylene polyoxypropylene block polymer, alkylpolyoxyethylene polypropylene block polymer ether, polyoxyethylene alkylamine, polyoxyethylene fatty acid amide, polyoxyethylene fatty acid bisphenyl ether, polyalkylene benzylphenyl ether, polyoxyalkylene styrylphenyl ether, acetylene diol, polyoxyalkylene-added acetylene diol, polyoxyethylene ether silicone, ester silicone, fluorine-based surface active agent, polyoxyethylene castor oil, and polyoxyethylene hydrogenated castor oil; anionic surface active agents such as alkyl sulfate, polyoxyethylene alkyl ether sulfate, polyoxyethylene alkylphenyl ether sulfate, polyoxyethylene styrylphenyl ether sulfate, alkyl benzene sulfonate, lignin sulfonate, alkyl sulfosuccinate, naphthalene sulfonate, alkyl naphthalene sulfonate, naphthalenesulfonic acid formaldehyde condensate salt, alkylnaphthalenesulfonic acid formaldehyde condensate salt, fatty acid salt, polycarboxylate, N-methyl-fatty acid sarcosinate, resin acid salt, polyoxyethylene alkyl ether phosphate, and polyoxyethylene alkylphenyl ether phosphate; cationic surface active agents such as laurylamine hydrochloride, stearylamine hydrochloride, oleylamine hydrochloride, stearylamine acetate, stearylaminopropylamine acetate, alkyltrimethylammonium chloride, and alkyldimethylbenzalkonium chloride; amino acid or betaine type amphoteric surface active agents; and the like.

These surface active agents may be used alone or in combination of two or more kinds.

Examples of the binder or tackifier include carboxymethyl cellulose and a salt thereof, dextrin, water-soluble starch, xanthan gum, guar gum, sucrose, polyvinylpyrrolidone, gum arabic, polyvinyl alcohol, polyvinyl acetate, sodium polyacrylate, polyethylene glycol having an average molecular weight of 6,000 to 20,000, polyethylene oxide having an average molecular weight of 100,000 to 5,000,000 natural phospholipids (for instance, cephalic acid, lecithin) and the like.

Examples of the thickener include water-soluble polymers such as xanthan gum, guar gum, carboxymethyl cellulose, polyvinylpyrrolidone, carboxy vinyl polymer, acrylic polymer, starch derivative and polysaccharide; fine inorganic powders such as high purity bentonite and white carbon; and the like.

Examples of the coloring agent include inorganic pigments such as iron oxide, titanium oxide and Prussian blue; organic dyes such as alizarin dye, azo dye and metal phthalocyanine dye; and the like.

Examples of the extender agent include silicone surface active agent, cellulose powder, dextrin, processed starch, polyaminocarboxylic acid chelate compound, crosslinked polyvinylpyrrolidone, maleic acid-styrenes-methacrylic acid copolymer, half ester of polyhydric alcohol polymer with dicarboxylic anhydride, water-soluble salt of polystyrene sulfonate and the like.

Examples of the spreader include various surface active agents such as diallyl sodium sulfosuccinate, polyoxyethylene alkyl ether, polyoxyethylene alkylphenyl ether and polyoxyethylene fatty acid ester, paraffin, terpene, polyamide resin, polyacrylate, polyoxyethylene, wax, polyvinylalkyl ether, alkylphenol-formaldehyde condensate, synthetic resin emulsion and the like.

Examples of the antifreezing agent include polyhydric alcohols such as ethylene glycol, diethylene glycol, propylene glycol, glycerin, and the like.

Examples of the anticaking agent include polysaccharides such as starch, alginic acid, mannose and galactose, polyvinylpyrrolidone, white carbon, ester gum, petroleum resin and the like.

Examples of the collapsing agent include sodium tripolyphosphate, sodium hexametaphosphate, metal stearate, cellulose powder, dextrin, copolymer of methacrylic acid ester, polyvinylpyrrolidone, polyaminocarboxylic chelate compound, sulfonated styrene-isobutylene-maleic anhydride copolymer, starch-polyacrylonitrile graft copolymer and the like.

Examples of the decomposition inhibitor include desiccants such as zeolite, quicklime and magnesium oxide; antioxidants that are based on phenol, amine, sulfur and phosphoric acid; ultraviolet absorbers that are based on salicylic acid, benzophenone or the like; and the like.

Examples of the antiseptic agent include potassium sorbate, 1,2-benzthiazolin-3-one and the like.

According to the agrochemical composition of the invention, in the case where the additive components described above are included, the content ratio of the carrier (weight base) is generally selected from 5 to 95%, preferably from 20 to 90%, the content ratio of the surface active agent is generally selected from 0.1 to 30%, preferably from 0.5 to 10%, and the content ratio of other additives are selected from 0.1 to 30%, preferably from 0.5 to 10%.

The agrochemical composition of the invention can be used in any forms such as liquid formulation, emulsifiable concentrate, wettable powder, dust, oil solution, water dispersible granule, flowable, granule, Jumbo formulation, and suspoemulsion.

On the occasion of use, the agrochemical composition can be sprayed after being diluted in an adequate concentration or be used directly.

The agrochemical composition of the invention can be used for foliage application, soil application, water-surface application or the like. The agrochemical composition of the invention, in particular the herbicides, is used for soils, i.e., farmland of fields and paddy fields in which agrohorticultural plants are cultivated.

For the agrochemical composition of the invention, the blending ratio of active component according to the invention is arbitrarily selected as needed. In the case of dust, granule or the like, the ratio should be arbitrarily selected from 0.01 to 10% (by weight), preferably from 0.05 to 5% (by weight). In the case of emulsifiable concentrate, wettable powder or the like, the ratio should be arbitrarily selected from 1 to 50% (by weight), preferably from 5 to 30% (by weight). In addition, in the case of a flowable agent or the like, the ratio should be arbitrarily selected from 1 to 40% (by weight), preferably from 5 to 30% (by weight).

The application amount of the agrochemical composition according to the invention varies depending on a kind of a compound to be used, target weed, growth pattern, environmental conditions, formulation for use or the like. In the case of a direct use of dust, granule or the like, the amount should be arbitrarily selected from 1 g to 50 kg, preferably from 10 g to 10 kg per hectare as an active component. Further, in the case of using in a liquid form, for example, in the case of emulsifiable concentrate, wettable powder, flowable agent or the like, the amount should be arbitrarily selected from 0.1 to 50,000 ppm, preferably from 10 to 10,000 ppm.

The agrochemical composition of the invention has an excellent herbicidal activity, and therefore is useful as herbicides in particular.

According to purpose of use, the agrochemical composition of the invention may be formulated, mixed or used in combination with at least one additional agrochemically active component, for example, a plant disease control component, a pesticidal component, an acaricidal component, an nematocidal component, a synergistic agent component, an attracting component, a repellent component, a herbicidal component, a safener component, a microbial pesticidal component, a plant growth control component, a fertilizer component, a soil improving agent, etc.

When the composition is used in combination with other agrochemically active component or fertilizer, the preparation of each individual component may be mixed with others at the time of use. Further, each preparation of an individual component may be used in order, or used with an interval of some days. When the preparations are used with an interval of some days, they may be applied with an interval of 1 day to 40 days, for example, although it may vary depending on each component to be used.

According to the agrochemical composition of the invention, when a mixture of at least one compound selected from the triazine derivatives represented by Formula 1 and their salt and at least one kind selected from other agrochemically active components is used, they are generally used in weight ratio of 100:1 to 1:100, preferably 20:1 to 1:20, and particularly 10:1 to 1:10.

Among other agrochemically active components that may be mixed or used in combination with the compound of the invention in the agrochemical composition of the invention, examples of known herbicides or plant growth control agents are described below, but the invention is not limited thereto.

[Herbicides]

A1. Acetyl CoA carboxylase (ACCase) inhibition type herbicides (A1-1) Aryl oxy phenoxy propionic acid-based compound: clodinafop-propargyl, cyhalofop-butyl, diclofop-methyl, diclofop-P-methyl, fenoxaprop-P-ethyl, fluazifop-butyl, fluazifop-P-butyl, haloxyfop, haloxyfop-etotyl, haloxyfop-P, metamifop, propaquizafop, quizalofop-ethyl, quizalofop-P-ethyl, quizalofop-P-tefuryl, and fenthiaprop-ethyl (A1-2) Cyclohexane dione-based compound: alloxydim, butroxydim, clethodim, cycloxydim, profoxydim, sethoxydim, tepraloxydim, and tralkoxydim (A1-3) Phenyl pyrazoline-based compound: aminopyralid, and pinoxaden B. Acetolactate synthase (ALS) inhibition type herbicides (B-1) Imidazolinone-based compound: imazamethabenz-methyl, imazamox, imazapic (including salts with amine or the like), imazapyr (including salts with isopropylamine or the like), imazaquin, and imazethapyr (B-2) Pyrimidinyloxy benzoic acid-based compound: bispyribac-sodium, pyribenzoxim, pyriftalid, pyriminobac-methyl, pyrithiobac-sodium, and pyrimisulfan (B-3) Sulfonylamino carbonyl triazolinone-based compound: flucarbazone-sodium, thiencarbazone (including sodium salt, methyl ester, or the like), propoxycarbazone-sodium, procarbazone-sodium (B-4) Sulfonylurea-based compound: amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, foramsulfuron, halosulfuron-methyl, imazosulfuron, iodosulfulon-methyl-sodium, mesosulfuron-methyl, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron-sodium, triflusulfuron-methyl, tritosulfuron, orthosulfamuron, propyrisulfuron, metazosulfuron, and flucetosulfuron (B-5) Triazolopyrimidine-based compound: cloransulam-methyl, diclosulam, florasulam, flumetsulam, metosulam, penoxsulam, pyroxsulam, and HNPC-C-9908 (code number)

C1. Herbicides 1 for photosystem II photosynthesis inhibition (C1-1) Phenylcarbamate-based compound: desmedipham and phenmedipham (C1-2) Pyridazinone-based compound: chloridazon and brompyrazon (C1-3) Triazine-based compound: ametryn, atrazine, cyanazine, desmetryne, dimethametryn, eglinazine-ethyl, prometon, prometryn, propazine, simazine, simetryn, terbumeton, terbuthylazine, terbutryn, and trietazine (C1-4) Triazinone-based compound: metamitron and metribuzin (C1-5) Triazolinone-based compound: amicarbazone (C1-6) Uracil-based compound: bromacil, lenacil, and terbacil C2. Herbicides 2 for photosystem II photosynthesis inhibition (C2-1) Amide-based compound: pentanochlor and propanil (C2-2) Urea-based compound: chlorbromuron, chlorotoluron, chloroxuron, dimefuron, diuron, ethidimuron, fenuron, fluometuron, isoproturon, isouron, linuron, methabenzthiazuron, metobromuron, metoxuron, monolinuron, neburon, siduron, tebuthiuron, and metobenzuron C3. Herbicides 3 for photosystem II photosynthesis inhibition (C3-1) Benzothiadiazone-based compound: bentazone (C3-2) Nitrile-based compound: bromofenoxim, bromoxynil (including ester form with butyric acid, octanoic acid and heptanoic acid), and ioxynil (C3-3) Phenyl pyrazine-based herbicide compound: pyridafol, and pyridate D. Photosystem I radical generation type herbicides (D-1) Bipyridinium-based compound: diquat and paraquat dichloride E. Protoporpyrinogen oxidase (PPO) inhibition herbicides (E-1) Diphenyl ether-based compound: acifluorfen-sodium, bifenox, chlomethoxyfen, ethoxyfen-ethyl, fluoroglycofen-ethyl, fomesafen, lactofen, and oxyfluorfen (E-2) N-Phenylphthalimide-based compound: cinidon-ethyl, flumiclorac-pentyl, flumioxazin, and chlorphthalim (E-3) Oxy diazole-based compound: oxadiargyl and oxadiazon (E-4) Oxazolidinedione-based compound: pentoxazone (E-5) Phenylpyrazole-based compound: fluazolate and pyraflufen-ethyl (E-6) Pyrimidinedione-based compound: benzfendizone, butafenacil, and saflufenacil (E-7) Thiadiazole-based compound: fluthiacet-methyl and thidiazimin (E-8) Triazolinone-based compound: azafenidin, carfentrazone-ethyl, sulfentrazone, and bencarbazone (E-9) Other compounds: flufenpyr-ethyl, profluazol, pyraclonil, SYP-298 (code number), and SYP-300 (code number)

F1. Phytoene desaturase (PDS) inhibition herbicides (F1-1) Pyridazinone-based compound: norflurazon (F1-2) Pyrimidine carboxamide-based compound: diflufenican and picolinafen (F1-3) Other compounds: beflubutamid, fluridone, fluorochloridone, and flurtamone F2. 4-Hydroxyphenylpyruvate deoxygenase (HPPD) inhibition herbicides (F2-1) Callistemon-based compound: mesotrione (F2-2) Isoxazole-based compound: pyrasulfotole, isoxaflutole, and isoxachlortole (F2-3) Pyrazole-based compound: benzofenap, pyrazolynate, and pyrazoxyfen (F2-4) Triketone-based compound: sulcotrione, tefuryltrion, ternbotrione, pyrasulfotole, topramezone, bicyclopyrone, and 4-chloro-5-(1,3-dioxocyclohexa-2-yl) carbonyl-2,3-dihydrobenzothiophene-1,1-dioxide F3. Carotenoid biosynthesis inhibition (unknown target) herbicides
  (F3-1) Diphenyl ether-based compound: aclonifen
  (F3-2) Isoxazolidinone-based compound: clomazone
  (F3-3) Triazole-based compound: amitrole
G. EPSP synthase synthesis inhibition (aromatic amino acid biosynthesis inhibition) type herbicides
  (G-1) Glycine-based compound: glyphosate (including salts with sodium, amine, propylamine, isopropylamine, dimethylamine, and trimesium)
H. Glutamine synthesis inhibition herbicides
  (H-1) Phosphinic acid-based compound: bilanafos, glufosinate (including salts with amine or sodium)
I. Dihydropteroic acid (DHP) inhibition herbicides
  (I-1) Carbamate-based compound: asulam
K1. Microtubule association inhibition type herbicides
  (K1-1) Benzamide-based compound: propyzamide and tebutam
  (K1-2) Benzoic acid-based compound: chlorthal-dimethyl
  (K1-3) Dinitroaniline-based compound: benfluralin, butralin, dinitramine, ethalfluralin, fluchloralin, oryzalin, pendimethalin, prodiamine, and trifluralin
  (K1-4) Phosphoroamidate-based compound: amiprofos-methyl and butamifos
  (K1-5) Pyridine-based compound: dithiopyr and thiazopyr
K2. Mitosis/Microtubule tissue formation inhibition herbicides
  (K2-1) Carbamate-based compound: carbetamide, chlorpropham, propham, swep, and karbutilate
K3. Very long-chain fatty acid (VLCFA) synthase inhibition herbicides
  (K3-1) Acetamide-based compound: diphenamid, napropamide, and naproanilide
  (K3-2) Chloroacetamide-based compound: acetochlor, alachlor, butachlor, butenachlor, diethatyl-ethyl, dimethachlor, dimethenamid, dimethenamid-P, metazachlor, metolachlor, pethoxamid, pretilachlor, propachlor, propisochlor, S-metolachlor, and thenylchlor
  (K3-3) Oxyacetamide-based compound: flufenacet and mefenacet
  (K3-4) Tetrazolinone-based compound: fentrazamide
  (K3-5) Other compounds: anilofos, bromobutide, cafenstrole, indanofan, piperophos, fenoxasulfone, pyroxasulfone, and ipfencarbazone
L. Cellulose synthesis inhibition herbicides
  (L-1) Benzamide-based compound: isoxaben
  (L-2) Nitrile-based compound: dichlobenil, chlorthiamid
  (L-3) Triazolocarboxamide-based compound: flupoxame
M. Uncoupler (cell membrane distruction) type herbicides
  (M-1) Dinitrophenol-based compound: dinoterb and DNOC (including salts with amine or sodium)
N. Lipid bioxynthesis (excluding ACCase inhibition) inhibition herbicides
  (N-1) Benzofuran-based compound: benfuresate and ethofumesate
  (N-2) Halogenated carboxylic acid-based compound: dalapon, flupropanate, and TCA (including salts with sodium, potassium, or ammonia)
  (N-3) Phosphorodithioate-based compound: bensulide
  (N-4) Thiocarbamate-based compound: butylate, cycloate, dimepiperate, EPTC, esprocarb, molinate, orbencarb, pebulate, prosulfocarb, thiobencarb, tiocarbazil, tri-allate, and vernolate
O. Auxin synthesis inhibition herbicides
  (O-1) Benzoic acid-based compound: chloramben, 2,3,6-TBA, and dicamba (including salts with amine, diethyl amine, triethanolamine, isopropylamine, sodium, or lithium)
  (O-2) Phenoxy carboxylic acid-based compound: 2,4,5-T, 2,4-D (including salts with amine, diethyl amine, isopropylamine, diglycolamine, sodium, or lithium), 2,4-DB, clomeprop, dichlorprop, dichlorprop-P, MCPA, MCPA-thioethyl, MCPB (including sodium salt and ethyl ester), mecoprop (including salts with sodium, potassium, isopropylamine, triethanol amine, and dimethylamine), and mecoprop-P
  (O-3) Pyridine carboxylic acid-based compound: clopyralid, fluoroxypyr, picloram, triclopyr, and triclopyr-butotyl
  (O-4) Quinoline carboxylic acid-based compound: quinclorac and quinmerac
  (O-5) Other compounds: benazolin
P. Auxin transport inhibition type herbicides
  (P-1) Phthalamates-based compound: naptalam (including salts with sodium)
  (P-2) Semicarbazone-based compound: diflufenzopyr
Z. Herbicides with unknown mode of action
Flamprop-M (including methyl, ethyl, and isopropyl ester), flamprop (including methyl, ethyl, and isopropyl ester), chlorflurenol-methyl, cinmethylin, cumyluron, daimuron, methyldymuron, difenzoquat, etobenzanid, fosamine, pyributicarb, oxaziclomefone, acrolein, AE-F-150944 (code number), aminocyclopyrachlor, cyanamide, heptamaloxyloglucan, indaziflam, triaziflam, quinoclamine, endothal-disodium, phenisopham, BDPT, BAU-9403 (code number), SYN-523 (code number, SYP-249 (code number), JS-913 (code number), IR-6396 (code number), metiozolin, Triafamone, HW-02 (code number), and BCS-AA10579 (code number)

[Plant Growth Controlling Compounds]
1-Methylcyclopropene, 1-naphthylacetamide, 2,6-diisopropylnaphthalene, 4-CPA, benzylaminopurine, ancymidol, aviglycine, carvone, chlormequat, cloprop, cloxyfonac, cloxyfonac-potassium, cyclanilide, cytokinins, daminodide, dikegulac, dimethipin, ethephon, ethychlozate, flumetralin, flurenol, flurprimidol, forchlorfenuron, gibberellin acid, inabenfide, indol acetic acid, indol butyric acid, maleic hydrazide, mefluidide, mepiquat chloride, n-decanol, paclobutrazol, prohexadione-calcium, prohydrojasmon, sintofen, thidiazuron, triacontanol, trinexapac-ethyl, uniconazole, uniconazole-P, and ecolyst Hereinbelow, known safeners which may be mixed or used in combination with the compound of the invention are exemplified, but the invention is not limited thereto: benoxacor, furilazole, dichlormid, dicyclonone, DKA-24 (N1,N2-diallyl-N2-dichloroacetylglycinamide), AD-67 (4-dichloroacetyl-1-oxa-4-azaspiro[4.5]decane), PPG-1292 (2,2-dichloro-N-(1,3-dioxan-2-ylmethyl)-N-(2-propenyl) acetamide), R-29148 (3-dichloroacetyl-2,2,5-trimethyl-1,3-oxazolidine), cloquintcet-mexyl, naphthalic anhydride (1,8-naphthalic anhydride), mefenpyr-diethyl, mefenpyr, mefenpyr-ethyl, fenchlorazole 0 ethyl, fenclorim, MG-191 (2-dichloromethyl-2-methyl-1,3-dioxane), cyometrinil, flurazole, fluxofenim, isoxadifen, isoxadifen-ethyl, mecoprop, MCPA, daimuron, 2,4-D, MON4660 (code number), oxabetrinil, cyprosulfamide, lower alkyl substituted benzoic acid, and TI-35 (code number).

Among other herbicidically active components that may be mixed or used in combination with the compound of the invention, known plant disease control agents are described below, but the invention is not limited thereto.
1. Nucleic acid biosynthesis inhibitor
  acyl alanine compound: benalaxyl, benalaxyl-M, furalaxyl, metalaxyl, and metalaxyl-M;
  oxazolidinone-based compound: oxadixyl;
  butylol lactone-based compound: clozylacon and ofurace;

hydroxy-(2-amino)pyrimidine-based compound: bupirimate, dimethirimol, and ethirimol;
isoxazole-based compound: hymexazol;
isotahiazolone-based compound: octhilinone;
carboxylic acid-based compound: oxolinic acid 2. Mitosis and cell differentiation inhibitor
benzimidazole-based compound: benomyl, carbendazim, fuberidazole, and thiabendazole;
thiophanate-based compound: thiophanate and thiophanate-methyl;
N-phenylcarbamate-based compound: diethofencarb;
toluamide-based compound: zoxamide;
phenylurea-based compound: pencycuron;
pyridinylmethyl benzamide-based compound: fluopicolide 3. Respiration inhibitor
pyrimidine amine-based compound: diflumetorim;
carboxamide-based compound: benodanil, flutolanil, mepronil, fluopyram, fenfuram, carboxin, oxycarboxin, thifluzamide, bixafen, furametpyr, isopyrazam, penflufen, penthiopyrad, sedaxane, and boscalid;
methoxy acrylate-based compound: azoxystrobin, enestroburin, picoxystrobin, and pyraoxystrobin;
methoxycarbamate-based compound: pyraclostrobin, pyrametostrobin;
oxyiminoacetate compound: kresoxim-methyl and trifloxystrobin;
oxyiminoacetamide-based compound: dimoxystrobin, metominostrobin, and orysastrobin;
oxazolidinedione-based compound: famoxadone;
dihydrodioxadine-based compound: fluoxastrobin;
imidazolinone-based compound: fenamidone;
benzylcarbamate-based compound: pyribencarb;
cyanoimidazole-based compound: cyazofamid;
sulfamoyltriazole-based compound: amisulbrom;
dinitrophenylcrotonic acid-based compound: binapacryl, meptyldinocap, and dinocap;
2,6-dinitroaniline-based compound: fluazinam;
pyrimidinone hydrazone-based compound: ferimzone;
triphenyl tin-based compound: TPTA, TPTC, TPTH;
thiophenecarboxamide-based compound: silthiofam;
triazolopyrimidyl amine-based compound: ametoctradin 4. Amino acid and protein synthesis inhibitor
anilino pyrimidine-based compound: cyprodinil, mepanipyrim, and pyrimethanil;
enopyranuronic acid-based antibiotics: blasticidin-S and mildiomycin;
hexopyranosyl-based antibiotics: kasugamycin;
glucopyranosyl-based antibiotics: streptomycin;
tetracycline-based antibiotics: oxytetracycline;
other antibiotics: gentamycin 5. Preparation acting on signal transduction pathway
quinoline-based compound: quinoxyfen;
quinazoline-based compound: proquinazid;
phenylpyrrol-based compound: fenpiclonil and fludioxonil;
dicarboxylmide-based compound: chlozolinate, iprodione, procymidone, and vinclozolin 6. Lipid and cell membrane synthesis inhibitor
phosphorothiorate-based compound: edifenphos, iprobenfos, and pyrazophos;
dithiolane-based compound: isoprothiolane;
aromatic hydrocarbon-based compound: biphenyl, chloroneb, dicloran, quintozene, tecnazene, and tolclofos-methyl;
1,2,4-thiadiazole-based compound: etridiazole;
carbamate-based compound: iodocarb, propamocarb-hydrochloride, and prothiocarb;
cinnamic amide-based compound: dimethomorph and flumorph;
valine amide carbamate-based compound: benthiavalicarb-isopropyl, iprovalicarb, and valifenalate;
mandelic amide-based compound: mandipropamid;
*Bascillus subtilis* and bactericidal lipopeptide product: *Bacillus subtilis* (strain: QST 713)

7. Sterol biosynthesis inhibitor
piperazine-based compound: triforine;
pyridine-based compound: pyrifenox;
pyrimidine-based compound: fenarimol and nuarimol;
imidazole-based compound: imazalil, oxpoconazole-fumarate, pefurazoate, prochloraz, and triflumizole;
triazole-based compound: azaconazole, bitertanol, bromuconazole, cyproconazole, difenoconazole, diniconazole, diniconazole-M, epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole, furconazole, furconazole-cis, and quinconazole;
morpholine-based compound: aldimorph, dodemorph, fenpropimorph, and tridemorph;
piperidine-based compound: fenpropidin and piperalin;
spiroketal amine-based compound: spiroxamine;
hydroxy anilide-based compound: fenhexamid;
thiocarbamate-based compound: pyributicarb;
aryl amine-based compound: naftifine and terbinafine 8. Glucan biosynthesis inhibitor
glucropyranosyl-based antibiotics: validamycin;
peptidyl pyridine nucleotide compound: polyoxin 9. Melanine synthesis inhibitor
isobenzofuranone-based compound: phthalide;
pyrroloquinoline-based compound: pyroquilon;
triazolobenzothiazole-based compound: tricyclazole;
carboxamide-based compound: carpropamid, diclocymet;
propionamide-based compound: fenoxanil 10. Preparation for inducing resistance to plant disease
benzothiadiazole-based compound: acibenzolar-S-methyl;
benzoisothiazole-based compound: probenazole;
thiadiazole carboxamide-based compound: tiadinil and isotianil;
natural product: laminarin 11. Preparation with unknown mode of action or multiple mode of action
copper compound: copper hydroxide, copper dioctanoate, copper oxychloride, copper sulfate, cuprous oxide, oxinecopper, Bordeaux mixture, and copper nonyl phenol sulphonate;
sulfur compound: sulfur;
dithiocarbamate-based compound: ferbam, mancozeb, maneb, metiram, propineb, thiram, zineb, ziram, and cufraneb;
phthalimide-based compound: captan, folpet, and captafol;
chloronitrile-based compound: chlorothalonil;
sulfamide-based compound: dichlofluanid, tolylfluanid;
guanidine-based compound: guazatine, iminoctadine-albesilate, and iminoctadine-triacetate, dodine;
other compounds: anilazine, dithianon, cymoxanil, vfosetyl (alminium, calcium, and sodium), phosphorous acid and salts, tecloftalam, triazoxide, flusulfamide, diclomezine, methasulfocarb, ethaboxam, cyflufenamid, metrafenone, potassium bicarbonate, sodium bicarbonate, BAF-045 (code number), BAG-010 (code number), benthiazole, bronopol, carvone, chinomethionat, dazomet, DBEDC, debacarb, dichlorophen, difenzoquat-methyl sulfate, dimethyl disulfide, diphenylamine, ethoxyquin, flumetover, fluoroimide, flutianil, fluxapyroxad, furancarboxylic acid, metam, nabam, natamycin, nitrapyrin, nitrothal-isopropyl, o-phenylphenol, oxazinylazole, oxyquinoline sulfate, phenazine oxide, polycarbamate, pyriofenone, S-2188 (code number), silver, SYP-Z-048 (code number), tebufloquin, tolnifanide, trichlamide, mineral oils, and organic oils 12. Microorganisms and products of microorganisms

*Agrobacterium* radiobacter, Fermented product from *Aspergillus* spp., *Bacillus* spp., Harpin protein, *Erwinia carotovora*, *Fusarium oxysporum*, *Gliocladium* spp., Laccase, *Pseudomonas* spp., *Talaromyces* spp., *Trichoderma* spp., Extract from mushroom, and Bacteriophage Among other herbicidically active components that may be mixed or used in combination with the compound of the invention, known pesticides, acaricides, nematocides, and synergistic agents are described below, but the invention is not limited thereto.

[Pesticides, Acaricids & Nematocides]

1. Acetylcholine esterase inhibitor:

(1A) carbamate compound: alanycarb, aldicarb, aldoxycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, 3,5-xylyl methylcarbamate(XMC), and xylylcarb (1B) organo phosphorus compound: acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diamidafos, diazinon, dichlorvos, dicrotophos, dimethoate, dimethylvinphos, dioxabenzofos, disulfoton, DSP, EPN, ethion, ethoprophos, etrimfos, famphur, fenamiphos, fenitrothion, fenthion, fonofos, fosthiazate, fosthietan, heptenophos, isamidofos, isazophos, isofenphos-methyl, isopropyl O-(methoxyaminothio-phosphoryl) salicylate, isoxathion, malathion, mecarbam, methamidophos, methidathion, mevinphos, monocrotophos, naled, omethoate, oxydemeton-methyl, oxydeprofos, parathion, parathion-methyl, phenthoate, phorate, phosalone, phosmet, phosphamidon, phoxim, pirimiphos-methyl, profenofos, propaphos, propetamphos, prothiofos, pyraclofos, pyridaphenthion, quinalphos, sulfotep, tebupirimfos, temephos, terbufos, tetrachlorvinphos, thiometon, thionazin, triazophos, trichlorfon, vamidothion, dichlofenthion, imicyafos, isocarbophos, mesulfenfos, and flupyrazofos 2. GABA receptor (chloride channel) inhibitor (2A) cyclodiene organic chloride-based compound: chlordane, endosulfan, and gamma-BCH (2B) phenylpyrazole-based compound: acetoprol, ethiprole, fipronil, pyrafluprole, pyriprole, and RZI-02-003 (code number)

3. Preparation acting on sodium channel (3A) pyrethroid-based compound: acrinathrin, allethrin [including d-cis-trans and d-trans], bifenthrin, bioallethrin, bioallethrin S-cyclopentenyl, bioresmethrin, cycloprothrin, and cyfluthrin [including beta-], cyhalothrin [including gamma- and lambda-], cypermethrin [including alpha-, beta-, theta-, and zeta-], cyphenothrin [including (1R)-trans-isomers], deltamethrin, empenthrin, esfenvalerate, etofenprox, fenpropathrin, fenvalerate, flucythrinate, flumethrin, and tau-fluvalinate [including tau-], halfenprox, imiprothrin, metofluthrin, permethrin, and phenothrin [including (1R)-trans-isomer], prallethrin, profluthrin, pyrethrine, resmethrin, RU15525 (code number), silafluofen, tefluthrin, tetramethrin, tralomethrin, transfluthrin, ZXI8901 (code number), fluvalinate, tetramethylfluthrin, and meperfluthrin (3B) DDT-based compound: DDT, methoxychlor 4. Nicotinic acetylchloine receptor agonistlantagonist (4A) neonicotinoid-based compound: acetamiprid, clothianidin, dinotefuran, imidacloprid, nitenpyram, thiacloprid, and thiamethoxam (4B) nicotine-based compound: nicotine-sulfate 5. Nicotinic acetylchloine receptor allosteric activator spinosyn-based compound: spinetoram and spinosad 6. Chloride channel activating preparation avermectin, milbemycin-based compound: abamectin, emamectin benzoate, lepimectin, milbemectin, ivermectin, and polynactins 7. Juvenile hormone preparation diofenolan, hydroprene, kinoprene, methothrin, fenoxycarb, and pyriproxyfen 8. Preparation with non-specific mode of action (multiple mode of action)

1,3-dichloropropene, DCIP, ethylene dibromide, methyl bromide, chloropicrin, and sulfuryl fluoride 9. Feeding inhibitor pymetrozine, flonicamid and pyrifluquinazon 10. Mite growth controlling agent clofentezine, diflovidazin, hexythiazox, and etoxazole 11. Preparation for disrupting insect intima BT preparation:

12. ATP biosynthesis enzyme inhibitor diafenthiuron;

organo tin compound: azocyclotin, cyhexatin, and fenbutatin oxide;

propargite, tetradifon

13. Uncoupler chlorfenapyr and DNOC

14. Preparation for blocking nicotinic acetylchloine channel nereistoxin-based compound: bensultap, cartap, thiocyclam, and thiosultap 15. Chitin biosynthesis inhibitor (type 0)

benzoylurea-based compound: bistrifluron, chlorfluazuron, diflubenzuron, flucycloxuron, flufenoxuron, hexaflumuron, lufenuron, novaluron, noviflumuron, teflubenzuron, triflumuron, and fluazuron 16. Chitin biosynthesis inhibitor (type 1)

buprofezin

17. Molting inhibitor (for Diptera)

cyromazine

18. Ecdysone agonist (for promoting molting)

diacylhydrazine-based compound: chromafenozide, halofenozide, methoxyfenozide, and tebufenozide 19. Octopamine agonist amitraz 20. Mitochondrial electron transport chain (complex III) inhibitor cyflumetofen, hydramethylnon, acequinocyl, fluacrypyrim, and cyenopyrafen 21. Mitochondrial electron transport chain (complex I) inhibitor METI acaricides: fenazaquin, fenpyroximate, pyridaben, pyrimidifen, tebufenpyrad, and tolfenpyrad others: rotenone 22. Sodium channel inhibitor indoxacarb and metaflumizon 23. Lipid biosynthesis inhibitor tetronic-based insecticides/acaricides: spirodiclofen, spiromesifen, and spirotetramat 24. Mitochondrial electron transport chain (complex IV) inhibitor aluminium phosphide, phosphine, zinc phosphide, calcium cyanide, and phosphine 25. Neuronal inhibitor preparation (unknown mode of action)

bifenazate

26. Aconitase inhibitor sodium fluoroacetate

27. Preparation acting on ryanodine receptor chlorantraniliprole, flubendiamide and cyantraniliprole 28. Other preparations (unknown mode of action)

azadirachtin, amidoflumet, benclothiaz, benzoximate, bromopropylate, chinomethionat, CL900167 (code number), cryolite, dicofol, dicyclanil, dienochlor, dinobuton, fenbutatin oxide, fenothiocarb, fluensulfone, flufenerim, flusulfamide, karanjin, metham, methoprene, methoxyfenozide, methyl isothiocyanate, pyridalyl, pyrifluquinazon, sulcofuron-sodium, sulflramid, and sulfoxaflor 29. Synergistic agent piperonyl butoxide and DEF.

Hereinafter, production methods of the compound of Formula 1 according to the compound of the invention, formulation examples, and applications will be described in detail with reference to Examples below. However, the invention is not limited to these Examples in any way. In the description below, "%" means "percent by weight" and "parts" means "parts by weight".

Example 1

Production of 6-(2-hydroxy-6-oxo cyclohexa-1-enecarbonyl)-2-methyl-4-phenyl-1,2,4-triazine-3,5 (2H, 4H)-dione (Compound No. 1-50)

(1) Production of 2-methyl-3,5-dioxo-4-phenyl-2,3,4,5-tetrahydro-1,2,4-triazine-6-carbonyl chloride 0.93 g (3.76 mmol) of 2-methyl-3,5-dioxo-4-phenyl-2,3,4,5-tetrahydro-1,2,4-triazine-6-carboxylic acid and 0.72 g (5.64 mmol) of oxalyl chloride were dissolved in dichloromethane (20 ml). To the mixture, a drop of N,N-dimethylformamide was added and stirred at room temperature for 2 hours. The reaction solution was concentrated to obtain 2-methyl-3,5-dioxo-4-phenyl-2,3,4,5-tetrahydro-1,2,4-triazine-6-carbonyl chloride as a pale yellow oily substance.

(2) Production 6-(2-hydroxy-6-oxo cyclohexa-1-enecarbonyl)-2-methyl-4-phenyl-1,2,4-triazine-3,5 (2H, 4H)-dione 0.63 g (5.64 mmol) of 1,3-cyclohexanedione and 0.57 g (5.64 mmol) of triethylamine were dissolved in dichloromethane (20 ml) under ice cooling. To the mixture, the dichloromethane solution (10 ml) of 2-methyl-3,5-dioxo-4-phenyl-2,3,4,5-tetrahydro-1,2,4-triazine-6-carbonyl chloride produced from the above (1) was slowly added dropwise, and stirred for 30 minutes under ice cooling. The reaction mixture was extracted with chloroform, and the organic layer was washed with water, dried over magnesium sulfate, and concentrated under reduced pressure. The residues obtained were dissolved in acetonitrile (20 ml), added with 0.57 g (5.64 mmol) of triethylamine and 0.03 g (0.38 mmol) of acetone cyanohydrin, and refluxed for 30 minutes under heating. After concentration under reduced pressure, the residues were dissolved in water and washed with ethyl acetate. The aqueous layer was acidified by using citric acid, extracted with chloroform, dried over magnesium sulfate, and concentrated under reduced pressure. The crystals obtained were washed with methanol to obtain 0.36 g of the target compound (yield 28%).

Melting point: 182 to 185° C.

Example 2

Production of 6-(5-hydroxy-1-methyl-1H-pyrazole-4-carbonyl)-2-methyl-4-phenyl-1,2,4-triazine-3,5 (2H, 4H)-dione (Compound No. 11-50)

1.50 g (6.07 mmol) of 2-methyl-3,5-dioxo-4-phenyl-2,3,4,5-tetrahydro-1,2,4-triazine-6-carboxylic acid and 1.16 g (9.10 mmol) of oxalyl chloride were dissolved in dichloromethane (30 ml). To the mixture, a drop of N,N-dimethylformamide was added and stirred at room temperature for 2 hours. The reaction solution was concentrated under reduced pressure to obtain 2-methyl-3,5-dioxo-4-phenyl-2,3,4,5-tetrahydro-1,2,4-triazine-6-carbonyl chloride as a pale yellow oily substance.

Next, 1.22 g (9.10 mmol) of 1-methyl-5-hydroxypyrazole hydrochloride and 1.53 g (15.17 mmol) of triethylamine were added to dichloromethane (30 ml) under ice cooling. To the mixture, the dichloromethane solution (15 ml) of 2-methyl-3,5-dioxo-4-phenyl-2,3,4,5-tetrahydro-1,2,4-triazine-6-carbonyl chloride was slowly added dropwise, and stirred for 30 minutes. The reaction mixture was extracted with chloroform, and the organic layer was washed with water, dried over magnesium sulfate, and concentrated under reduced pressure. The residues obtained were dissolved in acetonitrile (30 ml), added with 0.92 g (9.10 mmol) of triethylamine and 0.05 g (0.61 mmol) of acetone cyanohydrin, and refluxed for 30 minutes under heating. The reaction mixture was concentrated under reduced pressure, and then the residues were dissolved in water and washed with ethyl acetate. The aqueous layer was acidified by using citric acid, extracted with chloroform, dried over magnesium sulfate, and concentrated under reduced pressure. The crystals obtained were washed with methanol to obtain 0.40 g of the target compound (yield 20%).

Melting point: 197 to 199° C.

Example 3

Production of 6-(2-hydroxy-4-oxobicyclo [3.2.1] octa-2-en-yl carbonyl]-2-methyl-4-phenyl-1,2,4-triazine-3,5 (2H, 4H)-dione (Compound No. III-50)

1.00 g (4.04 mmol) of 2-methyl-3,5-dioxo-4-phenyl-2,3,4,5-tetrahydro-1,2,4-triazine-6-carboxylic acid and 1.03 g (8.09 mmol) of oxalyl chloride were dissolved in dichloromethane (20 ml). To the mixture, a drop of N,N-dimethylformamide was added and stirred at room temperature for 2 hours. The reaction solution was concentrated under reduced pressure to obtain 2-methyl-3,5-dioxo-4-phenyl-2,3,4,5-tetrahydro-1,2,4-triazine-6-carbonyl chloride as a pale yellow oily substance.

Next, 0.83 g (6.07 mmol) of bicyclo[3.2.1]octane-2,4-dione and 0.61 g (6.07 mmol) of triethylamine were dissolved in dichloromethane (20 ml) under ice cooling. To the solution, the dichloromethane solution (10 ml) of 2-methyl-3,5-dioxo-4-phenyl-2,3,4,5-tetrahydro-1,2,4-triazine-6-carbonyl chloride that is prepared previously was slowly added dropwise. After stirring for 30 minutes under ice cooling, the reaction mixture was extracted with chloroform, and the organic layer was washed with water, dried over magnesium sulfate, and concentrated under reduced pressure. The residues obtained were dissolved in acetonitrile (20 ml), added with 0.61 g (6.07 mmol) of triethylamine and 0.03 g (0.4 mmol) of acetone cyanohydrin, and refluxed for 30 minutes under heating. The reaction mixture was concentrated under reduced pressure, and then the residues were dissolved in water and washed with ethyl acetate. The aqueous layer was acidified by using citric acid, extracted with chloroform, dried over magnesium sulfate, and concentrated under reduced pressure. The crystals obtained were washed with methanol to obtain 0.70 g of the target compound (yield 47%).

Melting point: 163 to 165° C.

Example 4

Production of 1-isopropyl-4-(2-methyl-3,5-dioxo-4-phenyl-2,3,4,5-tetrahydro-1,2,4-triazine-6-yl carbonyl)-1H-pyrazole-5-yl propane-1-sulfonate (Compound No. 11-267)

0.85 g (2.60 mmol) of 6-(5-hydroxy-1-isopropyl-1H-pyrazol-4-yl carbonyl)-2-methyl-4-phenyl-1,2,4-triazine-3,5 (2H, 4H)-dione was dissolved in 20 ml of dichloromethane. To the solution, 0.27 g (2.60 mmol) of triethylamine and 0.37 g (2.60 mmol) of 1-propane sulfonyl chloride were added at room temperature and stirred overnight. The reaction mixture was concentrated under reduced pressure, and the residues were purified by silica gel column chromatography (hexane:ethyl acetate=1:1) to obtain 0.71 g of the target compound (yield 63%).

Melting point: 51 to 53° C.

Example 5

Production of 2-methyl-3,5-dioxo-4-(4-chlorophenyl)-2,3,4,5-tetrahydro-1,2,4-triazine-6-carboxylic acid (Compound No. V-53)

(1) Production of diethyl 2-(2-methylhydrazono) malonate 5.00 g (0.0287 mol) of diethyl ketomalonate was dissolved in 30 ml ethanol. To the solution, 1.45 g (0.0316 mol) of methyl hydrazine was added and stirred for 7 hours at 60° C. followed by further stirring overnight at room temperature. The reaction mixture was concentrated under reduced pressure and extracted with ethyl acetate. The organic layer was washed with water, dried over magnesium sulfate, and concentrated under reduced pressure. The resulting residues were purified by silica gel column chromatography (hexane:ethyl acetate=1:1) to obtain 5.28 g of the target compound (yield 91%).

(2) Production of ethyl 4-(4-chlorophenyl)-2-methyl-3,5-dioxo-2,3,4,5-tetrahydro-1,2,4-triazine-6-carboxylic acid ester 2.00 g (9.89 mmol) of diethyl 2-(2-methylhydrazono) malonate and 1.50 g (9.89 mmol) of DBU were dissolved in 50 ml of tetrahydrofuran. To the solution, the tetrahydrofuran (10 ml) solution of 4-chlorophenyl isocyanate (3.34 g, 21.7 mmol) was slowly added dropwise at room temperature, and stirred over night. The reaction mixture was concentrated under reduced pressure, and the residues were extracted with ethyl acetate, washed with water, dried over magnesium sulfate, and concentrated under reduced pressure. The resulting residues were purified by silica gel column chromatography (hexane:ethyl acetate=7:1) to obtain 2.00 g of the target compound (yield 65%).

(3) Production of 2-methyl-3,5-dioxo-4-(4-chlorophenyl)-2,3,4,5-tetrahydro-1,2,4-triazine-6-carboxylic acid 2.00 g (6.46 mmol) of ethyl 2-methyl-4-(4-chlorophenyl)-2,3,4,5-tetrahydro-1,2,4-triazine-6-carboxylic acid ester was stirred at room temperature for 2 days in a mixed solvent of acetic acid (30 ml) and conc. hydrochloric acid (30 ml). The reaction mixture was concentrated under reduced pressure to obtain 1.88 g of the target compound (yield, quantitative).

Melting point: 234 to 236° C.

Example 6

Production of 2,4-dimethyl-3,5-dioxo-2,3,4,5-tetrahydro-1,2,4-triazine-6-carboxylic acid (Compound No. V-1)

(1) Production of 2-methylsemicarbazide 13 g (282.1 mmol) of methyl hydrazine was dissolved in 60 ml of tetrahydrofuran. To the solution, 25 g (217 mmol) of trimethylsilyl isocyanate was slowly added dropwise at 0° C. and further stirred for 1 hour. To the reaction mixture, 40 ml of methanol was added and stirred for 5 hours at 40° C. The reaction mixture was concentrated to obtain 18 g of 2-methyl semicarbazide as a pale yellow solid (yield 93%).

$^1$H-NMR (CDCl$_3$, TMS) δ(ppm).
3.15 (3H, s), 3.80 (2H, br), 5.61 (2H, br)

(2) Production of ethyl 2-methyl-3,5-dioxo-2,3,4,5-tetrahydro-1,2,4-triazine-6-carboxylic acid ester 35.2 g (202 mmol) of diethyl ketomalonate and 18 g (202 mmol) of 2-methyl semicarbazide were dissolved in 200 ml ethanol, and then refluxed under heating for 36 hours. The reaction solution was concentrated to obtain 31 g of ethyl 2-methyl-3,5-dioxo-2,3,4,5-tetrahydro-1,2,4-triazine-6-carboxylic acid ester as a white solid (yield 78%).

$^1$H-NMR (CDCl$_3$, TMS) δ(ppm).
1.39 (3H, t, J=7.1 Hz), 3.72 (3H, s), 4.42 (2H, q, J7.1 Hz), 9.38 (1H, br)

(3) Production of ethyl 2,4-dimethyl-3,5-dioxo-2,3,4,5-tetrahydro-1,2,4-triazine-6-carboxylic acid ester 2.0 g (10.0 mmol) of ethyl 2-methyl-3,5-dioxo-2,3,4,5-tetrahydro-1,2,4-triazine-6-carboxylic acid ester, 1.9 g (13.5 mmol) of potassium carbonate, and 1.8 g (12.5 mmol) of methyl iodide were added to 20 ml of N,N-dimethylformamide, and stirred for 2 hours at 60° C. Upon the completion of the reaction, the reaction solution was added with water, and then extracted with ethyl acetate. The organic layer obtained was dried over anhydrous magnesium sulfate and concentrated to obtain 1.8 g of ethyl 2,4-dimethyl-3,5-dioxo-2,3,4,5-tetrahydro-1,2,4-triazine-6-carboxylic acid ester (yield 86%).

$^1$H-NMR (CDCl$_3$, TMS) δ(ppm).
1.40 (3H, t, J=7.1 Hz), 3.38 (3H, s), 3.74 (3H, s), 4.42 (2H, q, J=7.1 Hz)

(4) Production of 2,4-dimethyl-3,5-dioxo-2,3,4,5-tetrahydro-1,2,4-triazine-6-carboxylic acid 1.8 g (8.41 mmol) of ethyl 2,4-dimethyl-3,5-dioxo-2,3,4, 5-tetrahydro-1,2,4-triazine-6-carboxylic acid ester was stirred at room temperature for 24 hours in a mixed solvent of acetic acid (30 ml) and conc. hydrochloric acid (30 ml). The reaction solution was concentrated to obtain 1.40 g of 2,4-dimethyl-3,5-dioxo-2,3,4,5-tetrahydro-1,2,4-triazine-6-carboxylic acid as a white solid (yield 90%).

Melting point: 220 to 223° C.
$^1$H-NMR (CDCl$_3$, TMS) δ(ppm).
3.48 (3H, s), 3.88 (3H, s)

Example 7

Production of 2-ethyl-3,5-dioxo-4-phenyl-2,3,4,5-tetrahydro-1,2,4-triazine-6-carboxylic acid (Compound No. V-259)

(1) Production of ethyl 3,5-dioxo-4-phenyl-2,3,4,5-tetrahydro-1,2,4-triazine-6-carboxylic acid ester 9.0 g (0.0517 mol) of diethyl ketomalonate and 7.81 g (0.0517 mol) of 2-phenyl semicarbazide were stirred in 50 ml xylene for 1 hour at 100° C. The reaction mixture was refluxed under heating, and by adding sodium methoxide (8.37 g, 0.155 mol) in small portions, the reaction was completed. After cooling to room temperature, the reaction mixture was neutralized with 1N aqueous hydrochloric acid solution, extracted with ethyl acetate, and dried over magnesium sulfate. The reaction mixture was concentrated under reduced pressure and the residues were isolated and purified by silica gel column chromatography (hexane:ethyl acetate=2:1) to obtain 6.18 g of the target compound (yield 46%).

(2) Production of ethyl 2-ethyl-3,5-dioxo-4-phenyl-2,3,4,5-tetrahydro-1,2,4-triazine-6-carboxylic acid ester 1.50 g (5.74 mmol) of ethyl 3,5-dioxo-4-phenyl-2,3,4,5-tetrahydro-1,2,4-triazine-6-carboxylic acid ester was dissolved in 30 ml of N,N-dimethylformamide, added with 60% sodium hydride (0.23 g, 5.74 mmol) under ice cooling, and further stirred for 30 minutes. The mixture was added with ethyl iodide (0.90 g, 5.74 mmol) and stirred. After raising to room temperature, an aqueous solution of ammonium chloride was added to terminate the reaction. The resultant was extracted with diethyl ether, dried over magnesium chloride, and concentrated under reduced pressure. The residues were purified by silica gel column chromatography to obtain 1.33 g of the target compound (yield 80%).

(3) Production of 2-ethyl-3,5-dioxo-4-phenyl-2,3,4,5-tetrahydro-1,2,4-triazine-6-carboxylic acid 1.30 g (4.49 mmol) of ethyl 2-ethyl-3,5-dioxo-4-phenyl-2,3,4,5-tetrahydro-1,2,4-triazine-6-carboxylic acid ester was dissolved in 30 ml ethanol, added with a 25% aqueous solution of sodium hydroxide (1.29 g, 8.09 mmol), and stirred overnight. After dilution by adding water, the aqueous layer was washed with diethyl ether. The aqueous layer was acidified by adding 6 N aqueous hydrochloric acid solution, and then extracted with ethyl acetate. After drying over magnesium sulfate and concentration under reduced pressure, 1.10 g of the target compound was obtained (yield 94%).

Example 8

Production of 2,4-dimethyl-5-oxo-3-thioxo-2,3,4,5-tetrahydro-1,2,4-triazine-6-carboxylic acid (Compound No. V-265)

(1) Production of ethyl 2,4-dimethyl-5-oxo-3-thioxo-2,3,4,5-tetrahydro-1,2,4-triazine-6-carboxylic acid ester 2.00 g (9.89 mmol) of diethyl 2-(2-methylhydrazono) malonate and 1.50 g (9.89 mmol) of 1,8-diazabicyclo[5.4.0]undec-7-ene (DBU) were dissolved in 50 ml of tetrahydrofuran. To the solution, the tetrahydrofuran (10 ml) of methylisothiocyanate (1.58 g, 21.7 mmol) was slowly added dropwise and stirred overnight. The reaction mixture was concentrated under reduced pressure, extracted with ethyl acetate, washed with water, and dried over magnesium sulfate. The residues obtained after concentration under reduced pressure were purified by silica gel column chromatography (hexane:ethyl acetate=3:1) to obtain 2.20 g of the target compound (yield 97%).

(2) Production of 2,4-dimethyl-5-oxo-3-thioxo-2,3,4,5-tetrahydro-1,2,4-triazine-6-carboxylic acid 2.30 g (0.01 mol) of ethyl 2,4-dimethyl-5-oxo-3-thioxo-2,3,4,5-tetrahydro-1,2,4-triazine-6-carboxylic acid ester was stirred overnight at room temperature in a mixed solvent of acetic acid (30 ml) and conc. hydrochloric acid (30 ml). The reaction mixture was concentrated under reduced pressure to obtain 2.01 g of the target compound (yield; quantitative).

Example 9

Production of 2-methyl-3,5-dioxo-4-(2-cyanophenyl)-2,3,4,5-tetrahydro-1,2,4-triazine-6-carboxylic acid (Compound No. V-72)

(1) Production of ethyl 2-methyl-3,5-dioxo-4-(2-cyanophenyl)-2,3,4,5-tetrahydro-1,2,4-triazine-6-carboxylic acid ester 2.0 g (9.89 mmol) of diethyl 2-(2-methylhydrazono) malonate and 3.3 g (21.8 mmol) of 1,8-diazabicyclo[5.4.0]undec-7-ene (DBU) were dissolved in 20 ml of tetrahydrofuran. To the solution, 4.9 g (20.8 mmol) of phenyl-2-cyanophenylcarbamate was added at room temperature and stirred for 1 hour at the same temperature. After that, the mixture was refluxed under heating for 3 hours. The reaction solution was concentrated and the residues were extracted with ethyl acetate. The organic layer obtained was washed with water and an aqueous solution of citric acid in order, dried over anhydrous magnesium sulfate, and concentrated under reduced pressure. The residues were purified by silica gel column chromatography (hexane:ethyl acetate=2:1) to obtain 2.3 g of ethyl 2-methyl-3,5-dioxo-4-(2-cyanophenyl)-2,3,4,5-tetrahydro-1,2,4-triazine-6-carboxylic acid ester (yield 78%).

$^1$H-NMR (CDCl$_3$, TMS) δ(ppm).
1.40 (3H, t, J=7.1 Hz), 3.81 (3H, s), 4.45 (2H, q, J=7.1 Hz), 7.39 (1H, d, J=8.0 Hz), 7.60-7.64 (1H, m), 7.75-7.80 (1H, m), 7.85 (1H, d, J=7.6 Hz)

(2) Production of 2-methyl-3,5-dioxo-4-(2-cyanophenyl)-2,3,4,5-tetrahydro-1,2,4-triazine-6-carboxylic acid 2.3 g (7.65 mmol) of ethyl 2-methyl-3,5-dioxo-4-(2-cyanophenyl)-2,3,4,5-tetrahydro-1,2,4-triazine-6-carboxylic acid ester was stirred for 24 hours at room temperature in a mixed solvent of acetic acid (30 ml) and conc. hydrochloric acid (30 ml). The reaction solution was concentrated under reduced pressure to obtain 1.8 g of 2-methyl-3,5-dioxo-4-(2- cyanophenyl)-2,3,4,5-tetrahydro-1,2,4-triazine-6-carboxylic acid as a white solid (yield 90%).
Melting point: 213 to 215° C.
$^1$H-NMR (DMSO-$d_6$, TMS) δ(ppm).
3.65 (3H, s), 7.67 (1H, d, J=8.0 Hz), 7.70-7.75 (1H, m), 7.90-7.96 (1H, m), 8.09 (1H, d, J=7.4 Hz), 14.02 (1H, br)

Example 10

Production of 2-methyl-3,5-dioxo-4-phenyl-2,3,4,5-tetrahydro-1,2,4-triazine-6-carboxylic acid (Compound No. V-50)

(1) Production of ethyl 2-methyl-3,5-dioxo-4-phenyl-2,3,4,5-tetrahydro-1,2,4-triazine-6-carboxylic acid ester 2.0 g (9.89 mmol) of diethyl 2-oxomalonate and 0.04 g (0.2 mmol) of p-toluene sulfonic acid were dissolved in 50 ml of toluene. To the solution, 2.5 g (15.2 mmol) of 1-methyl-N-phenylhydrazine carboxamides was added at room temperature, and then stirred for 2 hours with reflux under heating. The reaction mixture was cooled to room temperature and added with 0.08 g (0.5 mmol) of 1,8-diazabicyclo[5.4.0]undec-7-ene (DBU) followed by stirring at room temperature for two hours. The reaction solution was washed with water and dried over magnesium sulfate. The solvent was distilled off to obtain ethyl 2-methyl-3,5-dioxo-4-phenyl-2,3,4,5-tetrahydro-1,2,4-triazine-6-carboxylic acid ester.

(2) Production of 2-methyl-3,5-dioxo-4-phenyl-2,3,4,5-tetrahydro-1,2,4-triazine-6-carboxylic acid Ethyl 2-methyl-3,5-dioxo-4-phenyl-2,3,4,5-tetrahydro-1,2,4-triazine-6-carboxylic acid ester produced from the above (1) was stirred for 24 hours at room temperature in a mixed solvent of acetic acid (30 ml) and conc. hydrochloric acid (30 ml). The reaction mixture was concentrated under reduced pressure, extracted with a saturated aqueous solution of sodium hydrogen carbonate, washed with ethyl acetate, and then adjusted to be weakly acidic by using diluted hydrochloric acid. After that, the mixture was extracted with ethyl acetate and dried over magnesium sulfate, and the solvent was distilled off to obtain 2.6 g of 2-methyl-3,5-dioxo-4-phenyl-2,3,4,5-tetrahydro-1,2,4-triazine-6-carboxylic acid as a white solid (2-step yield 70%).
Melting point: 195 to 198° C.
$^1$H-NMR (DMSO-$d_6$, TMS) δ(ppm).
3.59 (3H, s), 7.29-7.31 (2H, m), 7.43-7.54 (3H, m), 13.64 (1H, bs)

Physical property values (melting point or refractive index) of the compound of the invention represented by Formula 1, which has been synthesized according to the above Examples, are shown in Table 68 to Table 70 including above Examples. Herein, * means refractive index.

TABLE 68

| Compound No. | Melting Point (° C.) or Refractive Index ($n_D^{20}$) |
|---|---|
| I-2 | 87-89 |
| I-3 | 1.5530* |
| I-5 | 1.5630* |
| I-9 | 1.5380* |
| I-10 | 124-125 |
| I-11 | 97-98 |
| I-14 | 126-129 |
| I-16 | 116-118 |
| I-19 | 132-134 |
| I-27 | 1.5460* |
| I-41 | 1.5495* |
| I-43 | 98-101 |
| I-47 | 155-157 |
| I-50 | 182-185 |
| I-51 | 184-185 |
| I-52 | 187-190 |
| I-53 | 182-183 |
| I-54 | 174-176 |
| I-55 | 209-212 |
| I-56 | 181-183 |
| I-57 | 135-136 |
| I-58 | 198-199 |
| I-59 | 190-193 |
| I-60 | 190-191 |
| I-61 | 186-187 |
| I-62 | 137-139 |
| I-63 | 166-169 |
| I-64 | 89-92 |
| I-65 | 184-187 |
| I-66 | 151-152 |
| I-67 | 174-177 |
| I-68 | 208-210 |
| I-71 | 130-131 |
| I-72 | 166-169 |
| I-73 | 181-184 |
| I-74 | 108-111 |
| I-75 | 173-176 |
| I-76 | 242-245 |
| I-77 | 192-194 |
| I-78 | 149-151 |
| I-79 | 161-163 |
| I-80 | 98-101 |
| I-81 | 158-161 |
| I-82 | 212-215 |
| I-83 | 191-194 |
| I-84 | 124-127 |
| I-85 | 235-238 |
| I-86 | 199-202 |
| I-87 | 197-198 |
| I-88 | 160-163 |
| I-89 | 190-193 |
| I-90 | 164-166 |
| I-91 | 89-91 |
| I-92 | 245-247 |
| I-93 | 168-169 |
| I-94 | 155-157 |
| I-96 | 151-153 |
| I-98 | 155-157 |
| I-99 | 178-181 |
| I-105 | 186-188 |
| I-106 | 228-231 |
| I-107 | 212-215 |
| I-108 | 167-169 |
| I-109 | 166-168 |
| I-110 | 151-152 |
| I-111 | 196-199 |
| I-115 | 144-147 |
| I-116 | 176-179 |
| I-117 | 140-143 |
| I-118 | 140-143 |
| I-119 | 191-194 |
| I-120 | 191-194 |
| I-125 | 148-151 |
| I-126 | 126-129 |
| I-127 | 237-240 |
| I-128 | 217-220 |
| I-129 | 155-158 |
| I-131 | 204-205 |
| I-134 | 215-217 |
| I-135 | 152-154 |
| I-136 | 156-157 |
| I-137 | 154-157 |
| I-138 | 123-126 |
| I-149 | 175-178 |

TABLE 68-continued

| Compound No. | Melting Point (° C.) or Refractive Index ($n_D^{20}$) |
|---|---|
| I-155 | 196-199 |
| I-167 | 183-185 |
| I-169 | 178-180 |
| I-170 | 213-215 |

TABLE 69

| Compound No. | Melting Point (° C.) or Refractive Index ($n_D^{20}$) |
|---|---|
| I-179 | 215-218 |
| I-182 | 159-161 |
| I-183 | 138-141 |
| I-184 | 100-103 |
| I-185 | 108-111 |
| I-187 | 180-183 |
| I-189 | 190-193 |
| I-198 | 135-137 |
| I-199 | 169-170 |
| I-202 | 161-162 |
| I-203 | 188-191 |
| I-204 | 201-204 |
| I-205 | 87-90 |
| I-259 | 150-153 |
| I-260 | 152-154 |
| I-261 | 190-193 |
| I-262 | 103-106 |
| I-263 | 174-176 |
| I-265 | 164-167 |
| I-268 | 201-204 |
| I-269 | 112-115 |
| I-270 | 172-175 |
| I-271 | 251-254 |
| I-272 | 204-207 |
| I-274 | 101-103 |
| I-275 | 89-92 |
| I-276 | 167-170 |
| I-277 | 96-99 |
| I-278 | 98-101 |
| I-279 | 218-220 |
| I-280 | 168-171 |
| I-281 | 146-147 |
| I-282 | 148-151 |
| I-283 | 172-175 |
| I-284 | 160-162 |
| I-285 | 149-152 |
| I-286 | 88-91 |
| I-287 | 155-158 |
| I-288 | 94-97 |
| I-289 | 215-218 |
| I-290 | 138-141 |
| I-291 | 194-197 |
| I-292 | 167-169 |
| I-293 | 158-160 |
| I-294 | 113-115 |
| I-295 | 1.5360* |
| I-296 | 1.5300* |
| I-297 | 89-92 |
| I-298 | 148-150 |
| I-299 | 212-215 |
| I-300 | 203-205 |
| I-301 | 274-277 |
| I-302 | 222-224 |
| I-303 | 62-65 |
| I-304 | 148-151 |
| I-307 | 58-61 |
| I-328 | 58-61 |
| I-463 | 131-134 |
| I-464 | 168-170 |
| I-465 | 211-213 |
| I-466 | 89-92 |
| I-467 | 211-214 |
| I-468 | 128-130 |
| I-469 | 172-174 |

TABLE 69-continued

| Compound No. | Melting Point (° C.) or Refractive Index ($n_D^{20}$) |
|---|---|
| I-470 | 147-148 |
| I-471 | 1.5620* |
| I-472 | 162-164 |
| I-473 | 143-146 |
| I-474 | 70-73 |
| I-475 | 83-86 |
| I-476 | 191-193 |
| I-477 | 149-151 |
| I-478 | 1.5270* |
| I-479 | 1.5450* |
| I-480 | 179-181 |
| II-50 | 197-199 |
| II-267 | 51-53 |
| III-50 | 163-165 |
| III-62 | 158-159 |
| VI-1 | 151-154 |
| VI-5 | 145-148 |
| VI-6 | 145-146 |
| VI-7 | 163-166 |
| VI-65 | 93-96 |
| VI-97 | 158-160 |

Compound number and $^1$H-NMR data (standard; TMS, δ (ppm) value) are given below. Data without a name of solvent are measured by using $CDCl_3$.

Compound No. I-1:
2.04-2.10 (2H, m), 2.45-2.49 (2H, m), 2.76-2.80 (2H, m), 3.56 (3H, s),
3.65 (3H, s), 16.05 (1H, br)

Compound No. I-3:
0.92 (3H, t, J=6.00 Hz), 1.69 (2H, q, J=6.00 Hz), 2.03-2.11 (2H, m),
2.45-2.49 (2H, m), 2.75-2.79 (2H, m), 3.64 (3H, s), 3.89 (2H, t, J=6.00 Hz),
16.05 (1H, br)

Compound No. I-4:
1.49 (6H, d, J=, 6.00 Hz), 2.03-2.11 (2H, m), 2.44-2.49 (2H, m), 2.74-2.79 (2H, m),
3.61 (3H, s), 5.07 (1H, sept, J=6.00 Hz), 16.08 (1H, br)

Compound No. I-5:
0.95 (3H, t, J=7.2 Hz), 1.32-1.43 (2H, m), 1.59-1.68 (2H, m), 2.03-2.10 (2H, m),
2.45-2.49 (2H, m), 2.75-2.79 (2H, m), 3.64 (3H, s), 3.92 (2H, t, J=6.9 Hz),
16.05 (1H, br)

Compound No. I-9:
0.88 (3H, t, J=6.6 Hz), 1.20-1.40 (6H, m), 1.58-1.64 (2H, m), 2.03-2.12 (2H, m),
2.44-2.48 (2H, m), 2.75-2.79 (2H, m), 3.64 (3H, s), 3.89-3.94 (2H, m), 16.04 (1H, br)

Compound No. I-27:
1.65 (3H, t, J=3.00 Hz), 2.03-2.09 (2H, m), 2.31-2.36 (2H, m), 2.44-2.49 (2H, m),
2.74-2.79 (2H, m), 3.64 (3H, s), 4.01 (2H, t, J=6.00), 16.00 (1H br)

Compound No. I-41:
1.89-1.97 (2H, m), 2.04-2.11 (2H, m), 2.44-2.48 (2H, m), 3.31 (3H, s),
3.44 (2H, t, J=6.0 Hz), 3.64 (3H, s), 4.03 (2H, t, J=7.0 Hz), 16.04 (1H, br)

Compound No. I-75:
2.05-2.11 (2H, m), 2.45-2.49 (2H, m), 2.75-2.80 (2H, m), 3.69 (3H, s),
7.05-7.09 (1H, m), 7.14-7.21 (1H, m), 7.24-7.33 (1H, m), 15.99 (1H, s)

Compound No. I-76:
  2.04-2.09 (2H, m), 2.46-2.50 (2H, m), 2.75-2.80 (2H, m), 3.69 (3H, s),
  6.88-6.96 (3H, m), 15.97 (1H, s)
Compound No. I-77:
  2.03-2.09 (2H, m), 2.45-2.49 (2H, m), 2.75-2.78 (2H, m), 3.71 (3H, s),
  7.11-7.14 (1H, m), 7.18-7.33 (2H, m), 15.95 (1H, s)
Compound No. I-79:
  2.04-2.10 (2H, m), 2.45-2.50 (2H, m), 2.75-2.79 (2H, m), 3.70 (3H, s),
  7.10-7.24 (3H, m), 15.96 (1H, s)
Compound No. I-80:
  2.01-2.08 (2H, m), 2.46-2.49 (2H, m), 2.75-2.78 (2H, m), 3.71 (3H, s),
Compound No. I-81:
  2.05-2.0 (2H, m), 2.45-2.50 (2H, m), 2.75-2.80 (2H, m), 3.69 (3H, s),
  7.14-7.19 (1H, m), 7.43 (1H, d, J=2.5), 7.57 (1H, d, J=8.5), 15.97 (1H, s)
Compound No. I-295:
  0.85-0.89 (3H, m), 1.26-1.32 (10H, m), 1.57-1.65 (2H, m), 2.05-2.12 (2H, m),
  2.44-2.49 (2H, m), 2.75-2.79 (2H, m), 3.64 (3H, s) 3.88-3.93 (2H, m)
Compound No. I-296:
  0.85-0.90 (3H, m), 1.25-1.36 (14H, m), 1.59-1.69 (2H, m), 2.05-2.09 (2H, m),
  2.44-2.49 (2H, m), 2.74-2.79 (2H, m), 3.64 (3H, s), 3.88-3.93 (2H, m),
Compound No. I-306:
  0.96 (3H, t, J=7.15), 1.39-1.46 (2H, m), 1.69-1.71 (2H, m), 2.05-2.09 (2H, m),
  2.44-2.49 (2H, m), 4.01 (2H, t, J=7.69), 7.32-7.36 (2H, m), 7.56-7.59 (1H, m),
  7.83-7.88 (1H, m), 8.61-8.63 (1H, m), 16.05 (1H, br)
Compound No. I-308:
  0.88-0.92 (3H, m), 0.35-0.37 (4H, m), 0.79-1.82 (2H, m), 2.03-2.07 (2H, m),
  2.44-2.49 (2H, m), 2.73-2.78 (2H, m), 4.01 (2H, t, J=7.69), 7.28-7.30 (2H, m),
  7.43-7.53 (3H, m), 16.06 (1H, br)
Compound No. I-339:
  1.84-2.11 (4H, m), 2.44-2.48 (2H, m), 2.74-2.78 (2H, m), 3.64 (3H, s),
  3.69-3.92 (3H, m), 4.07-4.34 (2H, m), 16.04 (1H, br)
Compound No. I-462:
  1.30 (3H, t, J=7.66), 2.03-2.07 (2H, m), 2.45-2.49 (2H, m), 2.69-2.77 (4H, m),
  3.68 (3H, s), 7.28-7.30 (1H, m), 7.77-7.73 (1H, m), 8.51 (1H, s), 16.03 (1H, br)

Physical property values of the production intermediate [13a] and [3b] are given in Table 70 and Table 71.

TABLE 70

| Compound No. | Melting Point (° C.) |
|---|---|
| IV-116 | 111-114 |
| IV-117 | 100-102 |
| IV-118 | 118-121 |
| IV-136 | 131-133 |
| IV-137 | 102-105 |
| IV-138 | 122-125 |
| IV-182 | 107-108 |
| IV-185 | 50-53 |
| IV-197 | 122-125 |
| IV-259 | 84-86 |

TABLE 70-continued

| Compound No. | Melting Point (° C.) |
|---|---|
| IV-260 | 107-109 |
| IV-261 | 132-135 |
| IV-275 | 102-103 |
| IV-276 | 46-49 |
| IV-278 | 171-172 |
| IV-280 | 137-140 |
| IV-284 | 136-137 |
| IV-285 | 112-114 |
| IV-287 | 140-142 |
| IV-288 | 101-102 |
| IV-290 | 124-127 |
| IV-291 | 137-138 |

TABLE 71

| Compound No. | Melting Point (° C.) |
|---|---|
| V-1 | 220-223 |
| V-2 | 165-168 |
| V-3 | 113-115 |
| V-4 | 122-125 |
| V-5 | 98-100 |
| V-9 | 99-102 |
| V-10 | 127-129 |
| V-11 | 82-84 |
| V-14 | 142-144 |
| V-16 | 155-158 |
| V-27 | 114-117 |
| V-41 | 90-91 |
| V-43 | 145-146 |
| V-47 | 144-147 |
| V-50 | 195-198 |
| V-51 | 154-157 |
| V-52 | 118-120 |
| V-53 | 234-236 |
| V-54 | 95-98 |
| V-55 | 95-98 |
| V-56 | 212-215 |
| V-57 | 150-152 |
| V-58 | 196-199 |
| V-60 | 145-146 |
| V-61 | 173-174 |
| V-66 | 164-166 |
| V-67 | 200-203 |
| V-68 | 206-209 |
| V-72 | 213-215 |
| V-73 | 221-224 |
| V-87 | 162-165 |
| V-88 | 227-230 |
| V-89 | 184-186 |
| V-90 | 156-159 |
| V-91 | 179-181 |
| V-92 | 207-210 |
| V-93 | 220-223 |
| V-99 | 166-169 |
| V-105 | 169-171 |
| V-106 | 231-234 |
| V-107 | 166-169 |
| V-108 | 153-156 |
| V-109 | 197-198 |
| V-110 | 194-197 |
| V-111 | 187-190 |
| V-115 | 188-191 |
| V-119 | 205-208 |
| V-125 | 173-175 |
| V-127 | 135-138 |
| V-128 | 186-188 |
| V-129 | 198-201 |
| V-131 | 201-204 |
| V-135 | 224-227 |
| V-149 | 216-218 |
| V-155 | 229-231 |
| V-167 | 211-212 |
| V-169 | 199-202 |
| V-170 | 177-180 |

TABLE 71-continued

| Compound No. | Melting Point (° C.) |
| --- | --- |
| V-179 | 237-240 |
| V-184 | 158-161 |
| V-189 | 200-201 |
| V-202 | 200-203 |
| V-203 | 164-167 |
| V-204 | 199-202 |
| V-268 | 201-204 |
| V-269 | 155-157 |
| V-270 | 184-187 |
| V-271 | 208-211 |
| V-272 | 100-102 |
| V-273 | 202-205 |
| V-275 | 166-169 |
| V-282 | 193-196 |
| V-283 | 186-189 |
| V-291 | 175-178 |
| V-294 | 204-207 |
| V-295 | 105-107 |
| V-296 | 106-108 |
| V-297 | 176-179 |
| V-298 | 145-146 |
| V-299 | 241-244 |
| V-300 | 245-248 |
| V-301 | 259-261 |
| V-302 | 211-212 |
| V-303 | 152-155 |
| V-304 | 140-143 |
| V-305 | 166-167 |
| V-328 | 143-146 |
| V-358 | 240-243 |
| V-359 | 91-94 |
| V-360 | 240-242 |
| V-361 | 155-158 |
| V-362 | 148-151 |
| V-363 | 189-192 |
| V-364 | 213-216 |
| V-365 | 75-78 |
| V-366 | 218-221 |
| V-367 | 192-195 |
| V-368 | 153-156 |
| V-369 | 111-113 |
| V-370 | 100-103 |
| V-371 | 80-83 |

Compound number and $^1$H-NMR data (standard; TMS, δ (ppm) value) for the production intermediates are given below. Data without a name of solvent are measured by using $CDCl_3$.

Compound No. IV-19:
1.19-1.41 (3H, m), 1.39 (3H, t, J=5.3 Hz), 1.56-1.66 (3H, m), 1.83-1.87 (2H, m),
2.37 (2H, dq, J=3.3 Hz, 12.1 Hz), 3.68 (3H, s), 4.41 (2H, q, J=7.1 Hz), 4.73 (1H, tt, J=3.3 Hz, 12.1 Hz)

Compound No. IV-50:
1.39 (3H, t, J=7.1 Hz), 3.71 (3H, s), 4.43 (2H, q, J=7.1 Hz), 7.24-7.26 (2H, m),
7.49-7.57 (3H, m)

Compound No. IV-53:
1.39 (3H, t, J=5.3 Hz), 3.77 (3H, s), 4.43 (2H, q, J=5.3 Hz), 7.18 (2H, d, J=6.4 Hz),
7.49 (2H, d, J=6.4 Hz)

Compound No. IV-56:
1.39 (3H, t, J=7.1 Hz), 3.77 (3H, s), 4.43 (2H, q, J=7.1 Hz), 7.20-7.22 (4H, m)

Compound No. IV-59:
1.39 (3H, t, J=7.1 Hz), 2.41 (3H, s), 3.77 (3H, s), 4.42 (2H, q, J=7.1 Hz),
7.10 (2H, d, J=8.3 Hz), 7.31 (2H, d, J=8.3 Hz)

Compound No. IV-62:
1.39 (3H, t, J=7.1 Hz), 3.76 (3H, s), 3.84 (3H, s), 4.43 (2H, q, J=7.1 Hz),
7.01 (2H, d, J=9.0 Hz), 7.14 (2H, d, J=9.0 Hz)

Compound No. IV-63:
1.39 (3H, t, J=7.1 Hz), 3.78 (3H, s), 4.43 (2H, q, J=7.1 Hz), 7.30 (1H, d, J=7.7 Hz),
7.67 (1H, t, J=7.7), 7.74 (1H, dt, J=1.1 Hz, 7.7 Hz), 7.84 (1H, dd, J=1.1 Hz, 7.7 Hz)

Compound No. IV-64:
1.40 (3H, t, J=7.1 Hz), 3.78 (3H, s), 4.44 (2H, q, J=7.1 Hz), 7.44 (1H, d, J=8.0 Hz),
7.54 (1H, s), 7.66 (1H, t, J=8.0 Hz), 7.75 (1H, d, J=8.0 Hz)

Compound No. IV-65:
1.40 (3H, t, J=5.3 Hz), 3.79 (3H, s), 4.44 (2H, q, J=5.3 Hz), 7.39 (2H, d, J=6.2 Hz),
7.79 (2H, d, J=6.2 Hz)

Compound No. IV-71:
1.39 (3H, t, J=7.1 Hz), 3.78 (3H, s), 4.43 (2H, q, J=7.1 Hz), 7.28 (2H, d, J=8.5 Hz), 7.36 (2H, d, J=8.5 Hz)

Compound No. IV-74:
1.39 (3H, t, J=7.1 Hz), 3.78 (3H, s), 4.44 (2H, q, J=7.1 Hz), 7.39 (2H, dd, J=1.9 Hz, 6.6 Hz), 7.82 (2H, dd, J=1.9 Hz, 6.6 Hz)

Compound No. IV-78:
1.40 (3H, t, J=7.1 Hz), 3.79 (3H, s), 4.43 (2H, q, J=7.1 Hz), 6.99-7.05 (2H, m),
7.22-7.28 (1H, m)

Compound No. IV-93:
1.39 (3H, t, J=7.1 Hz), 3.77 (3H, s), 3.78 (6H, s), 4.43 (2H, q, J=7.1 Hz),
6.35 (2H, d, J=2.2 Hz), 6.55 (1H, t, J=2.2 Hz)

Compound No. IV-96:
1.39 (3H, t, J=7.1 Hz), 3.76 (6H, s), 3.83 (3H, s), 4.42 (2H, q, J=7.1 Hz),
6.55-6.59 (2H, m), 7.05 (1H, d, J=9.1 Hz)

Compound No. IV-134:
1.40 (3H, t, J=5.3 Hz), 3.77 (3H, s), 3.79 (3H, s), 4.43 (2H, q, J=5.3 Hz),
6.97 (1H, d, J=6.8 Hz), 7.17 (1H, d, J=2.0 Hz), 7.41 (1H, dd, J=2.0 Hz, 6.8 Hz)

Compound No. IV-179:
1.39 (3H, t, J=5.3 Hz), 3.77 (3H, s), 4.43 (2H, q, J=5.3 Hz), 7.32 (1H, d, J=5.7 Hz),
7.46 (1H, dd, J=5.7 Hz, 3.7 Hz), 7.92 (1H, dt, J=1.1 Hz, 5.7 Hz),
8.68 (1H, dt, J=3.7 Hz, 1.1 Hz)

Compound No. IV-198:
1.40 (3H, t, J=5.3 Hz), 3.78 (3H, s), 4.43 (2H, q, J=5.3 Hz), 7.07-7.12 (2H, m),
7.42 (1H, dd, J=1.1 Hz, 4.0 Hz)

Compound No. IV-259:
1.39 (3H, t, J=7.1 Hz), 1.43 (3H, t, J=7.1 Hz), 4.17 (2H, q, J=7.1 Hz),
4.43 (2H, q, J=7.1 Hz), 7.21-7.26 (2H, m), 7.44-7.55 (3H, m)

Compound No. IV-260:
1.39 (3H, t, J=7.1 Hz), 1.43 (6H, d, J=6.8 Hz), 4.42 (2H, q, J=7.1 Hz),
5.01 (1H, p, J=6.8 Hz), 7.22-7.26 (2H, m), 7.46-7.55 (3H, m)

Compound No. IV-261:
1.40 (3H, t, J=7.1 Hz), 4.46 (2H, q, J=7.1 Hz), 7.23-7.26 (2H, m),
7.47 (1H, t, J=57.8 Hz), 7.51-7.66 (3H, m)

Compound No. IV-262:
1.39 (3H, t, J=7.1 Hz), 4.44 (2H, q, J=7.1 Hz), 7.26-7.60 (10H, m)

Compound No. IV-265:
1.40 (3H, t, J=7.1 Hz), 3.71 (3H, s), 4.05 (3H, s), 4.44 (2H, q, J=7.1 Hz)
Compound No. IV-286:
1.19-1.17 (6H, dd, J=7.0 Hz, J=2.2 Hz), 1.41-1.37 (3H, t, J=7.0 Hz),
2.65-2.58 (1H, sept., J=7.0 Hz), 3.78 (3H, s), 4.46-4.39 (2H, q, J=7.0 Hz),
7.05-7.03 (1H, d, J=8.0 Hz), 7.33-7.29 (1H, m), 7.47-7.46 (2H, d, J=4.0 Hz)
Compound No. V-19: (solvent for measurement: DMSO-$d_6$)
1.09-1.34 (3H, m), 1.59-1.64 (2H, m), 1.76-1.80 (2H, m), 2.22 (2H, dq, J=3.3 Hz, 12.3 Hz), 3.51 (3H, s), 4.54 (1H, tt, J=3.3 Hz, 12.3 Hz),
13.53 (1H, bs)
Compound No. V-50: (solvent for measurement: DMSO-$d_6$)
3.59 (3H, s), 729-7.31 (2H, m), 7.43-7.54 (3H, m), 13.64 (1H, bs)
Compound No. V-53: (solvent for measurement: DMSO-$d_6$)
3.59 (3H, s), 7.35 (2H, dd, J=1.6 Hz, 5.0 Hz), 7.59 (2H, dd, J=1.6 Hz, 5.0 Hz),
13.66 (1H, bs)
Compound No. V-56: (solvent for measurement: DMSO-$d_6$)
3.59 (3H, s), 7.34-7.37 (4H, m), 13.65 (1H, bs)
Compound No. V-59: (solvent for measurement: DMSO-$d_6$)
2.36 (3H, s), 3.58 (3H, s), 7.17 (2H, d, J=8.3 Hz), 7.30 (2H, d, J=8.3 Hz),
13.62 (1H, bs)
Compound No. V-62: (solvent for measurement: DMSO-$d_6$)
3.39 (3H, s), 3.74 (3H, s), 6.93 (2H, d, J=9.0), 7.39 (2H, d, J=9.0 Hz),
9.54 (1H, bs)
Compound No. V-63: (solvent for measurement: DMSO-$d_6$)
3.62 (3H, s), 7.64 (1H, d, J=7.7 Hz), 7.75 (1H, t, J=7.68 Hz), 7.87-7.94 (2H, m),
13.90 (1H, bs)
Compound No. V-64: (solvent for measurement: DMSO-$d_6$)
3.41 (3H, s), 7.46 (1H, d, J=6.0 Hz), 7.60 (1H, t, J5.0 Hz), 7.82 (1H, d, J=6.0 Hz),
7.97 (1H, s), 9.90 (1H, bs)
Compound No. V-65: (solvent for measurement: DMSO-$d_6$)
3.60 (3H, s), 7.58 (2H, d, J=8.3 Hz), 7.92 (2H, d, J=8.3 Hz), 13.69 (1H, bs) [0259]
Compound No. V-71: (solvent for measurement: DMSO-$d_6$)
3.59 (3H, s), 7.47 (2H, dt, J=9.3 Hz, 2.2 Hz), 7.54 (2H, d, J=9.3 Hz), 13.67 (1H, bs)
Compound No. V-75:
3.92 (3H, s), 7.03-7.06 (1H, m), 7.13-7.18 (1H, m), 7.35-7.41 (1H, m)
Compound No. V-76:
3.92 (3H, s), 7.85-7.87 (2H, m), 7.00-7.12 (1H, m)
Compound No. V-77:
3.94 (3H, s), 7.07-7.11 (1H, m), 7.29-7.31 (1H, m), 7.38-7.42 (1H, m)
Compound No. V-78: (solvent for measurement: DMSO-$d_6$)
3.61 (3H, s), 7.25-7.31 (1H, m), 7.49-7.58 (2H, m), 13.79 (1H, bs)
Compound No. V-79:
3.94 (3H, s), 7.05-7.07 (1H, m), 727-7.32 (2H, m)
Compound No. V-80:
3.94 (3H, s), 7.12-7.18 (1H, m), 7.52-7.61 (1H, m)
Compound No. V-81: (solvent for measurement: DMSO-$d_6$)
3.60 (3H, s), 7.37 (1H, d, J=8.5 Hz), 7.69 (1H, s), 7.82 (1H, d, J=7.7 Hz)
Compound No. V-82:
3.92 (3H, s), 7.20 (2H, s), 7.56 (1H, s)
Compound No. V-83:
3.93 (3H, s), 7.25 (1H, d, J=10.4), 7.44 (1H, t, J=8.0), 7.68 (1H, d, J=11.7)
Compound No. V-84:
3.93 (3H, s), 7.21 (1H, d, J=15.6), 7.45-7.48 (1H, m), 7.68 (1H, d, J=2.4 Hz)
Compound No. V-85:
3.93 (3H, s), 7.33 (1H, d, J=5.7), 7.49-7.58 (2H, m)
Compound No. V-86:
3.95 (3H, s), 7.45-7.56 (2H, m)
Compound No. V-93: (solvent for measurement: DMSO-$d_6$)
3.58 (3H, s), 3.74 (6H, s), 7.52 (2H, d, J=2.2 Hz), 6.59 (1H, t, J=2.2 Hz),
13.63 (1H, bs)
Compound No. V-96: (solvent for measurement: DMSO-$d_6$)
3.59 (3H, s), 3.73 (3H, s), 3.82 (3H, s), 7.62 (1H, dd, T=2.5 Hz, 8.8 Hz),
6.71 (1H, s), 7.16 (1H, d, J=8.5 Hz), 13.76 (1H, bs)
Compound No. V-134: (solvent for measurement: DMSO-$d_6$)
3.60 (3H, s), 3.76 (3H, s), 723 (1H, d, J=9.1 Hz), 7.43 (1H, d, J=2.8 Hz),
7.54 (1H, dd, J=2.8 Hz, 9.1 Hz), 13.84 (1H, bs)
Compound No. V-170: (solvent for measurement: DMSO-$d_6$)
3.58 (3H, s), 6.10 (2H, s), 6.78 (1H, dd, J=1.0 Hz, 6.2 Hz), 6.89 (1H, d, J=1.0 Hz),
7.01 (1H, d, J2 Hz), 13.63 (1H, bs)
Compound No. V-179: (solvent for measurement: DMSO-$d_6$)
3.60 (3H, s), 7.49 (1H, d, J=7.7 Hz), 7.55 (1H, ddd, J=1.1 Hz, 5.0 Hz, 7.7 Hz),
8.05 (1H, dt, J=1.9 Hz, 7.7 Hz), 8.62 (1H, dd, J=1.1 Hz, 5.0 Hz)
Compound No. V-198: (solvent for measurement: DMSO-$d_6$)
3.57 (3H, s), 7.07-7.10 (2H, m), 7.63 (1H, dd, J=1.9 Hz, 5.2 Hz)
Compound No. V-259: (solvent for measurement: DMSO-$d_6$)
1.09 (3H, t, J=5.3 Hz), 3.96 (2H, q, J=5.3 Hz), 7.32-7.37 (2H, m),
7.45-7.54 (3H, m), 9.51 (1H, bs)
Compound No. V-261: (solvent for measurement: DMSO-$d_6$)
7.36-7.53 (5H, m), 7.82 (1H, t, J=42.9 Hz)
Compound No. V-265: (solvent for measurement: DMSO-$d_6$)
3.53 (3H, s), 3.90 (3H, s)
Compound No. V-268: (solvent for measurement: DMSO-$d_6$)
1.45 (3H, t), 3.91 (3H, s), 4.09 (2H, d), 7.04 (2H, d), 7.15 (21-1, d) [0261]

Formulation Example 1

Wettable Powder 10 parts of the compound (I-1), 0.5 parts of polyoxyethylene octylphenyl ether, 0.5 parts of sodium β-naphthalene sulfonate formalin condensate, 20 parts of diatomaceous earth, and 69 parts of clay were mixed and pulverized to give a wettable powder.

Formulation Example 2

Flowable Agent 20 parts of roughly crushed compound (I-1) were dispersed in 69 parts of water, and added with 200 ppm of silicone AF-118N (trade name, manufactured by Asahi Kasei Corporation) while simultaneously adding 4 parts of polyoxyethylene styryl phenyl ether sulfonate and 7 parts of ethylene glycol. After mixing for 30 minutes by high-speed mixer, the mixture was pulverized using a wet-type pulverizer to give a flowable agent.

Formulation Example 3

Emulsifiable Concentrate 30 parts of the compound (I-1), 60 parts of a mixture of xylene and isophorone (1:1 mixture), and 10 parts of a mixture of polyoxyethylene sorbitan alkylate, polyoxyethylene alkylaryl polymer, and alkylaryl sulfonate were mixed well to give an emulsifiable concentrate.

Formulation Example 4

Granules 10 parts of the compound (I-1), 80 parts of extender in which talc and bentonite are mixed in ratio of 1 to 3, 5 parts of white carbon, and 5 parts of a mixture of polyoxyethylene sorbitan alkylate, polyoxyethylene alkylaryl polymer, and alkylaryl sulfonate were added with 10 parts of water. After kneading well, the resulting paste was extruded through a sieve (diameter; 0.7 mm) followed by drying. By cutting it to have length of 0.5 to 1 mm, granules were obtained.

Effect of the compounds of the invention is explained by way of following test examples.

Test Example 1

Test for Determining Herbicidal Activity by Paddy Field Soil Treatment

A 100 cm$^2$ wide plastic pot was filled with a paddy field soil and, after watering and shuffling, seeds of each of *Echinochloa oryzicola, Monochoria vaginalis*, and *Scirpus juncoides* Rocxb. were sowed and watered to a depth of 3 cm. On the next day, the wettable powder obtained in view of Formulation example 1 was diluted with water and applied on water surface. The application amount was 1000 g of effective component per hectare. After that, the plants were cultivated in a greenhouse, and on day 21 after the treatment, evaluation was made by the criteria of Table 72 for determining the herbicidal effects. The results are shown in Table 73 to Table 76.

TABLE 72

| Index Number | Herbicidal Effects |
| --- | --- |
| 10 | 100% of herbicidal effects (complete death) |
| 9 | 90% or more and less than 100% of herbicidal effects |
| 8 | 80% or more and less than 90% of herbicidal effects |
| 7 | 70% or more and less than 80% of herbicidal effects |
| 6 | 60% or more and less than 70% of herbicidal effects |
| 5 | 50% or more and less than 60% of herbicidal effects |
| 4 | 40% or more and less than 50% of herbicidal effects |
| 3 | 30% or more and less than 40% of herbicidal effects |
| 2 | 20% or more and less than 30% of herbicidal effects |
| 1 | 10% or more and less than 20% of herbicidal effects |
| 0 | 0% or more and less than 10% of herbicidal effects |

TABLE 73

| Compound No. | Echinochloa oryzicola |
| --- | --- |
| I-1 | 10 |
| I-2 | 10 |
| I-3 | 10 |
| I-4 | 9 |
| I-5 | 10 |

TABLE 73-continued

| Compound No. | Echinochloa oryzicola |
| --- | --- |
| I-9 | 8 |
| I-10 | 10 |
| I-11 | 10 |
| I-14 | 10 |
| I-16 | 9 |
| I-19 | 10 |
| I-27 | 10 |
| I-41 | 8 |
| I-43 | 10 |
| I-50 | 10 |
| I-51 | 10 |
| I-52 | 10 |
| I-53 | 10 |
| I-54 | 10 |
| I-55 | 10 |
| I-56 | 10 |
| I-57 | 10 |
| I-58 | 10 |
| I-59 | 10 |
| I-60 | 10 |
| I-61 | 8 |
| I-63 | 10 |
| I-64 | 10 |
| I-65 | 10 |
| I-66 | 10 |
| I-67 | 10 |
| I-68 | 10 |
| I-71 | 10 |
| I-72 | 10 |
| I-73 | 10 |
| I-74 | 10 |
| I-75 | 10 |
| I-76 | 10 |
| I-77 | 10 |
| I-78 | 10 |
| I-79 | 10 |
| I-80 | 10 |
| I-81 | 10 |
| I-82 | 8 |
| I-83 | 10 |
| I-84 | 10 |
| I-85 | 10 |
| I-86 | 10 |
| I-87 | 9 |
| I-88 | 10 |
| I-89 | 10 |
| I-90 | 9 |
| I-91 | 10 |
| I-92 | 10 |
| I-93 | 8 |
| I-96 | 8 |
| I-99 | 10 |
| I-105 | 10 |
| I-106 | 10 |
| I-107 | 10 |
| I-108 | 10 |
| I-109 | 10 |
| I-110 | 10 |
| I-111 | 10 |
| I-115 | 10 |
| I-116 | 10 |
| I-117 | 10 |
| I-118 | 10 |
| I-119 | 9 |
| I-120 | 8 |
| I-125 | 10 |
| I-126 | 10 |
| I-127 | 10 |
| I-128 | 8 |
| I-129 | 10 |
| I-131 | 9 |
| I-134 | 10 |
| I-135 | 10 |
| I-136 | 9 |
| I-137 | 10 |
| I-138 | 10 |
| I-149 | 9 |

TABLE 73-continued

| Compound No. | Echinochloa oryzicola |
|---|---|
| I-155 | 10 |
| I-169 | 10 |
| I-170 | 10 |
| I-179 | 10 |
| I-184 | 10 |
| I-185 | 8 |
| I-187 | 10 |
| I-198 | 8 |
| I-199 | 9 |
| I-202 | 10 |
| I-203 | 10 |
| I-205 | 7 |
| I-259 | 10 |
| I-260 | 10 |
| I-261 | 8 |
| I-263 | 10 |
| I-265 | 10 |
| I-268 | 10 |
| I-269 | 8 |
| I-270 | 8 |
| I-271 | 8 |
| I-272 | 7 |
| I-273 | 9 |
| I-274 | 8 |
| I-275 | 9 |
| I-276 | 8 |
| I-277 | 9 |
| I-278 | 8 |
| I-279 | 8 |
| I-280 | 10 |
| I-281 | 10 |
| I-282 | 10 |
| I-283 | 10 |
| I-284 | 10 |
| I-285 | 10 |
| I-286 | 10 |
| I-287 | 10 |
| I-288 | 10 |
| I-289 | 10 |
| I-292 | 10 |
| I-294 | 9 |
| I-297 | 10 |
| I-298 | 10 |
| I-299 | 10 |
| I-300 | 10 |
| I-301 | 10 |
| I-302 | 10 |
| I-303 | 10 |
| I-304 | 10 |
| I-307 | 8 |
| I-328 | 10 |
| I-339 | 10 |
| I-463 | 10 |
| I-464 | 10 |
| I-465 | 10 |
| I-466 | 8 |
| I-468 | 10 |
| I-469 | 10 |
| I-470 | 10 |
| I-471 | 10 |
| I-473 | 8 |
| I-474 | 10 |
| I-475 | 10 |
| I-476 | 10 |
| I-477 | 10 |
| I-478 | 10 |
| I-479 | 10 |
| I-480 | 10 |
| III-50 | 10 |
| III-62 | 8 |
| VI-1 | 10 |
| VI-5 | 10 |
| VI-6 | 10 |
| VI-7 | 10 |
| VI-65 | 10 |
| VI-97 | 10 |
| V-300 | 10 |
| V-358 | 10 |
| V-359 | 8 |
| V-362 | 10 |
| V-363 | 10 |
| V-364 | 10 |
| V-365 | 10 |
| V-367 | 8 |
| V-368 | 10 |
| V-369 | 10 |
| V-370 | 10 |
| V-371 | 10 |

TABLE 74

| Compound No. | Monochoria vaginalis |
|---|---|
| I-1 | 10 |
| I-2 | 10 |
| I-3 | 10 |
| I-4 | 9 |
| I-5 | 10 |
| I-9 | 8 |
| I-10 | 10 |
| I-11 | 10 |
| I-14 | 10 |
| I-16 | 9 |
| I-19 | 10 |
| I-27 | 10 |
| I-41 | 8 |
| I-43 | 10 |
| I-47 | 10 |
| I-50 | 10 |
| I-51 | 10 |
| I-52 | 10 |
| I-53 | 7 |
| I-54 | 10 |
| I-55 | 10 |
| I-56 | 10 |
| I-57 | 10 |
| I-58 | 10 |
| I-59 | 10 |
| I-60 | 10 |
| I-61 | 10 |
| I-62 | 8 |
| I-63 | 10 |
| I-64 | 10 |
| I-65 | 10 |
| I-66 | 10 |
| I-67 | 10 |
| I-68 | 10 |
| I-71 | 10 |
| I-72 | 10 |
| I-73 | 10 |
| I-74 | 10 |
| I-75 | 10 |
| I-76 | 10 |
| I-77 | 10 |
| I-78 | 10 |
| I-79 | 10 |
| I-80 | 10 |
| I-81 | 10 |
| I-82 | 10 |
| I-83 | 10 |
| I-84 | 10 |
| I-85 | 10 |
| I-86 | 10 |
| I-87 | 10 |
| I-88 | 10 |
| I-89 | 10 |
| I-90 | 10 |
| I-91 | 10 |
| I-92 | 10 |
| I-93 | 10 |

TABLE 74-continued

| Compound No. | Monochoria vaginalis |
|---|---|
| I-94 | 10 |
| I-96 | 10 |
| I-99 | 10 |
| I-105 | 10 |
| I-106 | 10 |
| I-107 | 10 |
| I-108 | 10 |
| I-109 | 10 |
| I-110 | 10 |
| I-111 | 10 |
| I-115 | 10 |
| I-116 | 10 |
| I-117 | 10 |
| I-118 | 10 |
| I-119 | 10 |
| I-120 | 10 |
| I-125 | 10 |
| I-126 | 10 |
| I-127 | 10 |
| I-128 | 9 |
| I-129 | 10 |
| I-131 | 10 |
| I-134 | 10 |
| I-135 | 10 |
| I-136 | 10 |
| I-137 | 10 |
| I-138 | 10 |
| I-149 | 10 |
| I-155 | 10 |
| I-169 | 10 |
| I-170 | 10 |
| I-179 | 10 |
| I-182 | 8 |
| I-183 | 10 |
| I-184 | 10 |
| I-185 | 9 |
| I-187 | 10 |
| I-189 | 10 |
| I-198 | 10 |
| I-199 | 8 |
| I-202 | 10 |
| I-203 | 10 |
| I-204 | 8 |
| I-205 | 10 |
| I-259 | 10 |
| I-260 | 10 |
| I-261 | 10 |
| I-262 | 8 |
| I-263 | 10 |
| I-265 | 10 |
| I-268 | 10 |
| I-269 | 8 |
| I-270 | 8 |
| I-271 | 8 |
| I-272 | 8 |
| I-273 | 9 |
| I-274 | 8 |
| I-275 | 10 |
| I-276 | 8 |
| I-277 | 9 |
| I-278 | 9 |
| I-279 | 8 |
| I-280 | 10 |
| I-281 | 10 |
| I-282 | 10 |
| I-283 | 10 |
| I-284 | 10 |
| I-285 | 10 |
| I-286 | 10 |
| I-287 | 10 |
| I-288 | 10 |
| I-289 | 10 |
| I-290 | 10 |
| I-291 | 10 |
| I-292 | 10 |
| I-293 | 10 |

TABLE 74-continued

| Compound No. | Monochoria vaginalis |
|---|---|
| I-294 | 9 |
| I-297 | 10 |

TABLE 75

| Compound No. | Monochoria vaginalis |
|---|---|
| I-298 | 10 |
| I-299 | 10 |
| I-300 | 10 |
| I-301 | 10 |
| I-302 | 10 |
| I-303 | 10 |
| I-304 | 10 |
| I-306 | 9 |
| I-307 | 9 |
| I-308 | 8 |
| I-328 | 10 |
| I-339 | 10 |
| I-462 | 10 |
| I-463 | 10 |
| I-464 | 10 |
| I-465 | 10 |
| I-466 | 10 |
| I-467 | 10 |
| I-468 | 10 |
| I-469 | 10 |
| I-470 | 10 |
| I-471 | 10 |
| I-472 | 10 |
| I-473 | 10 |
| I-474 | 10 |
| I-475 | 10 |
| I-476 | 10 |
| I-477 | 10 |
| I-478 | 10 |
| I-479 | 10 |
| II-50 | 8 |
| II-267 | 8 |
| III-50 | 10 |
| III-62 | 10 |
| VI-1 | 10 |
| VI-5 | 10 |
| VI-6 | 10 |
| VI-7 | 10 |
| VI-65 | 10 |
| VI-97 | 10 |
| V-291 | 8 |
| V-300 | 10 |
| V-358 | 10 |
| V-359 | 10 |
| V-360 | 10 |
| V-361 | 10 |
| V-362 | 10 |
| V-363 | 10 |
| V-364 | 10 |
| V-365 | 10 |
| V-366 | 10 |
| V-367 | 10 |
| V-368 | 10 |
| V-369 | 10 |
| V-370 | 10 |
| V-371 | 10 |

TABLE 76

| Compound No. | S. juncoides Rocxb. |
|---|---|
| I-1 | 10 |
| I-2 | 10 |
| I-3 | 10 |

TABLE 76-continued

| Compound No. | S. juncoides Rocxb. |
|---|---|
| I-4 | 10 |
| I-5 | 10 |
| I-9 | 8 |
| I-10 | 10 |
| I-11 | 10 |
| I-14 | 10 |
| I-16 | 10 |
| I-19 | 10 |
| I-27 | 10 |
| I-41 | 10 |
| I-43 | 10 |
| I-47 | 10 |
| I-50 | 10 |
| I-51 | 10 |
| I-52 | 10 |
| I-53 | 10 |
| I-54 | 10 |
| I-55 | 10 |
| I-56 | 10 |
| I-57 | 10 |
| I-58 | 10 |
| I-59 | 10 |
| I-60 | 10 |
| I-61 | 10 |
| I-63 | 10 |
| I-64 | 10 |
| I-65 | 10 |
| I-66 | 10 |
| I-67 | 10 |
| I-68 | 10 |
| I-71 | 10 |
| I-72 | 10 |
| I-73 | 10 |
| I-74 | 10 |
| I-75 | 10 |
| I-76 | 10 |
| I-77 | 10 |
| I-78 | 10 |
| I-79 | 10 |
| I-80 | 10 |
| I-81 | 10 |
| I-82 | 10 |
| I-83 | 10 |
| I-84 | 10 |
| I-85 | 10 |
| I-86 | 10 |
| I-87 | 10 |
| I-88 | 10 |
| I-89 | 10 |
| I-90 | 10 |
| I-91 | 10 |
| I-92 | 10 |
| I-93 | 10 |
| I-94 | 10 |
| I-96 | 10 |
| I-99 | 10 |
| I-105 | 10 |
| I-106 | 10 |
| I-107 | 10 |
| I-108 | 10 |
| I-109 | 10 |
| I-110 | 10 |
| I-111 | 10 |
| I-115 | 10 |
| I-116 | 10 |
| I-117 | 10 |
| I-118 | 10 |
| I-119 | 10 |
| I-120 | 10 |
| I-125 | 10 |
| I-126 | 10 |
| I-127 | 10 |
| I-128 | 10 |
| I-129 | 10 |
| I-131 | 10 |
| I-134 | 10 |
| I-135 | 10 |
| I-136 | 10 |
| I-137 | 10 |
| I-138 | 10 |
| I-149 | 10 |
| I-155 | 10 |
| I-169 | 10 |
| I-170 | 10 |
| I-179 | 10 |
| I-182 | 9 |
| I-183 | 10 |
| I-184 | 10 |
| I-185 | 9 |
| I-187 | 10 |
| I-189 | 10 |
| I-198 | 10 |
| I-199 | 9 |
| I-202 | 10 |
| I-203 | 10 |
| I-205 | 10 |
| I-259 | 10 |
| I-260 | 10 |
| I-261 | 8 |
| I-263 | 10 |
| I-265 | 10 |
| I-268 | 10 |
| I-269 | 10 |
| I-270 | 8 |
| I-271 | 10 |
| I-272 | 8 |
| I-273 | 10 |
| I-274 | 4 |
| I-275 | 8 |
| I-276 | 9 |
| I-277 | 10 |
| I-278 | 10 |
| I-279 | 10 |
| I-280 | 10 |
| I-281 | 10 |
| I-282 | 10 |
| I-283 | 10 |
| I-284 | 10 |
| I-285 | 10 |
| I-286 | 9 |
| I-287 | 10 |
| I-288 | 10 |
| I-289 | 10 |
| I-290 | 10 |
| I-291 | 10 |
| I-292 | 10 |
| I-293 | 10 |
| I-294 | 9 |
| I-297 | 10 |
| I-298 | 10 |
| I-299 | 10 |
| I-300 | 10 |
| I-301 | 10 |
| I-302 | 10 |
| I-303 | 10 |
| I-304 | 10 |
| I-307 | 8 |
| I-328 | 10 |
| I-339 | 10 |
| I-462 | 10 |
| I-463 | 10 |
| I-464 | 10 |
| I-465 | 10 |
| I-466 | 10 |
| I-467 | 10 |
| I-468 | 10 |
| I-469 | 10 |
| I-470 | 10 |
| I-471 | 10 |
| I-472 | 8 |
| I-473 | 8 |
| I-474 | 10 |
| I-475 | 10 |
| I-476 | 10 |

TABLE 76-continued

| Compound No. | S. juncoides Rocxb. |
|---|---|
| I-477 | 10 |
| I-478 | 9 |
| I-479 | 10 |
| I-480 | 10 |
| II-50 | 7 |
| III-50 | 10 |
| III-62 | 10 |
| VI-1 | 10 |
| VI-5 | 10 |
| VI-6 | 10 |
| VI-7 | 10 |
| VI-65 | 10 |
| VI-97 | 10 |
| V-300 | 10 |
| V-358 | 10 |
| V-359 | 10 |
| V-360 | 10 |
| V-361 | 10 |
| V-362 | 10 |
| V-363 | 10 |
| V-364 | 10 |
| V-365 | 10 |
| V-366 | 8 |
| V-367 | 8 |
| V-368 | 10 |
| V-369 | 10 |
| V-370 | 10 |
| V-371 | 9 |

Test example 2

Test for Determining Herbicidal Activity by Field Soil Treatment

A 80 cm² wide plastic pot was filled with a field soil and seeds of each of *Echinochloa crus-galli*, foxtail, Indian millet, and *A. retroflexus* were sowed and then covered with soil. The wettable powder produced with reference to the Formulation example 1 was diluted water, and applied on the soil surface by using a small sprayer in an amount of 1000 liters per hectare so that the effective component is 1000 g per hectare. After that, the plants were cultivated in a greenhouse, and on day 21 after the treatment, evaluation was made by the criteria described in Table 72 for determining the herbicidal effects. The results are shown in Table 77 to Table 80.

TABLE 77

| Compound No. | Echinochloacrus-galli |
|---|---|
| I-1 | 8 |
| I-2 | 10 |
| I-3 | 10 |
| I-4 | 9 |
| I-5 | 10 |
| I-9 | 7 |
| I-10 | 10 |
| I-11 | 10 |
| I-14 | 10 |
| I-16 | 9 |
| I-19 | 8 |
| I-27 | 10 |
| I-41 | 9 |
| I-43 | 10 |
| I-50 | 10 |
| I-51 | 10 |
| I-52 | 10 |
| I-53 | 8 |
| I-54 | 10 |

TABLE 77-continued

| Compound No. | Echinochloacrus-galli |
|---|---|
| I-55 | 10 |
| I-56 | 10 |
| I-57 | 10 |
| I-58 | 10 |
| I-60 | 10 |
| I-61 | 8 |
| I-63 | 10 |
| I-64 | 10 |
| I-65 | 10 |
| I-66 | 10 |
| I-67 | 10 |
| I-68 | 10 |
| I-71 | 10 |
| I-72 | 9 |
| I-73 | 9 |
| I-74 | 10 |
| I-75 | 9 |
| I-76 | 10 |
| I-77 | 9 |
| I-78 | 10 |
| I-79 | 9 |
| I-80 | 9 |
| I-81 | 9 |
| I-82 | 9 |
| I-83 | 9 |
| I-84 | 9 |
| I-85 | 9 |
| I-86 | 10 |
| I-87 | 9 |
| I-88 | 8 |
| I-89 | 9 |
| I-90 | 8 |
| I-91 | 9 |
| I-92 | 9 |
| I-93 | 7 |
| I-98 | 7 |
| I-99 | 8 |
| I-105 | 9 |
| I-106 | 10 |
| I-107 | 8 |
| I-109 | 9 |
| I-110 | 7 |
| I-111 | 9 |
| I-115 | 9 |
| I-116 | 10 |
| I-117 | 10 |
| I-118 | 10 |
| I-119 | 8 |
| I-120 | 8 |
| I-125 | 7 |
| I-127 | 10 |
| I-128 | 8 |
| I-129 | 9 |
| I-131 | 9 |
| I-134 | 10 |
| I-135 | 9 |
| I-137 | 10 |
| I-138 | 9 |
| I-149 | 8 |
| I-167 | 8 |
| I-169 | 10 |
| I-179 | 10 |
| I-182 | 7 |
| I-184 | 8 |
| I-185 | 9 |
| I-187 | 7 |
| I-198 | 7 |
| I-199 | 9 |
| I-202 | 10 |
| I-203 | 9 |
| I-259 | 10 |
| I-260 | 10 |
| I-265 | 10 |
| I-269 | 8 |
| I-270 | 8 |
| I-271 | 10 |
| I-273 | 9 |

TABLE 77-continued

| Compound No. | Echinochloa crus-galli |
|---|---|
| I-274 | 7 |
| I-275 | 8 |
| I-276 | 9 |
| I-277 | 8 |
| I-278 | 9 |
| I-279 | 7 |
| I-280 | 9 |
| I-281 | 9 |
| I-282 | 10 |
| I-283 | 9 |
| I-284 | 10 |
| I-285 | 10 |
| I-286 | 10 |
| I-287 | 10 |
| I-288 | 10 |
| I-289 | 9 |
| I-292 | 7 |
| I-294 | 9 |
| I-297 | 10 |
| I-298 | 7 |
| I-299 | 9 |
| I-302 | 7 |
| I-303 | 9 |
| I-304 | 10 |
| I-307 | 7 |
| I-339 | 8 |
| I-471 | 7 |
| I-474 | 7 |
| I-475 | 7 |
| I-476 | 7 |
| I-477 | 9 |
| I-478 | 9 |
| I-479 | 9 |
| I-480 | 8 |
| VI-5 | 8 |
| VI-7 | 10 |
| V-300 | 7 |
| V-365 | 7 |
| V-368 | 7 |
| V-369 | 7 |
| V-370 | 7 |
| V-371 | 9 |

TABLE 78

| Compound No. | Setaria viridis |
|---|---|
| I-1 | 7 |
| I-2 | 7 |
| I-3 | 10 |
| I-4 | 9 |
| I-5 | 7 |
| I-10 | 10 |
| I-11 | 7 |
| I-14 | 10 |
| I-16 | 9 |
| I-19 | 8 |
| I-41 | 7 |
| I-50 | 10 |
| I-51 | 10 |
| I-52 | 10 |
| I-54 | 10 |
| I-55 | 10 |
| I-56 | 10 |
| I-57 | 10 |
| I-58 | 8 |
| I-63 | 10 |
| I-66 | 10 |
| I-67 | 10 |
| I-68 | 10 |
| I-71 | 6 |
| I-72 | 10 |
| I-73 | 8 |
| I-74 | 7 |
| I-75 | 7 |
| I-76 | 9 |
| I-77 | 9 |
| I-79 | 10 |
| I-80 | 9 |
| I-81 | 7 |
| I-82 | 9 |
| I-83 | 9 |
| I-84 | 9 |
| I-85 | 9 |
| I-86 | 9 |
| I-87 | 6 |
| I-89 | 8 |
| I-91 | 10 |
| I-92 | 9 |
| I-93 | 6 |
| I-98 | 7 |
| I-99 | 6 |
| I-105 | 7 |
| I-109 | 6 |
| I-111 | 7 |
| I-116 | 9 |
| I-117 | 7 |
| I-118 | 9 |
| I-127 | 8 |
| I-128 | 9 |
| I-129 | 10 |
| I-131 | 7 |
| I-134 | 10 |
| I-136 | 8 |
| I-137 | 9 |
| I-155 | 7 |
| I-169 | 10 |
| I-179 | 10 |
| I-202 | 9 |
| I-260 | 5 |
| I-265 | 10 |
| I-269 | 9 |
| I-270 | 7 |
| I-271 | 10 |
| I-276 | 9 |
| I-277 | 8 |
| I-278 | 9 |
| I-280 | 8 |
| I-281 | 9 |
| I-282 | 10 |
| I-283 | 8 |
| I-284 | 8 |
| I-285 | 10 |
| I-286 | 9 |
| I-288 | 9 |
| I-289 | 7 |
| I-294 | 7 |
| I-297 | 9 |
| I-298 | 7 |
| I-299 | 10 |
| I-303 | 9 |
| I-304 | 9 |
| VI-7 | 10 |
| VI-65 | 7 |

TABLE 79

| Compound No. | Abutilon theophrasti |
|---|---|
| I-1 | 9 |
| I-2 | 10 |
| I-3 | 10 |
| I-4 | 9 |
| I-5 | 10 |
| I-10 | 10 |
| I-11 | 9 |

TABLE 79-continued

| Compound No. | Abutilon theophrasti |
|---|---|
| I-14 | 10 |
| I-16 | 9 |
| I-27 | 10 |
| I-41 | 8 |
| I-50 | 10 |
| I-51 | 10 |
| I-52 | 10 |
| I-53 | 10 |
| I-54 | 10 |
| I-55 | 10 |
| I-56 | 10 |
| I-57 | 10 |
| I-58 | 10 |
| I-59 | 10 |
| I-60 | 10 |
| I-61 | 10 |
| I-63 | 10 |
| I-64 | 10 |
| I-65 | 10 |
| I-66 | 10 |
| I-67 | 10 |
| I-68 | 10 |
| I-71 | 10 |
| I-72 | 10 |
| I-73 | 10 |
| I-74 | 10 |
| I-75 | 10 |
| I-76 | 10 |
| I-77 | 10 |
| I-78 | 10 |
| I-79 | 10 |
| I-80 | 9 |
| I-81 | 10 |
| I-82 | 9 |
| I-83 | 10 |
| I-84 | 10 |
| I-85 | 10 |
| I-86 | 9 |
| I-87 | 9 |
| I-88 | 10 |
| I-89 | 10 |
| I-90 | 10 |
| I-91 | 10 |
| I-92 | 10 |
| I-93 | 10 |
| I-94 | 10 |
| I-96 | 10 |
| I-98 | 7 |
| I-99 | 9 |
| I-105 | 9 |
| I-106 | 10 |
| I-107 | 10 |
| I-108 | 8 |
| I-109 | 10 |
| I-110 | 10 |
| I-111 | 9 |
| I-115 | 9 |
| I-116 | 10 |
| I-117 | 10 |
| I-118 | 9 |
| I-119 | 9 |
| I-120 | 9 |
| I-125 | 8 |
| I-126 | 10 |
| I-127 | 10 |
| I-128 | 10 |
| I-129 | 10 |
| I-131 | 9 |
| I-134 | 10 |
| I-135 | 9 |
| I-136 | 9 |
| I-137 | 10 |
| I-138 | 9 |
| I-149 | 10 |
| I-155 | 10 |
| I-167 | 10 |
| I-169 | 9 |
| I-170 | 10 |
| I-179 | 10 |
| I-182 | 10 |
| I-183 | 10 |
| I-184 | 10 |
| I-185 | 10 |
| I-187 | 9 |
| I-189 | 10 |
| I-198 | 10 |
| I-199 | 10 |
| I-202 | 9 |
| I-259 | 8 |
| I-260 | 10 |
| I-261 | 10 |
| I-263 | 8 |
| I-265 | 10 |
| I-268 | 8 |
| I-269 | 9 |
| I-271 | 10 |
| I-273 | 7 |
| I-274 | 8 |
| I-275 | 10 |
| I-276 | 10 |
| I-277 | 7 |
| I-279 | 10 |
| I-280 | 9 |
| I-281 | 9 |
| I-282 | 9 |
| I-283 | 9 |
| I-284 | 9 |
| I-285 | 10 |
| I-286 | 9 |
| I-287 | 9 |
| I-288 | 9 |
| I-289 | 9 |
| I-290 | 10 |
| I-291 | 10 |
| I-292 | 9 |
| I-293 | 10 |
| I-294 | 9 |
| I-297 | 9 |
| I-298 | 10 |
| I-299 | 10 |
| I-300 | 10 |
| I-302 | 10 |
| I-303 | 9 |
| I-304 | 10 |
| I-306 | 7 |
| I-307 | 9 |
| I-339 | 10 |
| I-462 | 10 |
| I-463 | 10 |
| I-465 | 10 |
| I-470 | 7 |
| I-471 | 10 |
| I-474 | 10 |
| I-475 | 7 |
| I-476 | 10 |
| I-477 | 10 |
| I-478 | 10 |
| I-479 | 10 |
| I-480 | 10 |
| VI-1 | 10 |
| VI-5 | 10 |
| VI-6 | 9 |
| VI-7 | 10 |
| VI-65 | 10 |
| V-61 | 8 |
| V-300 | 9 |
| V-358 | 10 |
| V-361 | 10 |
| V-364 | 7 |
| V-365 | 10 |
| V-368 | 10 |
| V-369 | 7 |

TABLE 79-continued

| Compound No. | Abutilon theophrasti |
|---|---|
| V-370 | 10 |
| V-371 | 10 |

TABLE 80

| Compound No. | Amaranthus retroflexus |
|---|---|
| I-1 | 10 |
| I-2 | 10 |
| I-3 | 10 |
| I-4 | 10 |
| I-5 | 10 |
| I-9 | 10 |
| I-10 | 10 |
| I-11 | 10 |
| I-14 | 10 |
| I-16 | 10 |
| I-19 | 8 |
| I-27 | 10 |
| I-41 | 10 |
| I-43 | 10 |
| I-47 | 10 |
| I-50 | 10 |
| I-51 | 10 |
| I-52 | 10 |
| I-53 | 10 |
| I-54 | 10 |
| I-55 | 10 |
| I-56 | 9 |
| I-57 | 10 |
| I-58 | 10 |
| I-59 | 10 |
| I-60 | 10 |
| I-61 | 10 |
| I-63 | 10 |
| I-64 | 10 |
| I-65 | 10 |
| I-66 | 10 |
| I-67 | 10 |
| I-68 | 10 |
| I-71 | 10 |
| I-72 | 10 |
| I-73 | 10 |
| I-74 | 10 |
| I-75 | 10 |
| I-76 | 10 |
| I-77 | 10 |
| I-78 | 10 |
| I-79 | 10 |
| I-80 | 10 |
| I-81 | 10 |
| I-82 | 10 |
| I-83 | 10 |
| I-84 | 10 |
| I-85 | 10 |
| I-86 | 10 |
| I-87 | 9 |
| I-88 | 10 |
| I-89 | 10 |
| I-90 | 10 |
| I-91 | 10 |
| I-92 | 10 |
| I-93 | 10 |
| I-94 | 10 |
| I-96 | 10 |
| I-99 | 10 |
| I-105 | 10 |
| I-106 | 10 |
| I-107 | 10 |
| I-108 | 10 |
| I-109 | 10 |
| I-110 | 10 |
| I-111 | 10 |

TABLE 80-continued

| Compound No. | Amaranthus retroflexus |
|---|---|
| I-115 | 9 |
| I-116 | 10 |
| I-117 | 10 |
| I-118 | 10 |
| I-119 | 10 |
| I-120 | 10 |
| I-125 | 10 |
| I-126 | 10 |
| I-127 | 10 |
| I-128 | 10 |
| I-129 | 10 |
| I-131 | 10 |
| I-134 | 10 |
| I-135 | 10 |
| I-136 | 9 |
| I-137 | 10 |
| I-138 | 10 |
| I-149 | 10 |
| I-155 | 10 |
| I-167 | 10 |
| I-169 | 10 |
| I-170 | 10 |
| I-179 | 9 |
| I-182 | 10 |
| I-183 | 8 |
| I-184 | 10 |
| I-185 | 10 |
| I-187 | 10 |
| I-189 | 10 |
| I-198 | 10 |
| I-199 | 10 |
| I-202 | 10 |
| I-203 | 7 |
| I-259 | 10 |
| I-260 | 10 |
| I-263 | 10 |
| I-265 | 10 |
| I-268 | 10 |
| I-269 | 10 |
| I-270 | 10 |
| I-271 | 10 |
| I-272 | 8 |
| I-273 | 10 |
| I-274 | 7 |
| I-275 | 10 |
| I-276 | 10 |
| I-277 | 8 |
| I-278 | 10 |
| I-279 | 10 |
| I-280 | 10 |
| I-281 | 10 |
| I-282 | 10 |
| I-283 | 10 |
| I-284 | 10 |
| I-285 | 10 |
| I-286 | 10 |
| I-287 | 10 |
| I-288 | 10 |
| I-289 | 10 |
| I-290 | 8 |
| I-291 | 8 |
| I-294 | 10 |
| I-297 | 10 |
| I-298 | 10 |
| I-299 | 10 |
| I-300 | 10 |
| I-302 | 10 |
| I-303 | 10 |
| I-304 | 10 |
| I-306 | 10 |
| I-307 | 10 |
| I-308 | 10 |
| I-339 | 10 |
| I-462 | 9 |
| I-463 | 7 |
| I-464 | 7 |
| I-465 | 10 |

TABLE 80-continued

| Compound No. | Amaranthus retroflexus |
|---|---|
| I-468 | 7 |
| I-470 | 8 |
| I-471 | 10 |
| I-474 | 10 |
| I-475 | 7 |
| I-476 | 10 |
| I-477 | 10 |
| I-478 | 10 |
| I-479 | 10 |
| I-480 | 10 |
| VI-1 | 10 |
| VI-5 | 10 |
| VI-6 | 10 |
| VI-7 | 10 |
| VI-65 | 10 |
| V-300 | 10 |
| V-358 | 10 |
| V-361 | 8 |
| V-362 | 7 |
| V-364 | 8 |
| V-365 | 10 |
| V-368 | 10 |
| V-369 | 7 |
| V-370 | 10 |
| V-371 | 10 |

Test example 3

Test for Determining Herbicidal Activity by Field Foliage Treatment

A 80 cm² wide plastic pot was filled with a field soil and seeds of each of Indian millet and *A. retroflexus* were sowed and then incubated for 2 weeks in a green house. The wettable powder produced with reference to the Formulation example 1 was diluted water, and applied from the air to entire body of the plant as foliage treatment by using a small sprayer in an amount of 1000 liters per hectare so that the effective component is 1000 g per hectare. After that, the plants were cultivated in a greenhouse, and on day 14 after the treatment, evaluation was made by the criteria described in Table 72 for determining the herbicidal effects. The results are shown in Table 81 to Table 84.

TABLE 81

| Compound No. | Echinochloa crus-galli |
|---|---|
| I-1 | 8 |
| I-2 | 9 |
| I-3 | 9 |
| I-4 | 9 |
| I-5 | 10 |
| I-9 | 10 |
| I-10 | 8 |
| I-11 | 9 |
| I-14 | 9 |
| I-16 | 9 |
| I-19 | 10 |
| I-27 | 9 |
| I-41 | 10 |
| I-43 | 8 |
| I-50 | 10 |
| I-51 | 10 |
| I-52 | 10 |
| I-53 | 8 |
| I-54 | 10 |
| I-55 | 10 |
| I-56 | 10 |

TABLE 81-continued

| Compound No. | Echinochloa crus-galli |
|---|---|
| I-57 | 10 |
| I-58 | 10 |
| I-59 | 7 |
| I-60 | 10 |
| I-61 | 9 |
| I-63 | 10 |
| I-64 | 10 |
| I-65 | 8 |
| I-66 | 10 |
| I-67 | 10 |
| I-68 | 10 |
| I-71 | 10 |
| I-72 | 10 |
| I-73 | 10 |
| I-74 | 9 |
| I-75 | 10 |
| I-76 | 10 |
| I-77 | 10 |
| I-78 | 10 |
| I-79 | 10 |
| I-80 | 10 |
| I-81 | 10 |
| I-82 | 10 |
| I-83 | 10 |
| I-84 | 9 |
| I-85 | 9 |
| I-86 | 9 |
| I-87 | 9 |
| I-88 | 8 |
| I-89 | 9 |
| I-90 | 8 |
| I-91 | 9 |
| I-92 | 10 |
| I-93 | 9 |
| I-96 | 7 |
| I-98 | 7 |
| I-99 | 9 |
| I-105 | 10 |
| I-106 | 10 |
| I-107 | 7 |
| I-109 | 10 |
| I-110 | 9 |
| I-111 | 10 |
| I-115 | 10 |
| I-116 | 9 |
| I-117 | 9 |
| I-118 | 9 |
| I-119 | 9 |
| I-120 | 9 |
| I-125 | 10 |
| I-126 | 9 |
| I-127 | 10 |
| I-128 | 9 |
| I-129 | 10 |
| I-131 | 10 |
| I-134 | 10 |
| I-135 | 10 |
| I-136 | 9 |
| I-137 | 10 |
| I-138 | 8 |
| I-149 | 8 |
| I-155 | 9 |
| I-167 | 10 |
| I-169 | 9 |
| I-170 | 10 |
| I-179 | 10 |
| I-182 | 8 |
| I-184 | 10 |
| I-185 | 10 |
| I-187 | 8 |
| I-198 | 10 |
| I-199 | 10 |
| I-202 | 9 |
| I-203 | 6 |
| I-259 | 10 |
| I-260 | 8 |
| I-263 | 9 |

TABLE 81-continued

| Compound No. | Echinochloa crus-galli |
|---|---|
| I-265 | 8 |
| I-268 | 7 |
| I-269 | 10 |
| I-270 | 9 |
| I-271 | 10 |
| I-272 | 6 |
| I-273 | 10 |
| I-274 | 9 |
| I-275 | 9 |
| I-276 | 10 |
| I-277 | 10 |
| I-278 | 10 |
| I-279 | 9 |
| I-280 | 9 |
| I-281 | 9 |
| I-282 | 8 |
| I-283 | 8 |
| I-284 | 9 |
| I-285 | 9 |
| I-286 | 10 |
| I-287 | 8 |
| I-288 | 9 |
| I-289 | 9 |
| I-292 | 8 |
| I-294 | 9 |
| I-297 | 9 |
| I-298 | 10 |
| I-299 | 8 |
| I-300 | 9 |
| I-302 | 10 |
| I-303 | 8 |
| I-304 | 10 |
| I-328 | 7 |
| I-339 | 9 |
| I-463 | 7 |
| I-465 | 8 |
| I-467 | 8 |
| I-468 | 9 |
| I-469 | 10 |
| I-470 | 8 |
| I-471 | 9 |
| I-474 | 7 |
| I-475 | 9 |
| I-476 | 7 |
| I-477 | 9 |
| I-478 | 8 |
| I-479 | 9 |
| I-480 | 9 |
| III-50 | 10 |
| VI-1 | 10 |
| VI-5 | 10 |
| VI-6 | 8 |
| VI-7 | 10 |
| VI-65 | 9 |
| VI-97 | 7 |
| V-300 | 8 |
| V-358 | 8 |
| V-360 | 8 |
| V-362 | 9 |
| V-363 | 10 |
| V-364 | 8 |
| V-365 | 9 |
| V-368 | 7 |
| V-369 | 9 |
| V-370 | 7 |
| V-371 | 8 |

TABLE 82

| Compound No. | Setaria viridis |
|---|---|
| I-1 | 8 |
| I-2 | 10 |
| I-3 | 9 |
| I-4 | 9 |
| I-5 | 10 |
| I-10 | 7 |
| I-11 | 9 |
| I-14 | 10 |
| I-16 | 9 |
| I-19 | 10 |
| I-27 | 6 |
| I-41 | 10 |
| I-43 | 8 |
| I-50 | 10 |
| I-51 | 10 |
| I-52 | 10 |
| I-54 | 10 |
| I-55 | 10 |
| I-56 | 10 |
| I-57 | 10 |
| I-58 | 10 |
| I-60 | 9 |
| I-63 | 10 |
| I-66 | 10 |
| I-67 | 10 |
| I-68 | 8 |
| I-71 | 9 |
| I-72 | 10 |
| I-73 | 10 |
| I-74 | 9 |
| I-75 | 10 |
| I-76 | 9 |
| I-77 | 10 |
| I-78 | 10 |
| I-79 | 10 |
| I-80 | 7 |
| I-81 | 10 |
| I-82 | 10 |
| I-83 | 10 |
| I-84 | 10 |
| I-85 | 10 |
| I-86 | 9 |
| I-89 | 10 |
| I-90 | 7 |
| I-91 | 10 |
| I-92 | 10 |
| I-93 | 9 |
| I-105 | 7 |
| I-109 | 7 |
| I-116 | 9 |
| I-117 | 9 |
| I-118 | 10 |
| I-126 | 7 |
| I-127 | 10 |
| I-128 | 10 |
| I-129 | 9 |
| I-134 | 10 |
| I-136 | 9 |
| I-137 | 10 |
| I-138 | 8 |
| I-155 | 7 |
| I-167 | 8 |
| I-169 | 9 |
| I-179 | 10 |
| I-184 | 8 |
| I-185 | 9 |
| I-187 | 8 |
| I-199 | 8 |
| I-202 | 9 |
| I-261 | 7 |
| I-263 | 9 |
| I-265 | 9 |
| I-269 | 8 |
| I-271 | 7 |
| I-274 | 8 |
| I-275 | 8 |
| I-276 | 10 |
| I-277 | 9 |
| I-278 | 10 |

TABLE 82-continued

| Compound No. | Setaria viridis |
|---|---|
| I-281 | 7 |
| I-282 | 7 |
| I-284 | 7 |
| I-285 | 9 |
| I-286 | 10 |
| I-288 | 10 |
| I-289 | 7 |
| I-297 | 9 |
| I-298 | 8 |
| I-302 | 10 |
| I-303 | 10 |
| I-304 | 10 |
| I-328 | 7 |
| I-463 | 7 |
| I-464 | 7 |
| I-465 | 10 |
| I-468 | 9 |
| I-469 | 10 |
| I-470 | 9 |
| I-471 | 10 |
| I-475 | 7 |
| I-479 | 7 |
| VI-1 | 10 |
| VI-5 | 10 |
| VI-6 | 10 |
| VI-7 | 10 |
| VI-65 | 7 |
| VI-97 | 10 |
| V-300 | 8 |
| V-358 | 10 |
| V-362 | 9 |
| V-363 | 10 |
| V-364 | 9 |
| V-365 | 10 |
| V-369 | 7 |

TABLE 83

| Compound No. | Abutilon theophrasti |
|---|---|
| I-1 | 9 |
| I-2 | 10 |
| I-3 | 9 |
| I-4 | 9 |
| I-5 | 10 |
| I-9 | 10 |
| I-10 | 9 |
| I-11 | 9 |
| I-14 | 10 |
| I-16 | 9 |
| I-19 | 10 |
| I-27 | 9 |
| I-41 | 10 |
| I-43 | 9 |
| I-47 | 9 |
| I-50 | 10 |
| I-51 | 10 |
| I-52 | 10 |
| I-53 | 10 |
| I-54 | 10 |
| I-55 | 10 |
| I-56 | 10 |
| I-57 | 10 |
| I-58 | 10 |
| I-59 | 10 |
| I-60 | 10 |
| I-61 | 10 |
| I-62 | 9 |
| I-63 | 10 |
| I-64 | 10 |
| I-65 | 10 |
| I-66 | 10 |
| I-67 | 10 |

TABLE 83-continued

| Compound No. | Abutilon theophrasti |
|---|---|
| I-68 | 10 |
| I-71 | 9 |
| I-72 | 10 |
| I-73 | 10 |
| I-74 | 9 |
| I-75 | 10 |
| I-76 | 10 |
| I-77 | 10 |
| I-78 | 10 |
| I-79 | 10 |
| I-80 | 9 |
| I-81 | 10 |
| I-82 | 10 |
| I-83 | 10 |
| I-84 | 10 |
| I-85 | 10 |
| I-86 | 10 |
| I-87 | 9 |
| I-88 | 9 |
| I-89 | 10 |
| I-90 | 9 |
| I-91 | 10 |
| I-92 | 10 |
| I-93 | 10 |
| I-94 | 10 |
| I-96 | 9 |
| I-98 | 9 |
| I-99 | 10 |
| I-105 | 10 |
| I-106 | 9 |
| I-107 | 9 |
| I-108 | 9 |
| I-109 | 9 |
| I-110 | 9 |
| I-111 | 10 |
| I-115 | 10 |
| I-116 | 9 |
| I-117 | 9 |
| I-118 | 10 |
| I-119 | 9 |
| I-120 | 9 |
| I-125 | 10 |
| I-126 | 9 |
| I-127 | 9 |
| I-128 | 10 |
| I-129 | 9 |
| I-131 | 10 |
| I-134 | 10 |
| I-135 | 10 |
| I-136 | 9 |
| I-137 | 10 |
| I-138 | 9 |
| I-149 | 10 |
| I-155 | 10 |
| I-167 | 10 |
| I-169 | 9 |
| I-170 | 10 |
| I-179 | 10 |
| I-182 | 9 |
| I-183 | 9 |
| I-184 | 9 |
| I-185 | 9 |
| I-187 | 9 |
| I-189 | 9 |
| I-198 | 10 |
| I-199 | 9 |
| I-202 | 9 |
| I-203 | 9 |
| I-205 | 10 |
| I-259 | 10 |
| I-260 | 10 |
| I-261 | 10 |
| I-263 | 10 |
| I-265 | 9 |
| I-268 | 9 |
| I-269 | 9 |
| I-270 | 9 |

TABLE 83-continued

| Compound No. | Abutilon theophrasti |
|---|---|
| I-271 | 9 |
| I-272 | 9 |
| I-273 | 9 |
| I-274 | 8 |
| I-275 | 9 |
| I-276 | 9 |
| I-277 | 9 |
| I-278 | 9 |
| I-279 | 10 |
| I-280 | 9 |
| I-281 | 9 |
| I-282 | 9 |
| I-283 | 8 |
| I-284 | 8 |
| I-285 | 7 |
| I-286 | 9 |
| I-287 | 9 |
| I-288 | 10 |
| I-289 | 9 |
| I-290 | 9 |
| I-291 | 9 |
| I-292 | 10 |
| I-293 | 8 |
| I-294 | 7 |
| I-295 | 9 |
| I-297 | 8 |
| I-298 | 9 |
| I-299 | 9 |
| I-300 | 8 |
| I-301 | 7 |
| I-302 | 10 |
| I-303 | 9 |
| I-304 | 9 |
| I-306 | 9 |
| I-307 | 10 |
| I-308 | 8 |
| I-328 | 10 |
| I-339 | 10 |
| I-462 | 10 |
| I-463 | 9 |
| I-464 | 10 |
| I-465 | 10 |
| I-466 | 10 |
| I-467 | 7 |
| I-468 | 10 |
| I-469 | 10 |
| I-470 | 10 |
| I-471 | 10 |
| I-472 | 7 |
| I-473 | 10 |
| I-474 | 9 |
| I-475 | 8 |
| I-476 | 9 |
| I-477 | 9 |
| I-478 | 9 |
| I-479 | 9 |
| I-480 | 10 |
| II-50 | 8 |
| II-267 | 9 |
| III-50 | 10 |
| III-62 | 10 |
| VI-1 | 10 |
| VI-5 | 10 |
| VI-6 | 10 |
| VI-7 | 10 |
| VI-65 | 10 |
| VI-97 | 10 |
| V-300 | 9 |
| V-358 | 10 |
| V-359 | 10 |
| V-360 | 7 |
| V-361 | 9 |
| V-362 | 10 |
| V-363 | 10 |
| V-364 | 10 |
| V-365 | 10 |
| V-366 | 7 |
| V-367 | 10 |
| V-368 | 9 |
| V-369 | 8 |
| V-370 | 9 |
| V-371 | 9 |

TABLE 84

| Compound No. | Amaranthus retroflexus |
|---|---|
| I-1 | 10 |
| I-2 | 10 |
| I-3 | 9 |
| I-4 | 9 |
| I-5 | 10 |
| I-9 | 10 |
| I-10 | 10 |
| I-11 | 10 |
| I-14 | 10 |
| I-16 | 10 |
| I-19 | 10 |
| I-27 | 9 |
| I-41 | 10 |
| I-43 | 10 |
| I-47 | 10 |
| I-50 | 10 |
| I-51 | 10 |
| I-52 | 10 |
| I-53 | 10 |
| I-54 | 10 |
| I-55 | 10 |
| I-56 | 10 |
| I-57 | 10 |
| I-58 | 10 |
| I-59 | 10 |
| I-60 | 10 |
| I-61 | 10 |
| I-62 | 10 |
| I-63 | 10 |
| I-64 | 10 |
| I-65 | 10 |
| I-66 | 10 |
| I-67 | 10 |
| I-68 | 10 |
| I-71 | 10 |
| I-72 | 10 |
| I-73 | 10 |
| I-74 | 10 |
| I-75 | 10 |
| I-76 | 10 |
| I-77 | 10 |
| I-78 | 10 |
| I-79 | 10 |
| I-80 | 10 |
| I-81 | 10 |
| I-82 | 10 |
| I-83 | 10 |
| I-84 | 10 |
| I-85 | 10 |
| I-86 | 10 |
| I-87 | 10 |
| I-88 | 10 |
| I-89 | 10 |
| I-90 | 10 |
| I-91 | 10 |
| I-92 | 10 |
| I-93 | 10 |
| I-94 | 10 |
| I-96 | 10 |
| I-98 | 8 |
| I-99 | 10 |
| I-105 | 10 |
| I-106 | 10 |

TABLE 84-continued

| Compound No. | Amaranthus retroflexus |
|---|---|
| I-107 | 10 |
| I-108 | 10 |
| I-109 | 9 |
| I-110 | 9 |
| I-111 | 10 |
| I-115 | 10 |
| I-116 | 8 |
| I-117 | 8 |
| I-118 | 10 |
| I-119 | 10 |
| I-120 | 10 |
| I-125 | 10 |
| I-126 | 10 |
| I-127 | 10 |
| I-128 | 10 |
| I-129 | 10 |
| I-131 | 10 |
| I-134 | 10 |
| I-135 | 10 |
| I-136 | 10 |
| I-137 | 10 |
| I-138 | 10 |
| I-149 | 10 |
| I-155 | 10 |
| I-167 | 10 |
| I-169 | 8 |
| I-170 | 10 |
| I-179 | 10 |
| I-182 | 9 |
| I-183 | 10 |
| I-184 | 10 |
| I-185 | 10 |
| I-187 | 10 |
| I-189 | 10 |
| I-198 | 10 |
| I-199 | 9 |
| I-202 | 9 |
| I-203 | 10 |
| I-204 | 7 |
| I-205 | 10 |
| I-259 | 10 |
| I-260 | 10 |
| I-261 | 10 |
| I-263 | 10 |
| I-265 | 10 |
| I-268 | 10 |
| I-269 | 10 |
| I-270 | 10 |
| I-271 | 10 |
| I-272 | 10 |
| I-273 | 10 |
| I-274 | 9 |
| I-275 | 9 |
| I-276 | 10 |
| I-277 | 10 |
| I-278 | 10 |
| I-279 | 10 |
| I-280 | 10 |
| I-281 | 9 |
| I-282 | 8 |
| I-283 | 8 |
| I-284 | 9 |
| I-285 | 8 |
| I-286 | 10 |
| I-287 | 10 |
| I-288 | 10 |
| I-289 | 10 |
| I-290 | 10 |
| I-291 | 10 |
| I-292 | 10 |
| I-293 | 10 |
| I-294 | 8 |
| I-295 | 8 |
| I-297 | 8 |
| I-298 | 10 |
| I-299 | 10 |
| I-300 | 10 |
| I-301 | 10 |
| I-302 | 10 |
| I-303 | 10 |
| I-304 | 10 |
| I-306 | 7 |
| I-307 | 9 |
| I-328 | 10 |
| I-339 | 10 |
| I-462 | 10 |
| I-463 | 10 |
| I-464 | 10 |
| I-465 | 10 |
| I-466 | 10 |
| I-467 | 10 |
| I-468 | 10 |
| I-469 | 10 |
| I-470 | 10 |
| I-471 | 10 |
| I-472 | 10 |
| I-473 | 3 |
| I-474 | 9 |
| I-475 | 9 |
| I-476 | 10 |
| I-477 | 10 |
| I-478 | 10 |
| I-479 | 10 |
| I-480 | 10 |
| II-50 | 10 |
| III-50 | 10 |
| III-62 | 10 |
| VI-1 | 10 |
| VI-5 | 10 |
| VI-6 | 10 |
| VI-7 | 10 |
| VI-65 | 10 |
| VI-97 | 10 |
| V-300 | 10 |
| V-358 | 10 |
| V-359 | 10 |
| V-360 | 10 |
| V-361 | 10 |
| V-362 | 10 |
| V-363 | 10 |
| V-364 | 10 |
| V-365 | 10 |
| V-366 | 10 |
| V-368 | 9 |
| V-369 | 9 |
| V-370 | 10 |
| V-371 | 10 |

As a result of the tests, it was found that the compounds of the invention have an excellent herbicidal activity.

The invention claimed is:

1. A triazine derivative or a salt thereof represented by following Formula 1:

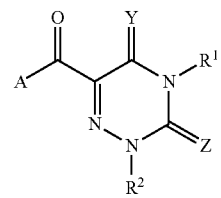

[1]

wherein $R^1$ is selected from the group consisting of a hydrogen atom; a $C_1$-$C_{12}$ alkyl group; a $C_2$-$C_6$ alkenyl group; a $C_2$-$C_6$ alkynyl group; a $C_3$-$C_6$ cycloalkyl group; a $C_3$-$C_6$ cycloalkenyl group; a $C_3$-$C_6$ cycloalkyl $C_1$-$C_6$ alkyl group; a $C_1$-$C_6$ haloalkyl group; a $C_2$-$C_6$ haloalkenyl group; a $C_2$-$C_6$ haloalkynyl group; a $C_3$-$C_6$ halocycloalkyl group; a $C_3$-$C_6$ halocycloalkyl $C_1$-$C_6$ alkyl group; an amino $C_1$-$C_6$ alkyl group; a nitro $C_1$-$C_6$ alkyl group; a $C_1$-$C_6$ alkylamino $C_1$-$C_6$ alkyl group; a di($C_1$-$C_6$ alkyl)amino $C_1$-$C_6$ alkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ haloalkylthio $C_1$-$C_6$ alkyl group; a $C_1$-$C_6$ haloalkylsulfinyl $C_1$-$C_6$ alkyl group; a $C_1$-$C_6$ haloalkylsulfonyl $C_1$-$C_6$ alkyl group; a $C_1$-$C_6$ alkoxy $C_1$-$C_6$ alkyl group; a hydroxy $C_1$-$C_6$ alkyl group; a phenyl $C_1$-$C_6$ alkoxy $C_1$-$C_6$ alkyl group wherein said phenyl in the group may be substituted with one substituent group selected from substituent group α or 2 to 5 substituent groups that are the same or different from each other and selected from substituent group α; a $C_1$-$C_6$ alkoxy $C_1$-$C_6$ alkoxy $C_1$-$C_6$ alkyl group; a $C_3$-$C_6$ cycloalkyloxy $C_1$-$C_6$ alkyl group; a $C_3$-$C_6$ cycloalkyl $C_1$-$C_6$ alkyloxy $C_1$-$C_6$ alkyl group; a phenyloxy $C_1$-$C_6$ alkyl group wherein the phenyl in the group may be substituted with 1 to 5 identical or different substituents selected from the substituent group α; a phenylthio $C_1$-$C_6$ alkyl group wherein the phenyl in the group may be substituted with 1 to 5 identical or different substituents selected from the substituent group α; a phenylsulfinyl $C_1$-$C_6$ alkyl group wherein the phenyl in the group may be substituted with 1 to 5 identical or different substituents selected from the substituent group α; a phenylsulfonyl $C_1$-$C_6$ alkyl group wherein the phenyl in the group may be substituted with 1 to 5 identical or different substituents selected from the substituent group α; a $C_1$-$C_6$ haloalkoxy $C_1$-$C_6$ alkyl group; a phenyl group which may be substituted with one or more substituents selected from the substituent group α; a phenyl $C_1$-$C_6$ alkyl group which may be substituted with one or more substituents selected from the substituent group α; a phenyl $C_2$-$C_6$ alkenyl group which may be substituted with one or more substituents selected from the substituent group α; a phenyl $C_2$-$C_6$ alkynyl group which may be substituted with one or more substituents selected from the substituent group α; a $C_1$-$C_6$ alkoxyimino $C_1$-$C_6$ alkyl group; a phenoxyimino $C_1$-$C_6$ alkyl group which may be substituted with one or more substituents selected from the substituent group α; a di($C_1$-$C_6$ alkoxy)$C_1$-$C_6$ alkyl group; a ($R^{31}R^{32}$N—C=O)$C_1$-$C_6$ alkyl group; a $C_1$-$C_6$ alkoxycarbonyl $C_1$-$C_6$ alkyl group; a $C_1$-$C_6$ alkylcarbonyl $C_1$-$C_6$ alkyl group; a $C_1$-$C_6$ alkylcarbonyloxy $C_1$-$C_6$ alkyl group; a $C_1$-$C_6$ alkylidene aminooxy $C_1$-$C_6$ alkyl group; a formyl $C_1$-$C_6$ alkyl group; a $C_1$-$C_6$ alkylthio $C_1$-$C_6$ alkoxy $C_1$-$C_6$ alkyl group; a $C_1$-$C_6$ alkylsulfinyl $C_1$-$C_6$ alkoxy $C_1$-$C_6$ alkyl group; a $C_1$-$C_6$ alkylsulfonyl $C_1$-$C_6$ alkoxy $C_1$-$C_6$ alkyl group; a cyano $C_1$-$C_6$ alkoxy $C_1$-$C_6$ alkyl group; a cyano $C_1$-$C_6$ alkyl group; a $C_2$-$C_6$ alkylidene amino group; a di($C_1$-$C_{10}$alkyl)amino $C_1$-$C_6$ alkylidene amino group; a $NR^{31}R^{32}$ group; a $C_1$-$C_6$ alkoxy group; a $C_2$-$C_6$ alkenyloxy group; a $C_2$-$C_6$ alkynyloxy group; a $C_3$-$C_6$ cycloalkyloxy group; a $C_3$-$C_6$ cycloalkyl $C_1$-$C_6$ alkyloxy group; a $C_1$-$C_6$ haloalkoxy group; a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α, and when the heteroatom in the heterocyclic group is a sulfur atom, the sulfur atom may be oxidized to sulfoxide or sulfone; a $C_1$-$C_6$ alkyl group substituted with a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α; a $C_1$-$C_6$ alkoxy $C_1$-$C_6$ alkyl group substituted with a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α; and a $C_1$-$C_6$ alkoxy $C_1$-$C_6$ alkyl group substituted with a heterocyclic-oxy group in which the heterocyclic group in the heterocyclic-oxy group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α;

$R^2$ is selected from the group consisting of a $C_1$-$C_6$ alkyl group; a $C_2$-$C_6$ alkenyl group; a $C_2$-$C_6$ alkynyl group; a $C_3$-$C_6$ cycloalkyl group; a $C_1$-$C_6$ haloalkyl group; a $C_2$-$C_6$ haloalkenyl group; a $C_2$-$C_6$ haloalkynyl group; a $C_1$-$C_6$ alkoxy $C_1$-$C_6$ alkyl group; a $C_3$-$C_6$ cycloalkyloxy $C_1$-$C_6$ alkyl group; a di($C_1$-$C_6$ alkoxy) $C_1$-$C_6$ alkyl group; a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α; a phenyl group which may be substituted with one or more substituents selected from the substituent group α; a phenyl $C_1$-$C_6$ alkyl group which may be substituted with one or more substituents selected from the substituent group α; a phenyl $C_2$-$C_6$ alkenyl group which may be substituted with one or more substituents selected from the substituent group α; and a phenyl $C_2$-$C_6$ alkynyl group which may be substituted with one or more substituents selected from the substituent group α, Y and Z are selected from the group consisting of an oxygen atom and a sulfur atom, A is selected from the group consisting of formula A-1 and A-3,

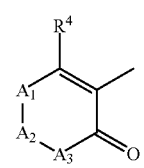

A-1

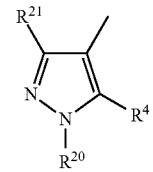

A-3

$R^4$ is selected from the group consisting of a hydroxyl group; O⁻M⁺ wherein M⁺ is an alkali metal cation or an ammonium cation; an amino group; a halogen atom; a cyano group; an isothiocyanate group; an isocyanate group; a hydroxycarbonyloxy group; a $C_1$-$C_6$ alkoxycarbonyloxy group; a benzyloxycarbonyloxy group which may be substituted with a substituent group selected from substituent group α; a $C_1$-$C_6$ alkoxy group; a $C_2$-$C_6$ alkenyloxy group; a $C_2$-$C_6$ alkynyloxy group; a $C_3$-$C_6$ cycloalkyloxy group; a cyanomethylene oxy group; a $C_3$-$C_6$ cycloalkyl $C_1$-$C_6$ alkyloxy group; a $C_1$-$C_6$ alkylcarbonyloxy group; a $C_1$-$C_6$ haloalkylcarbonyloxy group; a $C_2$-$C_6$ alkenylcarbonyloxy group; a $C_2$-$C_6$ haloalkenylcarbonyloxy group; a $C_2$-$C_6$ alkynylcarbonyloxy group; a $C_2$-$C_6$ haloalkynylcarbonyloxy group; a $C_1$-$C_6$ alkoxycarbonyl $C_1$-$C_6$ alkoxy group; a phenyloxy group which may be substituted with one or more substituents selected from the substituent group α; a benzyloxy group which may be substituted with one or more substituents selected from the substituent group α; a phenylcarbonyloxy group which may be substituted with one or more substituents selected from the substituent group α; a benzylcarbonyloxy group which may be substituted with one or more substituents selected from the substituent group α; a phenylcarbonyl $C_1$-$C_6$ alkyloxy group which may be substituted with one or more substituents selected from the substituent group α; a $C_1$-$C_{10}$ alkylsulfonlyoxy group; a $C_1$-$C_6$ haloalkylsulfonlyoxy group; a phenylsulfonyloxy group which may be substituted with one or more substituents selected from the substituent group α; a benzylsulfonyloxy group which may be substituted with one or more substituents selected from the substituent group α; a $C_1$-$C_{10}$ alkylthio group; a $C_1$-$C_{10}$ alkylsulfinyl group; a $C_1$-$C_{10}$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_2$-$C_6$ alkenylthio group; a $C_2$-$C_6$ alkenylsulfinyl group; a $C_2$-$C_6$ alkenylsulfonyl group; a $C_2$-$C_6$ alkynylthio group; a $C_2$-$C_6$ alkynylsulfinyl group; a $C_2$-$C_6$ alkynylsulfonyl group; a phenylthio group which may be substituted with one or more substituents selected from the substituent group α; a benzylthio group which may be substituted with one or more substituents selected from the substituent group α; a phenylsulfinyl group which may be substituted with one or more substituents selected from the substituent group α; a benzylsulfinyl group which may be substituted with one or more substituents selected from the substituent group α; a phenylsulfonyl group which may be substituted with one or more substituents selected from the substituent group α; a benzylsulfonyl group which may be substituted with one or more substituents selected from the substituent group α; a $C_1$-$C_{10}$ alkylamino group; a di($C_1$-$C_{10}$ alkyl)amino group; a $C_1$-$C_6$ alkoxycarbonylamino group; a $C_1$-$C_6$ alkoxy group substituted with a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α; a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α; or a heterocyclic-oxy group in which the heterocyclic group in the heterocyclic-oxy group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α, $A_1$ is $X_1$ or $X_2$:

[$X_1$]

[$X_2$]

$A_2$ is selected from the group consisting of $X_3$, $X_4$, $X_5$, $X_6$ and $X_7$:

[$X_3$]

[$X_4$]

[$X_5$]

[$X_6$]

[$X_7$]

$A_3$ is $X_8$ or $X_9$:

[$X_8$]

[$X_9$]

n is 0, 1, or 2, $R^5$, $R^6$, $R^8$, $R^9$, $R^{35}$ and $R^{36}$ each independently is a hydrogen atom or a $C_1$-$C_6$ alkyl group, $R^5$ and $R^8$ may be joined together to form a $C_2$-$C_5$ alkylene chain or a $C_2$-$C_5$ alkenylene chain, and may form a ring together with adjacent carbon atoms, and $R^5$ and $R^{35}$ may be joined together to form a $C_1$-$C_5$ alkylene chain to form a ring with adjacent carbon atoms, $R^7$, $R^{33}$, and $R^{34}$ each independently is a hydrogen atom, a $C_1$-$C_6$ alkyl group, a $C_1$-$C_6$ haloalkyl group, a $C_2$-$C_6$ alkenyl group, a $C_2$-$C_6$ alkynyl group, or a $C_1$-$C_6$ alkoxy group, $R^{20}$ is selected from the group consisting of a $C_1$-$C_6$ alkyl group, a $C_2$-$C_6$ alkenyl group, a $C_2$-$C_6$ alkynyl group, a $C_3$-$C_6$ cycloalkyl group, and a $C_3$-$C_6$ cycloalkyl $C_1$-$C_6$ alkyl group, $R^{21}$ is selected from the group consisting of a hydrogen atom, a $C_1$-$C_6$ alkyl group, and a halogen atom, $R^{31}$ and $R^{32}$ each independently is selected from the group consisting of a hydrogen atom; a $C_1$-$C_6$ alkyl group; a phenyl group which may be substituted with one or more substituents selected from the substituent group α; a benzyl group which may be substituted with one or more substituents selected from the substituent group α; a $C_1$-$C_6$ alkoxy $C_1$-$C_6$ alkyl group; a $C_1$-$C_6$ alkylcarbonyl group; a $C_1$-$C_{10}$ alkylthio carbonyl group; a $C_1$-$C_6$ alkoxycarbonyl group; a $C_1$-$C_6$ haloalkyl group; a $C_3$-$C_6$ cycloalkyl group; a $C_3$-$C_6$ cycloalkyl $C_1$-$C_6$ alkyl group; a $C_1$-$C_6$ alkylsulfonyl group; a phenylsulfonyl group which may be substituted with one or more substituents selected from the substituent group α; a benzylsulfonyl group which may be substituted with one or more substituents selected from the substituent group α; a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α; and a $C_1$-$C_6$ alkyl group substituted with a heterocyclic group in which the heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α, herein, $R^{31}$ and $R^{32}$ may be joined together to form a 5- to 6-membered ring with adjacent nitrogen atom, and the one or more carbon atoms in the ring may be substituted with a sulfur atom and/or an oxygen atom, wherein substituent group α is selected from the group consisting of:

a halogen atom; a hydroxyl group; a $C_1$-$C_6$ alkyl group; a $C_3$-$C_6$ cycloalkyl group; a $C_3$-$C_6$ cycloalkyl $C_1$-$C_6$ alkyl group; a $C_2$-$C_6$ alkenyl group; a $C_2$-$C_6$ alkynyl group; a $C_1$-$C_6$ haloalkyl group; a $C_2$-$C_6$ haloalkenyl group; a $C_2$-$C_6$ haloalkynyl group; a $C_3$-$C_6$ halocycloalkyl group; a $C_3$-$C_6$ halocycloalkyl $C_1$-$C_6$ alkyl group; a $C_1$-$C_6$ alkoxy group; a $C_3$-$C_6$ cycloalkyloxy group; a $C_2$-$C_6$ alkenyloxy group; a $C_2$-$C_6$ alkynyloxy group; a $C_1$-$C_6$ alkylcarbonyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a $C_1$-$C_6$ alkylcarbonylamino group; a mono($C_1$-$C_6$ alkyl)amino group; a di($C_1$-$C_6$ alkyl)amino group; a hydroxy $C_1$-$C_6$ alkyl group; a $C_1$-$C_6$ alkoxy $C_1$-$C_6$ alkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ haloalkylthio $C_1$-$C_6$ alkyl group; a $C_1$-$C_6$ haloalkylsulfinyl $C_1$-$C_6$ alkyl group; a $C_1$-$C_6$ haloalkylsulfonyl $C_1$-$C_6$ alkyl group; a cyano $C_1$-$C_6$ alkyl group; a $C_1$-$C_6$ alkoxy $C_1$-$C_6$ alkoxy group; a $C_3$-$C_6$ cycloalkyl $C_1$-$C_6$ alkyloxy group; a $C_1$-$C_6$ haloalkoxy $C_1$-$C_6$ alkoxy group; a cyano $C_1$-$C_6$ alkoxy group; a $C_1$-$C_6$ acyl group; a $C_1$-$C_6$ alkoxyimino $C_1$-$C_6$ alkyl group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; a nitro group; a cyano group; a phenyl group wherein the phenyl in the group may be substituted with 1 to 5 identical or different substituents selected from the substituent group β; a heterocyclic group comprising 2 to 10 carbon atoms and 1 to 5 identical or different heteroatoms selected from an oxygen atom, a sulfur atom, and a nitrogen atom wherein the group may be substituted with 1 to 5 identical or different substituents selected from the substituent group β; a heterocyclic oxy group comprising 2 to 10 carbon atoms and 1 to 5 identical or different heteroatoms selected from an oxygen atom, a sulfur atom, and a nitrogen atom wherein the group may be substituted with 1 to 5 identical or different substituents selected from the substituent group β; and a $C_3$-$C_6$ alkylene group formed with two adjacent substituent groups, wherein 1 to 3 carbon atoms in the alkylene group may be substituted with an atom selected from a group consisting of an oxygen atom, a sulfur atom, a nitrogen atom, and a carbon atom constituting an carbonyl group; and wherein substituent group β is selected from the group consisting of: a halogen atom, a nitro group, a cyano group, a $C_1$-$C_6$ alkyl group, a $C_1$-$C_6$ haloalkyl group, a $C_1$-$C_6$ alkoxy group, and a $C_1$-$C_6$ haloalkoxy group.

2. The triazine derivative or the salt thereof according to claim 1, wherein $R^1$ is selected from the group consisting of a $C_1$-$C_{12}$ alkyl group; a $C_2$-$C_6$ alkenyl group; a $C_2$-$C_6$ alkynyl group; a $C_3$-$C_6$ cycloalkyl group; a $C_3$-$C_6$ cycloalkenyl group; a $C_3$-$C_6$ cycloalkyl $C_1$-$C_6$ alkyl group; a $C_1$-$C_6$ haloalkyl group; a $C_2$-$C_6$ haloalkenyl group; a $C_2$-$C_6$ haloalkynyl group; a $C_3$-$C_6$ halocycloalkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ alkoxy $C_1$-$C_6$ alkyl group; a $C_1$-$C_6$ alkoxy $C_1$-$C_6$ alkoxy $C_1$-$C_6$ alkyl group; a $C_3$-$C_6$ cycloalkyloxy $C_1$-$C_6$ alkyl group; a phenyloxy $C_1$-$C_6$ alkyl group wherein the phenyl in the group may be substituted with 1 to 5 identical or different substituents selected from the substituent group α; a phenylthio $C_1$-$C_6$ alkyl group wherein the phenyl in the group may be substituted with 1 to 5 identical or different substituents selected from the substituent group α; a phenylsulfinyl $C_1$-$C_6$ alkyl group wherein the phenyl in the group may be substituted with 1 to 5 identical or different substituents selected from the substituent group α; a phenylsulfonyl $C_1$-$C_6$ alkyl group wherein the phenyl in the group may be substituted with 1 to 5 identical or different substituents selected from the substituent group α; a phenyl group which may be substituted with one or more substituents selected from the substituent group α; a phenyl $C_1$-$C_6$ alkyl group which may be substituted with one or more substituents selected from the substituent group α; a phenyl $C_2$-$C_6$ alkenyl group which may be substituted with one or more substituents selected from the substituent group α; a phenyl $C_2$-$C_6$ alkynyl group which may be substituted with one or more substituents selected from the substituent group α; a $C_1$-$C_6$ alkoxyimino $C_1$-$C_6$ alkyl group; a di($C_1$-$C_6$ alkoxy) $C_1$-$C_6$ alkyl group; a $C_1$-$C_6$ alkoxycarbonyl $C_1$-$C_6$ alkyl group; a $C_1$-$C_6$ alkylcarbonyl $C_1$-$C_6$ alkyl group; a $C_1$-$C_6$ alkylcarbonyloxy $C_1$-$C_6$ alkyl group; a $NR^{31}R^{32}$ group; a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α, and when the heteroatom in the heterocyclic group is a sulfur atom, the sulfur atom may be oxidized to sulfoxide or sulfone; and a $C_1$-$C_6$ alkyl group substituted with a heterocyclic group in which the heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α;

$R^2$ is selected from the group consisting of a $C_1$-$C_6$ alkyl group; a $C_2$-$C_6$ alkenyl group; a $C_2$-$C_6$ alkynyl group; a $C_3$-$C_6$ cycloalkyl group; a $C_1$-$C_6$ haloalkyl group; a $C_2$-$C_6$ haloalkenyl group; a $C_2$-$C_6$ haloalkynyl group; a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group cc; a phenyl group which may be substituted with one or more substituents selected from the substituent group cc; and a phenyl $C_1$-$C_6$ alkyl group which may be substituted with one or more substituents selected from the substituent group cc;

Y and Z are selected from the group consisting of an oxygen atom and a sulfur atom, A is selected from the group consisting of A-1 and A-3, $A_1$ is $X_1$, $A_2$ is $X_3$ or $X_4$, and $A_3$ is $X_9$, wherein in $X_1$, $R^5$ and $R^6$ each independently represent a hydrogen atom or a $C_1$-$C_6$ alkyl group, wherein in $X_3$, $R^8$ and $R^9$ each independently represent a hydrogen atom or a $C_1$-$C_6$ alkyl group, wherein in $X_9$, $R^{35}$ and $R^{36}$ each independently represent a hydrogen atom or a $C_1$-$C_6$ alkyl group, wherein $R^5$ and $R^8$ may be joined together to form a $C_2$-$C_5$ alkylene chain or a $C_2$-$C_5$ alkenylene chain, and may form a ring together with adjacent carbon atoms, and $R^5$ and $R^{35}$ may be joined together to form a $C_1$-$C_5$ alkylene chain to form a ring with adjacent carbon atoms, in A-3, $R^{20}$ is a $C_1$-$C_6$ alkyl group, $R^{21}$ is a hydrogen atom or a $C_1$-$C_6$ alkyl group, $R^4$ is selected from the group consisting of a hydroxyl group; $O^-M^+$ wherein $M^+$ is an alkali metal cation or an ammonium cation; and a $C_1$-$C_{10}$ alkylsulfonlyoxy group;

$R^{31}$ and $R^{32}$ each independently is selected from the group consisting of a hydrogen atom; a $C_1$-$C_6$ alkyl group; a phenyl group which may be substituted with one or more substituents selected from the substituent group α; and a benzyl group which may be substituted with one or more substituents selected from the substituent group α; wherein $R^{31}$ and $R^{32}$ may be joined together to form a 5- to 6-membered ring with adjacent nitrogen atom, and the one or more carbon atoms in the ring may be substituted with a sulfur atom and/or an oxygen atom, wherein substituent group α is selected from the group consisting of:

a halogen atom; a $C_1$-$C_6$ alkyl group; a $C_3$-$C_6$ cycloalkyl group; a $C_2$-$C_6$ alkenyl group; a $C_2$-$C_6$ alkynyl group; a $C_1$-$C_6$ haloalkyl group; a $C_2$-$C_6$ haloalkenyl group; a $C_2$-$C_6$ haloalkynyl group; a $C_3$-$C_6$ halocycloalkyl group; a $C_1$-$C_6$ alkoxy group; a $C_3$-$C_6$ cycloalkyloxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a nitro group; a cyano group; a phenyl group wherein the phenyl in the group may be substituted with 1 to 5 identical or different substituents selected from the substituent group β; a heterocyclic oxy group comprising 2 to 10 carbon atoms and 1 to 5 heteroatoms that are optionally selected from an oxygen atom, a sulfur atom, and a nitrogen atom wherein the group may be substituted with 1 to 5 identical or different substituents selected from the substituent group β; and a $C_3$-$C_6$ alkylene group formed with two adjacent substituent groups, wherein 1 to 3 carbon atoms in the alkylene group may be substituted with an atom selected from a group consisting of an oxygen atom, a sulfur atom, a nitrogen atom, and a carbon atom constituting an carbonyl group.

3. The triazine derivative or the salt thereof according to claim 1, wherein $R^1$ is a group selected from a group consisting of a $C_1$-$C_{12}$ alkyl group; a $C_2$-$C_6$ alkenyl group;

a $C_2$-$C_6$ alkynyl group; a $C_3$-$C_6$ cycloalkyl group; a $C_3$-$C_6$ cycloalkenyl group; a $C_1$-$C_6$ haloalkyl group; a $C_2$-$C_6$ haloalkenyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ alkoxy $C_1$-$C_6$ alkyl group; a phenyl group which may be substituted with one or more substituents selected from the substituent group α; a phenyl $C_1$-$C_6$ alkyl group which may be substituted with one or more substituents selected from the substituent group α; a $C_1$-$C_6$ alkoxyimino $C_1$-$C_6$ alkyl group; a $C_1$-$C_6$ alkoxycarbonyl $C_1$-$C_6$ alkyl group; a $C_1$-$C_6$ alkylcarbonyl $C_1$-$C_6$ alkyl group; a $NR^{31}R^{32}$ group; a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α, and when the heteroatom in the heterocyclic group is a sulfur atom, the sulfur atom may be oxidized to sulfoxide or sulfone; and, a $C_1$-$C_6$ alkyl group substituted with a heterocyclic group in which the heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α;

$R^{31}$ and $R^{32}$ each independently is a group selected from the group consisting of a hydrogen atom; a $C_1$-$C_6$ alkyl group; and a phenyl group which may be substituted with one or more substituents selected from the substituent group α;

$R^2$ is a group selected from the group consisting of a $C_1$-$C_6$ alkyl group; a $C_2$-$C_6$ alkenyl group; a $C_2$-$C_6$ alkynyl group; a $C_3$-$C_6$ cycloalkyl group; a $C_1$-$C_6$ haloalkyl group; a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α; and a phenyl group which may be substituted with 1 to 5 identical or different substituents selected from the substituent group α;

Y and Z are selected from the group consisting of an oxygen atom and a sulfur atom, A is selected from the group consisting of A-1 and A-3, $R^4$ in A-1 is selected from the group consisting of a hydroxyl group; $O^-M^+$ wherein $M^+$ is an alkali metal cation or an ammonium cation; and a $C_1$-$C_{10}$ alkylsulfonlyoxy group;

in A-1, $A_1$ is $X_1$, $A_2$ is $X_3$ or $X_4$, and $A_3$ is $X_9$, in $X_1$, $R^5$ and $R^6$ each independently is a hydrogen atom or a $C_1$-$C_6$ alkyl group, in $X_3$, $R^8$ and $R^9$ each independently is a hydrogen atom or a $C_1$-$C_6$ alkyl group, in $X_9$, $R^{35}$ and $R^{36}$ each independently is a hydrogen atom or a $C_1$-$C_6$ alkyl group, wherein $R^5$ and $R^8$ may bind to each other via a $C_2$-$C_5$ alkylene chain or a $C_2$-$C_5$ alkenylene chain to form a ring, and $R^5$ and $R^{35}$ may bind to each other via a $C_1$-$C_5$ alkylene chain to form a ring, in A-3, $R^{20}$ is a $C_1$-$C_6$ alkyl group, $R^{21}$ is a hydrogen atom or a $C_1$-$C_6$ alkyl group, and $R^4$ in A-1 is selected from the group consisting of a hydroxyl group; $O^-M^+$ wherein $M^+$ is an alkali metal cation or an ammonium cation; and a $C_1$-$C_{10}$ alkylsulfonlyoxy group;

wherein substituent group α is selected from the group consisting of: a halogen atom; a $C_1$-$C_6$ alkyl group; a $C_2$-$C_6$ alkenyl group; a $C_2$-$C_6$ alkynyl group; a $C_1$-$C_6$ haloalkyl group; a $C_1$-$C_6$ alkoxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a nitro group; a cyano group; a phenyl group; and a $C_3$-$C_6$ alkylene group formed with two adjacent substituent groups, wherein 1 to 3 carbon atoms in the alkylene group may be substituted with an atom selected from a group consisting of an oxygen atom, a sulfur atom, a nitrogen atom, and a carbon atom constituting an carbonyl group.

4. The triazine derivative or the salt thereof according to claim 1, wherein $R^1$ is selected from the group consisting of a $C_1$-$C_{12}$ alkyl group; a $C_2$-$C_6$ alkenyl group; a $C_2$-$C_6$ alkynyl group; a $C_3$-$C_6$ cycloalkyl group; a $C_3$-$C_6$ cycloalkenyl group; a $C_1$-$C_6$ haloalkyl group; a $C_2$-$C_6$ haloalkenyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ alkoxy $C_1$-$C_6$ alkyl group; a phenyl group which may be substituted with one or more substituents selected from the substituent group α; a phenyl $C_1$-$C_6$ alkyl group; a $C_1$-$C_6$ alkoxyimino $C_1$-$C_6$ alkyl group; a $C_1$-$C_6$ alkoxycarbonyl $C_1$-$C_6$ alkyl group; a $C_1$-$C_6$ alkylcarbonyl $C_1$-$C_6$ alkyl group; a $NR^{31}R^{32}$ group; a heterocyclic group selected from the group consisting of pyridyl group, pyrimidinyl group, pyridazinyl group, thienyl group, isoxazolyl group, pyrazolyl group, morpholinyl group, thiomorpholinyl group, pyrazinyl group, piperidinyl group, and pyperazinyl group wherein the heterocyclic group may be substituted with 1 to 5 identical or different substituents selected from the substituent group α, and when the heteroatom in the heterocyclic group is a sulfur atom, the sulfur atom may be oxidized to sulfoxide or sulfone; and, a tetrahydrofuryl-methyl group;

$R^{31}$ and $R^{32}$ each independently is selected from the group consisting of a hydrogen atom; a $C_1$-$C_6$ alkyl group; and a phenyl group;

$R^2$ is selected from the group consisting of a $C_1$-$C_6$ alkyl group; a $C_1$-$C_6$ haloalkyl group; a pyridyl group; and a phenyl group;

Y and Z represent an oxygen atom or a sulfur atom,

A represents any one of A-1 and A-3, $R^4$ in A-1 represents a hydroxyl group; or a $C_1$-$C_{10}$ alkylsulfonlyoxy group, in A-1, $A_1$ is $X_1$, $A_2$ is $X_3$ or $X_4$, and $A_3$ is $X_9$, in $X_1$, $R^5$ and $R^6$ are a hydrogen atom or a $C_1$-$C_6$ alkyl group, in $X_3$, $R^8$ and $R^9$ are a hydrogen atom or a $C_1$-$C_6$ alkyl group, in $X_9$, $R^{35}$ and $R^{36}$ are a hydrogen atom or a $C_1$-$C_6$ alkyl group, wherein $R^5$ and $R^8$ may be joined together to form a $C_2$-$C_5$ alkylene chain and to form a ring, and $R^5$ and $R^{35}$ may be joined together to form a $C_1$-$C_5$ alkylene chain and to form a ring, in A-3, $R^{20}$ is a $C_1$-$C_6$ alkyl group, $R^{21}$ is a hydrogen atom or a $C_1$-$C_6$ alkyl group, and $R^4$ represents a hydroxyl group or a $C_1$-$C_{10}$ alkylsulfonlyoxy group, and substituent group α is selected from the group consisting of: a halogen atom; a $C_1$-$C_6$ alkyl group; a $C_2$-$C_6$ alkenyl group; a $C_2$-$C_6$ alkynyl group; a $C_1$-$C_6$ haloalkyl group; a $C_1$-$C_6$ alkoxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a nitro group; a cyano group; a phenyl group; and a methylenedioxy group.

5. An agrochemical composition comprising the triazine derivative or the salt thereof described in claim 1, and an agriculturally acceptable carrier.

6. The agrochemical composition according to claim 5, in which the agrochemical composition further comprises a surface active agent.

7. A herbicide comprising the triazine derivative or the salt thereof described in claim 1 as an active component.

8. The herbicide according to claim 7, in which the herbicide has a herbicidal activity for weeds in a field or a paddy field in which agrohorticultural plants are cultivated.

9. The herbicide according to claim 8, in which the agrohorticultural plants are agrohorticultural plants given with resistance by a breeding method or a genetic recombination technique.

10. A method of eliminating weeds in soils by applying an effective amount of herbicides comprising the triazine derivative or the salt thereof described in claim 1.

11. The method according to claim 10, in which the soils are a farmland.

12. The method according to claim 11, in which the farmland is a field or a paddy field in which agrohorticultural plants are cultivated.

13. A triazine derivative or a salt thereof represented by following Formula 2:

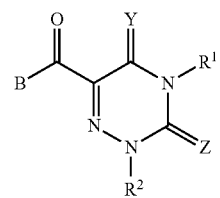

[2]

wherein B is a hydroxyl group or a $C_1$-$C_6$ alkoxy group, and Y and Z have the same definitions as those described in claim 1, and $R^1$ is selected from the group consisting of a $C_2$-$C_6$ alkenyl group; a $C_2$-$C_6$ alkynyl group; a $C_3$-$C_6$ cycloalkyl group; a $C_3$-$C_6$ cycloalkenyl group; a $C_3$-$C_6$ cycloalkyl $C_1$-$C_6$ alkyl group; a $C_1$-$C_6$ haloalkyl group; a $C_2$-$C_6$ haloalkenyl group; a $C_2$-$C_6$ haloalkynyl group; a $C_3$-$C_6$ halocycloalkyl group; a $C_3$-$C_6$ halocycloalkyl $C_1$-$C_6$ alkyl group; an amino $C_1$-$C_6$ alkyl group; a nitro $C_1$-$C_6$ alkyl group; a $C_1$-$C_6$ alkylamino $C_1$-$C_6$ alkyl group; a di($C_1$-$C_6$ alkyl)amino $C_1$-$C_6$ alkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ haloalkylthio $C_1$-$C_6$ alkyl group; a $C_1$-$C_6$ haloalkylsulfinyl $C_1$-$C_6$ alkyl group; a $C_1$-$C_6$ haloalkylsulfonyl $C_1$-$C_6$ alkyl group; a $C_1$-$C_6$ alkoxy $C_1$-$C_6$ alkyl group; a hydroxy $C_1$-$C_6$ alkyl group; a phenyl $C_1$-$C_6$ alkoxy $C_1$-$C_6$ alkyl group wherein phenyl in the group may be substituted with one substituent group selected from substituent group α or 2 to 5 substituent groups that are the same or different from each other and selected from substituent group α; a $C_1$-$C_6$ alkoxy $C_1$-$C_6$ alkoxy $C_1$-$C_6$ alkyl group; a $C_3$-$C_6$ cycloalkyloxy $C_1$-$C_6$ alkyl group; a $C_3$-$C_6$ cycloalkyl $C_1$-$C_6$ alkyloxy $C_1$-$C_6$ alkyl group; a phenyloxy $C_1$-$C_6$ alkyl group wherein the phenyl in the group may be substituted with 1 to 5 identical or different substituents selected from the substituent group α; a phenylthio $C_1$-$C_6$ alkyl group wherein the phenyl in the group may be substituted with 1 to 5 identical or different substituents selected from the substituent group α; a phenylsulfinyl $C_1$-$C_6$ alkyl group wherein the phenyl in the group may be substituted with 1 to 5 identical or different substituents selected from the substituent group α; a phenylsulfonyl $C_1$-$C_6$ alkyl group wherein the phenyl in the group may be substituted with 1 to 5 identical or different substituents selected from the substituent group α; a $C_1$-$C_6$ haloalkoxy $C_1$-$C_6$ alkyl group; a phenyl group which may be substituted with one or more substituents selected from the substituent group α; a phenyl $C_1$-$C_6$ alkyl group which may be substituted with one or more substituents selected from the substituent group α; a phenyl $C_2$-$C_6$ alkenyl group which may be substituted with one or more substituents selected from the substituent group α; a phenyl $C_2$-$C_6$ alkynyl group which may be substituted with one or more substituents selected from the substituent group α; a $C_1$-$C_6$ alkoxyimino $C_1$-$C_6$ alkyl group; a phenoxyimino $C_1$-$C_6$ alkyl group which may be substituted with one or more substituents selected from the substituent group α; a di($C_1$-$C_6$ alkoxy)$C_1$-$C_6$ alkyl group; a ($R^{31}R^{32}$N—C=O)$C_1$-$C_6$ alkyl group; a $C_1$-$C_6$ alkoxycarbonyl $C_1$-$C_6$ alkyl group; a $C_1$-$C_6$ alkylcarbonyl $C_1$-$C_6$ alkyl group;

a $C_1$-$C_6$ alkylcarbonyloxy $C_1$-$C_6$ alkyl group; a $C_1$-$C_6$ alkylidene aminooxy $C_1$-$C_6$ alkyl group; a formyl $C_1$-$C_6$ alkyl group; a $C_1$-$C_6$ alkylthio $C_1$-$C_6$ alkoxy $C_1$-$C_6$ alkyl group; a $C_1$-$C_6$ alkylsulfinyl $C_1$-$C_6$ alkoxy $C_1$-$C_6$ alkyl group; a $C_1$-$C_6$ alkylsulfonyl $C_1$-$C_6$ alkoxy $C_1$-$C_6$ alkyl group; a cyano $C_1$-$C_6$ alkoxy $C_1$-$C_6$ alkyl group; a cyano $C_1$-$C_6$ alkyl group; a $C_2$-$C_6$ alkylidene amino group; a di($C_1$-$C_{10}$ alk amino $C_1$-$C_6$ alkylidene amino group; a $NR^{31}R^{32}$ group; a $C_1$-$C_6$ alkoxy group; a $C_2$-$C_6$ alkenyloxy group; a $C_2$-$C_6$ alkynyloxy group; a $C_3$-$C_6$ cycloalkyloxy group;

a $C_3$-$C_6$ cycloalkyl $C_1$-$C_6$ alkyloxy group; a $C_1$-$C_6$ haloalkoxy group; a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α, and when the heteroatom in the heterocyclic group is a sulfur atom, the sulfur atom may be oxidized to sulfoxide or sulfone]; a $C_1$-$C_6$ alkyl group substituted with a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α; a $C_1$-$C_6$ alkoxy $C_1$-$C_6$ alkyl group substituted with a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α; or a $C_1$-$C_6$ alkoxy $C_1$-$C_6$ alkyl group substituted with a heterocyclic-oxy group in which the heterocyclic group in the heterocyclic-oxy group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α;

$R^{31}$ and $R^{32}$ each independently represent a hydrogen atom; a $C_1$-$C_6$ alkyl group; a phenyl group which may be substituted with one or more substituents selected from the substituent group α; a benzyl group which may be substituted with one or more substituents selected from the substituent group α; a $C_1$-$C_6$ alkoxy $C_1$-$C_6$ alkyl group; a $C_1$-$C_6$ alkylcarbonyl group; a $C_1$-$C_{10}$ alkylthio carbonyl group; a $C_1$-$C_6$ alkoxycarbonyl group; a $C_1$-$C_6$ haloalkyl group; a $C_3$-$C_6$ cycloalkyl group; a $C_3$-$C_6$ cycloalkyl $C_1$-$C_6$ alkyl group; a $C_1$-$C_6$ alkylsulfonyl group; a phenylsulfonyl group which may be substituted with one or more substituents selected from the substituent group α; a benzylsulfonyl group which may be substituted with one or more substituents selected from the substituent group α; a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α; or a $C_1$-$C_6$ alkyl group substituted with a heterocyclic group in which the heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α, herein, $R^{31}$ and $R^{32}$ may be joined together to form a 5- to 6-membered ring with adjacent nitrogen atom, and the one or more carbon atoms in the ring may be substituted with a sulfur atom and/or an oxygen atom, wherein substituent group α is selected from the group consisting of:

a halogen atom; a hydroxyl group; a $C_1$-$C_6$ alkyl group; a $C_3$-$C_6$ cycloalkyl group; a $C_3$-$C_6$ cycloalkyl $C_1$-$C_6$ alkyl group; a $C_2$-$C_6$ alkenyl group; a $C_2$-$C_6$ alkynyl group; a $C_1$-$C_6$ haloalkyl group; a $C_2$-$C_6$ haloalkenyl group; a $C_2$-$C_6$ haloalkynyl group; a $C_3$-$C_6$ halocycloalkyl group; a $C_3$-$C_6$ halocycloalkyl $C_1$-$C_6$ alkyl group; a $C_1$-$C_6$ alkoxy group; a $C_3$-$C_6$ cycloalkyloxy group; a $C_2$-$C_6$ alkenyloxy group; a $C_2$-$C_6$ alkynyloxy group; a $C_1$-$C_6$ alkylcarbonyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a $C_1$-$C_6$ alkylcarbonylamino group; a mono($C_1$-$C_6$ alkyl)amino group; a di($C_1$-$C_6$ alkyl)amino group; a hydroxy $C_1$-$C_6$ alkyl group; a $C_1$-$C_6$ alkoxy $C_1$-$C_6$ alkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ haloalkylthio $C_1$-$C_6$ alkyl group; a $C_1$-$C_6$ haloalkylsulfinyl $C_1$-$C_6$ alkyl group; a $C_1$-$C_6$ haloalkylsulfonyl $C_1$-$C_6$ alkyl group; a cyano $C_1$-$C_6$ alkyl group; a $C_1$-$C_6$ alkoxy $C_1$-$C_6$ alkoxy group; a $C_3$-$C_6$ cycloalkyl $C_1$-$C_6$ alkyloxy group; a $C_1$-$C_6$ haloalkoxy $C_1$-$C_6$ alkoxy group; a cyano $C_1$-$C_6$ alkoxy group; a $C_1$-$C_6$ acyl group; a $C_1$-$C_6$ alkoxyimino $C_1$-$C_6$ alkyl group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; a nitro group; a cyano group; a phenyl group wherein the phenyl in the group may be substituted with 1 to 5 identical or different substituents selected from the substituent group β; a heterocyclic group comprising 2 to 10 carbon atoms and 1 to 5 identical or different heteroatoms selected from an oxygen atom, a sulfur atom, and a nitrogen atom wherein the group may be substituted with 1 to 5 identical or different substituents selected from the substituent group β; a heterocyclic oxy group comprising 2 to 10 carbon atoms and 1 to 5 identical or different heteroatoms selected from an oxygen atom, a sulfur atom, and a nitrogen atom wherein the group may be substituted with 1 to 5 identical or different substituents selected from the substituent group β; and a $C_3$-$C_6$ alkylene group formed with two adjacent substituent groups, wherein 1 to 3 carbon atoms in the alkylene group may be substituted with an atom selected from a group consisting of an oxygen atom, a sulfur atom, a nitrogen atom, and a carbon atom constituting an carbonyl group; and wherein substituent group β is selected from the group consisting of: a halogen atom, a nitro group, a cyano group, a $C_1$-$C_6$ alkyl group, a $C_1$-$C_6$ haloalkyl group, a $C_1$-$C_6$ alkoxy group, and a $C_1$-$C_6$ haloalkoxy group, $R^2$ is selected from the group consisting of a hydrogen atom; a $C_1$-$C_6$ alkyl group; a $C_2$-$C_6$ alkenyl group; a $C_2$-$C_6$ alkynyl group; a $C_3$-$C_6$ cycloalkyl group; a $C_1$-$C_6$ haloalkyl group; a $C_2$-$C_6$ haloalkenyl group; a $C_2$-$C_6$ haloalkynyl group; a $C_1$-$C_6$ alkoxy $C_1$-$C_6$ alkyl group; a $C_3$-$C_6$ cycloalkyloxy $C_1$-$C_6$ alkyl group; a di($C_1$-$C_6$ alkoxy) $C_1$-$C_6$ alkyl group; a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α; a phenyl group; a phenyl $C_1$-$C_6$ alkyl group; a phenyl $C_2$-$C_6$ alkenyl group; and a phenyl $C_2$-$C_6$ alkynyl group.

14. The triazine derivative or the salt thereof according to claim 13, wherein Y in Formula 2 is an oxygen atom, $R^1$ in Formula 2 is selected from the group consisting of a $C_2$-$C_6$ alkenyl group; a $C_2$-$C_6$ alkynyl group; a $C_3$-$C_6$ cycloalkyl group; a $C_3$-$C_6$ cycloalkenyl group; a $C_1$-$C_6$ haloalkyl group; a $C_2$-$C_6$ haloalkenyl group; a $C_1$-$C_6$ alkoxy $C_1$-$C_6$ alkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ alkoxyimino $C_1$-$C_6$ alkyl group; a $C_1$-$C_6$ alkoxycarbonyl $C_1$-$C_6$ alkyl group; a $C_1$-$C_6$ alkylcarbonyl $C_1$-$C_6$ alkyl group; a phenyl group which may be substituted with one or more substituents selected from the substituent group α; a phenyl $C_1$-$C_6$ alkyl group which may be substituted with one or more substituents selected from the substituent group α; and a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α, and when the heteroatom in the heterocyclic group is a sulfur atom, the sulfur atom may be oxidized to sulfoxide or sulfone; and $R^2$ in Formula 2 is selected from the group consisting of a $C_1$-$C_6$ alkyl group; a $C_1$-$C_6$ haloalkyl group; a phenyl group; and a heterocyclic group comprising 3 to 10 carbon atoms and one or more identical or different heteroatoms selected from an oxygen atom, a sulfur atom, and a nitrogen atom wherein the group may be substituted with 1 to 5 identical or different substituents selected from the substituent group α.

15. The triazine derivative or the salt thereof according to claim 14, wherein Y in Formula 2 is an oxygen atom, $R^1$ in Formula 2 is selected from the group consisting of a $C_2$-$C_6$ alkenyl group; a $C_2$-$C_6$ alkynyl group; a $C_3$-$C_6$ cycloalkyl group; a $C_3$-$C_6$ cycloalkenyl group; a $C_1$-$C_6$ haloalkyl group; a $C_2$-$C_6$ haloalkenyl group; a $C_1$-$C_6$ alkoxy $C_1$-$C_6$ alkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ alkoxyimino $C_1$-$C_6$ alkyl group; a $C_1$-$C_6$ alkoxycarbonyl $C_1$-$C_6$ alkyl group; a $C_1$-$C_6$ alkylcarbonyl $C_1$-$C_6$ alkyl group; a phenyl group which may be substituted with one or more substituents selected from the substituent group α; a phenyl $C_1$-$C_6$ alkyl group which may be substituted with one or more substituents selected from the substituent group α; and a heterocyclic group selected from the group consisting of pyridyl group, pyrimidinyl group, pyrazinyl group, pyridazinyl group, thienyl group, thiazolyl group, isoxazolyl group, pyrazolyl group, morpholinyl group, thiomorpholinyl group, and pyperazinyl group wherein the group may be substituted with 1 to 5 identical or different substituents selected from the substituent group α, and when the heteroatom in the heterocyclic group is a sulfur atom, the sulfur atom may be oxidized to sulfoxide or sulfone;

$R^2$ is a group selected from a group consisting of a $C_1$-$C_6$ alkyl group; a $C_1$-$C_6$ haloalkyl group; and a pyridyl group; and, substituent group α is selected from the group consisting of a halogen atom; a $C_1$-$C_6$ alkyl group; a $C_2$-$C_6$ alkenyl group; a $C_2$-$C_6$ alkynyl group; a $C_1$-$C_6$ haloalkyl group; a $C_1$-$C_6$ alkoxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a nitro group; a cyano group; a phenyl group; and a methylenedioxy group.

* * * * *

UNITED STATES PATENT AND TRADEMARK OFFICE
CERTIFICATE OF CORRECTION

PATENT NO.        : 8,969,554 B2
APPLICATION NO.   : 13/807590
DATED             : March 3, 2015
INVENTOR(S)       : Shibayama et al.

It is certified that error appears in the above-identified patent and that said Letters Patent is hereby corrected as shown below:

On the title page item [57]

Formula 1, replace 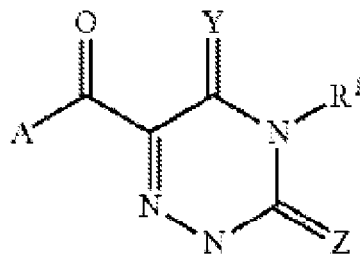

with 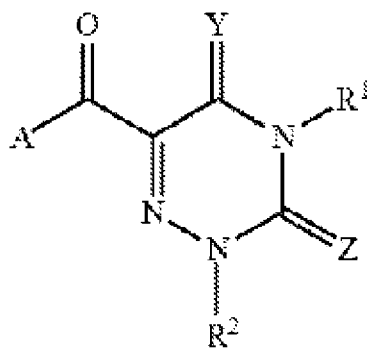

Signed and Sealed this
Thirty-first Day of May, 2016

Michelle K. Lee
*Director of the United States Patent and Trademark Office*